US009815869B2

(12) United States Patent
Notter et al.

(10) Patent No.: US 9,815,869 B2
(45) Date of Patent: Nov. 14, 2017

(54) SP-B AND SP-C PEPTIDES, SYNTHETIC LUNG SURFACTANTS, AND USE THEREOF

(71) Applicants: UNIVERSITY OF ROCHESTER, Rochester, NY (US); LOS ANGELES BIOMEDICAL RESEARCH INSTITUTE AT HARBOR—UCLA MEDICAL CENTER, Torrance, CA (US)

(72) Inventors: Robert H. Notter, Pittsford, NY (US); Alan J. Waring, Irvine, CA (US); Frans J. Walther, Redondo Beach, CA (US); Larry M. Gordon, Torrance, CA (US); Zhengdong Wang, Rochester, NY (US)

(73) Assignees: University of Rochester, Rochester, NY (US); Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 14/376,726

(22) PCT Filed: Feb. 11, 2013

(86) PCT No.: PCT/US2013/025532
§ 371 (c)(1),
(2) Date: Aug. 5, 2014

(87) PCT Pub. No.: WO2013/120058
PCT Pub. Date: Aug. 15, 2013

(65) Prior Publication Data
US 2015/0125515 A1 May 7, 2015

Related U.S. Application Data

(60) Provisional application No. 61/596,913, filed on Feb. 9, 2012.

(51) Int. Cl.
| | | |
|---|---|---|
| *C07K 14/00* | (2006.01) | |
| *C07K 14/47* | (2006.01) | |
| *A61K 38/16* | (2006.01) | |
| *A61K 45/06* | (2006.01) | |
| *C07K 7/08* | (2006.01) | |
| *A61K 38/00* | (2006.01) | |

(52) U.S. Cl.
CPC ............ *C07K 14/001* (2013.01); *A61K 38/16* (2013.01); *A61K 45/06* (2013.01); *C07K 7/08* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,538,090 B1 | 5/2009 | Waring et al. | |
| 2008/0045449 A1* | 2/2008 | Johansson ............ | A61K 9/0073 514/15.5 |
| 2010/0004173 A1 | 1/2010 | Johansson et al. | |
| 2010/0055164 A1 | 3/2010 | Notter et al. | |

FOREIGN PATENT DOCUMENTS

| | | | | |
|---|---|---|---|---|
| EP | 0335133 A2 | * | 10/1989 | ........... A61K 9/0082 |
| IT | WO 2009018908 A1 | * | 2/2009 | ........... C07K 14/785 |
| WO | 2008/011559 A2 | | 1/2008 | |
| WO | 2010/139442 A1 | | 12/2010 | |
| WO | 2011/115538 A1 | | 9/2011 | |

OTHER PUBLICATIONS

Gorecke, "Pulmonary surfactant: functions and molecule composition", Biochmica et Biophysica Acta, 1998, pp. 79-89.*
Almlen et al., "Synthetic Surfactant Based on Analogues of SP-B and SP-C Is Superior to Single-Peptide Surfactants in Ventilated Premature Rabbits," Neonatology 98:91-99 (2010).
Johansson et al., "A Synthetic Surfactant Based on a Poly-Leu SP-C Analog and Phospholipids: Effects on Tidal Volumes and Lung Gas Volumes in Ventilated Immature Newborn Rabbits," J. Appl. Physiol. 95:2055-2063 (2003).
Partial Supplementary EP Search Report for EP13746107.5 dated Jun. 15, 2016.
Raghavendran et al., "Surfactant Therapy of ALI and ARDS," Crit. Care Clin. 27(3):525-559 (2011).
Walther et al., "Critical Structural and Functional Roles for the N-Terminal Insertion Sequence in Surfactant Protein B Analogs," PLoS One 5(1):e8672 (2010).
Wang et al., "Activity and Inhibition Resistance of a Phospholipase-Resistant Synthetic Surfactant in Rat Lungs," Am Respir Cell Mol Biol. 37:387-394 (2007).
Walther et al., "Dynamic Surface Activity of a Fully Synthetic Phospholipase-Resistant Lipid/Peptide Lung Surfactant," PLoSOne 2(10):e1039 (2007).
PCT International Search Report and Written Opinion for PCT/US2013/025532, dated Aug. 2, 2013.
Willson et al., "Surfactant for Pediatric Acute Lung Injury," Pediatr. Clin. N. Am., 55:546-575 (2008).
Raghavendran et al., "Pharmacotherapy of Acute Lung Injury and Acute Respiratory Distress Syndrome," Curr. Med. Chem. 15:1911-1924 (2008).
Chess et al., "Surfactant Replacement Therapy to Lung Injury," in Notter et al., eds., Lung Injury: Mechanisms, Pathophysiology and Therapy, pp. 617-663 (2005).

(Continued)

*Primary Examiner* — Lianko Garyu
(74) *Attorney, Agent, or Firm* — LeClairRyan, a Professional Corporation

(57) ABSTRACT

The present invention relates to synthetic lung surfactant compositions that include a novel surface active peptide and a phospholipid, including phospholipase-resistant phosphoglycerol derivatives, phospholipase-resistant phospho-choline derivatives, naturally occurring phospholipids, or a combination thereof. Uses of the surfactant compositions of the present invention to treat endogenous surfactant dysfunctional or deficient lung tissue and to deliver therapeutic agents are also disclosed.

15 Claims, 2 Drawing Sheets

(56) References Cited

OTHER PUBLICATIONS

Extended European Search Report for European Patent Application No. 13746107.5 (dated Sep. 16, 2016).

* cited by examiner

SEQUENCE LISTING

```
<160> NUMBER OF SEQ ID NOS: 504

<210> SEQ ID NO 1
<211> LENGTH: 34
<212> TYPE: PRT
<213> ORGANISM: artificial
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: Xaa is an uncharged amino acid
<220> FEATURE:
<221> NAME/KEY: MISC_FEATURE
<222> LOCATION: (4)..(4)
<223> OTHER INFORMATION: Xaa is an uncharged amino acid
<220> FEATURE:
<221> NAME/KEY: MISC_FEATURE
<222> LOCATION: (16)..(19)
<223> OTHER INFORMATION: Xaa represents a turn or loop sequence
      containing four to ten amino acids, which can include Pro Lys Gly
      Gly, Asp Ala Thr Lys, Asp His Gly Ser, His Ser Gly Asp, or Glu
      Ala Gly Asp
<220> FEATURE:
<221> NAME/KEY: MISC_FEATURE
<222> LOCATION: (27)..(27)
<223> OTHER INFORMATION: Xaa is an uncharged amino acid
<220> FEATURE:
<221> NAME/KEY: MISC_FEATURE
<222> LOCATION: (33)..(33)
<223> OTHER INFORMATION: Xaa is an uncharged amino acid

<400> SEQUENCE: 1
```

```
Xaa Trp Leu Xaa Arg Ala Leu Ile Lys Arg Ile Gln Ala Met Ile Xaa
1               5                   10                  15

Xaa Xaa Xaa Arg Met Leu Pro Gln Leu Val Xaa Arg Leu Val Leu Arg
            20                  25                  30

Xaa Ser

<210> SEQ ID NO 2
<211> LENGTH: 34
<212> TYPE: PRT
<213> ORGANISM: artificial
<220> FEATURE:
<223> OTHER INFORMATION: MB_ala

<400> SEQUENCE: 2

Ala Trp Leu Ala Arg Ala Leu Ile Lys Arg Ile Gln Ala Met Ile Pro
1               5                   10                  15

Lys Gly Gly Arg Met Leu Pro Gln Leu Val Ala Arg Leu Val Leu Arg
            20                  25                  30

Ala Ser

<210> SEQ ID NO 3
<211> LENGTH: 34
<212> TYPE: PRT
<213> ORGANISM: artificial
<220> FEATURE:
<223> OTHER INFORMATION: MB_ser

<400> SEQUENCE: 3

Ser Trp Leu Ser Arg Ala Leu Ile Lys Arg Ile Gln Ala Met Ile Pro
1               5                   10                  15

Lys Gly Gly Arg Met Leu Pro Gln Leu Val Ser Arg Leu Val Leu Arg
            20                  25                  30

Ser Ser

<210> SEQ ID NO 4
<211> LENGTH: 34
<212> TYPE: PRT
<213> ORGANISM: artificial
<220> FEATURE:
<223> OTHER INFORMATION: MB_datk

<400> SEQUENCE: 4

Cys Trp Leu Cys Arg Ala Leu Ile Lys Arg Ile Gln Ala Met Ile Asp
1               5                   10                  15

Ala Thr Lys Arg Met Leu Pro Gln Leu Val Cys Arg Leu Val Leu Arg
            20                  25                  30

Cys Ser

<210> SEQ ID NO 5
<211> LENGTH: 34
<212> TYPE: PRT
<213> ORGANISM: artificial
<220> FEATURE:
<223> OTHER INFORMATION: MB_datk_ala

<400> SEQUENCE: 5

Ala Trp Leu Ala Arg Ala Leu Ile Lys Arg Ile Gln Ala Met Ile Asp
1               5                   10                  15

Ala Thr Lys Arg Met Leu Pro Gln Leu Val Ala Arg Leu Val Leu Arg
            20                  25                  30
```

-continued

Ala Ser

<210> SEQ ID NO 6
<211> LENGTH: 34
<212> TYPE: PRT
<213> ORGANISM: artificial
<220> FEATURE:
<223> OTHER INFORMATION: MB_datk_ser

<400> SEQUENCE: 6

Ser Trp Leu Ser Arg Ala Leu Ile Lys Arg Ile Gln Ala Met Ile Asp
1               5                   10                  15

Ala Thr Lys Arg Met Leu Pro Gln Leu Val Ser Arg Leu Val Leu Arg
            20                  25                  30

Ser Ser

<210> SEQ ID NO 7
<211> LENGTH: 34
<212> TYPE: PRT
<213> ORGANISM: artificial
<220> FEATURE:
<223> OTHER INFORMATION: MB_dhgs

<400> SEQUENCE: 7

Cys Trp Leu Cys Arg Ala Leu Ile Lys Arg Ile Gln Ala Met Ile Asp
1               5                   10                  15

His Gly Ser Arg Met Leu Pro Gln Leu Val Cys Arg Leu Val Leu Arg
            20                  25                  30

Cys Ser

<210> SEQ ID NO 8
<211> LENGTH: 34
<212> TYPE: PRT
<213> ORGANISM: artificial
<220> FEATURE:
<223> OTHER INFORMATION: MB_dhgs_ala

<400> SEQUENCE: 8

Ala Trp Leu Ala Arg Ala Leu Ile Lys Arg Ile Gln Ala Met Ile Asp
1               5                   10                  15

His Gly Ser Arg Met Leu Pro Gln Leu Val Ala Arg Leu Val Leu Arg
            20                  25                  30

Ala Ser

<210> SEQ ID NO 9
<211> LENGTH: 34
<212> TYPE: PRT
<213> ORGANISM: artificial
<220> FEATURE:
<223> OTHER INFORMATION: MB_dhgs_ser

<400> SEQUENCE: 9

Ser Trp Leu Ser Arg Ala Leu Ile Lys Arg Ile Gln Ala Met Ile Asp
1               5                   10                  15

His Gly Ser Arg Met Leu Pro Gln Leu Val Ser Arg Leu Val Leu Arg
            20                  25                  30

Ser Ser

<210> SEQ ID NO 10
<211> LENGTH: 34
<212> TYPE: PRT
<213> ORGANISM: artificial

```
<220> FEATURE:
<223> OTHER INFORMATION: MB_hsgd

<400> SEQUENCE: 10

Cys Trp Leu Cys Arg Ala Leu Ile Lys Arg Ile Gln Ala Met Ile His
1               5                   10                  15

Ser Gly Asp Arg Met Leu Pro Gln Leu Val Cys Arg Leu Val Leu Arg
            20                  25                  30

Cys Ser

<210> SEQ ID NO 11
<211> LENGTH: 34
<212> TYPE: PRT
<213> ORGANISM: artificial
<220> FEATURE:
<223> OTHER INFORMATION: MB_hsgd_ala

<400> SEQUENCE: 11

Ala Trp Leu Ala Arg Ala Leu Ile Lys Arg Ile Gln Ala Met Ile His
1               5                   10                  15

Ser Gly Asp Arg Met Leu Pro Gln Leu Val Ala Arg Leu Val Leu Arg
            20                  25                  30

Ala Ser

<210> SEQ ID NO 12
<211> LENGTH: 34
<212> TYPE: PRT
<213> ORGANISM: artificial
<220> FEATURE:
<223> OTHER INFORMATION: MB_hsgd_ser

<400> SEQUENCE: 12

Ser Trp Leu Ser Arg Ala Leu Ile Lys Arg Ile Gln Ala Met Ile His
1               5                   10                  15

Ser Gly Asp Arg Met Leu Pro Gln Leu Val Ser Arg Leu Val Leu Arg
            20                  25                  30

Ser Ser

<210> SEQ ID NO 13
<211> LENGTH: 34
<212> TYPE: PRT
<213> ORGANISM: artificial
<220> FEATURE:
<223> OTHER INFORMATION: MB_eagd

<400> SEQUENCE: 13

Cys Trp Leu Cys Arg Ala Leu Ile Lys Arg Ile Gln Ala Met Ile Glu
1               5                   10                  15

Ala Gly Asp Arg Met Leu Pro Gln Leu Val Cys Arg Leu Val Leu Arg
            20                  25                  30

Cys Ser

<210> SEQ ID NO 14
<211> LENGTH: 34
<212> TYPE: PRT
<213> ORGANISM: artificial
<220> FEATURE:
<223> OTHER INFORMATION: MB_eagd_ala

<400> SEQUENCE: 14

Ala Trp Leu Ala Arg Ala Leu Ile Lys Arg Ile Gln Ala Met Ile Glu
1               5                   10                  15
```

```
Ala Gly Asp Arg Met Leu Pro Gln Leu Val Ala Arg Leu Val Leu Arg
            20                  25                  30

Ala Ser

<210> SEQ ID NO 15
<211> LENGTH: 34
<212> TYPE: PRT
<213> ORGANISM: artificial
<220> FEATURE:
<223> OTHER INFORMATION: MB_eagd_ser

<400> SEQUENCE: 15

Ser Trp Leu Ser Arg Ala Leu Ile Lys Arg Ile Gln Ala Met Ile Glu
1               5                   10                  15

Ala Gly Asp Arg Met Leu Pro Gln Leu Val Ser Arg Leu Val Leu Arg
            20                  25                  30

Ser Ser

<210> SEQ ID NO 16
<211> LENGTH: 41
<212> TYPE: PRT
<213> ORGANISM: artificial
<220> FEATURE:
<223> OTHER INFORMATION: SMB_ala

<400> SEQUENCE: 16

Phe Pro Ile Pro Leu Pro Tyr Ala Trp Leu Ala Arg Ala Leu Ile Lys
1               5                   10                  15

Arg Ile Gln Ala Met Ile Pro Lys Gly Gly Arg Met Leu Pro Gln Leu
            20                  25                  30

Val Ala Arg Leu Val Leu Arg Ala Ser
        35                  40

<210> SEQ ID NO 17
<211> LENGTH: 41
<212> TYPE: PRT
<213> ORGANISM: artificial
<220> FEATURE:
<223> OTHER INFORMATION: SMB_ser

<400> SEQUENCE: 17

Phe Pro Ile Pro Leu Pro Tyr Ser Trp Leu Ser Arg Ala Leu Ile Lys
1               5                   10                  15

Arg Ile Gln Ala Met Ile Pro Lys Gly Gly Arg Met Leu Pro Gln Leu
            20                  25                  30

Val Ser Arg Leu Val Leu Arg Ser Ser
        35                  40

<210> SEQ ID NO 18
<211> LENGTH: 41
<212> TYPE: PRT
<213> ORGANISM: artificial
<220> FEATURE:
<223> OTHER INFORMATION: SMB_datk

<400> SEQUENCE: 18

Phe Pro Ile Pro Leu Pro Tyr Cys Trp Leu Cys Arg Ala Leu Ile Lys
1               5                   10                  15

Arg Ile Gln Ala Met Ile Asp Ala Thr Lys Arg Met Leu Pro Gln Leu
            20                  25                  30

Val Cys Arg Leu Val Leu Arg Cys Ser
```

35                  40

<210> SEQ ID NO 19
<211> LENGTH: 41
<212> TYPE: PRT
<213> ORGANISM: artificial
<220> FEATURE:
<223> OTHER INFORMATION: SMB_datk_ala

<400> SEQUENCE: 19

Phe Pro Ile Pro Leu Pro Tyr Ala Trp Leu Ala Arg Ala Leu Ile Lys
1               5                   10                  15

Arg Ile Gln Ala Met Ile Asp Ala Thr Lys Arg Met Leu Pro Gln Leu
            20                  25                  30

Val Ala Arg Leu Val Leu Arg Ala Ser
        35                  40

<210> SEQ ID NO 20
<211> LENGTH: 41
<212> TYPE: PRT
<213> ORGANISM: artificial
<220> FEATURE:
<223> OTHER INFORMATION: SMB_datk_ser

<400> SEQUENCE: 20

Phe Pro Ile Pro Leu Pro Tyr Ser Trp Leu Ser Arg Ala Leu Ile Lys
1               5                   10                  15

Arg Ile Gln Ala Met Ile Asp Ala Thr Lys Arg Met Leu Pro Gln Leu
            20                  25                  30

Val Ser Arg Leu Val Leu Arg Ser Ser
        35                  40

<210> SEQ ID NO 21
<211> LENGTH: 41
<212> TYPE: PRT
<213> ORGANISM: artificial
<220> FEATURE:
<223> OTHER INFORMATION: SMB_dhgs

<400> SEQUENCE: 21

Phe Pro Ile Pro Leu Pro Tyr Cys Trp Leu Cys Arg Ala Leu Ile Lys
1               5                   10                  15

Arg Ile Gln Ala Met Ile Asp His Gly Ser Arg Met Leu Pro Gln Leu
            20                  25                  30

Val Cys Arg Leu Val Leu Arg Cys Ser
        35                  40

<210> SEQ ID NO 22
<211> LENGTH: 41
<212> TYPE: PRT
<213> ORGANISM: artificial
<220> FEATURE:
<223> OTHER INFORMATION: SMB_dhgs_ala

<400> SEQUENCE: 22

Phe Pro Ile Pro Leu Pro Tyr Ala Trp Leu Ala Arg Ala Leu Ile Lys
1               5                   10                  15

Arg Ile Gln Ala Met Ile Asp His Gly Ser Arg Met Leu Pro Gln Leu
            20                  25                  30

Val Ala Arg Leu Val Leu Arg Ala Ser
        35                  40

<210> SEQ ID NO 23
<211> LENGTH: 41
<212> TYPE: PRT
<213> ORGANISM: artificial
<220> FEATURE:
<223> OTHER INFORMATION: SMB_dhgs_ser

<400> SEQUENCE: 23

Phe Pro Ile Pro Leu Pro Tyr Ser Trp Leu Ser Arg Ala Leu Ile Lys
1               5                   10                  15

Arg Ile Gln Ala Met Ile Asp His Gly Ser Arg Met Leu Pro Gln Leu
            20                  25                  30

Val Ser Arg Leu Val Leu Arg Ser Ser
        35                  40

<210> SEQ ID NO 24
<211> LENGTH: 41
<212> TYPE: PRT
<213> ORGANISM: artificial
<220> FEATURE:
<223> OTHER INFORMATION: SMB_hsgd

<400> SEQUENCE: 24

Phe Pro Ile Pro Leu Pro Tyr Cys Trp Leu Cys Arg Ala Leu Ile Lys
1               5                   10                  15

Arg Ile Gln Ala Met Ile His Ser Gly Asp Arg Met Leu Pro Gln Leu
            20                  25                  30

Val Cys Arg Leu Val Leu Arg Cys Ser
        35                  40

<210> SEQ ID NO 25
<211> LENGTH: 41
<212> TYPE: PRT
<213> ORGANISM: artificial
<220> FEATURE:
<223> OTHER INFORMATION: SMB_hsgd_ala

<400> SEQUENCE: 25

Phe Pro Ile Pro Leu Pro Tyr Ala Trp Leu Ala Arg Ala Leu Ile Lys
1               5                   10                  15

Arg Ile Gln Ala Met Ile His Ser Gly Asp Arg Met Leu Pro Gln Leu
            20                  25                  30

Val Ala Arg Leu Val Leu Arg Ala Ser
        35                  40

<210> SEQ ID NO 26
<211> LENGTH: 41
<212> TYPE: PRT
<213> ORGANISM: artificial
<220> FEATURE:
<223> OTHER INFORMATION: SMB_hsgd_ser

<400> SEQUENCE: 26

Phe Pro Ile Pro Leu Pro Tyr Ser Trp Leu Ser Arg Ala Leu Ile Lys
1               5                   10                  15

Arg Ile Gln Ala Met Ile His Ser Gly Asp Arg Met Leu Pro Gln Leu
            20                  25                  30

Val Ser Arg Leu Val Leu Arg Ser Ser
        35                  40

<210> SEQ ID NO 27
<211> LENGTH: 41
<212> TYPE: PRT

<213> ORGANISM: artificial
<220> FEATURE:
<223> OTHER INFORMATION: SMB_eagd

<400> SEQUENCE: 27

Phe Pro Ile Pro Leu Pro Tyr Cys Trp Leu Cys Arg Ala Leu Ile Lys
1               5                   10                  15

Arg Ile Gln Ala Met Ile Glu Ala Gly Asp Arg Met Leu Pro Gln Leu
            20                  25                  30

Val Cys Arg Leu Val Leu Arg Cys Ser
        35                  40

<210> SEQ ID NO 28
<211> LENGTH: 41
<212> TYPE: PRT
<213> ORGANISM: artificial
<220> FEATURE:
<223> OTHER INFORMATION: SMB_eagd_ala

<400> SEQUENCE: 28

Phe Pro Ile Pro Leu Pro Tyr Ala Trp Leu Ala Arg Ala Leu Ile Lys
1               5                   10                  15

Arg Ile Gln Ala Met Ile Glu Ala Gly Asp Arg Met Leu Pro Gln Leu
            20                  25                  30

Val Ala Arg Leu Val Leu Arg Ala Ser
        35                  40

<210> SEQ ID NO 29
<211> LENGTH: 41
<212> TYPE: PRT
<213> ORGANISM: artificial
<220> FEATURE:
<223> OTHER INFORMATION: SMB_eagd_ser

<400> SEQUENCE: 29

Phe Pro Ile Pro Leu Pro Tyr Ser Trp Leu Ser Arg Ala Leu Ile Lys
1               5                   10                  15

Arg Ile Gln Ala Met Ile Glu Ala Gly Asp Arg Met Leu Pro Gln Leu
            20                  25                  30

Val Ser Arg Leu Val Leu Arg Ser Ser
        35                  40

<210> SEQ ID NO 30
<211> LENGTH: 19
<212> TYPE: PRT
<213> ORGANISM: artificial
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: Xaa is optional and can be Leu or Phe
<220> FEATURE:
<221> NAME/KEY: MISC_FEATURE
<222> LOCATION: (2)..(2)
<223> OTHER INFORMATION: Xaa is optional and can be Gly or Arg
<220> FEATURE:
<221> NAME/KEY: MISC_FEATURE
<222> LOCATION: (5)..(5)
<223> OTHER INFORMATION: Xaa is Phe, Cys, or Tyr
<220> FEATURE:
<221> NAME/KEY: MISC_FEATURE
<222> LOCATION: (6)..(6)
<223> OTHER INFORMATION: Xaa is Phe or Tyr
<220> FEATURE:
<221> NAME/KEY: MISC_FEATURE
<222> LOCATION: (8)..(8)

```
<223> OTHER INFORMATION: Xaa is Ser or Val
<220> FEATURE:
<221> NAME/KEY: MISC_FEATURE
<222> LOCATION: (9)..(9)
<223> OTHER INFORMATION: Xaa is Ser or His
<220> FEATURE:
<221> NAME/KEY: MISC_FEATURE
<222> LOCATION: (14)..(14)
<223> OTHER INFORMATION: Xaa is Leu or Lys
<220> FEATURE:
<221> NAME/KEY: MISC_FEATURE
<222> LOCATION: (15)..(16)
<223> OTHER INFORMATION: Xaa is independently Ile, Leu, or Val
<220> FEATURE:
<221> NAME/KEY: MISC_FEATURE
<222> LOCATION: (17)..(19)
<223> OTHER INFORMATION: Xaa is independently Val or Leu

<400> SEQUENCE: 30

Xaa Xaa Ile Pro Xaa Xaa Pro Xaa Xaa Leu Lys Arg Leu Leu Xaa Xaa
1               5                   10                  15

Xaa Xaa Xaa

<210> SEQ ID NO 31
<211> LENGTH: 19
<212> TYPE: PRT
<213> ORGANISM: artificial
<220> FEATURE:
<223> OTHER INFORMATION: Mini-SPCff_dog

<400> SEQUENCE: 31

Leu Gly Ile Pro Phe Phe Pro Ser Ser Leu Lys Arg Leu Leu Ile Ile
1               5                   10                  15

Val Val Val

<210> SEQ ID NO 32
<211> LENGTH: 19
<212> TYPE: PRT
<213> ORGANISM: artificial
<220> FEATURE:
<223> OTHER INFORMATION: Mini-SPCff_dog_leu

<400> SEQUENCE: 32

Leu Gly Ile Pro Phe Phe Pro Ser Ser Leu Lys Arg Leu Leu Ile Ile
1               5                   10                  15

Leu Leu Leu

<210> SEQ ID NO 33
<211> LENGTH: 19
<212> TYPE: PRT
<213> ORGANISM: artificial
<220> FEATURE:
<223> OTHER INFORMATION: Mini-C dog cf_cys5

<400> SEQUENCE: 33

Leu Gly Ile Pro Cys Phe Pro Ser Ser Leu Lys Arg Leu Leu Ile Ile
1               5                   10                  15

Val Val Val

<210> SEQ ID NO 34
<211> LENGTH: 19
<212> TYPE: PRT
<213> ORGANISM: artificial
<220> FEATURE:
<223> OTHER INFORMATION: Mini-SPCff_2_leu

<400> SEQUENCE: 34
```

```
Phe Gly Ile Pro Phe Phe Pro Val His Leu Lys Arg Leu Leu Ile Leu
1               5                   10                  15

Leu Leu Leu

<210> SEQ ID NO 35
<211> LENGTH: 28
<212> TYPE: PRT
<213> ORGANISM: artificial
<220> FEATURE:
<223> OTHER INFORMATION: Super Mini-C

<400> SEQUENCE: 35

Phe Arg Ile Pro Tyr Tyr Pro Val His Leu Lys Arg Leu Leu Val Val
1               5                   10                  15

Val Val Val Ile Val Gly Ala Leu Leu Met Gly Leu
            20                  25

<210> SEQ ID NO 36
<211> LENGTH: 33
<212> TYPE: PRT
<213> ORGANISM: artificial
<220> FEATURE:
<223> OTHER INFORMATION: consensus
<220> FEATURE:
<221> NAME/KEY: MISC_FEATURE
<222> LOCATION: (4)..(5)
<223> OTHER INFORMATION: Xaa is independently Ser or Phe
<220> FEATURE:
<221> NAME/KEY: MISC_FEATURE
<222> LOCATION: (7)..(7)
<223> OTHER INFORMATION: Xaa is Val or Ser
<220> FEATURE:
<221> NAME/KEY: MISC_FEATURE
<222> LOCATION: (8)..(8)
<223> OTHER INFORMATION: Xaa is His or Ser
<220> FEATURE:
<221> NAME/KEY: MISC_FEATURE
<222> LOCATION: (15)..(15)
<223> OTHER INFORMATION: Xaa is an ion lock pair with the amino acid at
      position 19, or Leu, Ile, or Val
<220> FEATURE:
<221> NAME/KEY: MISC_FEATURE
<222> LOCATION: (19)..(19)
<223> OTHER INFORMATION: Xaa is an ion lock pair with the amino acid at
      position 15, or Leu, Ile, or Val
<220> FEATURE:
<221> NAME/KEY: MISC_FEATURE
<222> LOCATION: (20)..(20)
<223> OTHER INFORMATION: Xaa is an ion lock pair with the amino acid at
      position 24, or Leu, Ile, or Val
<220> FEATURE:
<221> NAME/KEY: MISC_FEATURE
<222> LOCATION: (22)..(22)
<223> OTHER INFORMATION: Xaa is Ile or Val
<220> FEATURE:
<221> NAME/KEY: MISC_FEATURE
<222> LOCATION: (24)..(24)
<223> OTHER INFORMATION: Xaa is an ion lock pair with the amino acid at
      position 20, or Leu, Ile, or Val

<400> SEQUENCE: 36

Gly Ile Pro Xaa Xaa Pro Xaa Xaa Leu Lys Arg Leu Leu Ile Xaa Val
1               5                   10                  15

Val Val Xaa Xaa Leu Xaa Val Xaa Val Ile Val Gly Ala Leu Leu Met
            20                  25                  30

Gly

<210> SEQ ID NO 37
<211> LENGTH: 33
```

```
<212> TYPE: PRT
<213> ORGANISM: artificial
<220> FEATURE:
<223> OTHER INFORMATION: SP-C SS Ion Lock E20/K24

<400> SEQUENCE: 37

Gly Ile Pro Ser Ser Pro Val His Leu Lys Arg Leu Leu Ile Val Val
1               5                   10                  15

Val Val Val Glu Leu Ile Val Lys Val Ile Val Gly Ala Leu Leu Met
            20                  25                  30

Gly

<210> SEQ ID NO 38
<211> LENGTH: 33
<212> TYPE: PRT
<213> ORGANISM: artificial
<220> FEATURE:
<223> OTHER INFORMATION: SP-C SS Ion Lock E20/R24

<400> SEQUENCE: 38

Gly Ile Pro Ser Ser Pro Val His Leu Lys Arg Leu Leu Ile Val Val
1               5                   10                  15

Val Val Val Glu Leu Ile Val Arg Val Ile Val Gly Ala Leu Leu Met
            20                  25                  30

Gly

<210> SEQ ID NO 39
<211> LENGTH: 33
<212> TYPE: PRT
<213> ORGANISM: artificial
<220> FEATURE:
<223> OTHER INFORMATION: SP-C SS Ion Lock D20/K24

<400> SEQUENCE: 39

Gly Ile Pro Ser Ser Pro Val His Leu Lys Arg Leu Leu Ile Val Val
1               5                   10                  15

Val Val Val Asp Leu Ile Val Lys Val Ile Val Gly Ala Leu Leu Met
            20                  25                  30

Gly

<210> SEQ ID NO 40
<211> LENGTH: 33
<212> TYPE: PRT
<213> ORGANISM: artificial
<220> FEATURE:
<223> OTHER INFORMATION: SP-C SS Ion LockD20/R24

<400> SEQUENCE: 40

Gly Ile Pro Ser Ser Pro Val His Leu Lys Arg Leu Leu Ile Val Val
1               5                   10                  15

Val Val Val Asp Leu Ile Val Arg Val Ile Val Gly Ala Leu Leu Met
            20                  25                  30

Gly

<210> SEQ ID NO 41
<211> LENGTH: 33
<212> TYPE: PRT
<213> ORGANISM: artificial
<220> FEATURE:
<223> OTHER INFORMATION: SP-C SS Ion Lock K20/E24

<400> SEQUENCE: 41
```

```
Gly Ile Pro Ser Ser Pro Val His Leu Lys Arg Leu Leu Ile Val Val
1               5                   10                  15

Val Val Val Lys Leu Ile Val Glu Val Ile Val Gly Ala Leu Leu Met
            20                  25                  30

Gly
```

<210> SEQ ID NO 42
<211> LENGTH: 33
<212> TYPE: PRT
<213> ORGANISM: artificial
<220> FEATURE:
<223> OTHER INFORMATION: SP-C SS Ion Lock R20/E24

<400> SEQUENCE: 42

```
Gly Ile Pro Ser Ser Pro Val His Leu Lys Arg Leu Leu Ile Val Val
1               5                   10                  15

Val Val Val Arg Leu Ile Val Glu Val Ile Val Gly Ala Leu Leu Met
            20                  25                  30

Gly
```

<210> SEQ ID NO 43
<211> LENGTH: 33
<212> TYPE: PRT
<213> ORGANISM: artificial
<220> FEATURE:
<223> OTHER INFORMATION: SP-C SS Ion Lock K20/D24

<400> SEQUENCE: 43

```
Gly Ile Pro Ser Ser Pro Val His Leu Lys Arg Leu Leu Ile Val Val
1               5                   10                  15

Val Val Val Lys Leu Ile Val Asp Val Ile Val Gly Ala Leu Leu Met
            20                  25                  30

Gly
```

<210> SEQ ID NO 44
<211> LENGTH: 33
<212> TYPE: PRT
<213> ORGANISM: artificial
<220> FEATURE:
<223> OTHER INFORMATION: SP-C SS Ion Lock R20/D24

<400> SEQUENCE: 44

```
Gly Ile Pro Ser Ser Pro Val His Leu Lys Arg Leu Leu Ile Val Val
1               5                   10                  15

Val Val Val Arg Leu Ile Val Asp Val Ile Val Gly Ala Leu Leu Met
            20                  25                  30

Gly
```

<210> SEQ ID NO 45
<211> LENGTH: 34
<212> TYPE: PRT
<213> ORGANISM: artificial
<220> FEATURE:
<223> OTHER INFORMATION: SP-C SS Ion Lock + L E20/K24

<400> SEQUENCE: 45

```
Gly Ile Pro Ser Ser Pro Val His Leu Lys Arg Leu Leu Ile Val Val
1               5                   10                  15

Val Val Val Glu Leu Ile Val Lys Val Ile Val Gly Ala Leu Leu Met
            20                  25                  30

Gly Leu
```

<210> SEQ ID NO 46
<211> LENGTH: 34
<212> TYPE: PRT
<213> ORGANISM: artificial
<220> FEATURE:
<223> OTHER INFORMATION: SP-C SS Ion Lock + L E20/R24

<400> SEQUENCE: 46

Gly Ile Pro Ser Ser Pro Val His Leu Lys Arg Leu Leu Ile Val Val
1               5                   10                  15

Val Val Val Glu Leu Ile Val Arg Val Ile Val Gly Ala Leu Leu Met
            20                  25                  30

Gly Leu

<210> SEQ ID NO 47
<211> LENGTH: 34
<212> TYPE: PRT
<213> ORGANISM: artificial
<220> FEATURE:
<223> OTHER INFORMATION: SP-C SS Ion Lock + L D20/K24

<400> SEQUENCE: 47

Gly Ile Pro Ser Ser Pro Val His Leu Lys Arg Leu Leu Ile Val Val
1               5                   10                  15

Val Val Val Asp Leu Ile Val Lys Val Ile Val Gly Ala Leu Leu Met
            20                  25                  30

Gly Leu

<210> SEQ ID NO 48
<211> LENGTH: 34
<212> TYPE: PRT
<213> ORGANISM: artificial
<220> FEATURE:
<223> OTHER INFORMATION: SP-C SS Ion Lock + L D20/R24

<400> SEQUENCE: 48

Gly Ile Pro Ser Ser Pro Val His Leu Lys Arg Leu Leu Ile Val Val
1               5                   10                  15

Val Val Val Asp Leu Ile Val Arg Val Ile Val Gly Ala Leu Leu Met
            20                  25                  30

Gly Leu

<210> SEQ ID NO 49
<211> LENGTH: 34
<212> TYPE: PRT
<213> ORGANISM: artificial
<220> FEATURE:
<223> OTHER INFORMATION: SP-C SS Ion Lock + L K20/E24

<400> SEQUENCE: 49

Gly Ile Pro Ser Ser Pro Val His Leu Lys Arg Leu Leu Ile Val Val
1               5                   10                  15

Val Val Val Lys Leu Ile Val Glu Val Ile Val Gly Ala Leu Leu Met
            20                  25                  30

Gly Leu

<210> SEQ ID NO 50
<211> LENGTH: 34
<212> TYPE: PRT
<213> ORGANISM: artificial
<220> FEATURE:

<223> OTHER INFORMATION: SP-C SS Ion Lock + L R20/E24

<400> SEQUENCE: 50

Gly Ile Pro Ser Ser Pro Val His Leu Lys Arg Leu Leu Ile Val Val
1               5                   10                  15

Val Val Val Arg Leu Ile Val Glu Val Ile Val Gly Ala Leu Leu Met
            20                  25                  30

Gly Leu

<210> SEQ ID NO 51
<211> LENGTH: 34
<212> TYPE: PRT
<213> ORGANISM: artificial
<220> FEATURE:
<223> OTHER INFORMATION: SP-C SS Ion Lock + L K20/D24

<400> SEQUENCE: 51

Gly Ile Pro Ser Ser Pro Val His Leu Lys Arg Leu Leu Ile Val Val
1               5                   10                  15

Val Val Val Lys Leu Ile Val Asp Val Ile Val Gly Ala Leu Leu Met
            20                  25                  30

Gly Leu

<210> SEQ ID NO 52
<211> LENGTH: 34
<212> TYPE: PRT
<213> ORGANISM: artificial
<220> FEATURE:
<223> OTHER INFORMATION: SP-C SS Ion Lock + L R20/D24

<400> SEQUENCE: 52

Gly Ile Pro Ser Ser Pro Val His Leu Lys Arg Leu Leu Ile Val Val
1               5                   10                  15

Val Val Val Arg Leu Ile Val Asp Val Ile Val Gly Ala Leu Leu Met
            20                  25                  30

Gly Leu

<210> SEQ ID NO 53
<211> LENGTH: 33
<212> TYPE: PRT
<213> ORGANISM: artificial
<220> FEATURE:
<223> OTHER INFORMATION: SP-C SF Ion Lock E20/K24

<400> SEQUENCE: 53

Gly Ile Pro Ser Phe Pro Ser Ser Leu Lys Arg Leu Leu Ile Val Val
1               5                   10                  15

Val Val Val Glu Leu Ile Val Lys Val Ile Val Gly Ala Leu Leu Met
            20                  25                  30

Gly

<210> SEQ ID NO 54
<211> LENGTH: 33
<212> TYPE: PRT
<213> ORGANISM: artificial
<220> FEATURE:
<223> OTHER INFORMATION: SP-C SF Ion Lock E20/R24

<400> SEQUENCE: 54

Gly Ile Pro Ser Phe Pro Ser Ser Leu Lys Arg Leu Leu Ile Val Val
1               5                   10                  15

```
Val Val Val Glu Leu Ile Val Arg Ile Val Gly Ala Leu Leu Met
            20                  25                  30

Gly

<210> SEQ ID NO 55
<211> LENGTH: 33
<212> TYPE: PRT
<213> ORGANISM: artificial
<220> FEATURE:
<223> OTHER INFORMATION: SP-C SF Ion Lock D20/K24

<400> SEQUENCE: 55

Gly Ile Pro Ser Phe Pro Ser Ser Leu Lys Arg Leu Leu Ile Val Val
1               5                   10                  15

Val Val Val Asp Leu Ile Val Lys Val Ile Val Gly Ala Leu Leu Met
            20                  25                  30

Gly

<210> SEQ ID NO 56
<211> LENGTH: 33
<212> TYPE: PRT
<213> ORGANISM: artificial
<220> FEATURE:
<223> OTHER INFORMATION: SP-C SF Ion Lock D20/R24

<400> SEQUENCE: 56

Gly Ile Pro Ser Phe Pro Ser Ser Leu Lys Arg Leu Leu Ile Val Val
1               5                   10                  15

Val Val Val Asp Leu Ile Val Arg Val Ile Val Gly Ala Leu Leu Met
            20                  25                  30

Gly

<210> SEQ ID NO 57
<211> LENGTH: 33
<212> TYPE: PRT
<213> ORGANISM: artificial
<220> FEATURE:
<223> OTHER INFORMATION: SP-C SF Ion Lock K20/E24

<400> SEQUENCE: 57

Gly Ile Pro Ser Phe Pro Ser Ser Leu Lys Arg Leu Leu Ile Val Val
1               5                   10                  15

Val Val Val Lys Leu Ile Val Glu Val Ile Val Gly Ala Leu Leu Met
            20                  25                  30

Gly

<210> SEQ ID NO 58
<211> LENGTH: 33
<212> TYPE: PRT
<213> ORGANISM: artificial
<220> FEATURE:
<223> OTHER INFORMATION: SP-C SF Ion Lock R20/E24

<400> SEQUENCE: 58

Gly Ile Pro Ser Phe Pro Ser Ser Leu Lys Arg Leu Leu Ile Val Val
1               5                   10                  15

Val Val Val Arg Leu Ile Val Glu Val Ile Val Gly Ala Leu Leu Met
            20                  25                  30

Gly

<210> SEQ ID NO 59
```

<211> LENGTH: 33
<212> TYPE: PRT
<213> ORGANISM: artificial
<220> FEATURE:
<223> OTHER INFORMATION: SP-C SF Ion Lock K20/D24

<400> SEQUENCE: 59

Gly Ile Pro Ser Phe Pro Ser Ser Leu Lys Arg Leu Leu Ile Val Val
1               5                   10                  15

Val Val Val Lys Leu Ile Val Asp Val Ile Val Gly Ala Leu Leu Met
            20                  25                  30

Gly

<210> SEQ ID NO 60
<211> LENGTH: 33
<212> TYPE: PRT
<213> ORGANISM: artificial
<220> FEATURE:
<223> OTHER INFORMATION: SP-C SF Ion Lock R20/D24

<400> SEQUENCE: 60

Gly Ile Pro Ser Phe Pro Ser Ser Leu Lys Arg Leu Leu Ile Val Val
1               5                   10                  15

Val Val Val Arg Leu Ile Val Asp Val Ile Val Gly Ala Leu Leu Met
            20                  25                  30

Gly

<210> SEQ ID NO 61
<211> LENGTH: 34
<212> TYPE: PRT
<213> ORGANISM: artificial
<220> FEATURE:
<223> OTHER INFORMATION: SP-C SF ion Lock + L E20/K24

<400> SEQUENCE: 61

Gly Ile Pro Ser Phe Pro Ser Ser Leu Lys Arg Leu Leu Ile Val Val
1               5                   10                  15

Val Val Val Glu Leu Ile Val Lys Val Ile Val Gly Ala Leu Leu Met
            20                  25                  30

Gly Leu

<210> SEQ ID NO 62
<211> LENGTH: 34
<212> TYPE: PRT
<213> ORGANISM: artificial
<220> FEATURE:
<223> OTHER INFORMATION: SP-C SF ion Lock + L E20/R24

<400> SEQUENCE: 62

Gly Ile Pro Ser Phe Pro Ser Ser Leu Lys Arg Leu Leu Ile Val Val
1               5                   10                  15

Val Val Val Glu Leu Ile Val Arg Val Ile Val Gly Ala Leu Leu Met
            20                  25                  30

Gly Leu

<210> SEQ ID NO 63
<211> LENGTH: 34
<212> TYPE: PRT
<213> ORGANISM: artificial
<220> FEATURE:
<223> OTHER INFORMATION: SP-C SF ion Lock + L D20/K24

<400> SEQUENCE: 63

```
Gly Ile Pro Ser Phe Pro Ser Ser Leu Lys Arg Leu Leu Ile Val Val
1               5                   10                  15

Val Val Val Asp Leu Ile Val Lys Val Ile Val Gly Ala Leu Leu Met
            20                  25                  30

Gly Leu

<210> SEQ ID NO 64
<211> LENGTH: 34
<212> TYPE: PRT
<213> ORGANISM: artificial
<220> FEATURE:
<223> OTHER INFORMATION: SP-C SF ion Lock + L D20/R24

<400> SEQUENCE: 64

Gly Ile Pro Ser Phe Pro Ser Ser Leu Lys Arg Leu Leu Ile Val Val
1               5                   10                  15

Val Val Val Asp Leu Ile Val Arg Val Ile Val Gly Ala Leu Leu Met
            20                  25                  30

Gly Leu

<210> SEQ ID NO 65
<211> LENGTH: 34
<212> TYPE: PRT
<213> ORGANISM: artificial
<220> FEATURE:
<223> OTHER INFORMATION: SP-C SF ion Lock + L K20/E24

<400> SEQUENCE: 65

Gly Ile Pro Ser Phe Pro Ser Ser Leu Lys Arg Leu Leu Ile Val Val
1               5                   10                  15

Val Val Val Lys Leu Ile Val Glu Val Ile Val Gly Ala Leu Leu Met
            20                  25                  30

Gly Leu

<210> SEQ ID NO 66
<211> LENGTH: 34
<212> TYPE: PRT
<213> ORGANISM: artificial
<220> FEATURE:
<223> OTHER INFORMATION: SP-C SF ion Lock + L R20/E24

<400> SEQUENCE: 66

Gly Ile Pro Ser Phe Pro Ser Ser Leu Lys Arg Leu Leu Ile Val Val
1               5                   10                  15

Val Val Val Arg Leu Ile Val Glu Val Ile Val Gly Ala Leu Leu Met
            20                  25                  30

Gly Leu

<210> SEQ ID NO 67
<211> LENGTH: 34
<212> TYPE: PRT
<213> ORGANISM: artificial
<220> FEATURE:
<223> OTHER INFORMATION: SP-C SF ion Lock + L K20/D24

<400> SEQUENCE: 67

Gly Ile Pro Ser Phe Pro Ser Ser Leu Lys Arg Leu Leu Ile Val Val
1               5                   10                  15

Val Val Val Lys Leu Ile Val Asp Val Ile Val Gly Ala Leu Leu Met
            20                  25                  30
```

Gly Leu

<210> SEQ ID NO 68
<211> LENGTH: 34
<212> TYPE: PRT
<213> ORGANISM: artificial
<220> FEATURE:
<223> OTHER INFORMATION: SP-C SF ion Lock + L R20/D24

<400> SEQUENCE: 68

Gly Ile Pro Ser Phe Pro Ser Ser Leu Lys Arg Leu Leu Ile Val Val
1               5                   10                  15

Val Val Val Arg Leu Ile Val Asp Val Ile Val Gly Ala Leu Leu Met
                20                  25                  30

Gly Leu

<210> SEQ ID NO 69
<211> LENGTH: 34
<212> TYPE: PRT
<213> ORGANISM: artificial
<220> FEATURE:
<223> OTHER INFORMATION: SP-C FF Ion Lock2 K15/E19;E20/K24

<400> SEQUENCE: 69

Gly Ile Pro Phe Phe Pro Val His Leu Lys Arg Leu Leu Ile Lys Val
1               5                   10                  15

Val Val Glu Glu Leu Ile Val Lys Val Ile Val Gly Ala Leu Leu Met
                20                  25                  30

Gly Leu

<210> SEQ ID NO 70
<211> LENGTH: 34
<212> TYPE: PRT
<213> ORGANISM: artificial
<220> FEATURE:
<223> OTHER INFORMATION: SP-C FF Ion Lock2 K15/D19;E20/K24

<400> SEQUENCE: 70

Gly Ile Pro Phe Phe Pro Val His Leu Lys Arg Leu Leu Ile Lys Val
1               5                   10                  15

Val Val Asp Glu Leu Ile Val Lys Val Ile Val Gly Ala Leu Leu Met
                20                  25                  30

Gly Leu

<210> SEQ ID NO 71
<211> LENGTH: 34
<212> TYPE: PRT
<213> ORGANISM: artificial
<220> FEATURE:
<223> OTHER INFORMATION: SP-C FF Ion Lock2 K15/E19;D20/K24

<400> SEQUENCE: 71

Gly Ile Pro Phe Phe Pro Val His Leu Lys Arg Leu Leu Ile Lys Val
1               5                   10                  15

Val Val Glu Asp Leu Ile Val Lys Val Ile Val Gly Ala Leu Leu Met
                20                  25                  30

Gly Leu

<210> SEQ ID NO 72
<211> LENGTH: 34
<212> TYPE: PRT
<213> ORGANISM: artificial

-continued

```
<220> FEATURE:
<223> OTHER INFORMATION: SP-C FF Ion Lock2 K15/D19;D20/K24

<400> SEQUENCE: 72

Gly Ile Pro Phe Phe Pro Val His Leu Lys Arg Leu Leu Ile Lys Val
1               5                   10                  15

Val Val Asp Asp Leu Ile Val Lys Val Ile Val Gly Ala Leu Leu Met
            20                  25                  30

Gly Leu

<210> SEQ ID NO 73
<211> LENGTH: 34
<212> TYPE: PRT
<213> ORGANISM: artificial
<220> FEATURE:
<223> OTHER INFORMATION: SP-C FF Ion Lock2 K15/E19;E20/R24

<400> SEQUENCE: 73

Gly Ile Pro Phe Phe Pro Val His Leu Lys Arg Leu Leu Ile Lys Val
1               5                   10                  15

Val Val Glu Glu Leu Ile Val Arg Val Ile Val Gly Ala Leu Leu Met
            20                  25                  30

Gly Leu

<210> SEQ ID NO 74
<211> LENGTH: 34
<212> TYPE: PRT
<213> ORGANISM: artificial
<220> FEATURE:
<223> OTHER INFORMATION: SP-C FF Ion Lock2 K15/D19;E20/R24

<400> SEQUENCE: 74

Gly Ile Pro Phe Phe Pro Val His Leu Lys Arg Leu Leu Ile Lys Val
1               5                   10                  15

Val Val Asp Glu Leu Ile Val Arg Val Ile Val Gly Ala Leu Leu Met
            20                  25                  30

Gly Leu

<210> SEQ ID NO 75
<211> LENGTH: 34
<212> TYPE: PRT
<213> ORGANISM: artificial
<220> FEATURE:
<223> OTHER INFORMATION: SP-C FF Ion Lock2 K15/E19;D20/R24

<400> SEQUENCE: 75

Gly Ile Pro Phe Phe Pro Val His Leu Lys Arg Leu Leu Ile Lys Val
1               5                   10                  15

Val Val Glu Asp Leu Ile Val Arg Val Ile Val Gly Ala Leu Leu Met
            20                  25                  30

Gly Leu

<210> SEQ ID NO 76
<211> LENGTH: 34
<212> TYPE: PRT
<213> ORGANISM: artificial
<220> FEATURE:
<223> OTHER INFORMATION: SP-C FF Ion Lock2 K15/D19;D20/R24

<400> SEQUENCE: 76

Gly Ile Pro Phe Phe Pro Val His Leu Lys Arg Leu Leu Ile Lys Val
1               5                   10                  15
```

```
Val Val Asp Asp Leu Ile Val Arg Val Ile Val Gly Ala Leu Leu Met
            20                  25                  30

Gly Leu

<210> SEQ ID NO 77
<211> LENGTH: 34
<212> TYPE: PRT
<213> ORGANISM: artificial
<220> FEATURE:
<223> OTHER INFORMATION: SP-C FF Ion Lock2 K15/E19;K20/E24

<400> SEQUENCE: 77

Gly Ile Pro Phe Phe Pro Val His Leu Lys Arg Leu Leu Ile Lys Val
1               5                   10                  15

Val Val Glu Lys Leu Ile Val Glu Val Ile Val Gly Ala Leu Leu Met
            20                  25                  30

Gly Leu

<210> SEQ ID NO 78
<211> LENGTH: 34
<212> TYPE: PRT
<213> ORGANISM: artificial
<220> FEATURE:
<223> OTHER INFORMATION: SP-C FF Ion Lock2 K15/D19;K20/E24

<400> SEQUENCE: 78

Gly Ile Pro Phe Phe Pro Val His Leu Lys Arg Leu Leu Ile Lys Val
1               5                   10                  15

Val Val Asp Lys Leu Ile Val Glu Val Ile Val Gly Ala Leu Leu Met
            20                  25                  30

Gly Leu

<210> SEQ ID NO 79
<211> LENGTH: 34
<212> TYPE: PRT
<213> ORGANISM: artificial
<220> FEATURE:
<223> OTHER INFORMATION: SP-C FF Ion Lock2 K15/E19;K20/D24

<400> SEQUENCE: 79

Gly Ile Pro Phe Phe Pro Val His Leu Lys Arg Leu Leu Ile Lys Val
1               5                   10                  15

Val Val Glu Lys Leu Ile Val Asp Val Ile Val Gly Ala Leu Leu Met
            20                  25                  30

Gly Leu

<210> SEQ ID NO 80
<211> LENGTH: 34
<212> TYPE: PRT
<213> ORGANISM: artificial
<220> FEATURE:
<223> OTHER INFORMATION: SP-C FF Ion Lock2 K15/D19;K20/D24

<400> SEQUENCE: 80

Gly Ile Pro Phe Phe Pro Val His Leu Lys Arg Leu Leu Ile Lys Val
1               5                   10                  15

Val Val Asp Lys Leu Ile Val Asp Val Ile Val Gly Ala Leu Leu Met
            20                  25                  30

Gly Leu
```

```
<210> SEQ ID NO 81
<211> LENGTH: 34
<212> TYPE: PRT
<213> ORGANISM: artificial
<220> FEATURE:
<223> OTHER INFORMATION: SP-C FF Ion Lock2 K15/E19;R20/E24

<400> SEQUENCE: 81

Gly Ile Pro Phe Phe Pro Val His Leu Lys Arg Leu Leu Ile Lys Val
1               5                   10                  15
Val Val Glu Arg Leu Ile Val Glu Val Ile Val Gly Ala Leu Leu Met
            20                  25                  30
Gly Leu

<210> SEQ ID NO 82
<211> LENGTH: 34
<212> TYPE: PRT
<213> ORGANISM: artificial
<220> FEATURE:
<223> OTHER INFORMATION: SP-C FF Ion Lock2 K15/D19;R20/E24

<400> SEQUENCE: 82

Gly Ile Pro Phe Phe Pro Val His Leu Lys Arg Leu Leu Ile Lys Val
1               5                   10                  15
Val Val Asp Arg Leu Ile Val Glu Val Ile Val Gly Ala Leu Leu Met
            20                  25                  30
Gly Leu

<210> SEQ ID NO 83
<211> LENGTH: 34
<212> TYPE: PRT
<213> ORGANISM: artificial
<220> FEATURE:
<223> OTHER INFORMATION: SP-C FF Ion Lock2 K15/E19;R20/D24

<400> SEQUENCE: 83

Gly Ile Pro Phe Phe Pro Val His Leu Lys Arg Leu Leu Ile Lys Val
1               5                   10                  15
Val Val Glu Arg Leu Ile Val Asp Val Ile Val Gly Ala Leu Leu Met
            20                  25                  30
Gly Leu

<210> SEQ ID NO 84
<211> LENGTH: 34
<212> TYPE: PRT
<213> ORGANISM: artificial
<220> FEATURE:
<223> OTHER INFORMATION: SP-C FF Ion Lock2 K15/D19;R20/D24

<400> SEQUENCE: 84

Gly Ile Pro Phe Phe Pro Val His Leu Lys Arg Leu Leu Ile Lys Val
1               5                   10                  15
Val Val Asp Arg Leu Ile Val Asp Val Ile Val Gly Ala Leu Leu Met
            20                  25                  30
Gly Leu

<210> SEQ ID NO 85
<211> LENGTH: 34
<212> TYPE: PRT
<213> ORGANISM: artificial
<220> FEATURE:
<223> OTHER INFORMATION: SP-C FF Ion Lock2 R15/E19;E20/K24
```

```
<400> SEQUENCE: 85

Gly Ile Pro Phe Phe Pro Val His Leu Lys Arg Leu Leu Ile Arg Val
1               5                   10                  15

Val Val Glu Glu Leu Ile Val Lys Val Ile Val Gly Ala Leu Leu Met
            20                  25                  30

Gly Leu

<210> SEQ ID NO 86
<211> LENGTH: 34
<212> TYPE: PRT
<213> ORGANISM: artificial
<220> FEATURE:
<223> OTHER INFORMATION: SP-C FF Ion Lock2 R15/D19;E20/K24

<400> SEQUENCE: 86

Gly Ile Pro Phe Phe Pro Val His Leu Lys Arg Leu Leu Ile Arg Val
1               5                   10                  15

Val Val Asp Glu Leu Ile Val Lys Val Ile Val Gly Ala Leu Leu Met
            20                  25                  30

Gly Leu

<210> SEQ ID NO 87
<211> LENGTH: 34
<212> TYPE: PRT
<213> ORGANISM: artificial
<220> FEATURE:
<223> OTHER INFORMATION: SP-C FF Ion Lock2 R15/E19;D20/K24

<400> SEQUENCE: 87

Gly Ile Pro Phe Phe Pro Val His Leu Lys Arg Leu Leu Ile Arg Val
1               5                   10                  15

Val Val Glu Asp Leu Ile Val Lys Val Ile Val Gly Ala Leu Leu Met
            20                  25                  30

Gly Leu

<210> SEQ ID NO 88
<211> LENGTH: 34
<212> TYPE: PRT
<213> ORGANISM: artificial
<220> FEATURE:
<223> OTHER INFORMATION: SP-C FF Ion Lock2 R15/D19;D20/K24

<400> SEQUENCE: 88

Gly Ile Pro Phe Phe Pro Val His Leu Lys Arg Leu Leu Ile Arg Val
1               5                   10                  15

Val Val Asp Asp Leu Ile Val Lys Val Ile Val Gly Ala Leu Leu Met
            20                  25                  30

Gly Leu

<210> SEQ ID NO 89
<211> LENGTH: 34
<212> TYPE: PRT
<213> ORGANISM: artificial
<220> FEATURE:
<223> OTHER INFORMATION: SP-C FF Ion Lock2 R15/E19;E20/R24

<400> SEQUENCE: 89

Gly Ile Pro Phe Phe Pro Val His Leu Lys Arg Leu Leu Ile Arg Val
1               5                   10                  15

Val Val Glu Glu Leu Ile Val Arg Val Ile Val Gly Ala Leu Leu Met
            20                  25                  30
```

<210> SEQ ID NO 90
<211> LENGTH: 34
<212> TYPE: PRT
<213> ORGANISM: artificial
<220> FEATURE:
<223> OTHER INFORMATION: SP-C FF Ion Lock2 R15/D19;E20/R24

<400> SEQUENCE: 90

Gly Ile Pro Phe Phe Pro Val His Leu Lys Arg Leu Leu Ile Arg Val
1               5                   10                  15

Val Val Asp Glu Leu Ile Val Arg Val Ile Val Gly Ala Leu Leu Met
            20                  25                  30

Gly Leu

<210> SEQ ID NO 91
<211> LENGTH: 34
<212> TYPE: PRT
<213> ORGANISM: artificial
<220> FEATURE:
<223> OTHER INFORMATION: SP-C FF Ion Lock2 R15/E19;D20/R24

<400> SEQUENCE: 91

Gly Ile Pro Phe Phe Pro Val His Leu Lys Arg Leu Leu Ile Arg Val
1               5                   10                  15

Val Val Glu Asp Leu Ile Val Arg Val Ile Val Gly Ala Leu Leu Met
            20                  25                  30

Gly Leu

<210> SEQ ID NO 92
<211> LENGTH: 34
<212> TYPE: PRT
<213> ORGANISM: artificial
<220> FEATURE:
<223> OTHER INFORMATION: SP-C FF Ion Lock2 R15/D19;D20/R24

<400> SEQUENCE: 92

Gly Ile Pro Phe Phe Pro Val His Leu Lys Arg Leu Leu Ile Arg Val
1               5                   10                  15

Val Val Asp Asp Leu Ile Val Arg Val Ile Val Gly Ala Leu Leu Met
            20                  25                  30

Gly Leu

<210> SEQ ID NO 93
<211> LENGTH: 34
<212> TYPE: PRT
<213> ORGANISM: artificial
<220> FEATURE:
<223> OTHER INFORMATION: SP-C FF Ion Lock2 R15/E19;K20/E24

<400> SEQUENCE: 93

Gly Ile Pro Phe Phe Pro Val His Leu Lys Arg Leu Leu Ile Arg Val
1               5                   10                  15

Val Val Glu Lys Leu Ile Val Glu Val Ile Val Gly Ala Leu Leu Met
            20                  25                  30

Gly Leu

<210> SEQ ID NO 94
<211> LENGTH: 34
<212> TYPE: PRT

```
<213> ORGANISM: artificial
<220> FEATURE:
<223> OTHER INFORMATION: SP-C FF Ion Lock2 R15/D19;K20/E24

<400> SEQUENCE: 94

Gly Ile Pro Phe Phe Pro Val His Leu Lys Arg Leu Leu Ile Arg Val
1               5                   10                  15

Val Val Asp Lys Leu Ile Val Glu Val Ile Val Gly Ala Leu Leu Met
            20                  25                  30

Gly Leu

<210> SEQ ID NO 95
<211> LENGTH: 34
<212> TYPE: PRT
<213> ORGANISM: artificial
<220> FEATURE:
<223> OTHER INFORMATION: SP-C FF Ion Lock2 R15/E19;K20/D24

<400> SEQUENCE: 95

Gly Ile Pro Phe Phe Pro Val His Leu Lys Arg Leu Leu Ile Arg Val
1               5                   10                  15

Val Val Glu Lys Leu Ile Val Asp Val Ile Val Gly Ala Leu Leu Met
            20                  25                  30

Gly Leu

<210> SEQ ID NO 96
<211> LENGTH: 34
<212> TYPE: PRT
<213> ORGANISM: artificial
<220> FEATURE:
<223> OTHER INFORMATION: SP-C FF Ion Lock2 R15/D19;K20/D24

<400> SEQUENCE: 96

Gly Ile Pro Phe Phe Pro Val His Leu Lys Arg Leu Leu Ile Arg Val
1               5                   10                  15

Val Val Asp Lys Leu Ile Val Asp Val Ile Val Gly Ala Leu Leu Met
            20                  25                  30

Gly Leu

<210> SEQ ID NO 97
<211> LENGTH: 34
<212> TYPE: PRT
<213> ORGANISM: artificial
<220> FEATURE:
<223> OTHER INFORMATION: SP-C FF Ion Lock2 R15/E19;R20/E24

<400> SEQUENCE: 97

Gly Ile Pro Phe Phe Pro Val His Leu Lys Arg Leu Leu Ile Arg Val
1               5                   10                  15

Val Val Glu Arg Leu Ile Val Glu Val Ile Val Gly Ala Leu Leu Met
            20                  25                  30

Gly Leu

<210> SEQ ID NO 98
<211> LENGTH: 34
<212> TYPE: PRT
<213> ORGANISM: artificial
<220> FEATURE:
<223> OTHER INFORMATION: SP-C FF Ion Lock2 R15/D19;R20/E24

<400> SEQUENCE: 98

Gly Ile Pro Phe Phe Pro Val His Leu Lys Arg Leu Leu Ile Arg Val
```

```
                1               5                  10                  15
Val Val Asp Arg Leu Ile Val Glu Val Ile Val Gly Ala Leu Leu Met
            20                  25                  30

Gly Leu

<210> SEQ ID NO 99
<211> LENGTH: 34
<212> TYPE: PRT
<213> ORGANISM: artificial
<220> FEATURE:
<223> OTHER INFORMATION: SP-C FF Ion Lock2 R15/E19;R20/D24

<400> SEQUENCE: 99

Gly Ile Pro Phe Phe Pro Val His Leu Lys Arg Leu Leu Ile Arg Val
1               5                  10                  15

Val Val Glu Arg Leu Ile Val Asp Val Ile Val Gly Ala Leu Leu Met
            20                  25                  30

Gly Leu

<210> SEQ ID NO 100
<211> LENGTH: 34
<212> TYPE: PRT
<213> ORGANISM: artificial
<220> FEATURE:
<223> OTHER INFORMATION: SP-C FF Ion Lock2 R15/D19;R20/D24

<400> SEQUENCE: 100

Gly Ile Pro Phe Phe Pro Val His Leu Lys Arg Leu Leu Ile Arg Val
1               5                  10                  15

Val Val Asp Arg Leu Ile Val Asp Val Ile Val Gly Ala Leu Leu Met
            20                  25                  30

Gly Leu

<210> SEQ ID NO 101
<211> LENGTH: 34
<212> TYPE: PRT
<213> ORGANISM: artificial
<220> FEATURE:
<223> OTHER INFORMATION: SP-C FF Ion Lock2 E15/K19;E20/K24

<400> SEQUENCE: 101

Gly Ile Pro Phe Phe Pro Val His Leu Lys Arg Leu Leu Ile Glu Val
1               5                  10                  15

Val Val Lys Glu Leu Ile Val Lys Val Ile Val Gly Ala Leu Leu Met
            20                  25                  30

Gly Leu

<210> SEQ ID NO 102
<211> LENGTH: 34
<212> TYPE: PRT
<213> ORGANISM: artificial
<220> FEATURE:
<223> OTHER INFORMATION: SP-C FF Ion Lock2 E15/R19;E20/K24

<400> SEQUENCE: 102

Gly Ile Pro Phe Phe Pro Val His Leu Lys Arg Leu Leu Ile Glu Val
1               5                  10                  15

Val Val Arg Glu Leu Ile Val Lys Val Ile Val Gly Ala Leu Leu Met
            20                  25                  30

Gly Leu
```

<210> SEQ ID NO 103
<211> LENGTH: 34
<212> TYPE: PRT
<213> ORGANISM: artificial
<220> FEATURE:
<223> OTHER INFORMATION: SP-C FF Ion Lock2 E15/K19;D20/K24

<400> SEQUENCE: 103

Gly Ile Pro Phe Phe Pro Val His Leu Lys Arg Leu Leu Ile Glu Val
1               5                   10                  15

Val Val Lys Asp Leu Ile Val Lys Val Ile Val Gly Ala Leu Leu Met
            20                  25                  30

Gly Leu

<210> SEQ ID NO 104
<211> LENGTH: 34
<212> TYPE: PRT
<213> ORGANISM: artificial
<220> FEATURE:
<223> OTHER INFORMATION: SP-C FF Ion Lock2 E15/R19;D20/K24

<400> SEQUENCE: 104

Gly Ile Pro Phe Phe Pro Val His Leu Lys Arg Leu Leu Ile Glu Val
1               5                   10                  15

Val Val Arg Asp Leu Ile Val Lys Val Ile Val Gly Ala Leu Leu Met
            20                  25                  30

Gly Leu

<210> SEQ ID NO 105
<211> LENGTH: 34
<212> TYPE: PRT
<213> ORGANISM: artificial
<220> FEATURE:
<223> OTHER INFORMATION: SP-C FF Ion Lock2 E15/K19;E20/R24

<400> SEQUENCE: 105

Gly Ile Pro Phe Phe Pro Val His Leu Lys Arg Leu Leu Ile Glu Val
1               5                   10                  15

Val Val Lys Glu Leu Ile Val Arg Val Ile Val Gly Ala Leu Leu Met
            20                  25                  30

Gly Leu

<210> SEQ ID NO 106
<211> LENGTH: 34
<212> TYPE: PRT
<213> ORGANISM: artificial
<220> FEATURE:
<223> OTHER INFORMATION: SP-C FF Ion Lock2 E15/R19;E20/R24

<400> SEQUENCE: 106

Gly Ile Pro Phe Phe Pro Val His Leu Lys Arg Leu Leu Ile Glu Val
1               5                   10                  15

Val Val Arg Glu Leu Ile Val Arg Val Ile Val Gly Ala Leu Leu Met
            20                  25                  30

Gly Leu

<210> SEQ ID NO 107
<211> LENGTH: 34
<212> TYPE: PRT
<213> ORGANISM: artificial
<220> FEATURE:
<223> OTHER INFORMATION: SP-C FF Ion Lock2 E15/K19;D20/R24

-continued

```
<400> SEQUENCE: 107

Gly Ile Pro Phe Phe Pro Val His Leu Lys Arg Leu Leu Ile Glu Val
1               5                   10                  15

Val Val Lys Asp Leu Ile Val Arg Val Ile Val Gly Ala Leu Leu Met
            20                  25                  30

Gly Leu

<210> SEQ ID NO 108
<211> LENGTH: 34
<212> TYPE: PRT
<213> ORGANISM: artificial
<220> FEATURE:
<223> OTHER INFORMATION: SP-C FF Ion Lock2 E15/R19;D20/R24

<400> SEQUENCE: 108

Gly Ile Pro Phe Phe Pro Val His Leu Lys Arg Leu Leu Ile Glu Val
1               5                   10                  15

Val Val Arg Asp Leu Ile Val Arg Val Ile Val Gly Ala Leu Leu Met
            20                  25                  30

Gly Leu

<210> SEQ ID NO 109
<211> LENGTH: 34
<212> TYPE: PRT
<213> ORGANISM: artificial
<220> FEATURE:
<223> OTHER INFORMATION: SP-C FF Ion Lock2 E15/K19;K20/E24

<400> SEQUENCE: 109

Gly Ile Pro Phe Phe Pro Val His Leu Lys Arg Leu Leu Ile Glu Val
1               5                   10                  15

Val Val Lys Lys Leu Ile Val Glu Val Ile Val Gly Ala Leu Leu Met
            20                  25                  30

Gly Leu

<210> SEQ ID NO 110
<211> LENGTH: 34
<212> TYPE: PRT
<213> ORGANISM: artificial
<220> FEATURE:
<223> OTHER INFORMATION: SP-C FF Ion Lock2 E15/R19;K20/E24

<400> SEQUENCE: 110

Gly Ile Pro Phe Phe Pro Val His Leu Lys Arg Leu Leu Ile Glu Val
1               5                   10                  15

Val Val Arg Lys Leu Ile Val Glu Val Ile Val Gly Ala Leu Leu Met
            20                  25                  30

Gly Leu

<210> SEQ ID NO 111
<211> LENGTH: 34
<212> TYPE: PRT
<213> ORGANISM: artificial
<220> FEATURE:
<223> OTHER INFORMATION: SP-C FF Ion Lock2 E15/K19;K20/D24

<400> SEQUENCE: 111

Gly Ile Pro Phe Phe Pro Val His Leu Lys Arg Leu Leu Ile Glu Val
1               5                   10                  15

Val Val Lys Lys Leu Ile Val Asp Val Ile Val Gly Ala Leu Leu Met
```

<210> SEQ ID NO 112
<211> LENGTH: 34
<212> TYPE: PRT
<213> ORGANISM: artificial
<220> FEATURE:
<223> OTHER INFORMATION: SP-C FF Ion Lock2 E15/R19;K20/D24

<400> SEQUENCE: 112

Gly Ile Pro Phe Phe Pro Val His Leu Lys Arg Leu Leu Ile Glu Val
1               5                   10                  15

Val Val Arg Lys Leu Ile Val Asp Val Ile Val Gly Ala Leu Leu Met
            20                  25                  30

Gly Leu

<210> SEQ ID NO 113
<211> LENGTH: 34
<212> TYPE: PRT
<213> ORGANISM: artificial
<220> FEATURE:
<223> OTHER INFORMATION: SP-C FF Ion Lock2 E15/K19;R20/E24

<400> SEQUENCE: 113

Gly Ile Pro Phe Phe Pro Val His Leu Lys Arg Leu Leu Ile Glu Val
1               5                   10                  15

Val Val Lys Arg Leu Ile Val Glu Val Ile Val Gly Ala Leu Leu Met
            20                  25                  30

Gly Leu

<210> SEQ ID NO 114
<211> LENGTH: 34
<212> TYPE: PRT
<213> ORGANISM: artificial
<220> FEATURE:
<223> OTHER INFORMATION: SP-C FF Ion Lock2 E15/R19;R20/E24

<400> SEQUENCE: 114

Gly Ile Pro Phe Phe Pro Val His Leu Lys Arg Leu Leu Ile Glu Val
1               5                   10                  15

Val Val Arg Arg Leu Ile Val Glu Val Ile Val Gly Ala Leu Leu Met
            20                  25                  30

Gly Leu

<210> SEQ ID NO 115
<211> LENGTH: 34
<212> TYPE: PRT
<213> ORGANISM: artificial
<220> FEATURE:
<223> OTHER INFORMATION: SP-C FF Ion Lock2 E15/K19;R20/D24

<400> SEQUENCE: 115

Gly Ile Pro Phe Phe Pro Val His Leu Lys Arg Leu Leu Ile Glu Val
1               5                   10                  15

Val Val Lys Arg Leu Ile Val Asp Val Ile Val Gly Ala Leu Leu Met
            20                  25                  30

Gly Leu

<210> SEQ ID NO 116
<211> LENGTH: 34

```
<212> TYPE: PRT
<213> ORGANISM: artificial
<220> FEATURE:
<223> OTHER INFORMATION: SP-C FF Ion Lock2 E15/R19;R20/D24

<400> SEQUENCE: 116

Gly Ile Pro Phe Phe Pro Val His Leu Lys Arg Leu Leu Ile Glu Val
1               5                   10                  15

Val Val Arg Arg Leu Ile Val Asp Val Ile Val Gly Ala Leu Leu Met
            20                  25                  30

Gly Leu

<210> SEQ ID NO 117
<211> LENGTH: 34
<212> TYPE: PRT
<213> ORGANISM: artificial
<220> FEATURE:
<223> OTHER INFORMATION: SP-C FF Ion Lock2 D15/K19;E20/K24

<400> SEQUENCE: 117

Gly Ile Pro Phe Phe Pro Val His Leu Lys Arg Leu Leu Ile Asp Val
1               5                   10                  15

Val Val Lys Glu Leu Ile Val Lys Val Ile Val Gly Ala Leu Leu Met
            20                  25                  30

Gly Leu

<210> SEQ ID NO 118
<211> LENGTH: 34
<212> TYPE: PRT
<213> ORGANISM: artificial
<220> FEATURE:
<223> OTHER INFORMATION: SP-C FF Ion Lock2 D15/R19;E20/K24

<400> SEQUENCE: 118

Gly Ile Pro Phe Phe Pro Val His Leu Lys Arg Leu Leu Ile Asp Val
1               5                   10                  15

Val Val Arg Glu Leu Ile Val Lys Val Ile Val Gly Ala Leu Leu Met
            20                  25                  30

Gly Leu

<210> SEQ ID NO 119
<211> LENGTH: 34
<212> TYPE: PRT
<213> ORGANISM: artificial
<220> FEATURE:
<223> OTHER INFORMATION: SP-C FF Ion Lock2 D15/K19;D20/K24

<400> SEQUENCE: 119

Gly Ile Pro Phe Phe Pro Val His Leu Lys Arg Leu Leu Ile Asp Val
1               5                   10                  15

Val Val Lys Asp Leu Ile Val Lys Val Ile Val Gly Ala Leu Leu Met
            20                  25                  30

Gly Leu

<210> SEQ ID NO 120
<211> LENGTH: 34
<212> TYPE: PRT
<213> ORGANISM: artificial
<220> FEATURE:
<223> OTHER INFORMATION: SP-C FF Ion Lock2 D15/R19;D20/K24

<400> SEQUENCE: 120
```

```
Gly Ile Pro Phe Phe Pro Val His Leu Lys Arg Leu Leu Ile Asp Val
1               5                   10                  15

Val Val Arg Asp Leu Ile Val Lys Val Ile Val Gly Ala Leu Leu Met
            20                  25                  30

Gly Leu

<210> SEQ ID NO 121
<211> LENGTH: 34
<212> TYPE: PRT
<213> ORGANISM: artificial
<220> FEATURE:
<223> OTHER INFORMATION: SP-C FF Ion Lock2 D15/K19;E20/R24

<400> SEQUENCE: 121

Gly Ile Pro Phe Phe Pro Val His Leu Lys Arg Leu Leu Ile Asp Val
1               5                   10                  15

Val Val Lys Glu Leu Ile Val Arg Val Ile Val Gly Ala Leu Leu Met
            20                  25                  30

Gly Leu

<210> SEQ ID NO 122
<211> LENGTH: 34
<212> TYPE: PRT
<213> ORGANISM: artificial
<220> FEATURE:
<223> OTHER INFORMATION: SP-C FF Ion Lock2 D15/R19;E20/R24

<400> SEQUENCE: 122

Gly Ile Pro Phe Phe Pro Val His Leu Lys Arg Leu Leu Ile Asp Val
1               5                   10                  15

Val Val Arg Glu Leu Ile Val Arg Val Ile Val Gly Ala Leu Leu Met
            20                  25                  30

Gly Leu

<210> SEQ ID NO 123
<211> LENGTH: 34
<212> TYPE: PRT
<213> ORGANISM: artificial
<220> FEATURE:
<223> OTHER INFORMATION: SP-C FF Ion Lock2 D15/K19;D20/R24

<400> SEQUENCE: 123

Gly Ile Pro Phe Phe Pro Val His Leu Lys Arg Leu Leu Ile Asp Val
1               5                   10                  15

Val Val Lys Asp Leu Ile Val Arg Val Ile Val Gly Ala Leu Leu Met
            20                  25                  30

Gly Leu

<210> SEQ ID NO 124
<211> LENGTH: 34
<212> TYPE: PRT
<213> ORGANISM: artificial
<220> FEATURE:
<223> OTHER INFORMATION: SP-C FF Ion Lock2 D15/R19;D20/R24

<400> SEQUENCE: 124

Gly Ile Pro Phe Phe Pro Val His Leu Lys Arg Leu Leu Ile Asp Val
1               5                   10                  15

Val Val Arg Asp Leu Ile Val Arg Val Ile Val Gly Ala Leu Leu Met
            20                  25                  30

Gly Leu
```

<210> SEQ ID NO 125
<211> LENGTH: 34
<212> TYPE: PRT
<213> ORGANISM: artificial
<220> FEATURE:
<223> OTHER INFORMATION: SP-C FF Ion Lock2 D15/K19;K20/E24

<400> SEQUENCE: 125

Gly Ile Pro Phe Phe Pro Val His Leu Lys Arg Leu Leu Ile Asp Val
1               5                   10                  15

Val Val Lys Lys Leu Ile Val Glu Val Ile Val Gly Ala Leu Leu Met
            20                  25                  30

Gly Leu

<210> SEQ ID NO 126
<211> LENGTH: 34
<212> TYPE: PRT
<213> ORGANISM: artificial
<220> FEATURE:
<223> OTHER INFORMATION: SP-C FF Ion Lock2 D15/R19;K20/E24

<400> SEQUENCE: 126

Gly Ile Pro Phe Phe Pro Val His Leu Lys Arg Leu Leu Ile Asp Val
1               5                   10                  15

Val Val Arg Lys Leu Ile Val Glu Val Ile Val Gly Ala Leu Leu Met
            20                  25                  30

Gly Leu

<210> SEQ ID NO 127
<211> LENGTH: 34
<212> TYPE: PRT
<213> ORGANISM: artificial
<220> FEATURE:
<223> OTHER INFORMATION: SP-C FF Ion Lock2 D15/K19;R20/D24

<400> SEQUENCE: 127

Gly Ile Pro Phe Phe Pro Val His Leu Lys Arg Leu Leu Ile Asp Val
1               5                   10                  15

Val Val Lys Arg Leu Ile Val Asp Val Ile Val Gly Ala Leu Leu Met
            20                  25                  30

Gly Leu

<210> SEQ ID NO 128
<211> LENGTH: 34
<212> TYPE: PRT
<213> ORGANISM: artificial
<220> FEATURE:
<223> OTHER INFORMATION: SP-C FF Ion Lock2 D15/R19;K20/D24

<400> SEQUENCE: 128

Gly Ile Pro Phe Phe Pro Val His Leu Lys Arg Leu Leu Ile Asp Val
1               5                   10                  15

Val Val Arg Lys Leu Ile Val Asp Val Ile Val Gly Ala Leu Leu Met
            20                  25                  30

Gly Leu

<210> SEQ ID NO 129
<211> LENGTH: 34
<212> TYPE: PRT
<213> ORGANISM: artificial
<220> FEATURE:

<223> OTHER INFORMATION: SP-C FF Ion Lock2 D15/K19;R20/E24

<400> SEQUENCE: 129

Gly Ile Pro Phe Phe Pro Val His Leu Lys Arg Leu Leu Ile Asp Val
1               5                   10                  15

Val Val Lys Arg Leu Ile Val Glu Val Ile Val Gly Ala Leu Leu Met
            20                  25                  30

Gly Leu

<210> SEQ ID NO 130
<211> LENGTH: 34
<212> TYPE: PRT
<213> ORGANISM: artificial
<220> FEATURE:
<223> OTHER INFORMATION: SP-C FF Ion Lock2 D15/R19;R20/E24

<400> SEQUENCE: 130

Gly Ile Pro Phe Phe Pro Val His Leu Lys Arg Leu Leu Ile Asp Val
1               5                   10                  15

Val Val Arg Arg Leu Ile Val Glu Val Ile Val Gly Ala Leu Leu Met
            20                  25                  30

Gly Leu

<210> SEQ ID NO 131
<211> LENGTH: 34
<212> TYPE: PRT
<213> ORGANISM: artificial
<220> FEATURE:
<223> OTHER INFORMATION: SP-C FF Ion Lock2 D15/K19;K20/D24

<400> SEQUENCE: 131

Gly Ile Pro Phe Phe Pro Val His Leu Lys Arg Leu Leu Ile Asp Val
1               5                   10                  15

Val Val Lys Lys Leu Ile Val Asp Val Ile Val Gly Ala Leu Leu Met
            20                  25                  30

Gly Leu

<210> SEQ ID NO 132
<211> LENGTH: 34
<212> TYPE: PRT
<213> ORGANISM: artificial
<220> FEATURE:
<223> OTHER INFORMATION: SP-C FF Ion Lock2 D15/R19;R20/D24

<400> SEQUENCE: 132

Gly Ile Pro Phe Phe Pro Val His Leu Lys Arg Leu Leu Ile Asp Val
1               5                   10                  15

Val Val Arg Arg Leu Ile Val Asp Val Ile Val Gly Ala Leu Leu Met
            20                  25                  30

Gly Leu

<210> SEQ ID NO 133
<211> LENGTH: 33
<212> TYPE: PRT
<213> ORGANISM: artificial
<220> FEATURE:
<223> OTHER INFORMATION: SP-C FF Ion Lock2 - L K15/E19;E20/K24

<400> SEQUENCE: 133

Gly Ile Pro Phe Phe Pro Val His Leu Lys Arg Leu Leu Ile Lys Val
1               5                   10                  15

```
Val Val Glu Glu Leu Ile Val Lys Val Ile Val Gly Ala Leu Leu Met
            20                  25                  30

Gly

<210> SEQ ID NO 134
<211> LENGTH: 33
<212> TYPE: PRT
<213> ORGANISM: artificial
<220> FEATURE:
<223> OTHER INFORMATION: SP-C FF Ion Lock2 - L K15/D19;E20/K24

<400> SEQUENCE: 134

Gly Ile Pro Phe Phe Pro Val His Leu Lys Arg Leu Leu Ile Lys Val
1               5                   10                  15

Val Val Asp Glu Leu Ile Val Lys Val Ile Val Gly Ala Leu Leu Met
            20                  25                  30

Gly

<210> SEQ ID NO 135
<211> LENGTH: 33
<212> TYPE: PRT
<213> ORGANISM: artificial
<220> FEATURE:
<223> OTHER INFORMATION: SP-C FF Ion Lock2 - L K15/E19;D20/K24

<400> SEQUENCE: 135

Gly Ile Pro Phe Phe Pro Val His Leu Lys Arg Leu Leu Ile Lys Val
1               5                   10                  15

Val Val Glu Asp Leu Ile Val Lys Val Ile Val Gly Ala Leu Leu Met
            20                  25                  30

Gly

<210> SEQ ID NO 136
<211> LENGTH: 33
<212> TYPE: PRT
<213> ORGANISM: artificial
<220> FEATURE:
<223> OTHER INFORMATION: SP-C FF Ion Lock2 - L K15/D19;D20/K24

<400> SEQUENCE: 136

Gly Ile Pro Phe Phe Pro Val His Leu Lys Arg Leu Leu Ile Lys Val
1               5                   10                  15

Val Val Asp Asp Leu Ile Val Lys Val Ile Val Gly Ala Leu Leu Met
            20                  25                  30

Gly

<210> SEQ ID NO 137
<211> LENGTH: 33
<212> TYPE: PRT
<213> ORGANISM: artificial
<220> FEATURE:
<223> OTHER INFORMATION: SP-C FF Ion Lock2 - L K15/E19;E20/R24

<400> SEQUENCE: 137

Gly Ile Pro Phe Phe Pro Val His Leu Lys Arg Leu Leu Ile Lys Val
1               5                   10                  15

Val Val Glu Glu Leu Ile Val Arg Val Ile Val Gly Ala Leu Leu Met
            20                  25                  30

Gly

<210> SEQ ID NO 138
```

```
<211> LENGTH: 33
<212> TYPE: PRT
<213> ORGANISM: artificial
<220> FEATURE:
<223> OTHER INFORMATION: SP-C FF Ion Lock2 - L K15/D19;E20/R24

<400> SEQUENCE: 138

Gly Ile Pro Phe Phe Pro Val His Leu Lys Arg Leu Leu Ile Lys Val
1               5                   10                  15

Val Val Asp Glu Leu Ile Val Arg Val Ile Val Gly Ala Leu Leu Met
            20                  25                  30

Gly

<210> SEQ ID NO 139
<211> LENGTH: 33
<212> TYPE: PRT
<213> ORGANISM: artificial
<220> FEATURE:
<223> OTHER INFORMATION: SP-C FF Ion Lock2 - L K15/E19;D20/R24

<400> SEQUENCE: 139

Gly Ile Pro Phe Phe Pro Val His Leu Lys Arg Leu Leu Ile Lys Val
1               5                   10                  15

Val Val Glu Asp Leu Ile Val Arg Val Ile Val Gly Ala Leu Leu Met
            20                  25                  30

Gly

<210> SEQ ID NO 140
<211> LENGTH: 33
<212> TYPE: PRT
<213> ORGANISM: artificial
<220> FEATURE:
<223> OTHER INFORMATION: SP-C FF Ion Lock2 - L K15/D19;D20/R24

<400> SEQUENCE: 140

Gly Ile Pro Phe Phe Pro Val His Leu Lys Arg Leu Leu Ile Lys Val
1               5                   10                  15

Val Val Asp Asp Leu Ile Val Arg Val Ile Val Gly Ala Leu Leu Met
            20                  25                  30

Gly

<210> SEQ ID NO 141
<211> LENGTH: 33
<212> TYPE: PRT
<213> ORGANISM: artificial
<220> FEATURE:
<223> OTHER INFORMATION: SP-C FF Ion Lock2 - L K15/E19;K20/E24

<400> SEQUENCE: 141

Gly Ile Pro Phe Phe Pro Val His Leu Lys Arg Leu Leu Ile Lys Val
1               5                   10                  15

Val Val Glu Lys Leu Ile Val Glu Val Ile Val Gly Ala Leu Leu Met
            20                  25                  30

Gly

<210> SEQ ID NO 142
<211> LENGTH: 33
<212> TYPE: PRT
<213> ORGANISM: artificial
<220> FEATURE:
<223> OTHER INFORMATION: SP-C FF Ion Lock2 - L K15/D19;K20/E24

<400> SEQUENCE: 142
```

```
Gly Ile Pro Phe Phe Pro Val His Leu Lys Arg Leu Leu Ile Lys Val
1               5                   10                  15

Val Val Asp Lys Leu Ile Val Glu Val Ile Val Gly Ala Leu Leu Met
            20                  25                  30

Gly

<210> SEQ ID NO 143
<211> LENGTH: 33
<212> TYPE: PRT
<213> ORGANISM: artificial
<220> FEATURE:
<223> OTHER INFORMATION: SP-C FF Ion Lock2 - L K15/E19;K20/D24

<400> SEQUENCE: 143

Gly Ile Pro Phe Phe Pro Val His Leu Lys Arg Leu Leu Ile Lys Val
1               5                   10                  15

Val Val Glu Lys Leu Ile Val Asp Val Ile Val Gly Ala Leu Leu Met
            20                  25                  30

Gly

<210> SEQ ID NO 144
<211> LENGTH: 33
<212> TYPE: PRT
<213> ORGANISM: artificial
<220> FEATURE:
<223> OTHER INFORMATION: SP-C FF Ion Lock2 - L K15/D19;K20/D24

<400> SEQUENCE: 144

Gly Ile Pro Phe Phe Pro Val His Leu Lys Arg Leu Leu Ile Lys Val
1               5                   10                  15

Val Val Asp Lys Leu Ile Val Asp Val Ile Val Gly Ala Leu Leu Met
            20                  25                  30

Gly

<210> SEQ ID NO 145
<211> LENGTH: 33
<212> TYPE: PRT
<213> ORGANISM: artificial
<220> FEATURE:
<223> OTHER INFORMATION: SP-C FF Ion Lock2 - L K15/E19;R20/E24

<400> SEQUENCE: 145

Gly Ile Pro Phe Phe Pro Val His Leu Lys Arg Leu Leu Ile Lys Val
1               5                   10                  15

Val Val Glu Arg Leu Ile Val Glu Val Ile Val Gly Ala Leu Leu Met
            20                  25                  30

Gly

<210> SEQ ID NO 146
<211> LENGTH: 33
<212> TYPE: PRT
<213> ORGANISM: artificial
<220> FEATURE:
<223> OTHER INFORMATION: SP-C FF Ion Lock2 - L K15/D19;R20/E24

<400> SEQUENCE: 146

Gly Ile Pro Phe Phe Pro Val His Leu Lys Arg Leu Leu Ile Lys Val
1               5                   10                  15

Val Val Asp Arg Leu Ile Val Glu Val Ile Val Gly Ala Leu Leu Met
            20                  25                  30
```

Gly

<210> SEQ ID NO 147
<211> LENGTH: 33
<212> TYPE: PRT
<213> ORGANISM: artificial
<220> FEATURE:
<223> OTHER INFORMATION: SP-C FF Ion Lock2 - L K15/E19;R20/D24

<400> SEQUENCE: 147

Gly Ile Pro Phe Phe Pro Val His Leu Lys Arg Leu Leu Ile Lys Val
1               5                   10                  15

Val Val Glu Arg Leu Ile Val Asp Val Ile Val Gly Ala Leu Leu Met
            20                  25                  30

Gly

<210> SEQ ID NO 148
<211> LENGTH: 33
<212> TYPE: PRT
<213> ORGANISM: artificial
<220> FEATURE:
<223> OTHER INFORMATION: SP-C FF Ion Lock2 - L K15/D19;R20/D24

<400> SEQUENCE: 148

Gly Ile Pro Phe Phe Pro Val His Leu Lys Arg Leu Leu Ile Lys Val
1               5                   10                  15

Val Val Asp Arg Leu Ile Val Asp Val Ile Val Gly Ala Leu Leu Met
            20                  25                  30

Gly

<210> SEQ ID NO 149
<211> LENGTH: 33
<212> TYPE: PRT
<213> ORGANISM: artificial
<220> FEATURE:
<223> OTHER INFORMATION: SP-C FF Ion Lock2 - L R15/E19;E20/K24

<400> SEQUENCE: 149

Gly Ile Pro Phe Phe Pro Val His Leu Lys Arg Leu Leu Ile Arg Val
1               5                   10                  15

Val Val Glu Glu Leu Ile Val Lys Val Ile Val Gly Ala Leu Leu Met
            20                  25                  30

Gly

<210> SEQ ID NO 150
<211> LENGTH: 33
<212> TYPE: PRT
<213> ORGANISM: artificial
<220> FEATURE:
<223> OTHER INFORMATION: SP-C FF Ion Lock2 - L R15/D19;E20/K24

<400> SEQUENCE: 150

Gly Ile Pro Phe Phe Pro Val His Leu Lys Arg Leu Leu Ile Arg Val
1               5                   10                  15

Val Val Asp Glu Leu Ile Val Lys Val Ile Val Gly Ala Leu Leu Met
            20                  25                  30

Gly

<210> SEQ ID NO 151
<211> LENGTH: 33
<212> TYPE: PRT
<213> ORGANISM: artificial

```
<220> FEATURE:
<223> OTHER INFORMATION: SP-C FF Ion Lock2 - L R15/E19;D20/K24

<400> SEQUENCE: 151

Gly Ile Pro Phe Phe Pro Val His Leu Lys Arg Leu Leu Ile Arg Val
1               5                   10                  15

Val Val Glu Asp Leu Ile Val Lys Val Ile Val Gly Ala Leu Leu Met
            20                  25                  30

Gly

<210> SEQ ID NO 152
<211> LENGTH: 33
<212> TYPE: PRT
<213> ORGANISM: artificial
<220> FEATURE:
<223> OTHER INFORMATION: SP-C FF Ion Lock2 - L R15/D19;D20/K24

<400> SEQUENCE: 152

Gly Ile Pro Phe Phe Pro Val His Leu Lys Arg Leu Leu Ile Arg Val
1               5                   10                  15

Val Val Asp Asp Leu Ile Val Lys Val Ile Val Gly Ala Leu Leu Met
            20                  25                  30

Gly

<210> SEQ ID NO 153
<211> LENGTH: 33
<212> TYPE: PRT
<213> ORGANISM: artificial
<220> FEATURE:
<223> OTHER INFORMATION: SP-C FF Ion Lock2 - L R15/E19;E20/R24

<400> SEQUENCE: 153

Gly Ile Pro Phe Phe Pro Val His Leu Lys Arg Leu Leu Ile Arg Val
1               5                   10                  15

Val Val Glu Glu Leu Ile Val Arg Val Ile Val Gly Ala Leu Leu Met
            20                  25                  30

Gly

<210> SEQ ID NO 154
<211> LENGTH: 33
<212> TYPE: PRT
<213> ORGANISM: artificial
<220> FEATURE:
<223> OTHER INFORMATION: SP-C FF Ion Lock2 - L R15/D19;E20/R24

<400> SEQUENCE: 154

Gly Ile Pro Phe Phe Pro Val His Leu Lys Arg Leu Leu Ile Arg Val
1               5                   10                  15

Val Val Asp Glu Leu Ile Val Arg Val Ile Val Gly Ala Leu Leu Met
            20                  25                  30

Gly

<210> SEQ ID NO 155
<211> LENGTH: 33
<212> TYPE: PRT
<213> ORGANISM: artificial
<220> FEATURE:
<223> OTHER INFORMATION: SP-C FF Ion Lock2 - L R15/E19;D20/R24

<400> SEQUENCE: 155

Gly Ile Pro Phe Phe Pro Val His Leu Lys Arg Leu Leu Ile Arg Val
1               5                   10                  15
```

-continued

Val Val Glu Asp Leu Ile Val Arg Val Ile Val Gly Ala Leu Leu Met
            20                  25                  30

Gly

<210> SEQ ID NO 156
<211> LENGTH: 33
<212> TYPE: PRT
<213> ORGANISM: artificial
<220> FEATURE:
<223> OTHER INFORMATION: SP-C FF Ion Lock2 - L R15/D19;D20/R24

<400> SEQUENCE: 156

Gly Ile Pro Phe Phe Pro Val His Leu Lys Arg Leu Leu Ile Arg Val
1               5                   10                  15

Val Val Asp Asp Leu Ile Val Arg Val Ile Val Gly Ala Leu Leu Met
            20                  25                  30

Gly

<210> SEQ ID NO 157
<211> LENGTH: 33
<212> TYPE: PRT
<213> ORGANISM: artificial
<220> FEATURE:
<223> OTHER INFORMATION: SP-C FF Ion Lock2 - L R15/E19;K20/E24

<400> SEQUENCE: 157

Gly Ile Pro Phe Phe Pro Val His Leu Lys Arg Leu Leu Ile Arg Val
1               5                   10                  15

Val Val Glu Lys Leu Ile Val Glu Val Ile Val Gly Ala Leu Leu Met
            20                  25                  30

Gly

<210> SEQ ID NO 158
<211> LENGTH: 33
<212> TYPE: PRT
<213> ORGANISM: artificial
<220> FEATURE:
<223> OTHER INFORMATION: SP-C FF Ion Lock2 - L R15/D19;K20/E24

<400> SEQUENCE: 158

Gly Ile Pro Phe Phe Pro Val His Leu Lys Arg Leu Leu Ile Arg Val
1               5                   10                  15

Val Val Asp Lys Leu Ile Val Glu Val Ile Val Gly Ala Leu Leu Met
            20                  25                  30

Gly

<210> SEQ ID NO 159
<211> LENGTH: 33
<212> TYPE: PRT
<213> ORGANISM: artificial
<220> FEATURE:
<223> OTHER INFORMATION: SP-C FF Ion Lock2 - L R15/E19;K20/D24

<400> SEQUENCE: 159

Gly Ile Pro Phe Phe Pro Val His Leu Lys Arg Leu Leu Ile Arg Val
1               5                   10                  15

Val Val Glu Lys Leu Ile Val Asp Val Ile Val Gly Ala Leu Leu Met
            20                  25                  30

Gly

```
<210> SEQ ID NO 160
<211> LENGTH: 33
<212> TYPE: PRT
<213> ORGANISM: artificial
<220> FEATURE:
<223> OTHER INFORMATION: SP-C FF Ion Lock2 - L R15/D19;K20/D24

<400> SEQUENCE: 160

Gly Ile Pro Phe Phe Pro Val His Leu Lys Arg Leu Leu Ile Arg Val
1               5                   10                  15

Val Val Asp Lys Leu Ile Val Asp Val Ile Val Gly Ala Leu Leu Met
            20                  25                  30

Gly

<210> SEQ ID NO 161
<211> LENGTH: 33
<212> TYPE: PRT
<213> ORGANISM: artificial
<220> FEATURE:
<223> OTHER INFORMATION: SP-C FF Ion Lock2 - L R15/E19;R20/E24

<400> SEQUENCE: 161

Gly Ile Pro Phe Phe Pro Val His Leu Lys Arg Leu Leu Ile Arg Val
1               5                   10                  15

Val Val Glu Arg Leu Ile Val Glu Val Ile Val Gly Ala Leu Leu Met
            20                  25                  30

Gly

<210> SEQ ID NO 162
<211> LENGTH: 33
<212> TYPE: PRT
<213> ORGANISM: artificial
<220> FEATURE:
<223> OTHER INFORMATION: SP-C FF Ion Lock2 - L R15/D19;R20/E24

<400> SEQUENCE: 162

Gly Ile Pro Phe Phe Pro Val His Leu Lys Arg Leu Leu Ile Arg Val
1               5                   10                  15

Val Val Asp Arg Leu Ile Val Glu Val Ile Val Gly Ala Leu Leu Met
            20                  25                  30

Gly

<210> SEQ ID NO 163
<211> LENGTH: 33
<212> TYPE: PRT
<213> ORGANISM: artificial
<220> FEATURE:
<223> OTHER INFORMATION: SP-C FF Ion Lock2 - L R15/E19;R20/D24

<400> SEQUENCE: 163

Gly Ile Pro Phe Phe Pro Val His Leu Lys Arg Leu Leu Ile Arg Val
1               5                   10                  15

Val Val Glu Arg Leu Ile Val Asp Val Ile Val Gly Ala Leu Leu Met
            20                  25                  30

Gly

<210> SEQ ID NO 164
<211> LENGTH: 33
<212> TYPE: PRT
<213> ORGANISM: artificial
<220> FEATURE:
<223> OTHER INFORMATION: SP-C FF Ion Lock2 - L R15/D19;R20/D24
```

```
<400> SEQUENCE: 164

Gly Ile Pro Phe Phe Pro Val His Leu Lys Arg Leu Leu Ile Arg Val
1               5                   10                  15

Val Val Asp Arg Leu Ile Val Asp Val Ile Val Gly Ala Leu Leu Met
            20                  25                  30

Gly

<210> SEQ ID NO 165
<211> LENGTH: 33
<212> TYPE: PRT
<213> ORGANISM: artificial
<220> FEATURE:
<223> OTHER INFORMATION: SP-C FF Ion Lock2 - L E15/K19;E20/K24

<400> SEQUENCE: 165

Gly Ile Pro Phe Phe Pro Val His Leu Lys Arg Leu Leu Ile Glu Val
1               5                   10                  15

Val Val Lys Glu Leu Ile Val Lys Val Ile Val Gly Ala Leu Leu Met
            20                  25                  30

Gly

<210> SEQ ID NO 166
<211> LENGTH: 33
<212> TYPE: PRT
<213> ORGANISM: artificial
<220> FEATURE:
<223> OTHER INFORMATION: SP-C FF Ion Lock2 - L E15/R19;E20/K24

<400> SEQUENCE: 166

Gly Ile Pro Phe Phe Pro Val His Leu Lys Arg Leu Leu Ile Glu Val
1               5                   10                  15

Val Val Arg Glu Leu Ile Val Lys Val Ile Val Gly Ala Leu Leu Met
            20                  25                  30

Gly

<210> SEQ ID NO 167
<211> LENGTH: 33
<212> TYPE: PRT
<213> ORGANISM: artificial
<220> FEATURE:
<223> OTHER INFORMATION: SP-C FF Ion Lock2 - L E15/K19;D20/K24

<400> SEQUENCE: 167

Gly Ile Pro Phe Phe Pro Val His Leu Lys Arg Leu Leu Ile Glu Val
1               5                   10                  15

Val Val Lys Asp Leu Ile Val Lys Val Ile Val Gly Ala Leu Leu Met
            20                  25                  30

Gly

<210> SEQ ID NO 168
<211> LENGTH: 33
<212> TYPE: PRT
<213> ORGANISM: artificial
<220> FEATURE:
<223> OTHER INFORMATION: SP-C FF Ion Lock2 - L E15/R19;D20/K24

<400> SEQUENCE: 168

Gly Ile Pro Phe Phe Pro Val His Leu Lys Arg Leu Leu Ile Glu Val
1               5                   10                  15

Val Val Arg Asp Leu Ile Val Lys Val Ile Val Gly Ala Leu Leu Met
            20                  25                  30
```

Gly

<210> SEQ ID NO 169
<211> LENGTH: 33
<212> TYPE: PRT
<213> ORGANISM: artificial
<220> FEATURE:
<223> OTHER INFORMATION: SP-C FF Ion Lock2 - L E15/K19;E20/R24

<400> SEQUENCE: 169

Gly Ile Pro Phe Phe Pro Val His Leu Lys Arg Leu Leu Ile Glu Val
1               5                   10                  15

Val Val Lys Glu Leu Ile Val Arg Val Ile Val Gly Ala Leu Leu Met
            20                  25                  30

Gly

<210> SEQ ID NO 170
<211> LENGTH: 33
<212> TYPE: PRT
<213> ORGANISM: artificial
<220> FEATURE:
<223> OTHER INFORMATION: SP-C FF Ion Lock2 - L E15/R19;E20/R24

<400> SEQUENCE: 170

Gly Ile Pro Phe Phe Pro Val His Leu Lys Arg Leu Leu Ile Glu Val
1               5                   10                  15

Val Val Arg Glu Leu Ile Val Arg Val Ile Val Gly Ala Leu Leu Met
            20                  25                  30

Gly

<210> SEQ ID NO 171
<211> LENGTH: 33
<212> TYPE: PRT
<213> ORGANISM: artificial
<220> FEATURE:
<223> OTHER INFORMATION: SP-C FF Ion Lock2 - L E15/K19;D20/R24

<400> SEQUENCE: 171

Gly Ile Pro Phe Phe Pro Val His Leu Lys Arg Leu Leu Ile Glu Val
1               5                   10                  15

Val Val Lys Asp Leu Ile Val Arg Val Ile Val Gly Ala Leu Leu Met
            20                  25                  30

Gly

<210> SEQ ID NO 172
<211> LENGTH: 33
<212> TYPE: PRT
<213> ORGANISM: artificial
<220> FEATURE:
<223> OTHER INFORMATION: SP-C FF Ion Lock2 - L E15/R19;D20/R24

<400> SEQUENCE: 172

Gly Ile Pro Phe Phe Pro Val His Leu Lys Arg Leu Leu Ile Glu Val
1               5                   10                  15

Val Val Arg Asp Leu Ile Val Arg Val Ile Val Gly Ala Leu Leu Met
            20                  25                  30

Gly

<210> SEQ ID NO 173
<211> LENGTH: 33
<212> TYPE: PRT

<213> ORGANISM: artificial
<220> FEATURE:
<223> OTHER INFORMATION: SP-C FF Ion Lock2 - L E15/K19;K20/E24

<400> SEQUENCE: 173

Gly Ile Pro Phe Phe Pro Val His Leu Lys Arg Leu Leu Ile Glu Val
1               5                   10                  15

Val Val Lys Lys Leu Ile Val Glu Val Ile Val Gly Ala Leu Leu Met
            20                  25                  30

Gly

<210> SEQ ID NO 174
<211> LENGTH: 33
<212> TYPE: PRT
<213> ORGANISM: artificial
<220> FEATURE:
<223> OTHER INFORMATION: SP-C FF Ion Lock2 - L E15/R19;K20/E24

<400> SEQUENCE: 174

Gly Ile Pro Phe Phe Pro Val His Leu Lys Arg Leu Leu Ile Glu Val
1               5                   10                  15

Val Val Arg Lys Leu Ile Val Glu Val Ile Val Gly Ala Leu Leu Met
            20                  25                  30

Gly

<210> SEQ ID NO 175
<211> LENGTH: 33
<212> TYPE: PRT
<213> ORGANISM: artificial
<220> FEATURE:
<223> OTHER INFORMATION: SP-C FF Ion Lock2 - L E15/K19;K20/D24

<400> SEQUENCE: 175

Gly Ile Pro Phe Phe Pro Val His Leu Lys Arg Leu Leu Ile Glu Val
1               5                   10                  15

Val Val Lys Lys Leu Ile Val Asp Val Ile Val Gly Ala Leu Leu Met
            20                  25                  30

Gly

<210> SEQ ID NO 176
<211> LENGTH: 33
<212> TYPE: PRT
<213> ORGANISM: artificial
<220> FEATURE:
<223> OTHER INFORMATION: SP-C FF Ion Lock2 - L E15/R19;K20/D24

<400> SEQUENCE: 176

Gly Ile Pro Phe Phe Pro Val His Leu Lys Arg Leu Leu Ile Glu Val
1               5                   10                  15

Val Val Arg Lys Leu Ile Val Asp Val Ile Val Gly Ala Leu Leu Met
            20                  25                  30

Gly

<210> SEQ ID NO 177
<211> LENGTH: 33
<212> TYPE: PRT
<213> ORGANISM: artificial
<220> FEATURE:
<223> OTHER INFORMATION: SP-C FF Ion Lock2 - L E15/K19;R20/E24

<400> SEQUENCE: 177

Gly Ile Pro Phe Phe Pro Val His Leu Lys Arg Leu Leu Ile Glu Val

```
                1               5                   10                  15
Val Val Lys Arg Leu Ile Val Glu Val Ile Val Gly Ala Leu Leu Met
                20                  25                  30

Gly

<210> SEQ ID NO 178
<211> LENGTH: 33
<212> TYPE: PRT
<213> ORGANISM: artificial
<220> FEATURE:
<223> OTHER INFORMATION: SP-C FF Ion Lock2 - L E15/R19;R20/E24

<400> SEQUENCE: 178

Gly Ile Pro Phe Phe Pro Val His Leu Lys Arg Leu Leu Ile Glu Val
1               5                   10                  15

Val Val Arg Arg Leu Ile Val Glu Val Ile Val Gly Ala Leu Leu Met
                20                  25                  30

Gly

<210> SEQ ID NO 179
<211> LENGTH: 33
<212> TYPE: PRT
<213> ORGANISM: artificial
<220> FEATURE:
<223> OTHER INFORMATION: SP-C FF Ion Lock2 - L E15/K19;R20/D24

<400> SEQUENCE: 179

Gly Ile Pro Phe Phe Pro Val His Leu Lys Arg Leu Leu Ile Glu Val
1               5                   10                  15

Val Val Lys Arg Leu Ile Val Asp Val Ile Val Gly Ala Leu Leu Met
                20                  25                  30

Gly

<210> SEQ ID NO 180
<211> LENGTH: 33
<212> TYPE: PRT
<213> ORGANISM: artificial
<220> FEATURE:
<223> OTHER INFORMATION: SP-C FF Ion Lock2 - L E15/R19;R20/D24

<400> SEQUENCE: 180

Gly Ile Pro Phe Phe Pro Val His Leu Lys Arg Leu Leu Ile Glu Val
1               5                   10                  15

Val Val Arg Arg Leu Ile Val Asp Val Ile Val Gly Ala Leu Leu Met
                20                  25                  30

Gly

<210> SEQ ID NO 181
<211> LENGTH: 33
<212> TYPE: PRT
<213> ORGANISM: artificial
<220> FEATURE:
<223> OTHER INFORMATION: SP-C FF Ion Lock2 - L D15/K19;E20/K24

<400> SEQUENCE: 181

Gly Ile Pro Phe Phe Pro Val His Leu Lys Arg Leu Leu Ile Asp Val
1               5                   10                  15

Val Val Lys Glu Leu Ile Val Lys Val Ile Val Gly Ala Leu Leu Met
                20                  25                  30

Gly
```

<210> SEQ ID NO 182
<211> LENGTH: 33
<212> TYPE: PRT
<213> ORGANISM: artificial
<220> FEATURE:
<223> OTHER INFORMATION: SP-C FF Ion Lock2 - L D15/R19;E20/K24

<400> SEQUENCE: 182

Gly Ile Pro Phe Phe Pro Val His Leu Lys Arg Leu Leu Ile Asp Val
1               5                   10                  15

Val Val Arg Glu Leu Ile Val Lys Val Ile Val Gly Ala Leu Leu Met
            20                  25                  30

Gly

<210> SEQ ID NO 183
<211> LENGTH: 33
<212> TYPE: PRT
<213> ORGANISM: artificial
<220> FEATURE:
<223> OTHER INFORMATION: SP-C FF Ion Lock2 - L D15/K19;D20/K24

<400> SEQUENCE: 183

Gly Ile Pro Phe Phe Pro Val His Leu Lys Arg Leu Leu Ile Asp Val
1               5                   10                  15

Val Val Lys Asp Leu Ile Val Lys Val Ile Val Gly Ala Leu Leu Met
            20                  25                  30

Gly

<210> SEQ ID NO 184
<211> LENGTH: 33
<212> TYPE: PRT
<213> ORGANISM: artificial
<220> FEATURE:
<223> OTHER INFORMATION: SP-C FF Ion Lock2 - L D15/R19;D20/K24

<400> SEQUENCE: 184

Gly Ile Pro Phe Phe Pro Val His Leu Lys Arg Leu Leu Ile Asp Val
1               5                   10                  15

Val Val Arg Asp Leu Ile Val Lys Val Ile Val Gly Ala Leu Leu Met
            20                  25                  30

Gly

<210> SEQ ID NO 185
<211> LENGTH: 33
<212> TYPE: PRT
<213> ORGANISM: artificial
<220> FEATURE:
<223> OTHER INFORMATION: SP-C FF Ion Lock2 - L D15/K19;E20/R24

<400> SEQUENCE: 185

Gly Ile Pro Phe Phe Pro Val His Leu Lys Arg Leu Leu Ile Asp Val
1               5                   10                  15

Val Val Lys Glu Leu Ile Val Arg Val Ile Val Gly Ala Leu Leu Met
            20                  25                  30

Gly

<210> SEQ ID NO 186
<211> LENGTH: 33
<212> TYPE: PRT
<213> ORGANISM: artificial
<220> FEATURE:
<223> OTHER INFORMATION: SP-C FF Ion Lock2 - L D15/R19;E20/R24

```
<400> SEQUENCE: 186

Gly Ile Pro Phe Phe Pro Val His Leu Lys Arg Leu Leu Ile Asp Val
1               5                   10                  15

Val Val Arg Glu Leu Ile Val Arg Val Ile Val Gly Ala Leu Leu Met
            20                  25                  30

Gly

<210> SEQ ID NO 187
<211> LENGTH: 33
<212> TYPE: PRT
<213> ORGANISM: artificial
<220> FEATURE:
<223> OTHER INFORMATION: SP-C FF Ion Lock2 - L D15/K19;D20/R24

<400> SEQUENCE: 187

Gly Ile Pro Phe Phe Pro Val His Leu Lys Arg Leu Leu Ile Asp Val
1               5                   10                  15

Val Val Lys Asp Leu Ile Val Arg Val Ile Val Gly Ala Leu Leu Met
            20                  25                  30

Gly

<210> SEQ ID NO 188
<211> LENGTH: 33
<212> TYPE: PRT
<213> ORGANISM: artificial
<220> FEATURE:
<223> OTHER INFORMATION: SP-C FF Ion Lock2 - L D15/R19;D20/R24

<400> SEQUENCE: 188

Gly Ile Pro Phe Phe Pro Val His Leu Lys Arg Leu Leu Ile Asp Val
1               5                   10                  15

Val Val Arg Asp Leu Ile Val Arg Val Ile Val Gly Ala Leu Leu Met
            20                  25                  30

Gly

<210> SEQ ID NO 189
<211> LENGTH: 33
<212> TYPE: PRT
<213> ORGANISM: artificial
<220> FEATURE:
<223> OTHER INFORMATION: SP-C FF Ion Lock2 - L D15/K19;K20/E24

<400> SEQUENCE: 189

Gly Ile Pro Phe Phe Pro Val His Leu Lys Arg Leu Leu Ile Asp Val
1               5                   10                  15

Val Val Lys Lys Leu Ile Val Glu Val Ile Val Gly Ala Leu Leu Met
            20                  25                  30

Gly

<210> SEQ ID NO 190
<211> LENGTH: 33
<212> TYPE: PRT
<213> ORGANISM: artificial
<220> FEATURE:
<223> OTHER INFORMATION: SP-C FF Ion Lock2 - L D15/R19;K20/E24

<400> SEQUENCE: 190

Gly Ile Pro Phe Phe Pro Val His Leu Lys Arg Leu Leu Ile Asp Val
1               5                   10                  15

Val Val Arg Lys Leu Ile Val Glu Val Ile Val Gly Ala Leu Leu Met
```

-continued

```
                20                  25                  30
Gly

<210> SEQ ID NO 191
<211> LENGTH: 33
<212> TYPE: PRT
<213> ORGANISM: artificial
<220> FEATURE:
<223> OTHER INFORMATION: SP-C FF Ion Lock2 - L D15/K19;D20/D24

<400> SEQUENCE: 191

Gly Ile Pro Phe Phe Pro Val His Leu Lys Arg Leu Leu Ile Asp Val
1               5                   10                  15

Val Val Lys Arg Leu Ile Val Asp Val Ile Val Gly Ala Leu Leu Met
            20                  25                  30

Gly

<210> SEQ ID NO 192
<211> LENGTH: 33
<212> TYPE: PRT
<213> ORGANISM: artificial
<220> FEATURE:
<223> OTHER INFORMATION: SP-C FF Ion Lock2 - L D15/R19;K20/D24

<400> SEQUENCE: 192

Gly Ile Pro Phe Phe Pro Val His Leu Lys Arg Leu Leu Ile Asp Val
1               5                   10                  15

Val Val Arg Lys Leu Ile Val Asp Val Ile Val Gly Ala Leu Leu Met
            20                  25                  30

Gly

<210> SEQ ID NO 193
<211> LENGTH: 33
<212> TYPE: PRT
<213> ORGANISM: artificial
<220> FEATURE:
<223> OTHER INFORMATION: SP-C FF Ion Lock2 - L D15/K19;R20/E24

<400> SEQUENCE: 193

Gly Ile Pro Phe Phe Pro Val His Leu Lys Arg Leu Leu Ile Asp Val
1               5                   10                  15

Val Val Lys Arg Leu Ile Val Glu Val Ile Val Gly Ala Leu Leu Met
            20                  25                  30

Gly

<210> SEQ ID NO 194
<211> LENGTH: 33
<212> TYPE: PRT
<213> ORGANISM: artificial
<220> FEATURE:
<223> OTHER INFORMATION: SP-C FF Ion Lock2 - L D15/R19;R20/E24

<400> SEQUENCE: 194

Gly Ile Pro Phe Phe Pro Val His Leu Lys Arg Leu Leu Ile Asp Val
1               5                   10                  15

Val Val Arg Arg Leu Ile Val Glu Val Ile Val Gly Ala Leu Leu Met
            20                  25                  30

Gly

<210> SEQ ID NO 195
<211> LENGTH: 33
```

```
<212> TYPE: PRT
<213> ORGANISM: artificial
<220> FEATURE:
<223> OTHER INFORMATION: SP-C FF Ion Lock2 - L D15/K19;K20/D24

<400> SEQUENCE: 195

Gly Ile Pro Phe Phe Pro Val His Leu Lys Arg Leu Leu Ile Asp Val
1               5                   10                  15

Val Val Lys Lys Leu Ile Val Asp Val Ile Val Gly Ala Leu Leu Met
            20                  25                  30

Gly

<210> SEQ ID NO 196
<211> LENGTH: 33
<212> TYPE: PRT
<213> ORGANISM: artificial
<220> FEATURE:
<223> OTHER INFORMATION: SP-C FF Ion Lock2 - L D15/R19;R20/D24

<400> SEQUENCE: 196

Gly Ile Pro Phe Phe Pro Val His Leu Lys Arg Leu Leu Ile Asp Val
1               5                   10                  15

Val Val Arg Arg Leu Ile Val Asp Val Ile Val Gly Ala Leu Leu Met
            20                  25                  30

Gly

<210> SEQ ID NO 197
<211> LENGTH: 34
<212> TYPE: PRT
<213> ORGANISM: artificial
<220> FEATURE:
<223> OTHER INFORMATION: SP-C SS Ion Lock2 K15/E19;E20/K24

<400> SEQUENCE: 197

Gly Ile Pro Ser Ser Pro Val His Leu Lys Arg Leu Leu Ile Lys Val
1               5                   10                  15

Val Val Glu Glu Leu Ile Val Lys Val Ile Val Gly Ala Leu Leu Met
            20                  25                  30

Gly Leu

<210> SEQ ID NO 198
<211> LENGTH: 34
<212> TYPE: PRT
<213> ORGANISM: artificial
<220> FEATURE:
<223> OTHER INFORMATION: SP-C SS Ion Lock2 K15/D19;E20/K24

<400> SEQUENCE: 198

Gly Ile Pro Ser Ser Pro Val His Leu Lys Arg Leu Leu Ile Lys Val
1               5                   10                  15

Val Val Asp Glu Leu Ile Val Lys Val Ile Val Gly Ala Leu Leu Met
            20                  25                  30

Gly Leu

<210> SEQ ID NO 199
<211> LENGTH: 34
<212> TYPE: PRT
<213> ORGANISM: artificial
<220> FEATURE:
<223> OTHER INFORMATION: SP-C SS Ion Lock2 K15/E19;D20/K24

<400> SEQUENCE: 199
```

```
Gly Ile Pro Ser Ser Pro Val His Leu Lys Arg Leu Leu Ile Lys Val
1               5                   10                  15

Val Val Glu Asp Leu Ile Val Lys Val Ile Val Gly Ala Leu Leu Met
            20                  25                  30

Gly Leu

<210> SEQ ID NO 200
<211> LENGTH: 34
<212> TYPE: PRT
<213> ORGANISM: artificial
<220> FEATURE:
<223> OTHER INFORMATION: SP-C SS Ion Lock2 K15/D19;D20/K24

<400> SEQUENCE: 200

Gly Ile Pro Ser Ser Pro Val His Leu Lys Arg Leu Leu Ile Lys Val
1               5                   10                  15

Val Val Asp Asp Leu Ile Val Lys Val Ile Val Gly Ala Leu Leu Met
            20                  25                  30

Gly Leu

<210> SEQ ID NO 201
<211> LENGTH: 34
<212> TYPE: PRT
<213> ORGANISM: artificial
<220> FEATURE:
<223> OTHER INFORMATION: SP-C SS Ion Lock2 K15/E19;E20/R24

<400> SEQUENCE: 201

Gly Ile Pro Ser Ser Pro Val His Leu Lys Arg Leu Leu Ile Lys Val
1               5                   10                  15

Val Val Glu Glu Leu Ile Val Arg Val Ile Val Gly Ala Leu Leu Met
            20                  25                  30

Gly Leu

<210> SEQ ID NO 202
<211> LENGTH: 34
<212> TYPE: PRT
<213> ORGANISM: artificial
<220> FEATURE:
<223> OTHER INFORMATION: SP-C SS Ion Lock2 K15/D19;E20/R24

<400> SEQUENCE: 202

Gly Ile Pro Ser Ser Pro Val His Leu Lys Arg Leu Leu Ile Lys Val
1               5                   10                  15

Val Val Asp Glu Leu Ile Val Arg Val Ile Val Gly Ala Leu Leu Met
            20                  25                  30

Gly Leu

<210> SEQ ID NO 203
<211> LENGTH: 34
<212> TYPE: PRT
<213> ORGANISM: artificial
<220> FEATURE:
<223> OTHER INFORMATION: SP-C SS Ion Lock2 K15/E19;D20/R24

<400> SEQUENCE: 203

Gly Ile Pro Ser Ser Pro Val His Leu Lys Arg Leu Leu Ile Lys Val
1               5                   10                  15

Val Val Glu Asp Leu Ile Val Arg Val Ile Val Gly Ala Leu Leu Met
            20                  25                  30

Gly Leu
```

<210> SEQ ID NO 204
<211> LENGTH: 34
<212> TYPE: PRT
<213> ORGANISM: artificial
<220> FEATURE:
<223> OTHER INFORMATION: SP-C SS Ion Lock2 K15/D19;D20/R24

<400> SEQUENCE: 204

Gly Ile Pro Ser Ser Pro Val His Leu Lys Arg Leu Leu Ile Lys Val
1               5                   10                  15

Val Val Asp Asp Leu Ile Val Arg Val Ile Val Gly Ala Leu Leu Met
            20                  25                  30

Gly Leu

<210> SEQ ID NO 205
<211> LENGTH: 34
<212> TYPE: PRT
<213> ORGANISM: artificial
<220> FEATURE:
<223> OTHER INFORMATION: SP-C SS Ion Lock2 K15/E19;K20/E24

<400> SEQUENCE: 205

Gly Ile Pro Ser Ser Pro Val His Leu Lys Arg Leu Leu Ile Lys Val
1               5                   10                  15

Val Val Glu Lys Leu Ile Val Glu Val Ile Val Gly Ala Leu Leu Met
            20                  25                  30

Gly Leu

<210> SEQ ID NO 206
<211> LENGTH: 34
<212> TYPE: PRT
<213> ORGANISM: artificial
<220> FEATURE:
<223> OTHER INFORMATION: SP-C SS Ion Lock2 K15/D19;K20/E24

<400> SEQUENCE: 206

Gly Ile Pro Ser Ser Pro Val His Leu Lys Arg Leu Leu Ile Lys Val
1               5                   10                  15

Val Val Asp Lys Leu Ile Val Glu Val Ile Val Gly Ala Leu Leu Met
            20                  25                  30

Gly Leu

<210> SEQ ID NO 207
<211> LENGTH: 34
<212> TYPE: PRT
<213> ORGANISM: artificial
<220> FEATURE:
<223> OTHER INFORMATION: SP-C SS Ion Lock2 K15/E19;K20/D24

<400> SEQUENCE: 207

Gly Ile Pro Ser Ser Pro Val His Leu Lys Arg Leu Leu Ile Lys Val
1               5                   10                  15

Val Val Glu Lys Leu Ile Val Asp Val Ile Val Gly Ala Leu Leu Met
            20                  25                  30

Gly Leu

<210> SEQ ID NO 208
<211> LENGTH: 34
<212> TYPE: PRT
<213> ORGANISM: artificial
<220> FEATURE:

-continued

<223> OTHER INFORMATION: SP-C SS Ion Lock2 K15/D19;K20/D24

<400> SEQUENCE: 208

Gly Ile Pro Ser Ser Pro Val His Leu Lys Arg Leu Leu Ile Lys Val
1               5                   10                  15

Val Val Asp Lys Leu Ile Val Asp Val Ile Val Gly Ala Leu Leu Met
            20                  25                  30

Gly Leu

<210> SEQ ID NO 209
<211> LENGTH: 34
<212> TYPE: PRT
<213> ORGANISM: artificial
<220> FEATURE:
<223> OTHER INFORMATION: SP-C SS Ion Lock2 K15/E19;R20/E24

<400> SEQUENCE: 209

Gly Ile Pro Ser Ser Pro Val His Leu Lys Arg Leu Leu Ile Lys Val
1               5                   10                  15

Val Val Glu Arg Leu Ile Val Glu Val Ile Val Gly Ala Leu Leu Met
            20                  25                  30

Gly Leu

<210> SEQ ID NO 210
<211> LENGTH: 34
<212> TYPE: PRT
<213> ORGANISM: artificial
<220> FEATURE:
<223> OTHER INFORMATION: SP-C SS Ion Lock2 K15/D19;R20/E24

<400> SEQUENCE: 210

Gly Ile Pro Ser Ser Pro Val His Leu Lys Arg Leu Leu Ile Lys Val
1               5                   10                  15

Val Val Asp Arg Leu Ile Val Glu Val Ile Val Gly Ala Leu Leu Met
            20                  25                  30

Gly Leu

<210> SEQ ID NO 211
<211> LENGTH: 34
<212> TYPE: PRT
<213> ORGANISM: artificial
<220> FEATURE:
<223> OTHER INFORMATION: SP-C SS Ion Lock2 K15/E19;R20/D24

<400> SEQUENCE: 211

Gly Ile Pro Ser Ser Pro Val His Leu Lys Arg Leu Leu Ile Lys Val
1               5                   10                  15

Val Val Glu Arg Leu Ile Val Asp Val Ile Val Gly Ala Leu Leu Met
            20                  25                  30

Gly Leu

<210> SEQ ID NO 212
<211> LENGTH: 34
<212> TYPE: PRT
<213> ORGANISM: artificial
<220> FEATURE:
<223> OTHER INFORMATION: SP-C SS Ion Lock2 K15/D19;R20/D24

<400> SEQUENCE: 212

Gly Ile Pro Ser Ser Pro Val His Leu Lys Arg Leu Leu Ile Lys Val
1               5                   10                  15

Val Val Asp Arg Leu Ile Val Asp Val Ile Val Gly Ala Leu Leu Met
            20                  25                  30

Gly Leu

<210> SEQ ID NO 213
<211> LENGTH: 34
<212> TYPE: PRT
<213> ORGANISM: artificial
<220> FEATURE:
<223> OTHER INFORMATION: SP-C SS Ion Lock2 R15/E19;E20/K24

<400> SEQUENCE: 213

Gly Ile Pro Ser Ser Pro Val His Leu Lys Arg Leu Leu Ile Arg Val
1               5                   10                  15

Val Val Glu Glu Leu Ile Val Lys Val Ile Val Gly Ala Leu Leu Met
            20                  25                  30

Gly Leu

<210> SEQ ID NO 214
<211> LENGTH: 34
<212> TYPE: PRT
<213> ORGANISM: artificial
<220> FEATURE:
<223> OTHER INFORMATION: SP-C SS Ion Lock2 R15/D19;E20/K24

<400> SEQUENCE: 214

Gly Ile Pro Ser Ser Pro Val His Leu Lys Arg Leu Leu Ile Arg Val
1               5                   10                  15

Val Val Asp Glu Leu Ile Val Lys Val Ile Val Gly Ala Leu Leu Met
            20                  25                  30

Gly Leu

<210> SEQ ID NO 215
<211> LENGTH: 34
<212> TYPE: PRT
<213> ORGANISM: artificial
<220> FEATURE:
<223> OTHER INFORMATION: SP-C SS Ion Lock2 R15/E19;D20/K24

<400> SEQUENCE: 215

Gly Ile Pro Ser Ser Pro Val His Leu Lys Arg Leu Leu Ile Arg Val
1               5                   10                  15

Val Val Glu Asp Leu Ile Val Lys Val Ile Val Gly Ala Leu Leu Met
            20                  25                  30

Gly Leu

<210> SEQ ID NO 216
<211> LENGTH: 34
<212> TYPE: PRT
<213> ORGANISM: artificial
<220> FEATURE:
<223> OTHER INFORMATION: SP-C SS Ion Lock2 R15/D19;D20/K24

<400> SEQUENCE: 216

Gly Ile Pro Ser Ser Pro Val His Leu Lys Arg Leu Leu Ile Arg Val
1               5                   10                  15

Val Val Asp Asp Leu Ile Val Lys Val Ile Val Gly Ala Leu Leu Met
            20                  25                  30

Gly Leu

<210> SEQ ID NO 217

```
<211> LENGTH: 34
<212> TYPE: PRT
<213> ORGANISM: artificial
<220> FEATURE:
<223> OTHER INFORMATION: SP-C SS Ion Lock2 R15/E19;E20/R24

<400> SEQUENCE: 217

Gly Ile Pro Ser Ser Pro Val His Leu Lys Arg Leu Leu Ile Arg Val
1               5                   10                  15

Val Val Glu Glu Leu Ile Val Arg Val Ile Val Gly Ala Leu Leu Met
            20                  25                  30

Gly Leu

<210> SEQ ID NO 218
<211> LENGTH: 34
<212> TYPE: PRT
<213> ORGANISM: artificial
<220> FEATURE:
<223> OTHER INFORMATION: SP-C SS Ion Lock2 R15/D19;E20/R24

<400> SEQUENCE: 218

Gly Ile Pro Ser Ser Pro Val His Leu Lys Arg Leu Leu Ile Arg Val
1               5                   10                  15

Val Val Asp Glu Leu Ile Val Arg Val Ile Val Gly Ala Leu Leu Met
            20                  25                  30

Gly Leu

<210> SEQ ID NO 219
<211> LENGTH: 34
<212> TYPE: PRT
<213> ORGANISM: artificial
<220> FEATURE:
<223> OTHER INFORMATION: SP-C SS Ion Lock2 R15/E19;D20/R24

<400> SEQUENCE: 219

Gly Ile Pro Ser Ser Pro Val His Leu Lys Arg Leu Leu Ile Arg Val
1               5                   10                  15

Val Val Glu Asp Leu Ile Val Arg Val Ile Val Gly Ala Leu Leu Met
            20                  25                  30

Gly Leu

<210> SEQ ID NO 220
<211> LENGTH: 34
<212> TYPE: PRT
<213> ORGANISM: artificial
<220> FEATURE:
<223> OTHER INFORMATION: SP-C SS Ion Lock2 R15/D19;D20/R24

<400> SEQUENCE: 220

Gly Ile Pro Ser Ser Pro Val His Leu Lys Arg Leu Leu Ile Arg Val
1               5                   10                  15

Val Val Asp Asp Leu Ile Val Arg Val Ile Val Gly Ala Leu Leu Met
            20                  25                  30

Gly Leu

<210> SEQ ID NO 221
<211> LENGTH: 34
<212> TYPE: PRT
<213> ORGANISM: artificial
<220> FEATURE:
<223> OTHER INFORMATION: SP-C SS Ion Lock2 R15/E19;K20/E24

<400> SEQUENCE: 221
```

```
Gly Ile Pro Ser Ser Pro Val His Leu Lys Arg Leu Leu Ile Arg Val
1               5                   10                  15

Val Val Glu Lys Leu Ile Val Glu Val Ile Val Gly Ala Leu Leu Met
            20                  25                  30

Gly Leu

<210> SEQ ID NO 222
<211> LENGTH: 34
<212> TYPE: PRT
<213> ORGANISM: artificial
<220> FEATURE:
<223> OTHER INFORMATION: SP-C SS Ion Lock2 R15/D19;K20/E24

<400> SEQUENCE: 222

Gly Ile Pro Ser Ser Pro Val His Leu Lys Arg Leu Leu Ile Arg Val
1               5                   10                  15

Val Val Asp Lys Leu Ile Val Glu Val Ile Val Gly Ala Leu Leu Met
            20                  25                  30

Gly Leu

<210> SEQ ID NO 223
<211> LENGTH: 34
<212> TYPE: PRT
<213> ORGANISM: artificial
<220> FEATURE:
<223> OTHER INFORMATION: SP-C SS Ion Lock2 R15/E19;K20/D24

<400> SEQUENCE: 223

Gly Ile Pro Ser Ser Pro Val His Leu Lys Arg Leu Leu Ile Arg Val
1               5                   10                  15

Val Val Glu Lys Leu Ile Val Asp Val Ile Val Gly Ala Leu Leu Met
            20                  25                  30

Gly Leu

<210> SEQ ID NO 224
<211> LENGTH: 34
<212> TYPE: PRT
<213> ORGANISM: artificial
<220> FEATURE:
<223> OTHER INFORMATION: SP-C SS Ion Lock2 R15/D19;K20/D24

<400> SEQUENCE: 224

Gly Ile Pro Ser Ser Pro Val His Leu Lys Arg Leu Leu Ile Arg Val
1               5                   10                  15

Val Val Asp Lys Leu Ile Val Asp Val Ile Val Gly Ala Leu Leu Met
            20                  25                  30

Gly Leu

<210> SEQ ID NO 225
<211> LENGTH: 34
<212> TYPE: PRT
<213> ORGANISM: artificial
<220> FEATURE:
<223> OTHER INFORMATION: SP-C SS Ion Lock2 R15/E19;R20/E24

<400> SEQUENCE: 225

Gly Ile Pro Ser Ser Pro Val His Leu Lys Arg Leu Leu Ile Arg Val
1               5                   10                  15

Val Val Glu Arg Leu Ile Val Glu Val Ile Val Gly Ala Leu Leu Met
            20                  25                  30
```

Gly Leu

<210> SEQ ID NO 226
<211> LENGTH: 34
<212> TYPE: PRT
<213> ORGANISM: artificial
<220> FEATURE:
<223> OTHER INFORMATION: SP-C SS Ion Lock2 R15/D19;R20/E24

<400> SEQUENCE: 226

Gly Ile Pro Ser Ser Pro Val His Leu Lys Arg Leu Leu Ile Arg Val
1               5                   10                  15

Val Val Asp Arg Leu Ile Val Glu Val Ile Val Gly Ala Leu Leu Met
            20                  25                  30

Gly Leu

<210> SEQ ID NO 227
<211> LENGTH: 34
<212> TYPE: PRT
<213> ORGANISM: artificial
<220> FEATURE:
<223> OTHER INFORMATION: SP-C SS Ion Lock2 R15/E19;R20/D24

<400> SEQUENCE: 227

Gly Ile Pro Ser Ser Pro Val His Leu Lys Arg Leu Leu Ile Arg Val
1               5                   10                  15

Val Val Glu Arg Leu Ile Val Asp Val Ile Val Gly Ala Leu Leu Met
            20                  25                  30

Gly Leu

<210> SEQ ID NO 228
<211> LENGTH: 34
<212> TYPE: PRT
<213> ORGANISM: artificial
<220> FEATURE:
<223> OTHER INFORMATION: SP-C SS Ion Lock2 R15/D19;R20/D24

<400> SEQUENCE: 228

Gly Ile Pro Ser Ser Pro Val His Leu Lys Arg Leu Leu Ile Arg Val
1               5                   10                  15

Val Val Asp Arg Leu Ile Val Asp Val Ile Val Gly Ala Leu Leu Met
            20                  25                  30

Gly Leu

<210> SEQ ID NO 229
<211> LENGTH: 34
<212> TYPE: PRT
<213> ORGANISM: artificial
<220> FEATURE:
<223> OTHER INFORMATION: SP-C SS Ion Lock2 E15/K19;E20/K24

<400> SEQUENCE: 229

Gly Ile Pro Ser Ser Pro Val His Leu Lys Arg Leu Leu Ile Glu Val
1               5                   10                  15

Val Val Lys Glu Leu Ile Val Lys Val Ile Val Gly Ala Leu Leu Met
            20                  25                  30

Gly Leu

<210> SEQ ID NO 230
<211> LENGTH: 34
<212> TYPE: PRT
<213> ORGANISM: artificial

```
<220> FEATURE:
<223> OTHER INFORMATION: SP-C SS Ion Lock2 E15/R19;E20/K24

<400> SEQUENCE: 230

Gly Ile Pro Ser Ser Pro Val His Leu Lys Arg Leu Leu Ile Glu Val
1               5                   10                  15

Val Val Arg Glu Leu Ile Val Lys Val Ile Val Gly Ala Leu Leu Met
            20                  25                  30

Gly Leu

<210> SEQ ID NO 231
<211> LENGTH: 34
<212> TYPE: PRT
<213> ORGANISM: artificial
<220> FEATURE:
<223> OTHER INFORMATION: SP-C SS Ion Lock2 E15/K19;D20/K24

<400> SEQUENCE: 231

Gly Ile Pro Ser Ser Pro Val His Leu Lys Arg Leu Leu Ile Glu Val
1               5                   10                  15

Val Val Lys Asp Leu Ile Val Lys Val Ile Val Gly Ala Leu Leu Met
            20                  25                  30

Gly Leu

<210> SEQ ID NO 232
<211> LENGTH: 34
<212> TYPE: PRT
<213> ORGANISM: artificial
<220> FEATURE:
<223> OTHER INFORMATION: SP-C SS Ion Lock2 E15/R19;D20/K24

<400> SEQUENCE: 232

Gly Ile Pro Ser Ser Pro Val His Leu Lys Arg Leu Leu Ile Glu Val
1               5                   10                  15

Val Val Arg Asp Leu Ile Val Lys Val Ile Val Gly Ala Leu Leu Met
            20                  25                  30

Gly Leu

<210> SEQ ID NO 233
<211> LENGTH: 34
<212> TYPE: PRT
<213> ORGANISM: artificial
<220> FEATURE:
<223> OTHER INFORMATION: SP-C SS Ion Lock2 E15/K19;E20/R24

<400> SEQUENCE: 233

Gly Ile Pro Ser Ser Pro Val His Leu Lys Arg Leu Leu Ile Glu Val
1               5                   10                  15

Val Val Lys Glu Leu Ile Val Arg Val Ile Val Gly Ala Leu Leu Met
            20                  25                  30

Gly Leu

<210> SEQ ID NO 234
<211> LENGTH: 34
<212> TYPE: PRT
<213> ORGANISM: artificial
<220> FEATURE:
<223> OTHER INFORMATION: SP-C SS Ion Lock2 E15/R19;E20/R24

<400> SEQUENCE: 234

Gly Ile Pro Ser Ser Pro Val His Leu Lys Arg Leu Leu Ile Glu Val
1               5                   10                  15
```

```
Val Val Arg Glu Leu Ile Val Arg Val Ile Val Gly Ala Leu Leu Met
            20                  25                  30

Gly Leu

<210> SEQ ID NO 235
<211> LENGTH: 34
<212> TYPE: PRT
<213> ORGANISM: artificial
<220> FEATURE:
<223> OTHER INFORMATION: SP-C SS Ion Lock2 E15/K19;D20/R24

<400> SEQUENCE: 235

Gly Ile Pro Ser Ser Pro Val His Leu Lys Arg Leu Leu Ile Glu Val
1               5                   10                  15

Val Val Lys Asp Leu Ile Val Arg Val Ile Val Gly Ala Leu Leu Met
            20                  25                  30

Gly Leu

<210> SEQ ID NO 236
<211> LENGTH: 34
<212> TYPE: PRT
<213> ORGANISM: artificial
<220> FEATURE:
<223> OTHER INFORMATION: SP-C SS Ion Lock2 E15/R19;D20/R24

<400> SEQUENCE: 236

Gly Ile Pro Ser Ser Pro Val His Leu Lys Arg Leu Leu Ile Glu Val
1               5                   10                  15

Val Val Arg Asp Leu Ile Val Arg Val Ile Val Gly Ala Leu Leu Met
            20                  25                  30

Gly Leu

<210> SEQ ID NO 237
<211> LENGTH: 34
<212> TYPE: PRT
<213> ORGANISM: artificial
<220> FEATURE:
<223> OTHER INFORMATION: SP-C SS Ion Lock2 E15/K19;K20/E24

<400> SEQUENCE: 237

Gly Ile Pro Ser Ser Pro Val His Leu Lys Arg Leu Leu Ile Glu Val
1               5                   10                  15

Val Val Lys Lys Leu Ile Val Glu Val Ile Val Gly Ala Leu Leu Met
            20                  25                  30

Gly Leu

<210> SEQ ID NO 238
<211> LENGTH: 34
<212> TYPE: PRT
<213> ORGANISM: artificial
<220> FEATURE:
<223> OTHER INFORMATION: SP-C SS Ion Lock2 E15/R19;K20/E24

<400> SEQUENCE: 238

Gly Ile Pro Ser Ser Pro Val His Leu Lys Arg Leu Leu Ile Glu Val
1               5                   10                  15

Val Val Arg Lys Leu Ile Val Glu Val Ile Val Gly Ala Leu Leu Met
            20                  25                  30

Gly Leu
```

-continued

```
<210> SEQ ID NO 239
<211> LENGTH: 34
<212> TYPE: PRT
<213> ORGANISM: artificial
<220> FEATURE:
<223> OTHER INFORMATION: SP-C SS Ion Lock2 E15/K19;K20/D24

<400> SEQUENCE: 239

Gly Ile Pro Ser Ser Pro Val His Leu Lys Arg Leu Leu Ile Glu Val
1               5                   10                  15

Val Val Lys Lys Leu Ile Val Asp Val Ile Val Gly Ala Leu Leu Met
            20                  25                  30

Gly Leu

<210> SEQ ID NO 240
<211> LENGTH: 34
<212> TYPE: PRT
<213> ORGANISM: artificial
<220> FEATURE:
<223> OTHER INFORMATION: SP-C SS Ion Lock2 E15/R19;K20/D24

<400> SEQUENCE: 240

Gly Ile Pro Ser Ser Pro Val His Leu Lys Arg Leu Leu Ile Glu Val
1               5                   10                  15

Val Val Arg Lys Leu Ile Val Asp Val Ile Val Gly Ala Leu Leu Met
            20                  25                  30

Gly Leu

<210> SEQ ID NO 241
<211> LENGTH: 34
<212> TYPE: PRT
<213> ORGANISM: artificial
<220> FEATURE:
<223> OTHER INFORMATION: SP-C SS Ion Lock2 E15/K19;R20/E24

<400> SEQUENCE: 241

Gly Ile Pro Ser Ser Pro Val His Leu Lys Arg Leu Leu Ile Glu Val
1               5                   10                  15

Val Val Lys Arg Leu Ile Val Glu Val Ile Val Gly Ala Leu Leu Met
            20                  25                  30

Gly Leu

<210> SEQ ID NO 242
<211> LENGTH: 34
<212> TYPE: PRT
<213> ORGANISM: artificial
<220> FEATURE:
<223> OTHER INFORMATION: SP-C SS Ion Lock2 E15/R19;R20/E24

<400> SEQUENCE: 242

Gly Ile Pro Ser Ser Pro Val His Leu Lys Arg Leu Leu Ile Glu Val
1               5                   10                  15

Val Val Arg Arg Leu Ile Val Glu Val Ile Val Gly Ala Leu Leu Met
            20                  25                  30

Gly Leu

<210> SEQ ID NO 243
<211> LENGTH: 34
<212> TYPE: PRT
<213> ORGANISM: artificial
<220> FEATURE:
<223> OTHER INFORMATION: SP-C SS Ion Lock2 E15/K19;R20/D24
```

-continued

```
<400> SEQUENCE: 243

Gly Ile Pro Ser Ser Pro Val His Leu Lys Arg Leu Leu Ile Glu Val
1               5                   10                  15

Val Val Lys Arg Leu Ile Val Asp Val Ile Val Gly Ala Leu Leu Met
            20                  25                  30

Gly Leu

<210> SEQ ID NO 244
<211> LENGTH: 34
<212> TYPE: PRT
<213> ORGANISM: artificial
<220> FEATURE:
<223> OTHER INFORMATION: SP-C SS Ion Lock2 E15/R19;R20/D24

<400> SEQUENCE: 244

Gly Ile Pro Ser Ser Pro Val His Leu Lys Arg Leu Leu Ile Glu Val
1               5                   10                  15

Val Val Arg Arg Leu Ile Val Asp Val Ile Val Gly Ala Leu Leu Met
            20                  25                  30

Gly Leu

<210> SEQ ID NO 245
<211> LENGTH: 34
<212> TYPE: PRT
<213> ORGANISM: artificial
<220> FEATURE:
<223> OTHER INFORMATION: SP-C SS Ion Lock2 D15/K19;E20/K24

<400> SEQUENCE: 245

Gly Ile Pro Ser Ser Pro Val His Leu Lys Arg Leu Leu Ile Asp Val
1               5                   10                  15

Val Val Lys Glu Leu Ile Val Lys Val Ile Val Gly Ala Leu Leu Met
            20                  25                  30

Gly Leu

<210> SEQ ID NO 246
<211> LENGTH: 34
<212> TYPE: PRT
<213> ORGANISM: artificial
<220> FEATURE:
<223> OTHER INFORMATION: SP-C SS Ion Lock2 D15/R19;E20/K24

<400> SEQUENCE: 246

Gly Ile Pro Ser Ser Pro Val His Leu Lys Arg Leu Leu Ile Asp Val
1               5                   10                  15

Val Val Arg Glu Leu Ile Val Lys Val Ile Val Gly Ala Leu Leu Met
            20                  25                  30

Gly Leu

<210> SEQ ID NO 247
<211> LENGTH: 34
<212> TYPE: PRT
<213> ORGANISM: artificial
<220> FEATURE:
<223> OTHER INFORMATION: SP-C SS Ion Lock2 D15/K19;D20/K24

<400> SEQUENCE: 247

Gly Ile Pro Ser Ser Pro Val His Leu Lys Arg Leu Leu Ile Asp Val
1               5                   10                  15

Val Val Lys Asp Leu Ile Val Lys Val Ile Val Gly Ala Leu Leu Met
            20                  25                  30
```

Gly Leu

<210> SEQ ID NO 248
<211> LENGTH: 34
<212> TYPE: PRT
<213> ORGANISM: artificial
<220> FEATURE:
<223> OTHER INFORMATION: SP-C SS Ion Lock2 D15/R19;D20/K24

<400> SEQUENCE: 248

Gly Ile Pro Ser Ser Pro Val His Leu Lys Arg Leu Leu Ile Asp Val
1               5                   10                  15

Val Val Arg Asp Leu Ile Val Lys Val Ile Val Gly Ala Leu Leu Met
            20                  25                  30

Gly Leu

<210> SEQ ID NO 249
<211> LENGTH: 34
<212> TYPE: PRT
<213> ORGANISM: artificial
<220> FEATURE:
<223> OTHER INFORMATION: SP-C SS Ion Lock2 D15/K19;E20/R24

<400> SEQUENCE: 249

Gly Ile Pro Ser Ser Pro Val His Leu Lys Arg Leu Leu Ile Asp Val
1               5                   10                  15

Val Val Lys Glu Leu Ile Val Arg Val Ile Val Gly Ala Leu Leu Met
            20                  25                  30

Gly Leu

<210> SEQ ID NO 250
<211> LENGTH: 34
<212> TYPE: PRT
<213> ORGANISM: artificial
<220> FEATURE:
<223> OTHER INFORMATION: SP-C SS Ion Lock2 D15/R19;E20/R24

<400> SEQUENCE: 250

Gly Ile Pro Ser Ser Pro Val His Leu Lys Arg Leu Leu Ile Asp Val
1               5                   10                  15

Val Val Arg Glu Leu Ile Val Arg Val Ile Val Gly Ala Leu Leu Met
            20                  25                  30

Gly Leu

<210> SEQ ID NO 251
<211> LENGTH: 34
<212> TYPE: PRT
<213> ORGANISM: artificial
<220> FEATURE:
<223> OTHER INFORMATION: SP-C SS Ion Lock2 D15/K19;D20/R24

<400> SEQUENCE: 251

Gly Ile Pro Ser Ser Pro Val His Leu Lys Arg Leu Leu Ile Asp Val
1               5                   10                  15

Val Val Lys Asp Leu Ile Val Arg Val Ile Val Gly Ala Leu Leu Met
            20                  25                  30

Gly Leu

<210> SEQ ID NO 252
<211> LENGTH: 34
<212> TYPE: PRT

-continued

<213> ORGANISM: artificial
<220> FEATURE:
<223> OTHER INFORMATION: SP-C SS Ion Lock2 D15/R19;D20/R24

<400> SEQUENCE: 252

Gly Ile Pro Ser Ser Pro Val His Leu Lys Arg Leu Leu Ile Asp Val
1               5                   10                  15

Val Val Arg Asp Leu Ile Val Arg Val Ile Val Gly Ala Leu Leu Met
            20                  25                  30

Gly Leu

<210> SEQ ID NO 253
<211> LENGTH: 34
<212> TYPE: PRT
<213> ORGANISM: artificial
<220> FEATURE:
<223> OTHER INFORMATION: SP-C SS Ion Lock2 D15/K19;K20/E24

<400> SEQUENCE: 253

Gly Ile Pro Ser Ser Pro Val His Leu Lys Arg Leu Leu Ile Asp Val
1               5                   10                  15

Val Val Lys Lys Leu Ile Val Glu Val Ile Val Gly Ala Leu Leu Met
            20                  25                  30

Gly Leu

<210> SEQ ID NO 254
<211> LENGTH: 34
<212> TYPE: PRT
<213> ORGANISM: artificial
<220> FEATURE:
<223> OTHER INFORMATION: SP-C SS Ion Lock2 D15/R19;K20/E24

<400> SEQUENCE: 254

Gly Ile Pro Ser Ser Pro Val His Leu Lys Arg Leu Leu Ile Asp Val
1               5                   10                  15

Val Val Arg Lys Leu Ile Val Glu Val Ile Val Gly Ala Leu Leu Met
            20                  25                  30

Gly Leu

<210> SEQ ID NO 255
<211> LENGTH: 34
<212> TYPE: PRT
<213> ORGANISM: artificial
<220> FEATURE:
<223> OTHER INFORMATION: SP-C SS Ion Lock2 D15/K19;R20/D24

<400> SEQUENCE: 255

Gly Ile Pro Ser Ser Pro Val His Leu Lys Arg Leu Leu Ile Asp Val
1               5                   10                  15

Val Val Lys Arg Leu Ile Val Asp Val Ile Val Gly Ala Leu Leu Met
            20                  25                  30

Gly Leu

<210> SEQ ID NO 256
<211> LENGTH: 34
<212> TYPE: PRT
<213> ORGANISM: artificial
<220> FEATURE:
<223> OTHER INFORMATION: SP-C SS Ion Lock2 D15/R19;K20/D24

<400> SEQUENCE: 256

Gly Ile Pro Ser Ser Pro Val His Leu Lys Arg Leu Leu Ile Asp Val

```
                1               5                  10                  15
Val Val Arg Lys Leu Ile Val Asp Val Ile Val Gly Ala Leu Leu Met
                20                  25                  30

Gly Leu

<210> SEQ ID NO 257
<211> LENGTH: 34
<212> TYPE: PRT
<213> ORGANISM: artificial
<220> FEATURE:
<223> OTHER INFORMATION: SP-C SS Ion Lock2 D15/K19;R20/E24

<400> SEQUENCE: 257

Gly Ile Pro Ser Ser Pro Val His Leu Lys Arg Leu Leu Ile Asp Val
1               5                  10                  15

Val Val Lys Arg Leu Ile Val Glu Val Ile Val Gly Ala Leu Leu Met
                20                  25                  30

Gly Leu

<210> SEQ ID NO 258
<211> LENGTH: 34
<212> TYPE: PRT
<213> ORGANISM: artificial
<220> FEATURE:
<223> OTHER INFORMATION: SP-C SS Ion Lock2 D15/R19;R20/E24

<400> SEQUENCE: 258

Gly Ile Pro Ser Ser Pro Val His Leu Lys Arg Leu Leu Ile Asp Val
1               5                  10                  15

Val Val Arg Arg Leu Ile Val Glu Val Ile Val Gly Ala Leu Leu Met
                20                  25                  30

Gly Leu

<210> SEQ ID NO 259
<211> LENGTH: 34
<212> TYPE: PRT
<213> ORGANISM: artificial
<220> FEATURE:
<223> OTHER INFORMATION: SP-C SS Ion Lock2 D15/K19;K20/D24

<400> SEQUENCE: 259

Gly Ile Pro Ser Ser Pro Val His Leu Lys Arg Leu Leu Ile Asp Val
1               5                  10                  15

Val Val Lys Lys Leu Ile Val Asp Val Ile Val Gly Ala Leu Leu Met
                20                  25                  30

Gly Leu

<210> SEQ ID NO 260
<211> LENGTH: 34
<212> TYPE: PRT
<213> ORGANISM: artificial
<220> FEATURE:
<223> OTHER INFORMATION: SP-C SS Ion Lock2 D15/R19;R20/D24

<400> SEQUENCE: 260

Gly Ile Pro Ser Ser Pro Val His Leu Lys Arg Leu Leu Ile Asp Val
1               5                  10                  15

Val Val Arg Arg Leu Ile Val Asp Val Ile Val Gly Ala Leu Leu Met
                20                  25                  30

Gly Leu
```

<210> SEQ ID NO 261
<211> LENGTH: 33
<212> TYPE: PRT
<213> ORGANISM: artificial
<220> FEATURE:
<223> OTHER INFORMATION: SP-C SS Ion Lock2 - L K15/E19;E20/K24

<400> SEQUENCE: 261

Gly Ile Pro Ser Ser Pro Val His Leu Lys Arg Leu Leu Ile Lys Val
1               5                   10                  15

Val Val Glu Glu Leu Ile Val Lys Val Ile Val Gly Ala Leu Leu Met
            20                  25                  30

Gly

<210> SEQ ID NO 262
<211> LENGTH: 33
<212> TYPE: PRT
<213> ORGANISM: artificial
<220> FEATURE:
<223> OTHER INFORMATION: SP-C SS Ion Lock2 - L K15/D19;E20/K24

<400> SEQUENCE: 262

Gly Ile Pro Ser Ser Pro Val His Leu Lys Arg Leu Leu Ile Lys Val
1               5                   10                  15

Val Val Asp Glu Leu Ile Val Lys Val Ile Val Gly Ala Leu Leu Met
            20                  25                  30

Gly

<210> SEQ ID NO 263
<211> LENGTH: 33
<212> TYPE: PRT
<213> ORGANISM: artificial
<220> FEATURE:
<223> OTHER INFORMATION: SP-C SS Ion Lock2 - L K15/E19;D20/K24

<400> SEQUENCE: 263

Gly Ile Pro Ser Ser Pro Val His Leu Lys Arg Leu Leu Ile Lys Val
1               5                   10                  15

Val Val Glu Asp Leu Ile Val Lys Val Ile Val Gly Ala Leu Leu Met
            20                  25                  30

Gly

<210> SEQ ID NO 264
<211> LENGTH: 33
<212> TYPE: PRT
<213> ORGANISM: artificial
<220> FEATURE:
<223> OTHER INFORMATION: SP-C SS Ion Lock2 - L K15/D19;D20/K24

<400> SEQUENCE: 264

Gly Ile Pro Ser Ser Pro Val His Leu Lys Arg Leu Leu Ile Lys Val
1               5                   10                  15

Val Val Asp Asp Leu Ile Val Lys Val Ile Val Gly Ala Leu Leu Met
            20                  25                  30

Gly

<210> SEQ ID NO 265
<211> LENGTH: 33
<212> TYPE: PRT
<213> ORGANISM: artificial
<220> FEATURE:
<223> OTHER INFORMATION: SP-C SS Ion Lock2 - L K15/E19;E20/R24

```
<400> SEQUENCE: 265

Gly Ile Pro Ser Ser Pro Val His Leu Lys Arg Leu Leu Ile Lys Val
1               5                   10                  15

Val Val Glu Glu Leu Ile Val Arg Val Ile Val Gly Ala Leu Leu Met
            20                  25                  30

Gly

<210> SEQ ID NO 266
<211> LENGTH: 33
<212> TYPE: PRT
<213> ORGANISM: artificial
<220> FEATURE:
<223> OTHER INFORMATION: SP-C SS Ion Lock2 - L K15/D19;E20/R24

<400> SEQUENCE: 266

Gly Ile Pro Ser Ser Pro Val His Leu Lys Arg Leu Leu Ile Lys Val
1               5                   10                  15

Val Val Asp Glu Leu Ile Val Arg Val Ile Val Gly Ala Leu Leu Met
            20                  25                  30

Gly

<210> SEQ ID NO 267
<211> LENGTH: 33
<212> TYPE: PRT
<213> ORGANISM: artificial
<220> FEATURE:
<223> OTHER INFORMATION: SP-C SS Ion Lock2 - L K15/E19;D20/R24

<400> SEQUENCE: 267

Gly Ile Pro Ser Ser Pro Val His Leu Lys Arg Leu Leu Ile Lys Val
1               5                   10                  15

Val Val Glu Asp Leu Ile Val Arg Val Ile Val Gly Ala Leu Leu Met
            20                  25                  30

Gly

<210> SEQ ID NO 268
<211> LENGTH: 33
<212> TYPE: PRT
<213> ORGANISM: artificial
<220> FEATURE:
<223> OTHER INFORMATION: SP-C SS Ion Lock2 - L K15/D19;D20/R24

<400> SEQUENCE: 268

Gly Ile Pro Ser Ser Pro Val His Leu Lys Arg Leu Leu Ile Lys Val
1               5                   10                  15

Val Val Asp Asp Leu Ile Val Arg Val Ile Val Gly Ala Leu Leu Met
            20                  25                  30

Gly

<210> SEQ ID NO 269
<211> LENGTH: 33
<212> TYPE: PRT
<213> ORGANISM: artificial
<220> FEATURE:
<223> OTHER INFORMATION: SP-C SS Ion Lock2 - L K15/E19;K20/E24

<400> SEQUENCE: 269

Gly Ile Pro Ser Ser Pro Val His Leu Lys Arg Leu Leu Ile Lys Val
1               5                   10                  15

Val Val Glu Lys Leu Ile Val Glu Val Ile Val Gly Ala Leu Leu Met
```

```
            20                  25                  30

Gly

<210> SEQ ID NO 270
<211> LENGTH: 33
<212> TYPE: PRT
<213> ORGANISM: artificial
<220> FEATURE:
<223> OTHER INFORMATION: SP-C SS Ion Lock2 - L K15/D19;K20/E24

<400> SEQUENCE: 270

Gly Ile Pro Ser Ser Pro Val His Leu Lys Arg Leu Leu Ile Lys Val
1               5                   10                  15

Val Val Asp Lys Leu Ile Val Glu Val Ile Val Gly Ala Leu Leu Met
            20                  25                  30

Gly

<210> SEQ ID NO 271
<211> LENGTH: 33
<212> TYPE: PRT
<213> ORGANISM: artificial
<220> FEATURE:
<223> OTHER INFORMATION: SP-C SS Ion Lock2 - L K15/E19;K20/D24

<400> SEQUENCE: 271

Gly Ile Pro Ser Ser Pro Val His Leu Lys Arg Leu Leu Ile Lys Val
1               5                   10                  15

Val Val Glu Lys Leu Ile Val Asp Val Ile Val Gly Ala Leu Leu Met
            20                  25                  30

Gly

<210> SEQ ID NO 272
<211> LENGTH: 33
<212> TYPE: PRT
<213> ORGANISM: artificial
<220> FEATURE:
<223> OTHER INFORMATION: SP-C SS Ion Lock2 - L K15/D19;K20/E24

<400> SEQUENCE: 272

Gly Ile Pro Ser Ser Pro Val His Leu Lys Arg Leu Leu Ile Lys Val
1               5                   10                  15

Val Val Asp Lys Leu Ile Val Asp Val Ile Val Gly Ala Leu Leu Met
            20                  25                  30

Gly

<210> SEQ ID NO 273
<211> LENGTH: 33
<212> TYPE: PRT
<213> ORGANISM: artificial
<220> FEATURE:
<223> OTHER INFORMATION: SP-C SS Ion Lock2 - L K15/E19;R20/E24

<400> SEQUENCE: 273

Gly Ile Pro Ser Ser Pro Val His Leu Lys Arg Leu Leu Ile Lys Val
1               5                   10                  15

Val Val Glu Arg Leu Ile Val Glu Val Ile Val Gly Ala Leu Leu Met
            20                  25                  30

Gly

<210> SEQ ID NO 274
<211> LENGTH: 33
```

```
<212> TYPE: PRT
<213> ORGANISM: artificial
<220> FEATURE:
<223> OTHER INFORMATION: SP-C SS Ion Lock2 - L K15/D19;R20/E24

<400> SEQUENCE: 274

Gly Ile Pro Ser Ser Pro Val His Leu Lys Arg Leu Leu Ile Lys Val
1               5                   10                  15

Val Val Asp Arg Leu Ile Val Glu Val Ile Val Gly Ala Leu Leu Met
            20                  25                  30

Gly

<210> SEQ ID NO 275
<211> LENGTH: 33
<212> TYPE: PRT
<213> ORGANISM: artificial
<220> FEATURE:
<223> OTHER INFORMATION: SP-C SS Ion Lock2 - L K15/E19;R20/D24

<400> SEQUENCE: 275

Gly Ile Pro Ser Ser Pro Val His Leu Lys Arg Leu Leu Ile Lys Val
1               5                   10                  15

Val Val Glu Arg Leu Ile Val Asp Val Ile Val Gly Ala Leu Leu Met
            20                  25                  30

Gly

<210> SEQ ID NO 276
<211> LENGTH: 33
<212> TYPE: PRT
<213> ORGANISM: artificial
<220> FEATURE:
<223> OTHER INFORMATION: SP-C SS Ion Lock2 - L K15/D19;R20/D24

<400> SEQUENCE: 276

Gly Ile Pro Ser Ser Pro Val His Leu Lys Arg Leu Leu Ile Lys Val
1               5                   10                  15

Val Val Asp Arg Leu Ile Val Asp Val Ile Val Gly Ala Leu Leu Met
            20                  25                  30

Gly

<210> SEQ ID NO 277
<211> LENGTH: 33
<212> TYPE: PRT
<213> ORGANISM: artificial
<220> FEATURE:
<223> OTHER INFORMATION: SP-C SS Ion Lock2 - L R15/E19;E20/K24

<400> SEQUENCE: 277

Gly Ile Pro Ser Ser Pro Val His Leu Lys Arg Leu Leu Ile Arg Val
1               5                   10                  15

Val Val Glu Glu Leu Ile Val Lys Val Ile Val Gly Ala Leu Leu Met
            20                  25                  30

Gly

<210> SEQ ID NO 278
<211> LENGTH: 33
<212> TYPE: PRT
<213> ORGANISM: artificial
<220> FEATURE:
<223> OTHER INFORMATION: SP-C SS Ion Lock2 - L R15/D19;E20/K24

<400> SEQUENCE: 278
```

```
Gly Ile Pro Ser Ser Pro Val His Leu Lys Arg Leu Leu Ile Arg Val
1               5                  10                  15

Val Val Asp Glu Leu Ile Val Lys Val Ile Val Gly Ala Leu Leu Met
            20                  25                  30

Gly

<210> SEQ ID NO 279
<211> LENGTH: 33
<212> TYPE: PRT
<213> ORGANISM: artificial
<220> FEATURE:
<223> OTHER INFORMATION: SP-C SS Ion Lock2 - L R15/E19;D20/K24

<400> SEQUENCE: 279

Gly Ile Pro Ser Ser Pro Val His Leu Lys Arg Leu Leu Ile Arg Val
1               5                  10                  15

Val Val Glu Asp Leu Ile Val Lys Val Ile Val Gly Ala Leu Leu Met
            20                  25                  30

Gly

<210> SEQ ID NO 280
<211> LENGTH: 33
<212> TYPE: PRT
<213> ORGANISM: artificial
<220> FEATURE:
<223> OTHER INFORMATION: SP-C SS Ion Lock2 - L R15/D19;D20/K24

<400> SEQUENCE: 280

Gly Ile Pro Ser Ser Pro Val His Leu Lys Arg Leu Leu Ile Arg Val
1               5                  10                  15

Val Val Asp Asp Leu Ile Val Lys Val Ile Val Gly Ala Leu Leu Met
            20                  25                  30

Gly

<210> SEQ ID NO 281
<211> LENGTH: 33
<212> TYPE: PRT
<213> ORGANISM: artificial
<220> FEATURE:
<223> OTHER INFORMATION: SP-C SS Ion Lock2 - L R15/E19;E20/R24

<400> SEQUENCE: 281

Gly Ile Pro Ser Ser Pro Val His Leu Lys Arg Leu Leu Ile Arg Val
1               5                  10                  15

Val Val Glu Glu Leu Ile Val Arg Val Ile Val Gly Ala Leu Leu Met
            20                  25                  30

Gly

<210> SEQ ID NO 282
<211> LENGTH: 33
<212> TYPE: PRT
<213> ORGANISM: artificial
<220> FEATURE:
<223> OTHER INFORMATION: SP-C SS Ion Lock2 - L R15/D19;E20/R24

<400> SEQUENCE: 282

Gly Ile Pro Ser Ser Pro Val His Leu Lys Arg Leu Leu Ile Arg Val
1               5                  10                  15

Val Val Asp Glu Leu Ile Val Arg Val Ile Val Gly Ala Leu Leu Met
            20                  25                  30

Gly
```

<210> SEQ ID NO 283
<211> LENGTH: 33
<212> TYPE: PRT
<213> ORGANISM: artificial
<220> FEATURE:
<223> OTHER INFORMATION: SP-C SS Ion Lock2 - L R15/E19;D20/R24

<400> SEQUENCE: 283

Gly Ile Pro Ser Ser Pro Val His Leu Lys Arg Leu Leu Ile Arg Val
1               5                   10                  15

Val Val Glu Asp Leu Ile Val Arg Val Ile Val Gly Ala Leu Leu Met
            20                  25                  30

Gly

<210> SEQ ID NO 284
<211> LENGTH: 33
<212> TYPE: PRT
<213> ORGANISM: artificial
<220> FEATURE:
<223> OTHER INFORMATION: SP-C SS Ion Lock2 - L R15/D19;D20/R24

<400> SEQUENCE: 284

Gly Ile Pro Ser Ser Pro Val His Leu Lys Arg Leu Leu Ile Arg Val
1               5                   10                  15

Val Val Asp Asp Leu Ile Val Arg Val Ile Val Gly Ala Leu Leu Met
            20                  25                  30

Gly

<210> SEQ ID NO 285
<211> LENGTH: 33
<212> TYPE: PRT
<213> ORGANISM: artificial
<220> FEATURE:
<223> OTHER INFORMATION: SP-C SS Ion Lock2 - L R15/E19;K20/E24

<400> SEQUENCE: 285

Gly Ile Pro Ser Ser Pro Val His Leu Lys Arg Leu Leu Ile Arg Val
1               5                   10                  15

Val Val Glu Lys Leu Ile Val Glu Val Ile Val Gly Ala Leu Leu Met
            20                  25                  30

Gly

<210> SEQ ID NO 286
<211> LENGTH: 33
<212> TYPE: PRT
<213> ORGANISM: artificial
<220> FEATURE:
<223> OTHER INFORMATION: SP-C SS Ion Lock2 - L R15/D19;K20/E24

<400> SEQUENCE: 286

Gly Ile Pro Ser Ser Pro Val His Leu Lys Arg Leu Leu Ile Arg Val
1               5                   10                  15

Val Val Asp Lys Leu Ile Val Glu Val Ile Val Gly Ala Leu Leu Met
            20                  25                  30

Gly

<210> SEQ ID NO 287
<211> LENGTH: 33
<212> TYPE: PRT
<213> ORGANISM: artificial
<220> FEATURE:

<223> OTHER INFORMATION: SP-C SS Ion Lock2 - L R15/E19;K20/D24

<400> SEQUENCE: 287

Gly Ile Pro Ser Ser Pro Val His Leu Lys Arg Leu Leu Ile Arg Val
1               5                   10                  15

Val Val Glu Lys Leu Ile Val Asp Val Ile Val Gly Ala Leu Leu Met
            20                  25                  30

Gly

<210> SEQ ID NO 288
<211> LENGTH: 33
<212> TYPE: PRT
<213> ORGANISM: artificial
<220> FEATURE:
<223> OTHER INFORMATION: SP-C SS Ion Lock2 - L R15/D19;K20/D24

<400> SEQUENCE: 288

Gly Ile Pro Ser Ser Pro Val His Leu Lys Arg Leu Leu Ile Arg Val
1               5                   10                  15

Val Val Asp Lys Leu Ile Val Asp Val Ile Val Gly Ala Leu Leu Met
            20                  25                  30

Gly

<210> SEQ ID NO 289
<211> LENGTH: 33
<212> TYPE: PRT
<213> ORGANISM: artificial
<220> FEATURE:
<223> OTHER INFORMATION: SP-C SS Ion Lock2 - L R15/E19;R20/E24

<400> SEQUENCE: 289

Gly Ile Pro Ser Ser Pro Val His Leu Lys Arg Leu Leu Ile Arg Val
1               5                   10                  15

Val Val Glu Arg Leu Ile Val Glu Val Ile Val Gly Ala Leu Leu Met
            20                  25                  30

Gly

<210> SEQ ID NO 290
<211> LENGTH: 33
<212> TYPE: PRT
<213> ORGANISM: artificial
<220> FEATURE:
<223> OTHER INFORMATION: SP-C SS Ion Lock2 - L R15/D19;R20/E24

<400> SEQUENCE: 290

Gly Ile Pro Ser Ser Pro Val His Leu Lys Arg Leu Leu Ile Arg Val
1               5                   10                  15

Val Val Asp Arg Leu Ile Val Glu Val Ile Val Gly Ala Leu Leu Met
            20                  25                  30

Gly

<210> SEQ ID NO 291
<211> LENGTH: 33
<212> TYPE: PRT
<213> ORGANISM: artificial
<220> FEATURE:
<223> OTHER INFORMATION: SP-C SS Ion Lock2 - L R15/E19;R20/D24

<400> SEQUENCE: 291

Gly Ile Pro Ser Ser Pro Val His Leu Lys Arg Leu Leu Ile Arg Val
1               5                   10                  15

```
Val Val Glu Arg Leu Ile Val Asp Val Ile Val Gly Ala Leu Leu Met
            20                  25                  30

Gly

<210> SEQ ID NO 292
<211> LENGTH: 33
<212> TYPE: PRT
<213> ORGANISM: artificial
<220> FEATURE:
<223> OTHER INFORMATION: SP-C SS Ion Lock2 - L R15/D19;R20/D24

<400> SEQUENCE: 292

Gly Ile Pro Ser Ser Pro Val His Leu Lys Arg Leu Leu Ile Arg Val
1               5                   10                  15

Val Val Asp Arg Leu Ile Val Asp Val Ile Val Gly Ala Leu Leu Met
            20                  25                  30

Gly

<210> SEQ ID NO 293
<211> LENGTH: 33
<212> TYPE: PRT
<213> ORGANISM: artificial
<220> FEATURE:
<223> OTHER INFORMATION: SP-C SS Ion Lock2 - L E15/K19;E20/K24

<400> SEQUENCE: 293

Gly Ile Pro Ser Ser Pro Val His Leu Lys Arg Leu Leu Ile Glu Val
1               5                   10                  15

Val Val Lys Glu Leu Ile Val Lys Val Ile Val Gly Ala Leu Leu Met
            20                  25                  30

Gly

<210> SEQ ID NO 294
<211> LENGTH: 33
<212> TYPE: PRT
<213> ORGANISM: artificial
<220> FEATURE:
<223> OTHER INFORMATION: SP-C SS Ion Lock2 - L E15/R19;E20/K24

<400> SEQUENCE: 294

Gly Ile Pro Ser Ser Pro Val His Leu Lys Arg Leu Leu Ile Glu Val
1               5                   10                  15

Val Val Arg Glu Leu Ile Val Lys Val Ile Val Gly Ala Leu Leu Met
            20                  25                  30

Gly

<210> SEQ ID NO 295
<211> LENGTH: 33
<212> TYPE: PRT
<213> ORGANISM: artificial
<220> FEATURE:
<223> OTHER INFORMATION: SP-C SS Ion Lock2 - L E15/K19;D20/K24

<400> SEQUENCE: 295

Gly Ile Pro Ser Ser Pro Val His Leu Lys Arg Leu Leu Ile Glu Val
1               5                   10                  15

Val Val Lys Asp Leu Ile Val Lys Val Ile Val Gly Ala Leu Leu Met
            20                  25                  30

Gly

<210> SEQ ID NO 296
```

```
<211> LENGTH: 33
<212> TYPE: PRT
<213> ORGANISM: artificial
<220> FEATURE:
<223> OTHER INFORMATION: SP-C SS Ion Lock2 - L E15/R19;D20/K24

<400> SEQUENCE: 296

Gly Ile Pro Ser Ser Pro Val His Leu Lys Arg Leu Leu Ile Glu Val
1               5                   10                  15

Val Val Arg Asp Leu Ile Val Lys Val Ile Val Gly Ala Leu Leu Met
            20                  25                  30

Gly

<210> SEQ ID NO 297
<211> LENGTH: 33
<212> TYPE: PRT
<213> ORGANISM: artificial
<220> FEATURE:
<223> OTHER INFORMATION: SP-C SS Ion Lock2 - L E15/K19;E20/R24

<400> SEQUENCE: 297

Gly Ile Pro Ser Ser Pro Val His Leu Lys Arg Leu Leu Ile Glu Val
1               5                   10                  15

Val Val Lys Glu Leu Ile Val Arg Val Ile Val Gly Ala Leu Leu Met
            20                  25                  30

Gly

<210> SEQ ID NO 298
<211> LENGTH: 33
<212> TYPE: PRT
<213> ORGANISM: artificial
<220> FEATURE:
<223> OTHER INFORMATION: SP-C SS Ion Lock2 - L E15/R19;E20/R24

<400> SEQUENCE: 298

Gly Ile Pro Ser Ser Pro Val His Leu Lys Arg Leu Leu Ile Glu Val
1               5                   10                  15

Val Val Arg Glu Leu Ile Val Arg Val Ile Val Gly Ala Leu Leu Met
            20                  25                  30

Gly

<210> SEQ ID NO 299
<211> LENGTH: 33
<212> TYPE: PRT
<213> ORGANISM: artificial
<220> FEATURE:
<223> OTHER INFORMATION: SP-C SS Ion Lock2 - L E15/K19;D20/R24

<400> SEQUENCE: 299

Gly Ile Pro Ser Ser Pro Val His Leu Lys Arg Leu Leu Ile Glu Val
1               5                   10                  15

Val Val Lys Asp Leu Ile Val Arg Val Ile Val Gly Ala Leu Leu Met
            20                  25                  30

Gly

<210> SEQ ID NO 300
<211> LENGTH: 33
<212> TYPE: PRT
<213> ORGANISM: artificial
<220> FEATURE:
<223> OTHER INFORMATION: SP-C SS Ion Lock2 - L E15/R19;D20/R24

<400> SEQUENCE: 300
```

```
Gly Ile Pro Ser Ser Pro Val His Leu Lys Arg Leu Leu Ile Glu Val
1               5                   10                  15

Val Val Arg Asp Leu Ile Val Arg Val Ile Val Gly Ala Leu Leu Met
            20                  25                  30

Gly

<210> SEQ ID NO 301
<211> LENGTH: 33
<212> TYPE: PRT
<213> ORGANISM: artificial
<220> FEATURE:
<223> OTHER INFORMATION: SP-C SS Ion Lock2 - L E15/K19;K20/E24

<400> SEQUENCE: 301

Gly Ile Pro Ser Ser Pro Val His Leu Lys Arg Leu Leu Ile Glu Val
1               5                   10                  15

Val Val Lys Lys Leu Ile Val Glu Val Ile Val Gly Ala Leu Leu Met
            20                  25                  30

Gly

<210> SEQ ID NO 302
<211> LENGTH: 33
<212> TYPE: PRT
<213> ORGANISM: artificial
<220> FEATURE:
<223> OTHER INFORMATION: SP-C SS Ion Lock2 - L E15/R19;K20/E24

<400> SEQUENCE: 302

Gly Ile Pro Ser Ser Pro Val His Leu Lys Arg Leu Leu Ile Glu Val
1               5                   10                  15

Val Val Arg Lys Leu Ile Val Glu Val Ile Val Gly Ala Leu Leu Met
            20                  25                  30

Gly

<210> SEQ ID NO 303
<211> LENGTH: 33
<212> TYPE: PRT
<213> ORGANISM: artificial
<220> FEATURE:
<223> OTHER INFORMATION: SP-C SS Ion Lock2 - L E15/K19;K20/D24

<400> SEQUENCE: 303

Gly Ile Pro Ser Ser Pro Val His Leu Lys Arg Leu Leu Ile Glu Val
1               5                   10                  15

Val Val Lys Lys Leu Ile Val Asp Val Ile Val Gly Ala Leu Leu Met
            20                  25                  30

Gly

<210> SEQ ID NO 304
<211> LENGTH: 33
<212> TYPE: PRT
<213> ORGANISM: artificial
<220> FEATURE:
<223> OTHER INFORMATION: SP-C SS Ion Lock2 - L E15/R19;K20/D24

<400> SEQUENCE: 304

Gly Ile Pro Ser Ser Pro Val His Leu Lys Arg Leu Leu Ile Glu Val
1               5                   10                  15

Val Val Arg Lys Leu Ile Val Asp Val Ile Val Gly Ala Leu Leu Met
            20                  25                  30
```

Gly

<210> SEQ ID NO 305
<211> LENGTH: 33
<212> TYPE: PRT
<213> ORGANISM: artificial
<220> FEATURE:
<223> OTHER INFORMATION: SP-C SS Ion Lock2 - L E15/K19;R20/E24

<400> SEQUENCE: 305

Gly Ile Pro Ser Ser Pro Val His Leu Lys Arg Leu Leu Ile Glu Val
1               5                   10                  15
Val Val Lys Arg Leu Ile Val Glu Val Ile Val Gly Ala Leu Leu Met
            20                  25                  30
Gly

<210> SEQ ID NO 306
<211> LENGTH: 33
<212> TYPE: PRT
<213> ORGANISM: artificial
<220> FEATURE:
<223> OTHER INFORMATION: SP-C SS Ion Lock2 - L E15/R19;R20/E24

<400> SEQUENCE: 306

Gly Ile Pro Ser Ser Pro Val His Leu Lys Arg Leu Leu Ile Glu Val
1               5                   10                  15
Val Val Arg Arg Leu Ile Val Glu Val Ile Val Gly Ala Leu Leu Met
            20                  25                  30
Gly

<210> SEQ ID NO 307
<211> LENGTH: 33
<212> TYPE: PRT
<213> ORGANISM: artificial
<220> FEATURE:
<223> OTHER INFORMATION: SP-C SS Ion Lock2 - L E15/K19;R20/D24

<400> SEQUENCE: 307

Gly Ile Pro Ser Ser Pro Val His Leu Lys Arg Leu Leu Ile Glu Val
1               5                   10                  15
Val Val Lys Arg Leu Ile Val Asp Val Ile Val Gly Ala Leu Leu Met
            20                  25                  30
Gly

<210> SEQ ID NO 308
<211> LENGTH: 33
<212> TYPE: PRT
<213> ORGANISM: artificial
<220> FEATURE:
<223> OTHER INFORMATION: SP-C SS Ion Lock2 - L E15/R19;R20/D24

<400> SEQUENCE: 308

Gly Ile Pro Ser Ser Pro Val His Leu Lys Arg Leu Leu Ile Glu Val
1               5                   10                  15
Val Val Arg Arg Leu Ile Val Asp Val Ile Val Gly Ala Leu Leu Met
            20                  25                  30
Gly

<210> SEQ ID NO 309
<211> LENGTH: 33
<212> TYPE: PRT
<213> ORGANISM: artificial

```
<220> FEATURE:
<223> OTHER INFORMATION: SP-C SS Ion Lock2 - L D15/K19;E20/K24

<400> SEQUENCE: 309

Gly Ile Pro Ser Ser Pro Val His Leu Lys Arg Leu Leu Ile Asp Val
1               5                   10                  15

Val Val Lys Glu Leu Ile Val Lys Val Ile Val Gly Ala Leu Leu Met
            20                  25                  30

Gly

<210> SEQ ID NO 310
<211> LENGTH: 33
<212> TYPE: PRT
<213> ORGANISM: artificial
<220> FEATURE:
<223> OTHER INFORMATION: SP-C SS Ion Lock2 - L D15/R19;E20/K24

<400> SEQUENCE: 310

Gly Ile Pro Ser Ser Pro Val His Leu Lys Arg Leu Leu Ile Asp Val
1               5                   10                  15

Val Val Arg Glu Leu Ile Val Lys Val Ile Val Gly Ala Leu Leu Met
            20                  25                  30

Gly

<210> SEQ ID NO 311
<211> LENGTH: 33
<212> TYPE: PRT
<213> ORGANISM: artificial
<220> FEATURE:
<223> OTHER INFORMATION: SP-C SS Ion Lock2 - L D15/K19;D20/K24

<400> SEQUENCE: 311

Gly Ile Pro Ser Ser Pro Val His Leu Lys Arg Leu Leu Ile Asp Val
1               5                   10                  15

Val Val Lys Asp Leu Ile Val Lys Val Ile Val Gly Ala Leu Leu Met
            20                  25                  30

Gly

<210> SEQ ID NO 312
<211> LENGTH: 33
<212> TYPE: PRT
<213> ORGANISM: artificial
<220> FEATURE:
<223> OTHER INFORMATION: SP-C SS Ion Lock2 - L D15/R19;D20/K24

<400> SEQUENCE: 312

Gly Ile Pro Ser Ser Pro Val His Leu Lys Arg Leu Leu Ile Asp Val
1               5                   10                  15

Val Val Arg Asp Leu Ile Val Lys Val Ile Val Gly Ala Leu Leu Met
            20                  25                  30

Gly

<210> SEQ ID NO 313
<211> LENGTH: 33
<212> TYPE: PRT
<213> ORGANISM: artificial
<220> FEATURE:
<223> OTHER INFORMATION: SP-C SS Ion Lock2 - L D15/K19;E20/R24

<400> SEQUENCE: 313

Gly Ile Pro Ser Ser Pro Val His Leu Lys Arg Leu Leu Ile Asp Val
1               5                   10                  15
```

-continued

```
Val Val Lys Glu Leu Ile Val Arg Val Ile Val Gly Ala Leu Leu Met
            20                  25                  30

Gly

<210> SEQ ID NO 314
<211> LENGTH: 33
<212> TYPE: PRT
<213> ORGANISM: artificial
<220> FEATURE:
<223> OTHER INFORMATION: SP-C SS Ion Lock2 - L D15/R19;E20/R24

<400> SEQUENCE: 314

Gly Ile Pro Ser Ser Pro Val His Leu Lys Arg Leu Leu Ile Asp Val
1               5                   10                  15

Val Val Arg Glu Leu Ile Val Arg Val Ile Val Gly Ala Leu Leu Met
            20                  25                  30

Gly

<210> SEQ ID NO 315
<211> LENGTH: 33
<212> TYPE: PRT
<213> ORGANISM: artificial
<220> FEATURE:
<223> OTHER INFORMATION: SP-C SS Ion Lock2 - L D15/K19;D20/R24

<400> SEQUENCE: 315

Gly Ile Pro Ser Ser Pro Val His Leu Lys Arg Leu Leu Ile Asp Val
1               5                   10                  15

Val Val Lys Asp Leu Ile Val Arg Val Ile Val Gly Ala Leu Leu Met
            20                  25                  30

Gly

<210> SEQ ID NO 316
<211> LENGTH: 33
<212> TYPE: PRT
<213> ORGANISM: artificial
<220> FEATURE:
<223> OTHER INFORMATION: SP-C SS Ion Lock2 - L D15/R19;D20/R24

<400> SEQUENCE: 316

Gly Ile Pro Ser Ser Pro Val His Leu Lys Arg Leu Leu Ile Asp Val
1               5                   10                  15

Val Val Arg Asp Leu Ile Val Arg Val Ile Val Gly Ala Leu Leu Met
            20                  25                  30

Gly

<210> SEQ ID NO 317
<211> LENGTH: 33
<212> TYPE: PRT
<213> ORGANISM: artificial
<220> FEATURE:
<223> OTHER INFORMATION: SP-C SS Ion Lock2 - L D15/K19;K20/E24

<400> SEQUENCE: 317

Gly Ile Pro Ser Ser Pro Val His Leu Lys Arg Leu Leu Ile Asp Val
1               5                   10                  15

Val Val Lys Lys Leu Ile Val Glu Val Ile Val Gly Ala Leu Leu Met
            20                  25                  30

Gly
```

```
<210> SEQ ID NO 318
<211> LENGTH: 33
<212> TYPE: PRT
<213> ORGANISM: artificial
<220> FEATURE:
<223> OTHER INFORMATION: SP-C SS Ion Lock2 - L D15/R19;K20/E24

<400> SEQUENCE: 318

Gly Ile Pro Ser Ser Pro Val His Leu Lys Arg Leu Leu Ile Asp Val
1               5                   10                  15

Val Val Arg Lys Leu Ile Val Glu Val Ile Val Gly Ala Leu Leu Met
            20                  25                  30

Gly

<210> SEQ ID NO 319
<211> LENGTH: 33
<212> TYPE: PRT
<213> ORGANISM: artificial
<220> FEATURE:
<223> OTHER INFORMATION: SP-C SS Ion Lock2 - L D15/K19;R20/D24

<400> SEQUENCE: 319

Gly Ile Pro Ser Ser Pro Val His Leu Lys Arg Leu Leu Ile Asp Val
1               5                   10                  15

Val Val Lys Arg Leu Ile Val Asp Val Ile Val Gly Ala Leu Leu Met
            20                  25                  30

Gly

<210> SEQ ID NO 320
<211> LENGTH: 33
<212> TYPE: PRT
<213> ORGANISM: artificial
<220> FEATURE:
<223> OTHER INFORMATION: SP-C SS Ion Lock2 - L D15/R19;K20/D24

<400> SEQUENCE: 320

Gly Ile Pro Ser Ser Pro Val His Leu Lys Arg Leu Leu Ile Asp Val
1               5                   10                  15

Val Val Arg Lys Leu Ile Val Asp Val Ile Val Gly Ala Leu Leu Met
            20                  25                  30

Gly

<210> SEQ ID NO 321
<211> LENGTH: 33
<212> TYPE: PRT
<213> ORGANISM: artificial
<220> FEATURE:
<223> OTHER INFORMATION: SP-C SS Ion Lock2 - L D15/K19;R20/E24

<400> SEQUENCE: 321

Gly Ile Pro Ser Ser Pro Val His Leu Lys Arg Leu Leu Ile Asp Val
1               5                   10                  15

Val Val Lys Arg Leu Ile Val Glu Val Ile Val Gly Ala Leu Leu Met
            20                  25                  30

Gly

<210> SEQ ID NO 322
<211> LENGTH: 33
<212> TYPE: PRT
<213> ORGANISM: artificial
<220> FEATURE:
<223> OTHER INFORMATION: SP-C SS Ion Lock2 - L D15/R19;R20/E24
```

```
<400> SEQUENCE: 322

Gly Ile Pro Ser Ser Pro Val His Leu Lys Arg Leu Leu Ile Asp Val
1               5                   10                  15

Val Val Arg Arg Leu Ile Val Glu Val Ile Val Gly Ala Leu Leu Met
                20                  25                  30

Gly

<210> SEQ ID NO 323
<211> LENGTH: 33
<212> TYPE: PRT
<213> ORGANISM: artificial
<220> FEATURE:
<223> OTHER INFORMATION: SP-C SS Ion Lock2 - L D15/K19;K20/D24

<400> SEQUENCE: 323

Gly Ile Pro Ser Ser Pro Val His Leu Lys Arg Leu Leu Ile Asp Val
1               5                   10                  15

Val Val Lys Lys Leu Ile Val Asp Val Ile Val Gly Ala Leu Leu Met
                20                  25                  30

Gly

<210> SEQ ID NO 324
<211> LENGTH: 33
<212> TYPE: PRT
<213> ORGANISM: artificial
<220> FEATURE:
<223> OTHER INFORMATION: SP-C SS Ion Lock2 - L D15/R19;R20/D24

<400> SEQUENCE: 324

Gly Ile Pro Ser Ser Pro Val His Leu Lys Arg Leu Leu Ile Asp Val
1               5                   10                  15

Val Val Arg Arg Leu Ile Val Asp Val Ile Val Gly Ala Leu Leu Met
                20                  25                  30

Gly

<210> SEQ ID NO 325
<211> LENGTH: 33
<212> TYPE: PRT
<213> ORGANISM: artificial
<220> FEATURE:
<223> OTHER INFORMATION: consensus
<220> FEATURE:
<221> NAME/KEY: MISC_FEATURE
<222> LOCATION: (3)..(4)
<223> OTHER INFORMATION: Xaa is independently Ser or Phe
<220> FEATURE:
<221> NAME/KEY: MISC_FEATURE
<222> LOCATION: (6)..(6)
<223> OTHER INFORMATION: Xaa is Val or Ser
<220> FEATURE:
<221> NAME/KEY: MISC_FEATURE
<222> LOCATION: (7)..(7)
<223> OTHER INFORMATION: Xaa is His or Ser
<220> FEATURE:
<221> NAME/KEY: MISC_FEATURE
<222> LOCATION: (15)..(15)
<223> OTHER INFORMATION: Xaa is an ion lock pair with the amino acid at
      position 19, or Leu, Ile, or Val
<220> FEATURE:
<221> NAME/KEY: MISC_FEATURE
<222> LOCATION: (19)..(19)
<223> OTHER INFORMATION: Xaa is an ion lock pair with the amino acid at
      position 15, or Leu, Ile, or Val
<220> FEATURE:
<221> NAME/KEY: MISC_FEATURE
<222> LOCATION: (20)..(20)
<223> OTHER INFORMATION: Xaa is an ion lock pair with the amino acid at
``` position 24, or Leu, Ile, or Val
<220> FEATURE:
<221> NAME/KEY: MISC_FEATURE
<222> LOCATION: (24)..(24)
<223> OTHER INFORMATION: Xaa is an ion lock pair with the amino acid at
       position 20, or Leu, Ile, or Val

<400> SEQUENCE: 325

Ile Pro Xaa Xaa Pro Xaa Xaa Leu Lys Arg Leu Lys Leu Leu Xaa Leu
1               5                   10                  15

Leu Leu Xaa Xaa Ile Leu Leu Xaa Ile Leu Gly Ala Leu Leu Met Gly
            20                  25                  30

Leu

<210> SEQ ID NO 326
<211> LENGTH: 33
<212> TYPE: PRT
<213> ORGANISM: artificial
<220> FEATURE:
<223> OTHER INFORMATION: SP-C33SS Ion Lock2 K15/E19;E20/K24

<400> SEQUENCE: 326

Ile Pro Ser Ser Pro Val His Leu Lys Arg Leu Lys Leu Leu Lys Leu
1               5                   10                  15

Leu Leu Glu Glu Ile Leu Leu Lys Ile Leu Gly Ala Leu Leu Met Gly
            20                  25                  30

Leu

<210> SEQ ID NO 327
<211> LENGTH: 33
<212> TYPE: PRT
<213> ORGANISM: artificial
<220> FEATURE:
<223> OTHER INFORMATION: SP-C33SS Ion Lock2 K15/D19;E20/K24

<400> SEQUENCE: 327

Ile Pro Ser Ser Pro Val His Leu Lys Arg Leu Lys Leu Leu Lys Leu
1               5                   10                  15

Leu Leu Asp Glu Ile Leu Leu Lys Ile Leu Gly Ala Leu Leu Met Gly
            20                  25                  30

Leu

<210> SEQ ID NO 328
<211> LENGTH: 33
<212> TYPE: PRT
<213> ORGANISM: artificial
<220> FEATURE:
<223> OTHER INFORMATION: SP-C33SS Ion Lock2 K15/E19;D20/K24

<400> SEQUENCE: 328

Ile Pro Ser Ser Pro Val His Leu Lys Arg Leu Lys Leu Leu Lys Leu
1               5                   10                  15

Leu Leu Glu Asp Ile Leu Leu Lys Ile Leu Gly Ala Leu Leu Met Gly
            20                  25                  30

Leu

<210> SEQ ID NO 329
<211> LENGTH: 33
<212> TYPE: PRT
<213> ORGANISM: artificial
<220> FEATURE:
<223> OTHER INFORMATION: SP-C33SS Ion Lock2 K15/D19;D20/K24

```
<400> SEQUENCE: 329

Ile Pro Ser Ser Pro Val His Leu Lys Arg Leu Lys Leu Leu Lys Leu
1               5                   10                  15

Leu Leu Asp Asp Ile Leu Leu Lys Ile Leu Gly Ala Leu Leu Met Gly
            20                  25                  30

Leu

<210> SEQ ID NO 330
<211> LENGTH: 33
<212> TYPE: PRT
<213> ORGANISM: artificial
<220> FEATURE:
<223> OTHER INFORMATION: SP-C33SS Ion Lock2 K15/E19;E20/R24

<400> SEQUENCE: 330

Ile Pro Ser Ser Pro Val His Leu Lys Arg Leu Lys Leu Leu Lys Leu
1               5                   10                  15

Leu Leu Glu Glu Ile Leu Leu Arg Ile Leu Gly Ala Leu Leu Met Gly
            20                  25                  30

Leu

<210> SEQ ID NO 331
<211> LENGTH: 33
<212> TYPE: PRT
<213> ORGANISM: artificial
<220> FEATURE:
<223> OTHER INFORMATION: SP-C33SS Ion Lock2 K15/D19;E20/R24

<400> SEQUENCE: 331

Ile Pro Ser Ser Pro Val His Leu Lys Arg Leu Lys Leu Leu Lys Leu
1               5                   10                  15

Leu Leu Asp Glu Ile Leu Leu Arg Ile Leu Gly Ala Leu Leu Met Gly
            20                  25                  30

Leu

<210> SEQ ID NO 332
<211> LENGTH: 33
<212> TYPE: PRT
<213> ORGANISM: artificial
<220> FEATURE:
<223> OTHER INFORMATION: SP-C33SS Ion Lock2 K15/E19;D20/R24

<400> SEQUENCE: 332

Ile Pro Ser Ser Pro Val His Leu Lys Arg Leu Lys Leu Leu Lys Leu
1               5                   10                  15

Leu Leu Glu Asp Ile Leu Leu Arg Ile Leu Gly Ala Leu Leu Met Gly
            20                  25                  30

Leu

<210> SEQ ID NO 333
<211> LENGTH: 33
<212> TYPE: PRT
<213> ORGANISM: artificial
<220> FEATURE:
<223> OTHER INFORMATION: SP-C33SS Ion Lock2 K15/D19;D20/R24

<400> SEQUENCE: 333

Ile Pro Ser Ser Pro Val His Leu Lys Arg Leu Lys Leu Leu Lys Leu
1               5                   10                  15

Leu Leu Asp Asp Ile Leu Leu Arg Ile Leu Gly Ala Leu Leu Met Gly
            20                  25                  30
```

Leu

<210> SEQ ID NO 334
<211> LENGTH: 33
<212> TYPE: PRT
<213> ORGANISM: artificial
<220> FEATURE:
<223> OTHER INFORMATION: SP-C33SS Ion Lock2 K15/E19;K20/E24

<400> SEQUENCE: 334

Ile Pro Ser Ser Pro Val His Leu Lys Arg Leu Lys Leu Leu Lys Leu
1               5                   10                  15

Leu Leu Glu Lys Ile Leu Leu Glu Ile Leu Gly Ala Leu Leu Met Gly
            20                  25                  30

Leu

<210> SEQ ID NO 335
<211> LENGTH: 33
<212> TYPE: PRT
<213> ORGANISM: artificial
<220> FEATURE:
<223> OTHER INFORMATION: SP-C33SS Ion Lock2 K15/D19;K20/E24

<400> SEQUENCE: 335

Ile Pro Ser Ser Pro Val His Leu Lys Arg Leu Lys Leu Leu Lys Leu
1               5                   10                  15

Leu Leu Asp Lys Ile Leu Leu Glu Ile Leu Gly Ala Leu Leu Met Gly
            20                  25                  30

Leu

<210> SEQ ID NO 336
<211> LENGTH: 33
<212> TYPE: PRT
<213> ORGANISM: artificial
<220> FEATURE:
<223> OTHER INFORMATION: SP-C33SS Ion Lock2 K15/E19;K20/D24

<400> SEQUENCE: 336

Ile Pro Ser Ser Pro Val His Leu Lys Arg Leu Lys Leu Leu Lys Leu
1               5                   10                  15

Leu Leu Glu Lys Ile Leu Leu Asp Ile Leu Gly Ala Leu Leu Met Gly
            20                  25                  30

Leu

<210> SEQ ID NO 337
<211> LENGTH: 33
<212> TYPE: PRT
<213> ORGANISM: artificial
<220> FEATURE:
<223> OTHER INFORMATION: SP-C33SS Ion Lock2 K15/D19;K20/D24

<400> SEQUENCE: 337

Ile Pro Ser Ser Pro Val His Leu Lys Arg Leu Lys Leu Leu Lys Leu
1               5                   10                  15

Leu Leu Asp Lys Ile Leu Leu Asp Ile Leu Gly Ala Leu Leu Met Gly
            20                  25                  30

Leu

<210> SEQ ID NO 338
<211> LENGTH: 33
<212> TYPE: PRT

<213> ORGANISM: artificial
<220> FEATURE:
<223> OTHER INFORMATION: SP-C33SS Ion Lock2 K15/E19;R20/E24

<400> SEQUENCE: 338

Ile Pro Ser Ser Pro Val His Leu Lys Arg Leu Lys Leu Leu Lys Leu
1               5                   10                  15

Leu Leu Glu Arg Ile Leu Leu Glu Ile Leu Gly Ala Leu Leu Met Gly
            20                  25                  30

Leu

<210> SEQ ID NO 339
<211> LENGTH: 33
<212> TYPE: PRT
<213> ORGANISM: artificial
<220> FEATURE:
<223> OTHER INFORMATION: SP-C33SS Ion Lock2 K15/D19;R20/E24

<400> SEQUENCE: 339

Ile Pro Ser Ser Pro Val His Leu Lys Arg Leu Lys Leu Leu Lys Leu
1               5                   10                  15

Leu Leu Glu Glu Ile Leu Leu Lys Ile Leu Gly Ala Leu Leu Met Gly
            20                  25                  30

Leu

<210> SEQ ID NO 340
<211> LENGTH: 33
<212> TYPE: PRT
<213> ORGANISM: artificial
<220> FEATURE:
<223> OTHER INFORMATION: SP-C33SS Ion Lock2 K15/E19;R20/D24

<400> SEQUENCE: 340

Ile Pro Ser Ser Pro Val His Leu Lys Arg Leu Lys Leu Leu Lys Leu
1               5                   10                  15

Leu Leu Glu Arg Ile Leu Leu Asp Ile Leu Gly Ala Leu Leu Met Gly
            20                  25                  30

Leu

<210> SEQ ID NO 341
<211> LENGTH: 33
<212> TYPE: PRT
<213> ORGANISM: artificial
<220> FEATURE:
<223> OTHER INFORMATION: SP-C33SS Ion Lock2 K15/D19;R20/D24

<400> SEQUENCE: 341

Ile Pro Ser Ser Pro Val His Leu Lys Arg Leu Lys Leu Leu Lys Leu
1               5                   10                  15

Leu Leu Asp Arg Ile Leu Leu Asp Ile Leu Gly Ala Leu Leu Met Gly
            20                  25                  30

Leu

<210> SEQ ID NO 342
<211> LENGTH: 33
<212> TYPE: PRT
<213> ORGANISM: artificial
<220> FEATURE:
<223> OTHER INFORMATION: SP-C33SS Ion Lock2 R15/E19;E20/K24

<400> SEQUENCE: 342

Ile Pro Ser Ser Pro Val His Leu Lys Arg Leu Lys Leu Leu Arg Leu

```
                1               5                  10                 15
Leu Leu Glu Glu Ile Leu Leu Lys Ile Leu Gly Ala Leu Leu Met Gly
            20                  25                 30

Leu
```

<210> SEQ ID NO 343
<211> LENGTH: 33
<212> TYPE: PRT
<213> ORGANISM: artificial
<220> FEATURE:
<223> OTHER INFORMATION: SP-C33SS Ion Lock2 R15/D19;E20/K24

<400> SEQUENCE: 343

```
Ile Pro Ser Ser Pro Val His Leu Lys Arg Leu Lys Leu Leu Arg Leu
1               5                   10                  15
Leu Leu Asp Glu Ile Leu Leu Lys Ile Leu Gly Ala Leu Leu Met Gly
            20                  25                  30
Leu
```

<210> SEQ ID NO 344
<211> LENGTH: 33
<212> TYPE: PRT
<213> ORGANISM: artificial
<220> FEATURE:
<223> OTHER INFORMATION: SP-C33SS Ion Lock2 R15/E19;D20/K24

<400> SEQUENCE: 344

```
Ile Pro Ser Ser Pro Val His Leu Lys Arg Leu Lys Leu Leu Arg Leu
1               5                   10                  15
Leu Leu Glu Asp Ile Leu Leu Lys Ile Leu Gly Ala Leu Leu Met Gly
            20                  25                  30
Leu
```

<210> SEQ ID NO 345
<211> LENGTH: 33
<212> TYPE: PRT
<213> ORGANISM: artificial
<220> FEATURE:
<223> OTHER INFORMATION: SP-C33SS Ion Lock2 R15/D19;D20/K24

<400> SEQUENCE: 345

```
Ile Pro Ser Ser Pro Val His Leu Lys Arg Leu Lys Leu Leu Arg Leu
1               5                   10                  15
Leu Leu Asp Asp Ile Leu Leu Lys Ile Leu Gly Ala Leu Leu Met Gly
            20                  25                  30
Leu
```

<210> SEQ ID NO 346
<211> LENGTH: 33
<212> TYPE: PRT
<213> ORGANISM: artificial
<220> FEATURE:
<223> OTHER INFORMATION: SP-C33SS Ion Lock2 R15/E19;E20/R24

<400> SEQUENCE: 346

```
Ile Pro Ser Ser Pro Val His Leu Lys Arg Leu Lys Leu Leu Arg Leu
1               5                   10                  15
Leu Leu Glu Glu Ile Leu Leu Arg Ile Leu Gly Ala Leu Leu Met Gly
            20                  25                  30
Leu
```

<210> SEQ ID NO 347
<211> LENGTH: 33
<212> TYPE: PRT
<213> ORGANISM: artificial
<220> FEATURE:
<223> OTHER INFORMATION: SP-C33SS Ion Lock2 R15/D19;E20/R24

<400> SEQUENCE: 347

Ile Pro Ser Ser Pro Val His Leu Lys Arg Leu Lys Leu Leu Arg Leu
1               5                   10                  15
Leu Leu Asp Glu Ile Leu Leu Arg Ile Leu Gly Ala Leu Leu Met Gly
            20                  25                  30
Leu

<210> SEQ ID NO 348
<211> LENGTH: 33
<212> TYPE: PRT
<213> ORGANISM: artificial
<220> FEATURE:
<223> OTHER INFORMATION: SP-C33SS Ion Lock2 R15/E19;D20/R24

<400> SEQUENCE: 348

Ile Pro Ser Ser Pro Val His Leu Lys Arg Leu Lys Leu Leu Arg Leu
1               5                   10                  15
Leu Leu Glu Asp Ile Leu Leu Arg Ile Leu Gly Ala Leu Leu Met Gly
            20                  25                  30
Leu

<210> SEQ ID NO 349
<211> LENGTH: 33
<212> TYPE: PRT
<213> ORGANISM: artificial
<220> FEATURE:
<223> OTHER INFORMATION: SP-C33SS Ion Lock2 R15/D19;D20/R24

<400> SEQUENCE: 349

Ile Pro Ser Ser Pro Val His Leu Lys Arg Leu Lys Leu Leu Arg Leu
1               5                   10                  15
Leu Leu Asp Asp Ile Leu Leu Arg Ile Leu Gly Ala Leu Leu Met Gly
            20                  25                  30
Leu

<210> SEQ ID NO 350
<211> LENGTH: 33
<212> TYPE: PRT
<213> ORGANISM: artificial
<220> FEATURE:
<223> OTHER INFORMATION: SP-C33SS Ion Lock2 R15/E19;K20/E24

<400> SEQUENCE: 350

Ile Pro Ser Ser Pro Val His Leu Lys Arg Leu Lys Leu Leu Arg Leu
1               5                   10                  15
Leu Leu Glu Lys Ile Leu Leu Glu Ile Leu Gly Ala Leu Leu Met Gly
            20                  25                  30
Leu

<210> SEQ ID NO 351
<211> LENGTH: 33
<212> TYPE: PRT
<213> ORGANISM: artificial
<220> FEATURE:
<223> OTHER INFORMATION: SP-C33SS Ion Lock2 R15/D19;K20/E24

-continued

```
<400> SEQUENCE: 351

Ile Pro Ser Ser Pro Val His Leu Lys Arg Leu Lys Leu Leu Arg Leu
1               5                   10                  15

Leu Leu Asp Lys Ile Leu Leu Glu Ile Leu Gly Ala Leu Leu Met Gly
            20                  25                  30

Leu

<210> SEQ ID NO 352
<211> LENGTH: 33
<212> TYPE: PRT
<213> ORGANISM: artificial
<220> FEATURE:
<223> OTHER INFORMATION: SP-C33SS Ion Lock2 R15/E19;K20/D24

<400> SEQUENCE: 352

Ile Pro Ser Ser Pro Val His Leu Lys Arg Leu Lys Leu Leu Arg Leu
1               5                   10                  15

Leu Leu Glu Lys Ile Leu Leu Asp Ile Leu Gly Ala Leu Leu Met Gly
            20                  25                  30

Leu

<210> SEQ ID NO 353
<211> LENGTH: 33
<212> TYPE: PRT
<213> ORGANISM: artificial
<220> FEATURE:
<223> OTHER INFORMATION: SP-C33SS Ion Lock2 R15/D19;K20/D24

<400> SEQUENCE: 353

Ile Pro Ser Ser Pro Val His Leu Lys Arg Leu Lys Leu Leu Arg Leu
1               5                   10                  15

Leu Leu Asp Lys Ile Leu Leu Asp Ile Leu Gly Ala Leu Leu Met Gly
            20                  25                  30

Leu

<210> SEQ ID NO 354
<211> LENGTH: 33
<212> TYPE: PRT
<213> ORGANISM: artificial
<220> FEATURE:
<223> OTHER INFORMATION: SP-C33SS Ion Lock2 R15/E19;R20/E24

<400> SEQUENCE: 354

Ile Pro Ser Ser Pro Val His Leu Lys Arg Leu Lys Leu Leu Arg Leu
1               5                   10                  15

Leu Leu Glu Arg Ile Leu Leu Glu Ile Leu Gly Ala Leu Leu Met Gly
            20                  25                  30

Leu

<210> SEQ ID NO 355
<211> LENGTH: 33
<212> TYPE: PRT
<213> ORGANISM: artificial
<220> FEATURE:
<223> OTHER INFORMATION: SP-C33SS Ion Lock2 R15/D19;R20/E24

<400> SEQUENCE: 355

Ile Pro Ser Ser Pro Val His Leu Lys Arg Leu Lys Leu Leu Arg Leu
1               5                   10                  15

Leu Leu Glu Glu Ile Leu Leu Lys Ile Leu Gly Ala Leu Leu Met Gly
```

-continued

Leu

<210> SEQ ID NO 356
<211> LENGTH: 33
<212> TYPE: PRT
<213> ORGANISM: artificial
<220> FEATURE:
<223> OTHER INFORMATION: SP-C33SS Ion Lock2 R15/E19;R20/D24

<400> SEQUENCE: 356

Ile Pro Ser Ser Pro Val His Leu Lys Arg Leu Lys Leu Leu Arg Leu
1               5                   10                  15

Leu Leu Glu Arg Ile Leu Leu Asp Ile Leu Gly Ala Leu Leu Met Gly
            20                  25                  30

Leu

<210> SEQ ID NO 357
<211> LENGTH: 33
<212> TYPE: PRT
<213> ORGANISM: artificial
<220> FEATURE:
<223> OTHER INFORMATION: SP-C33SS Ion Lock2 R15/D19;R20/D24

<400> SEQUENCE: 357

Ile Pro Ser Ser Pro Val His Leu Lys Arg Leu Lys Leu Leu Arg Leu
1               5                   10                  15

Leu Leu Asp Arg Ile Leu Leu Asp Ile Leu Gly Ala Leu Leu Met Gly
            20                  25                  30

Leu

<210> SEQ ID NO 358
<211> LENGTH: 33
<212> TYPE: PRT
<213> ORGANISM: artificial
<220> FEATURE:
<223> OTHER INFORMATION: SP-C33SS Ion Lock2 E15/K19;E20/K24

<400> SEQUENCE: 358

Ile Pro Ser Ser Pro Val His Leu Lys Arg Leu Lys Leu Leu Glu Leu
1               5                   10                  15

Leu Leu Lys Glu Ile Leu Leu Lys Ile Leu Gly Ala Leu Leu Met Gly
            20                  25                  30

Leu

<210> SEQ ID NO 359
<211> LENGTH: 33
<212> TYPE: PRT
<213> ORGANISM: artificial
<220> FEATURE:
<223> OTHER INFORMATION: SP-C33SS Ion Lock2 E15/R19;E20/K24

<400> SEQUENCE: 359

Ile Pro Ser Ser Pro Val His Leu Lys Arg Leu Lys Leu Leu Glu Leu
1               5                   10                  15

Leu Leu Arg Glu Ile Leu Leu Lys Ile Leu Gly Ala Leu Leu Met Gly
            20                  25                  30

Leu

<210> SEQ ID NO 360
<211> LENGTH: 33

-continued

```
<212> TYPE: PRT
<213> ORGANISM: artificial
<220> FEATURE:
<223> OTHER INFORMATION: SP-C33SS Ion Lock2 E15/K19;D20/K24

<400> SEQUENCE: 360

Ile Pro Ser Ser Pro Val His Leu Lys Arg Leu Lys Leu Leu Glu Leu
1               5                   10                  15

Leu Leu Lys Asp Ile Leu Leu Lys Ile Leu Gly Ala Leu Leu Met Gly
            20                  25                  30

Leu

<210> SEQ ID NO 361
<211> LENGTH: 33
<212> TYPE: PRT
<213> ORGANISM: artificial
<220> FEATURE:
<223> OTHER INFORMATION: SP-C33SS Ion Lock2 E15/R19;D20/K24

<400> SEQUENCE: 361

Ile Pro Ser Ser Pro Val His Leu Lys Arg Leu Lys Leu Leu Glu Leu
1               5                   10                  15

Leu Leu Arg Asp Ile Leu Leu Lys Ile Leu Gly Ala Leu Leu Met Gly
            20                  25                  30

Leu

<210> SEQ ID NO 362
<211> LENGTH: 33
<212> TYPE: PRT
<213> ORGANISM: artificial
<220> FEATURE:
<223> OTHER INFORMATION: SP-C33SS Ion Lock2 E15/K19;E20/R24

<400> SEQUENCE: 362

Ile Pro Ser Ser Pro Val His Leu Lys Arg Leu Lys Leu Leu Glu Leu
1               5                   10                  15

Leu Leu Lys Glu Ile Leu Leu Arg Ile Leu Gly Ala Leu Leu Met Gly
            20                  25                  30

Leu

<210> SEQ ID NO 363
<211> LENGTH: 33
<212> TYPE: PRT
<213> ORGANISM: artificial
<220> FEATURE:
<223> OTHER INFORMATION: SP-C33SS Ion Lock2 E15/R19;E20/R24

<400> SEQUENCE: 363

Ile Pro Ser Ser Pro Val His Leu Lys Arg Leu Lys Leu Leu Glu Leu
1               5                   10                  15

Leu Leu Arg Glu Ile Leu Leu Arg Ile Leu Gly Ala Leu Leu Met Gly
            20                  25                  30

Leu

<210> SEQ ID NO 364
<211> LENGTH: 33
<212> TYPE: PRT
<213> ORGANISM: artificial
<220> FEATURE:
<223> OTHER INFORMATION: SP-C33SS Ion Lock2 E15/K19;D20/R24

<400> SEQUENCE: 364
```

-continued

Ile Pro Ser Ser Pro Val His Leu Lys Arg Leu Lys Leu Leu Glu Leu
1               5                   10                  15

Leu Leu Lys Asp Ile Leu Leu Arg Ile Leu Gly Ala Leu Leu Met Gly
            20                  25                  30

Leu

<210> SEQ ID NO 365
<211> LENGTH: 33
<212> TYPE: PRT
<213> ORGANISM: artificial
<220> FEATURE:
<223> OTHER INFORMATION: SP-C33SS Ion Lock2 E15/R19;D20/R24

<400> SEQUENCE: 365

Ile Pro Ser Ser Pro Val His Leu Lys Arg Leu Lys Leu Leu Glu Leu
1               5                   10                  15

Leu Leu Arg Asp Ile Leu Leu Arg Ile Leu Gly Ala Leu Leu Met Gly
            20                  25                  30

Leu

<210> SEQ ID NO 366
<211> LENGTH: 33
<212> TYPE: PRT
<213> ORGANISM: artificial
<220> FEATURE:
<223> OTHER INFORMATION: SP-C33SS Ion Lock2 E15/K19;K20/E24

<400> SEQUENCE: 366

Ile Pro Ser Ser Pro Val His Leu Lys Arg Leu Lys Leu Leu Glu Leu
1               5                   10                  15

Leu Leu Lys Lys Ile Leu Leu Glu Ile Leu Gly Ala Leu Leu Met Gly
            20                  25                  30

Leu

<210> SEQ ID NO 367
<211> LENGTH: 33
<212> TYPE: PRT
<213> ORGANISM: artificial
<220> FEATURE:
<223> OTHER INFORMATION: SP-C33SS Ion Lock2 E15/R19;K20/E24

<400> SEQUENCE: 367

Ile Pro Ser Ser Pro Val His Leu Lys Arg Leu Lys Leu Leu Glu Leu
1               5                   10                  15

Leu Leu Arg Lys Ile Leu Leu Glu Ile Leu Gly Ala Leu Leu Met Gly
            20                  25                  30

Leu

<210> SEQ ID NO 368
<211> LENGTH: 33
<212> TYPE: PRT
<213> ORGANISM: artificial
<220> FEATURE:
<223> OTHER INFORMATION: SP-C33SS Ion Lock2 E15/K19;K20/D24

<400> SEQUENCE: 368

Ile Pro Ser Ser Pro Val His Leu Lys Arg Leu Lys Leu Leu Glu Leu
1               5                   10                  15

Leu Leu Lys Lys Ile Leu Leu Asp Ile Leu Gly Ala Leu Leu Met Gly
            20                  25                  30

Leu

<210> SEQ ID NO 369
<211> LENGTH: 33
<212> TYPE: PRT
<213> ORGANISM: artificial
<220> FEATURE:
<223> OTHER INFORMATION: SP-C33SS Ion Lock2 E15/R19;K20/D24

<400> SEQUENCE: 369

Ile Pro Ser Ser Pro Val His Leu Lys Arg Leu Lys Leu Leu Glu Leu
1               5                   10                  15

Leu Leu Arg Lys Ile Leu Leu Asp Ile Leu Gly Ala Leu Leu Met Gly
            20                  25                  30

Leu

<210> SEQ ID NO 370
<211> LENGTH: 33
<212> TYPE: PRT
<213> ORGANISM: artificial
<220> FEATURE:
<223> OTHER INFORMATION: SP-C33SS Ion Lock2 E15/K19;R20/E24

<400> SEQUENCE: 370

Ile Pro Ser Ser Pro Val His Leu Lys Arg Leu Lys Leu Leu Glu Leu
1               5                   10                  15

Leu Leu Lys Arg Ile Leu Leu Glu Ile Leu Gly Ala Leu Leu Met Gly
            20                  25                  30

Leu

<210> SEQ ID NO 371
<211> LENGTH: 33
<212> TYPE: PRT
<213> ORGANISM: artificial
<220> FEATURE:
<223> OTHER INFORMATION: SP-C33SS Ion Lock2 E15/R19;R20/E24

<400> SEQUENCE: 371

Ile Pro Ser Ser Pro Val His Leu Lys Arg Leu Lys Leu Leu Glu Leu
1               5                   10                  15

Leu Leu Arg Arg Ile Leu Leu Glu Ile Leu Gly Ala Leu Leu Met Gly
            20                  25                  30

Leu

<210> SEQ ID NO 372
<211> LENGTH: 33
<212> TYPE: PRT
<213> ORGANISM: artificial
<220> FEATURE:
<223> OTHER INFORMATION: SP-C33SS Ion Lock2 E15/K19;R20/D24

<400> SEQUENCE: 372

Ile Pro Ser Ser Pro Val His Leu Lys Arg Leu Lys Leu Leu Glu Leu
1               5                   10                  15

Leu Leu Lys Arg Ile Leu Leu Asp Ile Leu Gly Ala Leu Leu Met Gly
            20                  25                  30

Leu

<210> SEQ ID NO 373
<211> LENGTH: 33
<212> TYPE: PRT
<213> ORGANISM: artificial
<220> FEATURE:

-continued

<223> OTHER INFORMATION: SP-C33SS Ion Lock2 E15/R19;R20/D24

<400> SEQUENCE: 373

Ile Pro Ser Ser Pro Val His Leu Lys Arg Leu Lys Leu Leu Glu Leu
1               5                   10                  15

Leu Leu Arg Arg Ile Leu Leu Asp Ile Leu Gly Ala Leu Leu Met Gly
            20                  25                  30

Leu

<210> SEQ ID NO 374
<211> LENGTH: 33
<212> TYPE: PRT
<213> ORGANISM: artificial
<220> FEATURE:
<223> OTHER INFORMATION: SP-C33SS Ion Lock2 D15/K19;E20/K24

<400> SEQUENCE: 374

Ile Pro Ser Ser Pro Val His Leu Lys Arg Leu Lys Leu Leu Asp Leu
1               5                   10                  15

Leu Leu Lys Glu Ile Leu Leu Lys Ile Leu Gly Ala Leu Leu Met Gly
            20                  25                  30

Leu

<210> SEQ ID NO 375
<211> LENGTH: 33
<212> TYPE: PRT
<213> ORGANISM: artificial
<220> FEATURE:
<223> OTHER INFORMATION: SP-C33SS Ion Lock2 D15/R19;E20/K24

<400> SEQUENCE: 375

Ile Pro Ser Ser Pro Val His Leu Lys Arg Leu Lys Leu Leu Asp Leu
1               5                   10                  15

Leu Leu Arg Glu Ile Leu Leu Lys Ile Leu Gly Ala Leu Leu Met Gly
            20                  25                  30

Leu

<210> SEQ ID NO 376
<211> LENGTH: 33
<212> TYPE: PRT
<213> ORGANISM: artificial
<220> FEATURE:
<223> OTHER INFORMATION: SP-C33SS Ion Lock2 D15/K19;D20/K24

<400> SEQUENCE: 376

Ile Pro Ser Ser Pro Val His Leu Lys Arg Leu Lys Leu Leu Asp Leu
1               5                   10                  15

Leu Leu Lys Asp Ile Leu Leu Lys Ile Leu Gly Ala Leu Leu Met Gly
            20                  25                  30

Leu

<210> SEQ ID NO 377
<211> LENGTH: 33
<212> TYPE: PRT
<213> ORGANISM: artificial
<220> FEATURE:
<223> OTHER INFORMATION: SP-C33SS Ion Lock2 D15/R19;D20/K24

<400> SEQUENCE: 377

Ile Pro Ser Ser Pro Val His Leu Lys Arg Leu Lys Leu Leu Asp Leu
1               5                   10                  15

-continued

Leu Leu Arg Asp Ile Leu Leu Lys Ile Leu Gly Ala Leu Leu Met Gly
            20                  25                  30

Leu

<210> SEQ ID NO 378
<211> LENGTH: 33
<212> TYPE: PRT
<213> ORGANISM: artificial
<220> FEATURE:
<223> OTHER INFORMATION: SP-C33SS Ion Lock2 D15/K19;E20/R24

<400> SEQUENCE: 378

Ile Pro Ser Ser Pro Val His Leu Lys Arg Leu Lys Leu Leu Asp Leu
1               5                   10                  15

Leu Leu Lys Glu Ile Leu Leu Arg Ile Leu Gly Ala Leu Leu Met Gly
            20                  25                  30

Leu

<210> SEQ ID NO 379
<211> LENGTH: 33
<212> TYPE: PRT
<213> ORGANISM: artificial
<220> FEATURE:
<223> OTHER INFORMATION: SP-C33SS Ion Lock2 D15/R19;E20/R24

<400> SEQUENCE: 379

Ile Pro Ser Ser Pro Val His Leu Lys Arg Leu Lys Leu Leu Asp Leu
1               5                   10                  15

Leu Leu Arg Glu Ile Leu Leu Arg Ile Leu Gly Ala Leu Leu Met Gly
            20                  25                  30

Leu

<210> SEQ ID NO 380
<211> LENGTH: 33
<212> TYPE: PRT
<213> ORGANISM: artificial
<220> FEATURE:
<223> OTHER INFORMATION: SP-C33SS Ion Lock2 D15/K19;D20/R24

<400> SEQUENCE: 380

Ile Pro Ser Ser Pro Val His Leu Lys Arg Leu Lys Leu Leu Asp Leu
1               5                   10                  15

Leu Leu Lys Asp Ile Leu Leu Arg Ile Leu Gly Ala Leu Leu Met Gly
            20                  25                  30

Leu

<210> SEQ ID NO 381
<211> LENGTH: 33
<212> TYPE: PRT
<213> ORGANISM: artificial
<220> FEATURE:
<223> OTHER INFORMATION: SP-C33SS Ion Lock2 D15/R19;D20/R24

<400> SEQUENCE: 381

Ile Pro Ser Ser Pro Val His Leu Lys Arg Leu Lys Leu Leu Asp Leu
1               5                   10                  15

Leu Leu Arg Asp Ile Leu Leu Arg Ile Leu Gly Ala Leu Leu Met Gly
            20                  25                  30

Leu

<210> SEQ ID NO 382

```
<211> LENGTH: 33
<212> TYPE: PRT
<213> ORGANISM: artificial
<220> FEATURE:
<223> OTHER INFORMATION: SP-C33SS Ion Lock2 D15/K19;K20/E24

<400> SEQUENCE: 382

Ile Pro Ser Ser Pro Val His Leu Lys Arg Leu Lys Leu Leu Asp Leu
1               5                   10                  15
Leu Leu Lys Lys Ile Leu Leu Glu Ile Leu Gly Ala Leu Leu Met Gly
            20                  25                  30
Leu

<210> SEQ ID NO 383
<211> LENGTH: 33
<212> TYPE: PRT
<213> ORGANISM: artificial
<220> FEATURE:
<223> OTHER INFORMATION: SP-C33SS Ion Lock2 D15/R19;K20/E24

<400> SEQUENCE: 383

Ile Pro Ser Ser Pro Val His Leu Lys Arg Leu Lys Leu Leu Asp Leu
1               5                   10                  15
Leu Leu Arg Lys Ile Leu Leu Glu Ile Leu Gly Ala Leu Leu Met Gly
            20                  25                  30
Leu

<210> SEQ ID NO 384
<211> LENGTH: 33
<212> TYPE: PRT
<213> ORGANISM: artificial
<220> FEATURE:
<223> OTHER INFORMATION: SP-C33SS Ion Lock2 D15/K19;R20/D24

<400> SEQUENCE: 384

Ile Pro Ser Ser Pro Val His Leu Lys Arg Leu Lys Leu Leu Asp Leu
1               5                   10                  15
Leu Leu Lys Arg Ile Leu Leu Asp Ile Leu Gly Ala Leu Leu Met Gly
            20                  25                  30
Leu

<210> SEQ ID NO 385
<211> LENGTH: 33
<212> TYPE: PRT
<213> ORGANISM: artificial
<220> FEATURE:
<223> OTHER INFORMATION: SP-C33SS Ion Lock2 D15/R19;K20/D24

<400> SEQUENCE: 385

Ile Pro Ser Ser Pro Val His Leu Lys Arg Leu Lys Leu Leu Asp Leu
1               5                   10                  15
Leu Leu Arg Lys Ile Leu Leu Asp Ile Leu Gly Ala Leu Leu Met Gly
            20                  25                  30
Leu

<210> SEQ ID NO 386
<211> LENGTH: 33
<212> TYPE: PRT
<213> ORGANISM: artificial
<220> FEATURE:
<223> OTHER INFORMATION: SP-C33SS Ion Lock2 D15/K19;R20/E24

<400> SEQUENCE: 386
```

```
Ile Pro Ser Ser Pro Val His Leu Lys Arg Leu Lys Leu Leu Asp Leu
1               5                   10                  15

Leu Leu Lys Arg Ile Leu Leu Glu Ile Leu Gly Ala Leu Leu Met Gly
            20                  25                  30

Leu
```

<210> SEQ ID NO 387
<211> LENGTH: 33
<212> TYPE: PRT
<213> ORGANISM: artificial
<220> FEATURE:
<223> OTHER INFORMATION: SP-C33SS Ion Lock2 D15/R19;R20/E24

<400> SEQUENCE: 387

```
Ile Pro Ser Ser Pro Val His Leu Lys Arg Leu Lys Leu Leu Asp Leu
1               5                   10                  15

Leu Leu Arg Arg Ile Leu Leu Glu Ile Leu Gly Ala Leu Leu Met Gly
            20                  25                  30

Leu
```

<210> SEQ ID NO 388
<211> LENGTH: 33
<212> TYPE: PRT
<213> ORGANISM: artificial
<220> FEATURE:
<223> OTHER INFORMATION: SP-C33SS Ion Lock2 D15/K19;K20/D24

<400> SEQUENCE: 388

```
Ile Pro Ser Ser Pro Val His Leu Lys Arg Leu Lys Leu Leu Asp Leu
1               5                   10                  15

Leu Leu Lys Lys Ile Leu Leu Asp Ile Leu Gly Ala Leu Leu Met Gly
            20                  25                  30

Leu
```

<210> SEQ ID NO 389
<211> LENGTH: 33
<212> TYPE: PRT
<213> ORGANISM: artificial
<220> FEATURE:
<223> OTHER INFORMATION: SP-C33SS Ion Lock2 D15/R19;R20/D24

<400> SEQUENCE: 389

```
Ile Pro Ser Ser Pro Val His Leu Lys Arg Leu Lys Leu Leu Asp Leu
1               5                   10                  15

Leu Leu Arg Arg Ile Leu Leu Asp Ile Leu Gly Ala Leu Leu Met Gly
            20                  25                  30

Leu
```

<210> SEQ ID NO 390
<211> LENGTH: 33
<212> TYPE: PRT
<213> ORGANISM: artificial
<220> FEATURE:
<223> OTHER INFORMATION: SP-C33FF

<400> SEQUENCE: 390

```
Ile Pro Phe Phe Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30
```

Leu

```
<210> SEQ ID NO 391
<211> LENGTH: 102
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (1)..(3)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
<222> LOCATION: (10)..(12)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
<222> LOCATION: (46)..(48)
<223> OTHER INFORMATION: 3 n's can be any codon that encodes a turn or
      loop sequence containing at least four amino acids
<220> FEATURE:
<221> NAME/KEY: misc_feature
<222> LOCATION: (49)..(51)
<223> OTHER INFORMATION: 3 n's can be any codon that encodes a turn or
      loop sequence containing at least four amino acids
<220> FEATURE:
<221> NAME/KEY: misc_feature
<222> LOCATION: (52)..(54)
<223> OTHER INFORMATION: 3 n's can be any codon that encodes a turn or
      loop sequence containing at least four amino acids
<220> FEATURE:
<221> NAME/KEY: misc_feature
<222> LOCATION: (55)..(57)
<223> OTHER INFORMATION: 3 n's can be any codon that encodes a turn or
      loop sequence containing at least four amino acids
<220> FEATURE:
<221> NAME/KEY: misc_feature
<222> LOCATION: (79)..(81)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
<222> LOCATION: (97)..(99)
<223> OTHER INFORMATION: 3 n's can be GCT, GCC, GCA, GCG, TCT, TCC, TCA,
      TCG, AGT, AGC, TGT, or TGC

<400> SEQUENCE: 391
nnntggttan nnagagcatt aataaaaaga atacaagcaa tgatannnnn nnnnnnnaga      60
atgttaccac aattagtann nagattagta ttaagannna gt                       102

<210> SEQ ID NO 392
<211> LENGTH: 57
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (1)..(3)
<223> OTHER INFORMATION: 3 n's can be CTT, CTC, CTA, CTG, TTA, TTG, TTT,
      or TTC
<220> FEATURE:
<221> NAME/KEY: misc_feature
<222> LOCATION: (4)..(6)
<223> OTHER INFORMATION: 3 n's can be GGT, GGC, GGA, GGG, CGT, CGC, CGA,
      CGG, AGA, or AGG
<220> FEATURE:
<221> NAME/KEY: misc_feature
<222> LOCATION: (13)..(15)
<223> OTHER INFORMATION: 3 n's can be TTT, TTC, TGT, TGC, TAT, or TAC
<220> FEATURE:
<221> NAME/KEY: misc_feature
```

```
<222> LOCATION: (16)..(18)
<223> OTHER INFORMATION: 3 n's can be TTT, TTC, TAT, or TAC
<220> FEATURE:
<221> NAME/KEY: misc_feature
<222> LOCATION: (22)..(24)
<223> OTHER INFORMATION: 3 n's can be TCT, TCC, TCA, TCG, AGT, AGC, GTT,
      GTC, GTA, or GTG
<220> FEATURE:
<221> NAME/KEY: misc_feature
<222> LOCATION: (25)..(27)
<223> OTHER INFORMATION: 3 n's can be TCT, TCC, TCA, TCG, AGT, AGC, CAT,
      or CAC
<220> FEATURE:
<221> NAME/KEY: misc_feature
<222> LOCATION: (40)..(42)
<223> OTHER INFORMATION: 3 n's can be CTT, CTC, CTA, CTG, TTA, TTG, AAA,
      or AAG
<220> FEATURE:
<221> NAME/KEY: misc_feature
<222> LOCATION: (43)..(45)
<223> OTHER INFORMATION: 3 n's can be ATT, ATC, ATA, CTT, CTC, CTA, CTG,
      TTA, TTG, GTT, GTC, GTA, or GTG
<220> FEATURE:
<221> NAME/KEY: misc_feature
<222> LOCATION: (46)..(48)
<223> OTHER INFORMATION: 3 n's can be ATT, ATC, ATA, CTT, CTC, CTA, CTG,
      TTA, TTG, GTT, GTC, GTA, or GTG
<220> FEATURE:
<221> NAME/KEY: misc_feature
<222> LOCATION: (49)..(51)
<223> OTHER INFORMATION: 3 n's can be GTT, GTC, GTA, GTG, CTT, CTC, CTA,
      CTG, TTA, or TTG
<220> FEATURE:
<221> NAME/KEY: misc_feature
<222> LOCATION: (52)..(54)
<223> OTHER INFORMATION: 3 n's can be GTT, GTC, GTA, GTG, CTT, CTC, CTA,
      CTG, TTA, or TTG
<220> FEATURE:
<221> NAME/KEY: misc_feature
<222> LOCATION: (55)..(57)
<223> OTHER INFORMATION: 3 n's can be GTT, GTC, GTA, GTG, CTT, CTC, CTA,
      CTG, TTA, or TTG

<400> SEQUENCE: 392
nnnnnnatac cannnnnncc annnnnntta aaaagattan nnnnnnnnnn nnnnnnn        57

<210> SEQ ID NO 393
<211> LENGTH: 99
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (10)..(12)
<223> OTHER INFORMATION: 3 n's can be TCT, TCC, TCA, TCG, AGT, AGC, TTT,
      or TTC
<220> FEATURE:
<221> NAME/KEY: misc_feature
<222> LOCATION: (13)..(15)
<223> OTHER INFORMATION: 3 n's can be TCT, TCC, TCA, TCG, AGT, AGC, TTT,
      or TTC
<220> FEATURE:
<221> NAME/KEY: misc_feature
<222> LOCATION: (19)..(21)
<223> OTHER INFORMATION: 3 n's can be GTT, GTC, GTA, GTG, TCT, TCC, TCA,
      TCG, AGT, or AGC
<220> FEATURE:
<221> NAME/KEY: misc_feature
<222> LOCATION: (22)..(24)
<223> OTHER INFORMATION: 3 n's can be CAT, CAC, TCT, TCC, TCA, TCG, AGT,
      or AGC
<220> FEATURE:
<221> NAME/KEY: misc_feature
<222> LOCATION: (43)..(45)
<223> OTHER INFORMATION: 3 n's can be CTT, CTC, CTA, CTG, TTA, TTG, ATT,
      ATC, ATA, GTT, GTC, GTA, or GTG, or a codon that encodes an ion
``` lock pair with the codon at positions 55-57
<220> FEATURE:
<221> NAME/KEY: misc_feature
<222> LOCATION: (55)..(57)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 43-45
<220> FEATURE:
<221> NAME/KEY: misc_feature
<222> LOCATION: (58)..(60)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 70-72
<220> FEATURE:
<221> NAME/KEY: misc_feature
<222> LOCATION: (64)..(66)
<223> OTHER INFORMATION: 3 n's can be ATT, ATC, ATA, GTT, GTC, GTA, or
       GTG
<220> FEATURE:
<221> NAME/KEY: misc_feature
<222> LOCATION: (70)..(72)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 58-60

<400> SEQUENCE: 393
ggaataccan nnnnnccann nnnnttaaaa agattattaa tannngtagt agtannnnnn      60
ttannngtan nngtaatagt aggagcatta ttaatggga                            99

<210> SEQ ID NO 394
<211> LENGTH: 99
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (43)..(45)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 55-57
<220> FEATURE:
<221> NAME/KEY: misc_feature
<222> LOCATION: (55)..(57)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 43-45
<220> FEATURE:
<221> NAME/KEY: misc_feature
<222> LOCATION: (58)..(60)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 70-72
<220> FEATURE:
<221> NAME/KEY: misc_feature
<222> LOCATION: (70)..(72)
<223> OTHER INFORMATION: 3 n's can be CTT, CTC, CTA, CTG, TTA, TTG, ATT,
       ATC, ATA, GTT, GTC, GTA, or GTG, or a codon that encodes an ion
       lock pair with the codon at positions 58-60

<400> SEQUENCE: 394
ataccaagta gtccagtaca tttaaaaaga ttaaaattat tannnttatt attannnnnn      60
atattattan nnatattagg agcattatta atgggatta                            99

<210> SEQ ID NO 395
<211> LENGTH: 34
<212> TYPE: PRT
<213> ORGANISM: artificial
<220> FEATURE:
<223> OTHER INFORMATION: dog SP-C

<400> SEQUENCE: 395

```
Gly Ile Pro Cys Phe Pro Ser Ser Leu Lys Arg Leu Leu Ile Ile Val
1               5                   10                  15

Val Val Ile Val Leu Val Val Val Ile Val Gly Ala Leu Leu Met
            20                  25                  30

Gly Leu
```

<210> SEQ ID NO 396
<211> LENGTH: 34
<212> TYPE: PRT
<213> ORGANISM: artificial
<220> FEATURE:
<223> OTHER INFORMATION: SP-cff

<400> SEQUENCE: 396

```
Gly Ile Pro Phe Phe Pro Val His Leu Lys Arg Leu Leu Ile Val Val
1               5                   10                  15

Val Val Val Val Leu Ile Val Val Ile Val Gly Ala Leu Leu Met
            20                  25                  30

Gly Leu
```

<210> SEQ ID NO 397
<211> LENGTH: 33
<212> TYPE: PRT
<213> ORGANISM: artificial
<220> FEATURE:
<223> OTHER INFORMATION: SP-c33

<400> SEQUENCE: 397

```
Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30

Leu
```

<210> SEQ ID NO 398
<211> LENGTH: 33
<212> TYPE: PRT
<213> ORGANISM: artificial
<220> FEATURE:
<223> OTHER INFORMATION: SP-C FF Ion Lock E20/K24

<400> SEQUENCE: 398

```
Gly Ile Pro Phe Phe Pro Val His Leu Lys Arg Leu Leu Ile Val Val
1               5                   10                  15

Val Val Val Glu Leu Ile Val Lys Val Ile Val Gly Ala Leu Leu Met
            20                  25                  30

Gly
```

<210> SEQ ID NO 399
<211> LENGTH: 33
<212> TYPE: PRT
<213> ORGANISM: artificial
<220> FEATURE:
<223> OTHER INFORMATION: SP-C FF Ion Lock E20/R24

<400> SEQUENCE: 399

```
Gly Ile Pro Phe Phe Pro Val His Leu Lys Arg Leu Leu Ile Val Val
1               5                   10                  15

Val Val Val Glu Leu Ile Val Arg Val Ile Val Gly Ala Leu Leu Met
            20                  25                  30

Gly
```

<210> SEQ ID NO 400
<211> LENGTH: 33
<212> TYPE: PRT
<213> ORGANISM: artificial
<220> FEATURE:
<223> OTHER INFORMATION: SP-C FF Ion Lock D20/K24

<400> SEQUENCE: 400

Gly Ile Pro Phe Phe Pro Val His Leu Lys Arg Leu Leu Ile Val Val
1               5                   10                  15

Val Val Val Asp Leu Ile Val Lys Val Ile Val Gly Ala Leu Leu Met
            20                  25                  30

Gly

<210> SEQ ID NO 401
<211> LENGTH: 33
<212> TYPE: PRT
<213> ORGANISM: artificial
<220> FEATURE:
<223> OTHER INFORMATION: SP-C FF Ion Lock D20/R24

<400> SEQUENCE: 401

Gly Ile Pro Phe Phe Pro Val His Leu Lys Arg Leu Leu Ile Val Val
1               5                   10                  15

Val Val Val Asp Leu Ile Val Arg Val Ile Val Gly Ala Leu Leu Met
            20                  25                  30

Gly

<210> SEQ ID NO 402
<211> LENGTH: 33
<212> TYPE: PRT
<213> ORGANISM: artificial
<220> FEATURE:
<223> OTHER INFORMATION: SP-C FF Ion Lock K20/E24

<400> SEQUENCE: 402

Gly Ile Pro Phe Phe Pro Val His Leu Lys Arg Leu Leu Ile Val Val
1               5                   10                  15

Val Val Val Lys Leu Ile Val Glu Val Ile Val Gly Ala Leu Leu Met
            20                  25                  30

Gly

<210> SEQ ID NO 403
<211> LENGTH: 33
<212> TYPE: PRT
<213> ORGANISM: artificial
<220> FEATURE:
<223> OTHER INFORMATION: SP-C FF Ion Lock R20/E24

<400> SEQUENCE: 403

Gly Ile Pro Phe Phe Pro Val His Leu Lys Arg Leu Leu Ile Val Val
1               5                   10                  15

Val Val Val Arg Leu Ile Val Glu Val Ile Val Gly Ala Leu Leu Met
            20                  25                  30

Gly

<210> SEQ ID NO 404
<211> LENGTH: 33
<212> TYPE: PRT
<213> ORGANISM: artificial
<220> FEATURE:

-continued

<223> OTHER INFORMATION: SP-C FF Ion Lock K20/D24

<400> SEQUENCE: 404

Gly Ile Pro Phe Phe Pro Val His Leu Lys Arg Leu Leu Ile Val Val
1               5                   10                  15

Val Val Val Lys Leu Ile Val Asp Val Ile Val Gly Ala Leu Leu Met
            20                  25                  30

Gly

<210> SEQ ID NO 405
<211> LENGTH: 33
<212> TYPE: PRT
<213> ORGANISM: artificial
<220> FEATURE:
<223> OTHER INFORMATION: SP-C FF Ion Lock R20/D24

<400> SEQUENCE: 405

Gly Ile Pro Phe Phe Pro Val His Leu Lys Arg Leu Leu Ile Val Val
1               5                   10                  15

Val Val Val Arg Leu Ile Val Asp Val Ile Val Gly Ala Leu Leu Met
            20                  25                  30

Gly

<210> SEQ ID NO 406
<211> LENGTH: 34
<212> TYPE: PRT
<213> ORGANISM: artificial
<220> FEATURE:
<223> OTHER INFORMATION: SP-C FF Ion Lock + L E20/K24

<400> SEQUENCE: 406

Gly Ile Pro Phe Phe Pro Val His Leu Lys Arg Leu Leu Ile Val Val
1               5                   10                  15

Val Val Val Glu Leu Ile Val Lys Val Ile Val Gly Ala Leu Leu Met
            20                  25                  30

Gly Leu

<210> SEQ ID NO 407
<211> LENGTH: 34
<212> TYPE: PRT
<213> ORGANISM: artificial
<220> FEATURE:
<223> OTHER INFORMATION: SP-C FF Ion Lock + L E20/R24

<400> SEQUENCE: 407

Gly Ile Pro Phe Phe Pro Val His Leu Lys Arg Leu Leu Ile Val Val
1               5                   10                  15

Val Val Val Glu Leu Ile Val Arg Val Ile Val Gly Ala Leu Leu Met
            20                  25                  30

Gly Leu

<210> SEQ ID NO 408
<211> LENGTH: 34
<212> TYPE: PRT
<213> ORGANISM: artificial
<220> FEATURE:
<223> OTHER INFORMATION: SP-C FF Ion Lock + L D20/K24

<400> SEQUENCE: 408

Gly Ile Pro Phe Phe Pro Val His Leu Lys Arg Leu Leu Ile Val Val
1               5                   10                  15

Val Val Val Asp Leu Ile Val Lys Val Ile Val Gly Ala Leu Leu Met
            20                  25                  30

Gly Leu

<210> SEQ ID NO 409
<211> LENGTH: 34
<212> TYPE: PRT
<213> ORGANISM: artificial
<220> FEATURE:
<223> OTHER INFORMATION: SP-C FF Ion Lock + L D20/R24

<400> SEQUENCE: 409

Gly Ile Pro Phe Phe Pro Val His Leu Lys Arg Leu Leu Ile Val Val
1               5                   10                  15

Val Val Val Asp Leu Ile Val Arg Val Ile Val Gly Ala Leu Leu Met
            20                  25                  30

Gly Leu

<210> SEQ ID NO 410
<211> LENGTH: 34
<212> TYPE: PRT
<213> ORGANISM: artificial
<220> FEATURE:
<223> OTHER INFORMATION: SP-C FF Ion Lock + L K20/E24

<400> SEQUENCE: 410

Gly Ile Pro Phe Phe Pro Val His Leu Lys Arg Leu Leu Ile Val Val
1               5                   10                  15

Val Val Val Lys Leu Ile Val Glu Val Ile Val Gly Ala Leu Leu Met
            20                  25                  30

Gly Leu

<210> SEQ ID NO 411
<211> LENGTH: 34
<212> TYPE: PRT
<213> ORGANISM: artificial
<220> FEATURE:
<223> OTHER INFORMATION: SP-C FF Ion Lock + L R20/E24

<400> SEQUENCE: 411

Gly Ile Pro Phe Phe Pro Val His Leu Lys Arg Leu Leu Ile Val Val
1               5                   10                  15

Val Val Val Arg Leu Ile Val Glu Val Ile Val Gly Ala Leu Leu Met
            20                  25                  30

Gly Leu

<210> SEQ ID NO 412
<211> LENGTH: 34
<212> TYPE: PRT
<213> ORGANISM: artificial
<220> FEATURE:
<223> OTHER INFORMATION: SP-C FF Ion Lock + L K20/D24

<400> SEQUENCE: 412

Gly Ile Pro Phe Phe Pro Val His Leu Lys Arg Leu Leu Ile Val Val
1               5                   10                  15

Val Val Val Lys Leu Ile Val Asp Val Ile Val Gly Ala Leu Leu Met
            20                  25                  30

Gly Leu

<210> SEQ ID NO 413

```
<211> LENGTH: 34
<212> TYPE: PRT
<213> ORGANISM: artificial
<220> FEATURE:
<223> OTHER INFORMATION: SP-C FF Ion Lock + L R20/D24

<400> SEQUENCE: 413

Gly Ile Pro Phe Phe Pro Val His Leu Lys Arg Leu Leu Ile Val Val
1               5                   10                  15

Val Val Val Arg Leu Ile Val Asp Val Ile Val Gly Ala Leu Leu Met
            20                  25                  30

Gly Leu

<210> SEQ ID NO 414
<211> LENGTH: 34
<212> TYPE: PRT
<213> ORGANISM: artificial
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: Xaa is an uncharged amino acid
<220> FEATURE:
<221> NAME/KEY: MISC_FEATURE
<222> LOCATION: (4)..(4)
<223> OTHER INFORMATION: Xaa is an uncharged amino acid
<220> FEATURE:
<221> NAME/KEY: MISC_FEATURE
<222> LOCATION: (14)..(14)
<223> OTHER INFORMATION: Xaa is Leu, Ile, or Nle
<220> FEATURE:
<221> NAME/KEY: MISC_FEATURE
<222> LOCATION: (16)..(19)
<223> OTHER INFORMATION: Xaa represents a turn or loop sequence
      containing four to ten amino acids which can include Pro Lys Gly
      Gly, Asp Ala Thr Lys, Asp His Gly Ser, His Ser Gly Asp, or Glu
      Ala Gly Asp
<220> FEATURE:
<221> NAME/KEY: MISC_FEATURE
<222> LOCATION: (21)..(21)
<223> OTHER INFORMATION: Xaa is Leu, Ile, or Nle
<220> FEATURE:
<221> NAME/KEY: MISC_FEATURE
<222> LOCATION: (27)..(27)
<223> OTHER INFORMATION: Xaa is an uncharged amino acid
<220> FEATURE:
<221> NAME/KEY: MISC_FEATURE
<222> LOCATION: (33)..(33)
<223> OTHER INFORMATION: Xaa is an uncharged amino acid

<400> SEQUENCE: 414

Xaa Trp Leu Xaa Arg Ala Leu Ile Lys Arg Ile Gln Ala Xaa Ile Xaa
1               5                   10                  15

Xaa Xaa Xaa Arg Xaa Leu Pro Gln Leu Val Xaa Arg Leu Val Leu Arg
            20                  25                  30

Xaa Ser

<210> SEQ ID NO 415
<211> LENGTH: 34
<212> TYPE: PRT
<213> ORGANISM: artificial
<220> FEATURE:
<223> OTHER INFORMATION: L.MB_ala

<400> SEQUENCE: 415

Ala Trp Leu Ala Arg Ala Leu Ile Lys Arg Ile Gln Ala Leu Ile Pro
1               5                   10                  15

Lys Gly Gly Arg Leu Leu Pro Gln Leu Val Ala Arg Leu Val Leu Arg
```

20                  25                  30

Ala Ser

<210> SEQ ID NO 416
<211> LENGTH: 34
<212> TYPE: PRT
<213> ORGANISM: artificial
<220> FEATURE:
<223> OTHER INFORMATION: L.MB_ser

<400> SEQUENCE: 416

Ser Trp Leu Ser Arg Ala Leu Ile Lys Arg Ile Gln Ala Leu Ile Pro
1               5                   10                  15

Lys Gly Gly Arg Leu Leu Pro Gln Leu Val Ser Arg Leu Val Leu Arg
                    20                  25                  30

Ser Ser

<210> SEQ ID NO 417
<211> LENGTH: 34
<212> TYPE: PRT
<213> ORGANISM: artificial
<220> FEATURE:
<223> OTHER INFORMATION: L.MB_datk

<400> SEQUENCE: 417

Cys Trp Leu Cys Arg Ala Leu Ile Lys Arg Ile Gln Ala Leu Ile Asp
1               5                   10                  15

Ala Thr Lys Arg Leu Leu Pro Gln Leu Val Cys Arg Leu Val Leu Arg
                    20                  25                  30

Cys Ser

<210> SEQ ID NO 418
<211> LENGTH: 34
<212> TYPE: PRT
<213> ORGANISM: artificial
<220> FEATURE:
<223> OTHER INFORMATION: L.MB_datk_ala

<400> SEQUENCE: 418

Ala Trp Leu Ala Arg Ala Leu Ile Lys Arg Ile Gln Ala Leu Ile Asp
1               5                   10                  15

Ala Thr Lys Arg Leu Leu Pro Gln Leu Val Ala Arg Leu Val Leu Arg
                    20                  25                  30

Ala Ser

<210> SEQ ID NO 419
<211> LENGTH: 34
<212> TYPE: PRT
<213> ORGANISM: artificial
<220> FEATURE:
<223> OTHER INFORMATION: L.MB_datk_ser

<400> SEQUENCE: 419

Ser Trp Leu Ser Arg Ala Leu Ile Lys Arg Ile Gln Ala Leu Ile Asp
1               5                   10                  15

Ala Thr Lys Arg Leu Leu Pro Gln Leu Val Ser Arg Leu Val Leu Arg
                    20                  25                  30

Ser Ser

<210> SEQ ID NO 420
<211> LENGTH: 34

```
<212> TYPE: PRT
<213> ORGANISM: artificial
<220> FEATURE:
<223> OTHER INFORMATION: L.MB_dhgs

<400> SEQUENCE: 420

Cys Trp Leu Cys Arg Ala Leu Ile Lys Arg Ile Gln Ala Leu Ile Asp
1               5                   10                  15

His Gly Ser Arg Leu Leu Pro Gln Leu Val Cys Arg Leu Val Leu Arg
            20                  25                  30

Cys Ser

<210> SEQ ID NO 421
<211> LENGTH: 34
<212> TYPE: PRT
<213> ORGANISM: artificial
<220> FEATURE:
<223> OTHER INFORMATION: L.MB_dhgs_ala

<400> SEQUENCE: 421

Ala Trp Leu Ala Arg Ala Leu Ile Lys Arg Ile Gln Ala Leu Ile Asp
1               5                   10                  15

His Gly Ser Arg Leu Leu Pro Gln Leu Val Ala Arg Leu Val Leu Arg
            20                  25                  30

Ala Ser

<210> SEQ ID NO 422
<211> LENGTH: 34
<212> TYPE: PRT
<213> ORGANISM: artificial
<220> FEATURE:
<223> OTHER INFORMATION: L.MB_dhgs_ser

<400> SEQUENCE: 422

Ser Trp Leu Ser Arg Ala Leu Ile Lys Arg Ile Gln Ala Leu Ile Asp
1               5                   10                  15

His Gly Ser Arg Leu Leu Pro Gln Leu Val Ser Arg Leu Val Leu Arg
            20                  25                  30

Ser Ser

<210> SEQ ID NO 423
<211> LENGTH: 34
<212> TYPE: PRT
<213> ORGANISM: artificial
<220> FEATURE:
<223> OTHER INFORMATION: L.MB_hsgd

<400> SEQUENCE: 423

Cys Trp Leu Cys Arg Ala Leu Ile Lys Arg Ile Gln Ala Leu Ile His
1               5                   10                  15

Ser Gly Asp Arg Leu Leu Pro Gln Leu Val Cys Arg Leu Val Leu Arg
            20                  25                  30

Cys Ser

<210> SEQ ID NO 424
<211> LENGTH: 34
<212> TYPE: PRT
<213> ORGANISM: artificial
<220> FEATURE:
<223> OTHER INFORMATION: L.MB_hsgd_ala

<400> SEQUENCE: 424
```

```
Ala Trp Leu Ala Arg Ala Leu Ile Lys Arg Ile Gln Ala Leu Ile His
1               5                   10                  15

Ser Gly Asp Arg Leu Leu Pro Gln Leu Val Ala Arg Leu Val Leu Arg
            20                  25                  30

Ala Ser

<210> SEQ ID NO 425
<211> LENGTH: 34
<212> TYPE: PRT
<213> ORGANISM: artificial
<220> FEATURE:
<223> OTHER INFORMATION: L.MB_hsgd_ser

<400> SEQUENCE: 425

Ser Trp Leu Ser Arg Ala Leu Ile Lys Arg Ile Gln Ala Leu Ile His
1               5                   10                  15

Ser Gly Asp Arg Leu Leu Pro Gln Leu Val Ser Arg Leu Val Leu Arg
            20                  25                  30

Ser Ser

<210> SEQ ID NO 426
<211> LENGTH: 34
<212> TYPE: PRT
<213> ORGANISM: artificial
<220> FEATURE:
<223> OTHER INFORMATION: L.MB_eagd

<400> SEQUENCE: 426

Cys Trp Leu Cys Arg Ala Leu Ile Lys Arg Ile Gln Ala Leu Ile Glu
1               5                   10                  15

Ala Gly Asp Arg Leu Leu Pro Gln Leu Val Cys Arg Leu Val Leu Arg
            20                  25                  30

Cys Ser

<210> SEQ ID NO 427
<211> LENGTH: 34
<212> TYPE: PRT
<213> ORGANISM: artificial
<220> FEATURE:
<223> OTHER INFORMATION: L.MB_eagd_ala

<400> SEQUENCE: 427

Ala Trp Leu Ala Arg Ala Leu Ile Lys Arg Ile Gln Ala Leu Ile Glu
1               5                   10                  15

Ala Gly Asp Arg Leu Leu Pro Gln Leu Val Ala Arg Leu Val Leu Arg
            20                  25                  30

Ala Ser

<210> SEQ ID NO 428
<211> LENGTH: 34
<212> TYPE: PRT
<213> ORGANISM: artificial
<220> FEATURE:
<223> OTHER INFORMATION: L.MB_eagd_ser

<400> SEQUENCE: 428

Ser Trp Leu Ser Arg Ala Leu Ile Lys Arg Ile Gln Ala Leu Ile Glu
1               5                   10                  15

Ala Gly Asp Arg Leu Leu Pro Gln Leu Val Ser Arg Leu Val Leu Arg
            20                  25                  30

Ser Ser
```

<210> SEQ ID NO 429
<211> LENGTH: 41
<212> TYPE: PRT
<213> ORGANISM: artificial
<220> FEATURE:
<223> OTHER INFORMATION: L.SMB_ala

<400> SEQUENCE: 429

Phe Pro Ile Pro Leu Pro Tyr Ala Trp Leu Ala Arg Ala Leu Ile Lys
1               5                   10                  15

Arg Ile Gln Ala Leu Ile Pro Lys Gly Gly Arg Leu Leu Pro Gln Leu
            20                  25                  30

Val Ala Arg Leu Val Leu Arg Ala Ser
        35                  40

<210> SEQ ID NO 430
<211> LENGTH: 41
<212> TYPE: PRT
<213> ORGANISM: artificial
<220> FEATURE:
<223> OTHER INFORMATION: L.SMB_ser

<400> SEQUENCE: 430

Phe Pro Ile Pro Leu Pro Tyr Ser Trp Leu Ser Arg Ala Leu Ile Lys
1               5                   10                  15

Arg Ile Gln Ala Leu Ile Pro Lys Gly Gly Arg Leu Leu Pro Gln Leu
            20                  25                  30

Val Ser Arg Leu Val Leu Arg Ser Ser
        35                  40

<210> SEQ ID NO 431
<211> LENGTH: 41
<212> TYPE: PRT
<213> ORGANISM: artificial
<220> FEATURE:
<223> OTHER INFORMATION: L.SMB_datk

<400> SEQUENCE: 431

Phe Pro Ile Pro Leu Pro Tyr Cys Trp Leu Cys Arg Ala Leu Ile Lys
1               5                   10                  15

Arg Ile Gln Ala Leu Ile Asp Ala Thr Lys Arg Leu Leu Pro Gln Leu
            20                  25                  30

Val Cys Arg Leu Val Leu Arg Cys Ser
        35                  40

<210> SEQ ID NO 432
<211> LENGTH: 41
<212> TYPE: PRT
<213> ORGANISM: artificial
<220> FEATURE:
<223> OTHER INFORMATION: L.SMB_datk_ala

<400> SEQUENCE: 432

Phe Pro Ile Pro Leu Pro Tyr Ala Trp Leu Ala Arg Ala Leu Ile Lys
1               5                   10                  15

Arg Ile Gln Ala Leu Ile Asp Ala Thr Lys Arg Leu Leu Pro Gln Leu
            20                  25                  30

Val Ala Arg Leu Val Leu Arg Ala Ser
        35                  40

<210> SEQ ID NO 433

<211> LENGTH: 41
<212> TYPE: PRT
<213> ORGANISM: artificial
<220> FEATURE:
<223> OTHER INFORMATION: L.SMB_datk_ser

<400> SEQUENCE: 433

Phe Pro Ile Pro Leu Pro Tyr Ser Trp Leu Ser Arg Ala Leu Ile Lys
1               5                   10                  15
Arg Ile Gln Ala Leu Ile Asp Ala Thr Lys Arg Leu Leu Pro Gln Leu
            20                  25                  30
Val Ser Arg Leu Val Leu Arg Ser Ser
        35                  40

<210> SEQ ID NO 434
<211> LENGTH: 41
<212> TYPE: PRT
<213> ORGANISM: artificial
<220> FEATURE:
<223> OTHER INFORMATION: L.SMB_dhgs

<400> SEQUENCE: 434

Phe Pro Ile Pro Leu Pro Tyr Cys Trp Leu Cys Arg Ala Leu Ile Lys
1               5                   10                  15
Arg Ile Gln Ala Leu Ile Asp His Gly Ser Arg Leu Leu Pro Gln Leu
            20                  25                  30
Val Cys Arg Leu Val Leu Arg Cys Ser
        35                  40

<210> SEQ ID NO 435
<211> LENGTH: 41
<212> TYPE: PRT
<213> ORGANISM: artificial
<220> FEATURE:
<223> OTHER INFORMATION: L.SMB_dhgs_ala

<400> SEQUENCE: 435

Phe Pro Ile Pro Leu Pro Tyr Ala Trp Leu Ala Arg Ala Leu Ile Lys
1               5                   10                  15
Arg Ile Gln Ala Leu Ile Asp His Gly Ser Arg Leu Leu Pro Gln Leu
            20                  25                  30
Val Ala Arg Leu Val Leu Arg Ala Ser
        35                  40

<210> SEQ ID NO 436
<211> LENGTH: 41
<212> TYPE: PRT
<213> ORGANISM: artificial
<220> FEATURE:
<223> OTHER INFORMATION: L.SMB_dhgs_ser

<400> SEQUENCE: 436

Phe Pro Ile Pro Leu Pro Tyr Ser Trp Leu Ser Arg Ala Leu Ile Lys
1               5                   10                  15
Arg Ile Gln Ala Leu Ile Asp His Gly Ser Arg Leu Leu Pro Gln Leu
            20                  25                  30
Val Ser Arg Leu Val Leu Arg Ser Ser
        35                  40

<210> SEQ ID NO 437
<211> LENGTH: 41
<212> TYPE: PRT
<213> ORGANISM: artificial

```
<220> FEATURE:
<223> OTHER INFORMATION: L.SMB_hsgd

<400> SEQUENCE: 437

Phe Pro Ile Pro Leu Pro Tyr Cys Trp Leu Cys Arg Ala Leu Ile Lys
1               5                   10                  15

Arg Ile Gln Ala Leu Ile His Ser Gly Asp Arg Leu Leu Pro Gln Leu
            20                  25                  30

Val Cys Arg Leu Val Leu Arg Cys Ser
        35                  40

<210> SEQ ID NO 438
<211> LENGTH: 41
<212> TYPE: PRT
<213> ORGANISM: artificial
<220> FEATURE:
<223> OTHER INFORMATION: L.SMB_hsgd_ala

<400> SEQUENCE: 438

Phe Pro Ile Pro Leu Pro Tyr Ala Trp Leu Ala Arg Ala Leu Ile Lys
1               5                   10                  15

Arg Ile Gln Ala Leu Ile His Ser Gly Asp Arg Leu Leu Pro Gln Leu
            20                  25                  30

Val Ala Arg Leu Val Leu Arg Ala Ser
        35                  40

<210> SEQ ID NO 439
<211> LENGTH: 41
<212> TYPE: PRT
<213> ORGANISM: artificial
<220> FEATURE:
<223> OTHER INFORMATION: L.SMB_hsgd_ser

<400> SEQUENCE: 439

Phe Pro Ile Pro Leu Pro Tyr Ser Trp Leu Ser Arg Ala Leu Ile Lys
1               5                   10                  15

Arg Ile Gln Ala Leu Ile His Ser Gly Asp Arg Leu Leu Pro Gln Leu
            20                  25                  30

Val Ser Arg Leu Val Leu Arg Ser Ser
        35                  40

<210> SEQ ID NO 440
<211> LENGTH: 41
<212> TYPE: PRT
<213> ORGANISM: artificial
<220> FEATURE:
<223> OTHER INFORMATION: L.SMB_eagd

<400> SEQUENCE: 440

Phe Pro Ile Pro Leu Pro Tyr Cys Trp Leu Cys Arg Ala Leu Ile Lys
1               5                   10                  15

Arg Ile Gln Ala Leu Ile Glu Ala Gly Asp Arg Leu Leu Pro Gln Leu
            20                  25                  30

Val Cys Arg Leu Val Leu Arg Cys Ser
        35                  40

<210> SEQ ID NO 441
<211> LENGTH: 41
<212> TYPE: PRT
<213> ORGANISM: artificial
<220> FEATURE:
<223> OTHER INFORMATION: L.SMB_eagd_ala
```

-continued

<400> SEQUENCE: 441

Phe Pro Ile Pro Leu Pro Tyr Ala Trp Leu Ala Arg Ala Leu Ile Lys
1               5                   10                  15

Arg Ile Gln Ala Leu Ile Glu Ala Gly Asp Arg Leu Leu Pro Gln Leu
            20                  25                  30

Val Ala Arg Leu Val Leu Arg Ala Ser
        35                  40

<210> SEQ ID NO 442
<211> LENGTH: 41
<212> TYPE: PRT
<213> ORGANISM: artificial
<220> FEATURE:
<223> OTHER INFORMATION: L.SMB_eagd_ser

<400> SEQUENCE: 442

Phe Pro Ile Pro Leu Pro Tyr Ser Trp Leu Ser Arg Ala Leu Ile Lys
1               5                   10                  15

Arg Ile Gln Ala Leu Ile Glu Ala Gly Asp Arg Leu Leu Pro Gln Leu
            20                  25                  30

Val Ser Arg Leu Val Leu Arg Ser Ser
        35                  40

<210> SEQ ID NO 443
<211> LENGTH: 34
<212> TYPE: PRT
<213> ORGANISM: artificial
<220> FEATURE:
<223> OTHER INFORMATION: I.MB_ala

<400> SEQUENCE: 443

Ala Trp Leu Ala Arg Ala Leu Ile Lys Arg Ile Gln Ala Ile Ile Pro
1               5                   10                  15

Lys Gly Gly Arg Ile Leu Pro Gln Leu Val Ala Arg Leu Val Leu Arg
            20                  25                  30

Ala Ser

<210> SEQ ID NO 444
<211> LENGTH: 34
<212> TYPE: PRT
<213> ORGANISM: artificial
<220> FEATURE:
<223> OTHER INFORMATION: I.MB_ser

<400> SEQUENCE: 444

Ser Trp Leu Ser Arg Ala Leu Ile Lys Arg Ile Gln Ala Ile Ile Pro
1               5                   10                  15

Lys Gly Gly Arg Ile Leu Pro Gln Leu Val Ser Arg Leu Val Leu Arg
            20                  25                  30

Ser Ser

<210> SEQ ID NO 445
<211> LENGTH: 34
<212> TYPE: PRT
<213> ORGANISM: artificial
<220> FEATURE:
<223> OTHER INFORMATION: I.MB_datk

<400> SEQUENCE: 445

Cys Trp Leu Cys Arg Ala Leu Ile Lys Arg Ile Gln Ala Ile Ile Asp
1               5                   10                  15

Ala Thr Lys Arg Ile Leu Pro Gln Leu Val Cys Arg Leu Val Leu Arg
            20                  25                  30

Cys Ser

<210> SEQ ID NO 446
<211> LENGTH: 34
<212> TYPE: PRT
<213> ORGANISM: artificial
<220> FEATURE:
<223> OTHER INFORMATION: I.MB_datk_ala

<400> SEQUENCE: 446

Ala Trp Leu Ala Arg Ala Leu Ile Lys Arg Ile Gln Ala Ile Ile Asp
1               5                   10                  15

Ala Thr Lys Arg Ile Leu Pro Gln Leu Val Ala Arg Leu Val Leu Arg
            20                  25                  30

Ala Ser

<210> SEQ ID NO 447
<211> LENGTH: 34
<212> TYPE: PRT
<213> ORGANISM: artificial
<220> FEATURE:
<223> OTHER INFORMATION: I.MB_datk_ser

<400> SEQUENCE: 447

Ser Trp Leu Ser Arg Ala Leu Ile Lys Arg Ile Gln Ala Ile Ile Asp
1               5                   10                  15

Ala Thr Lys Arg Ile Leu Pro Gln Leu Val Ser Arg Leu Val Leu Arg
            20                  25                  30

Ser Ser

<210> SEQ ID NO 448
<211> LENGTH: 34
<212> TYPE: PRT
<213> ORGANISM: artificial
<220> FEATURE:
<223> OTHER INFORMATION: I.MB_dhgs

<400> SEQUENCE: 448

Cys Trp Leu Cys Arg Ala Leu Ile Lys Arg Ile Gln Ala Ile Ile Asp
1               5                   10                  15

His Gly Ser Arg Ile Leu Pro Gln Leu Val Cys Arg Leu Val Leu Arg
            20                  25                  30

Cys Ser

<210> SEQ ID NO 449
<211> LENGTH: 34
<212> TYPE: PRT
<213> ORGANISM: artificial
<220> FEATURE:
<223> OTHER INFORMATION: I.MB_dhgs_ala

<400> SEQUENCE: 449

Ala Trp Leu Ala Arg Ala Leu Ile Lys Arg Ile Gln Ala Ile Ile Asp
1               5                   10                  15

His Gly Ser Arg Ile Leu Pro Gln Leu Val Ala Arg Leu Val Leu Arg
            20                  25                  30

Ala Ser

<210> SEQ ID NO 450

-continued

```
<211> LENGTH: 34
<212> TYPE: PRT
<213> ORGANISM: artificial
<220> FEATURE:
<223> OTHER INFORMATION: I.MB_dhgs_ser

<400> SEQUENCE: 450

Ser Trp Leu Ser Arg Ala Leu Ile Lys Arg Ile Gln Ala Ile Ile Asp
1               5                   10                  15

His Gly Ser Arg Ile Leu Pro Gln Leu Val Ser Arg Leu Val Leu Arg
            20                  25                  30

Ser Ser

<210> SEQ ID NO 451
<211> LENGTH: 34
<212> TYPE: PRT
<213> ORGANISM: artificial
<220> FEATURE:
<223> OTHER INFORMATION: I.MB_hsgd

<400> SEQUENCE: 451

Cys Trp Leu Cys Arg Ala Leu Ile Lys Arg Ile Gln Ala Ile Ile His
1               5                   10                  15

Ser Gly Asp Arg Ile Leu Pro Gln Leu Val Cys Arg Leu Val Leu Arg
            20                  25                  30

Cys Ser

<210> SEQ ID NO 452
<211> LENGTH: 34
<212> TYPE: PRT
<213> ORGANISM: artificial
<220> FEATURE:
<223> OTHER INFORMATION: I.MB_hsgd_ala

<400> SEQUENCE: 452

Ala Trp Leu Ala Arg Ala Leu Ile Lys Arg Ile Gln Ala Ile Ile His
1               5                   10                  15

Ser Gly Asp Arg Ile Leu Pro Gln Leu Val Ala Arg Leu Val Leu Arg
            20                  25                  30

Ala Ser

<210> SEQ ID NO 453
<211> LENGTH: 34
<212> TYPE: PRT
<213> ORGANISM: artificial
<220> FEATURE:
<223> OTHER INFORMATION: I.MB_hsgd_ser

<400> SEQUENCE: 453

Ser Trp Leu Ser Arg Ala Leu Ile Lys Arg Ile Gln Ala Ile Ile His
1               5                   10                  15

Ser Gly Asp Arg Ile Leu Pro Gln Leu Val Ser Arg Leu Val Leu Arg
            20                  25                  30

Ser Ser

<210> SEQ ID NO 454
<211> LENGTH: 34
<212> TYPE: PRT
<213> ORGANISM: artificial
<220> FEATURE:
<223> OTHER INFORMATION: I.MB_eagd

<400> SEQUENCE: 454
```

Cys Trp Leu Cys Arg Ala Leu Ile Lys Arg Ile Gln Ala Ile Ile Glu
1               5                   10                  15

Ala Gly Asp Arg Ile Leu Pro Gln Leu Val Cys Arg Leu Val Leu Arg
            20                  25                  30

Cys Ser

<210> SEQ ID NO 455
<211> LENGTH: 34
<212> TYPE: PRT
<213> ORGANISM: artificial
<220> FEATURE:
<223> OTHER INFORMATION: I.MB_eagd_ala

<400> SEQUENCE: 455

Ala Trp Leu Ala Arg Ala Leu Ile Lys Arg Ile Gln Ala Ile Ile Glu
1               5                   10                  15

Ala Gly Asp Arg Ile Leu Pro Gln Leu Val Ala Arg Leu Val Leu Arg
            20                  25                  30

Ala Ser

<210> SEQ ID NO 456
<211> LENGTH: 34
<212> TYPE: PRT
<213> ORGANISM: artificial
<220> FEATURE:
<223> OTHER INFORMATION: I.MB_eagd_ser

<400> SEQUENCE: 456

Ser Trp Leu Ser Arg Ala Leu Ile Lys Arg Ile Gln Ala Ile Ile Glu
1               5                   10                  15

Ala Gly Asp Arg Ile Leu Pro Gln Leu Val Ser Arg Leu Val Leu Arg
            20                  25                  30

Ser Ser

<210> SEQ ID NO 457
<211> LENGTH: 41
<212> TYPE: PRT
<213> ORGANISM: artificial
<220> FEATURE:
<223> OTHER INFORMATION: I.SMB_ala

<400> SEQUENCE: 457

Phe Pro Ile Pro Leu Pro Tyr Ala Trp Leu Ala Arg Ala Leu Ile Lys
1               5                   10                  15

Arg Ile Gln Ala Ile Ile Pro Lys Gly Gly Arg Ile Leu Pro Gln Leu
            20                  25                  30

Val Ala Arg Leu Val Leu Arg Ala Ser
        35                  40

<210> SEQ ID NO 458
<211> LENGTH: 41
<212> TYPE: PRT
<213> ORGANISM: artificial
<220> FEATURE:
<223> OTHER INFORMATION: I.SMB_ser

<400> SEQUENCE: 458

Phe Pro Ile Pro Leu Pro Tyr Ser Trp Leu Ser Arg Ala Leu Ile Lys
1               5                   10                  15

Arg Ile Gln Ala Ile Ile Pro Lys Gly Gly Arg Ile Leu Pro Gln Leu
            20                  25                  30

Val Ser Arg Leu Val Leu Arg Ser Ser
        35                  40

<210> SEQ ID NO 459
<211> LENGTH: 41
<212> TYPE: PRT
<213> ORGANISM: artificial
<220> FEATURE:
<223> OTHER INFORMATION: I.SMB_datk

<400> SEQUENCE: 459

Phe Pro Ile Pro Leu Pro Tyr Cys Trp Leu Cys Arg Ala Leu Ile Lys
1               5                   10                  15

Arg Ile Gln Ala Ile Ile Asp Ala Thr Lys Arg Ile Leu Pro Gln Leu
            20                  25                  30

Val Cys Arg Leu Val Leu Arg Cys Ser
        35                  40

<210> SEQ ID NO 460
<211> LENGTH: 41
<212> TYPE: PRT
<213> ORGANISM: artificial
<220> FEATURE:
<223> OTHER INFORMATION: I.SMB_datk_ala

<400> SEQUENCE: 460

Phe Pro Ile Pro Leu Pro Tyr Ala Trp Leu Ala Arg Ala Leu Ile Lys
1               5                   10                  15

Arg Ile Gln Ala Ile Ile Asp Ala Thr Lys Arg Ile Leu Pro Gln Leu
            20                  25                  30

Val Ala Arg Leu Val Leu Arg Ala Ser
        35                  40

<210> SEQ ID NO 461
<211> LENGTH: 41
<212> TYPE: PRT
<213> ORGANISM: artificial
<220> FEATURE:
<223> OTHER INFORMATION: I.SMB_datk_ser

<400> SEQUENCE: 461

Phe Pro Ile Pro Leu Pro Tyr Ser Trp Leu Ser Arg Ala Leu Ile Lys
1               5                   10                  15

Arg Ile Gln Ala Ile Ile Asp Ala Thr Lys Arg Ile Leu Pro Gln Leu
            20                  25                  30

Val Ser Arg Leu Val Leu Arg Ser Ser
        35                  40

<210> SEQ ID NO 462
<211> LENGTH: 41
<212> TYPE: PRT
<213> ORGANISM: artificial
<220> FEATURE:
<223> OTHER INFORMATION: I.SMB_dhgs

<400> SEQUENCE: 462

Phe Pro Ile Pro Leu Pro Tyr Cys Trp Leu Cys Arg Ala Leu Ile Lys
1               5                   10                  15

Arg Ile Gln Ala Ile Ile Asp His Gly Ser Arg Ile Leu Pro Gln Leu
            20                  25                  30

Val Cys Arg Leu Val Leu Arg Cys Ser
        35                  40

<210> SEQ ID NO 463
<211> LENGTH: 41
<212> TYPE: PRT
<213> ORGANISM: artificial
<220> FEATURE:
<223> OTHER INFORMATION: I.SMB_dhgs_ala

<400> SEQUENCE: 463

Phe Pro Ile Pro Leu Pro Tyr Ala Trp Leu Ala Arg Ala Leu Ile Lys
1               5                   10                  15

Arg Ile Gln Ala Ile Ile Asp His Gly Ser Arg Ile Leu Pro Gln Leu
            20                  25                  30

Val Ala Arg Leu Val Leu Arg Ala Ser
        35                  40

<210> SEQ ID NO 464
<211> LENGTH: 41
<212> TYPE: PRT
<213> ORGANISM: artificial
<220> FEATURE:
<223> OTHER INFORMATION: I.SMB_dhgs_ser

<400> SEQUENCE: 464

Phe Pro Ile Pro Leu Pro Tyr Ser Trp Leu Ser Arg Ala Leu Ile Lys
1               5                   10                  15

Arg Ile Gln Ala Ile Ile Asp His Gly Ser Arg Ile Leu Pro Gln Leu
            20                  25                  30

Val Ser Arg Leu Val Leu Arg Ser Ser
        35                  40

<210> SEQ ID NO 465
<211> LENGTH: 41
<212> TYPE: PRT
<213> ORGANISM: artificial
<220> FEATURE:
<223> OTHER INFORMATION: I.SMB_hsgd

<400> SEQUENCE: 465

Phe Pro Ile Pro Leu Pro Tyr Cys Trp Leu Cys Arg Ala Leu Ile Lys
1               5                   10                  15

Arg Ile Gln Ala Ile Ile His Ser Gly Asp Arg Ile Leu Pro Gln Leu
            20                  25                  30

Val Cys Arg Leu Val Leu Arg Cys Ser
        35                  40

<210> SEQ ID NO 466
<211> LENGTH: 41
<212> TYPE: PRT
<213> ORGANISM: artificial
<220> FEATURE:
<223> OTHER INFORMATION: I.SMB_hsgd_ala

<400> SEQUENCE: 466

Phe Pro Ile Pro Leu Pro Tyr Ala Trp Leu Ala Arg Ala Leu Ile Lys
1               5                   10                  15

Arg Ile Gln Ala Ile Ile His Ser Gly Asp Arg Ile Leu Pro Gln Leu
            20                  25                  30

Val Ala Arg Leu Val Leu Arg Ala Ser
        35                  40

<210> SEQ ID NO 467

```
<211> LENGTH: 41
<212> TYPE: PRT
<213> ORGANISM: artificial
<220> FEATURE:
<223> OTHER INFORMATION: I.SMB_hsgd_ser

<400> SEQUENCE: 467

Phe Pro Ile Pro Leu Pro Tyr Ser Trp Leu Ser Arg Ala Leu Ile Lys
1               5                   10                  15

Arg Ile Gln Ala Ile Ile His Ser Gly Asp Arg Ile Leu Pro Gln Leu
            20                  25                  30

Val Ser Arg Leu Val Leu Arg Ser Ser
        35                  40

<210> SEQ ID NO 468
<211> LENGTH: 41
<212> TYPE: PRT
<213> ORGANISM: artificial
<220> FEATURE:
<223> OTHER INFORMATION: I.SMB_eagd

<400> SEQUENCE: 468

Phe Pro Ile Pro Leu Pro Tyr Cys Trp Leu Cys Arg Ala Leu Ile Lys
1               5                   10                  15

Arg Ile Gln Ala Ile Ile Glu Ala Gly Asp Arg Ile Leu Pro Gln Leu
            20                  25                  30

Val Cys Arg Leu Val Leu Arg Cys Ser
        35                  40

<210> SEQ ID NO 469
<211> LENGTH: 41
<212> TYPE: PRT
<213> ORGANISM: artificial
<220> FEATURE:
<223> OTHER INFORMATION: I.SMB_eagd_ala

<400> SEQUENCE: 469

Phe Pro Ile Pro Leu Pro Tyr Ala Trp Leu Ala Arg Ala Leu Ile Lys
1               5                   10                  15

Arg Ile Gln Ala Ile Ile Glu Ala Gly Asp Arg Ile Leu Pro Gln Leu
            20                  25                  30

Val Ala Arg Leu Val Leu Arg Ala Ser
        35                  40

<210> SEQ ID NO 470
<211> LENGTH: 41
<212> TYPE: PRT
<213> ORGANISM: artificial
<220> FEATURE:
<223> OTHER INFORMATION: I.SMB_eagd_ser

<400> SEQUENCE: 470

Phe Pro Ile Pro Leu Pro Tyr Ser Trp Leu Ser Arg Ala Leu Ile Lys
1               5                   10                  15

Arg Ile Gln Ala Ile Ile Glu Ala Gly Asp Arg Ile Leu Pro Gln Leu
            20                  25                  30

Val Ser Arg Leu Val Leu Arg Ser Ser
        35                  40

<210> SEQ ID NO 471
<211> LENGTH: 34
<212> TYPE: PRT
<213> ORGANISM: artificial
```

```
<220> FEATURE:
<223> OTHER INFORMATION: Nle.MB_ala
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 471

Ala Trp Leu Ala Arg Ala Leu Ile Lys Arg Ile Gln Ala Xaa Ile Pro
1               5                   10                  15

Lys Gly Gly Arg Xaa Leu Pro Gln Leu Val Ala Arg Leu Val Leu Arg
            20                  25                  30

Ala Ser

<210> SEQ ID NO 472
<211> LENGTH: 34
<212> TYPE: PRT
<213> ORGANISM: artificial
<220> FEATURE:
<223> OTHER INFORMATION: Nle.MB_ser
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 472

Ser Trp Leu Ser Arg Ala Leu Ile Lys Arg Ile Gln Ala Xaa Ile Pro
1               5                   10                  15

Lys Gly Gly Arg Xaa Leu Pro Gln Leu Val Ser Arg Leu Val Leu Arg
            20                  25                  30

Ser Ser

<210> SEQ ID NO 473
<211> LENGTH: 34
<212> TYPE: PRT
<213> ORGANISM: artificial
<220> FEATURE:
<223> OTHER INFORMATION: Nle.MB_datk
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 473

Cys Trp Leu Cys Arg Ala Leu Ile Lys Arg Ile Gln Ala Xaa Ile Asp
1               5                   10                  15

Ala Thr Lys Arg Xaa Leu Pro Gln Leu Val Cys Arg Leu Val Leu Arg
            20                  25                  30

Cys Ser

<210> SEQ ID NO 474
<211> LENGTH: 34
<212> TYPE: PRT
<213> ORGANISM: artificial
<220> FEATURE:
```

```
<223> OTHER INFORMATION: Nle.MB_datk_ala
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 474

Ala Trp Leu Ala Arg Ala Leu Ile Lys Arg Ile Gln Ala Xaa Ile Asp
1               5                   10                  15

Ala Thr Lys Arg Xaa Leu Pro Gln Leu Val Ala Arg Leu Val Leu Arg
            20                  25                  30

Ala Ser

<210> SEQ ID NO 475
<211> LENGTH: 34
<212> TYPE: PRT
<213> ORGANISM: artificial
<220> FEATURE:
<223> OTHER INFORMATION: Nle.MB_datk_ser
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 475

Ser Trp Leu Ser Arg Ala Leu Ile Lys Arg Ile Gln Ala Xaa Ile Asp
1               5                   10                  15

Ala Thr Lys Arg Xaa Leu Pro Gln Leu Val Ser Arg Leu Val Leu Arg
            20                  25                  30

Ser Ser

<210> SEQ ID NO 476
<211> LENGTH: 34
<212> TYPE: PRT
<213> ORGANISM: artificial
<220> FEATURE:
<223> OTHER INFORMATION: Nle.MB_dhgs
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 476

Cys Trp Leu Cys Arg Ala Leu Ile Lys Arg Ile Gln Ala Xaa Ile Asp
1               5                   10                  15

His Gly Ser Arg Xaa Leu Pro Gln Leu Val Cys Arg Leu Val Leu Arg
            20                  25                  30

Cys Ser

<210> SEQ ID NO 477
<211> LENGTH: 34
<212> TYPE: PRT
<213> ORGANISM: artificial
<220> FEATURE:
<223> OTHER INFORMATION: Nle.MB_dhgs_ala
```

-continued

```
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 477

Ala Trp Leu Ala Arg Ala Leu Ile Lys Arg Ile Gln Ala Xaa Ile Asp
1               5                   10                  15

His Gly Ser Arg Xaa Leu Pro Gln Leu Val Ala Arg Leu Val Leu Arg
            20                  25                  30

Ala Ser

<210> SEQ ID NO 478
<211> LENGTH: 34
<212> TYPE: PRT
<213> ORGANISM: artificial
<220> FEATURE:
<223> OTHER INFORMATION: Nle.MB_dhgs_ser
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 478

Ser Trp Leu Ser Arg Ala Leu Ile Lys Arg Ile Gln Ala Xaa Ile Asp
1               5                   10                  15

His Gly Ser Arg Xaa Leu Pro Gln Leu Val Ser Arg Leu Val Leu Arg
            20                  25                  30

Ser Ser

<210> SEQ ID NO 479
<211> LENGTH: 34
<212> TYPE: PRT
<213> ORGANISM: artificial
<220> FEATURE:
<223> OTHER INFORMATION: Nle.MB_hsgd
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 479

Cys Trp Leu Cys Arg Ala Leu Ile Lys Arg Ile Gln Ala Xaa Ile His
1               5                   10                  15

Ser Gly Asp Arg Xaa Leu Pro Gln Leu Val Cys Arg Leu Val Leu Arg
            20                  25                  30

Cys Ser

<210> SEQ ID NO 480
<211> LENGTH: 34
<212> TYPE: PRT
<213> ORGANISM: artificial
<220> FEATURE:
<223> OTHER INFORMATION: Nle.MB_hsgd_ala
<220> FEATURE:
```

```
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 480

Ala Trp Leu Ala Arg Ala Leu Ile Lys Arg Ile Gln Ala Xaa Ile His
1               5                   10                  15

Ser Gly Asp Arg Xaa Leu Pro Gln Leu Val Ala Arg Leu Val Leu Arg
            20                  25                  30

Ala Ser

<210> SEQ ID NO 481
<211> LENGTH: 34
<212> TYPE: PRT
<213> ORGANISM: artificial
<220> FEATURE:
<223> OTHER INFORMATION: Nle.MB_hsgd_ser
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 481

Ser Trp Leu Ser Arg Ala Leu Ile Lys Arg Ile Gln Ala Xaa Ile His
1               5                   10                  15

Ser Gly Asp Arg Xaa Leu Pro Gln Leu Val Ser Arg Leu Val Leu Arg
            20                  25                  30

Ser Ser

<210> SEQ ID NO 482
<211> LENGTH: 34
<212> TYPE: PRT
<213> ORGANISM: artificial
<220> FEATURE:
<223> OTHER INFORMATION: Nle.MB_eagd
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 482

Cys Trp Leu Cys Arg Ala Leu Ile Lys Arg Ile Gln Ala Xaa Ile Glu
1               5                   10                  15

Ala Gly Asp Arg Xaa Leu Pro Gln Leu Val Cys Arg Leu Val Leu Arg
            20                  25                  30

Cys Ser

<210> SEQ ID NO 483
<211> LENGTH: 34
<212> TYPE: PRT
<213> ORGANISM: artificial
<220> FEATURE:
<223> OTHER INFORMATION: Nle.MB_eagd_ala
<220> FEATURE:
<221> NAME/KEY: MISC_FEATURE
```

```
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 483

Ala Trp Leu Ala Arg Ala Leu Ile Lys Arg Ile Gln Ala Xaa Ile Glu
1               5                   10                  15

Ala Gly Asp Arg Xaa Leu Pro Gln Leu Val Ala Arg Leu Val Leu Arg
            20                  25                  30

Ala Ser

<210> SEQ ID NO 484
<211> LENGTH: 34
<212> TYPE: PRT
<213> ORGANISM: artificial
<220> FEATURE:
<223> OTHER INFORMATION: Nle.MB_eagd_ser
<220> FEATURE:
<221> NAME/KEY: MISC_FEATURE
<222> LOCATION: (14)..(14)
<223> OTHER INFORMATION: Xaa represents Nle
<220> FEATURE:
<221> NAME/KEY: MISC_FEATURE
<222> LOCATION: (21)..(21)
<223> OTHER INFORMATION: Xaa represents Nle

<400> SEQUENCE: 484

Ser Trp Leu Ser Arg Ala Leu Ile Lys Arg Ile Gln Ala Xaa Ile Glu
1               5                   10                  15

Ala Gly Asp Arg Xaa Leu Pro Gln Leu Val Ser Arg Leu Val Leu Arg
            20                  25                  30

Ser Ser

<210> SEQ ID NO 485
<211> LENGTH: 41
<212> TYPE: PRT
<213> ORGANISM: artificial
<220> FEATURE:
<223> OTHER INFORMATION: Nle.SMB_ala
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 485

Phe Pro Ile Pro Leu Pro Tyr Ala Trp Leu Ala Arg Ala Leu Ile Lys
1               5                   10                  15

Arg Ile Gln Ala Xaa Ile Pro Lys Gly Gly Arg Xaa Leu Pro Gln Leu
            20                  25                  30

Val Ala Arg Leu Val Leu Arg Ala Ser
            35                  40

<210> SEQ ID NO 486
<211> LENGTH: 41
<212> TYPE: PRT
<213> ORGANISM: artificial
<220> FEATURE:
<223> OTHER INFORMATION: Nle.SMB_ser
<220> FEATURE:
<221> NAME/KEY: MISC_FEATURE
```

<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 486

Phe Pro Ile Pro Leu Pro Tyr Ser Trp Leu Ser Arg Ala Leu Ile Lys
1               5                   10                  15

Arg Ile Gln Ala Xaa Ile Pro Lys Gly Gly Arg Xaa Leu Pro Gln Leu
            20                  25                  30

Val Ser Arg Leu Val Leu Arg Ser Ser
            35                  40

<210> SEQ ID NO 487
<211> LENGTH: 41
<212> TYPE: PRT
<213> ORGANISM: artificial
<220> FEATURE:
<223> OTHER INFORMATION: Nle.SMB_datk
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 487

Phe Pro Ile Pro Leu Pro Tyr Cys Trp Leu Cys Arg Ala Leu Ile Lys
1               5                   10                  15

Arg Ile Gln Ala Xaa Ile Asp Ala Thr Lys Arg Xaa Leu Pro Gln Leu
            20                  25                  30

Val Cys Arg Leu Val Leu Arg Cys Ser
            35                  40

<210> SEQ ID NO 488
<211> LENGTH: 41
<212> TYPE: PRT
<213> ORGANISM: artificial
<220> FEATURE:
<223> OTHER INFORMATION: Nle.SMB_datk_ala
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 488

Phe Pro Ile Pro Leu Pro Tyr Ala Trp Leu Ala Arg Ala Leu Ile Lys
1               5                   10                  15

Arg Ile Gln Ala Xaa Ile Asp Ala Thr Lys Arg Xaa Leu Pro Gln Leu
            20                  25                  30

Val Ala Arg Leu Val Leu Arg Ala Ser
            35                  40

<210> SEQ ID NO 489
<211> LENGTH: 41
<212> TYPE: PRT
<213> ORGANISM: artificial
<220> FEATURE:
<223> OTHER INFORMATION: Nle.SMB_datk_ser
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 489

Phe Pro Ile Pro Leu Pro Tyr Ser Trp Leu Ser Arg Ala Leu Ile Lys
1               5                   10                  15

Arg Ile Gln Ala Xaa Ile Asp Ala Thr Lys Arg Xaa Leu Pro Gln Leu
            20                  25                  30

Val Ser Arg Leu Val Leu Arg Ser Ser
        35                  40

<210> SEQ ID NO 490
<211> LENGTH: 41
<212> TYPE: PRT
<213> ORGANISM: artificial
<220> FEATURE:
<223> OTHER INFORMATION: Nle.SMB_dhgs
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 490

Phe Pro Ile Pro Leu Pro Tyr Cys Trp Leu Cys Arg Ala Leu Ile Lys
1               5                   10                  15

Arg Ile Gln Ala Xaa Ile Asp His Gly Ser Arg Xaa Leu Pro Gln Leu
            20                  25                  30

Val Cys Arg Leu Val Leu Arg Cys Ser
        35                  40

<210> SEQ ID NO 491
<211> LENGTH: 41
<212> TYPE: PRT
<213> ORGANISM: artificial
<220> FEATURE:
<223> OTHER INFORMATION: Nle.SMB_dhgs_ala
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 491

Phe Pro Ile Pro Leu Pro Tyr Ala Trp Leu Ala Arg Ala Leu Ile Lys
1               5                   10                  15

Arg Ile Gln Ala Xaa Ile Asp His Gly Ser Arg Xaa Leu Pro Gln Leu
            20                  25                  30

Val Ala Arg Leu Val Leu Arg Ala Ser
        35                  40

<210> SEQ ID NO 492
<211> LENGTH: 41
<212> TYPE: PRT
<213> ORGANISM: artificial

-continued

<220> FEATURE:
<223> OTHER INFORMATION: Nle.SMB_dhgs_ser
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 492

Phe Pro Ile Pro Leu Pro Tyr Ser Trp Leu Ser Arg Ala Leu Ile Lys
1               5                   10                  15

Arg Ile Gln Ala Xaa Ile Asp His Gly Ser Arg Xaa Leu Pro Gln Leu
            20                  25                  30

Val Ser Arg Leu Val Leu Arg Ser Ser
        35                  40

<210> SEQ ID NO 493
<211> LENGTH: 41
<212> TYPE: PRT
<213> ORGANISM: artificial
<220> FEATURE:
<223> OTHER INFORMATION: Nle.SMB_hsgd
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 493

Phe Pro Ile Pro Leu Pro Tyr Cys Trp Leu Cys Arg Ala Leu Ile Lys
1               5                   10                  15

Arg Ile Gln Ala Xaa Ile His Ser Gly Asp Arg Xaa Leu Pro Gln Leu
            20                  25                  30

Val Cys Arg Leu Val Leu Arg Cys Ser
        35                  40

<210> SEQ ID NO 494
<211> LENGTH: 41
<212> TYPE: PRT
<213> ORGANISM: artificial
<220> FEATURE:
<223> OTHER INFORMATION: Nle.SMB_hsgd_ala
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 494

Phe Pro Ile Pro Leu Pro Tyr Ala Trp Leu Ala Arg Ala Leu Ile Lys
1               5                   10                  15

Arg Ile Gln Ala Xaa Ile His Ser Gly Asp Arg Xaa Leu Pro Gln Leu
            20                  25                  30

Val Ala Arg Leu Val Leu Arg Ala Ser
        35                  40

<210> SEQ ID NO 495
<211> LENGTH: 41

```
<212> TYPE: PRT
<213> ORGANISM: artificial
<220> FEATURE:
<223> OTHER INFORMATION: Nle.SMB_hsgd_ser
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 495

Phe Pro Ile Pro Leu Pro Tyr Ser Trp Leu Ser Arg Ala Leu Ile Lys
1               5                   10                  15

Arg Ile Gln Ala Xaa Ile His Ser Gly Asp Arg Xaa Leu Pro Gln Leu
            20                  25                  30

Val Ser Arg Leu Val Leu Arg Ser Ser
            35                  40

<210> SEQ ID NO 496
<211> LENGTH: 41
<212> TYPE: PRT
<213> ORGANISM: artificial
<220> FEATURE:
<223> OTHER INFORMATION: Nle.SMB_eagd
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 496

Phe Pro Ile Pro Leu Pro Tyr Cys Trp Leu Cys Arg Ala Leu Ile Lys
1               5                   10                  15

Arg Ile Gln Ala Xaa Ile Glu Ala Gly Asp Arg Xaa Leu Pro Gln Leu
            20                  25                  30

Val Cys Arg Leu Val Leu Arg Cys Ser
            35                  40

<210> SEQ ID NO 497
<211> LENGTH: 41
<212> TYPE: PRT
<213> ORGANISM: artificial
<220> FEATURE:
<223> OTHER INFORMATION: Nle.SMB_eagd_ala
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 497

Phe Pro Ile Pro Leu Pro Tyr Ala Trp Leu Ala Arg Ala Leu Ile Lys
1               5                   10                  15

Arg Ile Gln Ala Xaa Ile Glu Ala Gly Asp Arg Xaa Leu Pro Gln Leu
            20                  25                  30

Val Ala Arg Leu Val Leu Arg Ala Ser
            35                  40
```

```
<210> SEQ ID NO 498
<211> LENGTH: 41
<212> TYPE: PRT
<213> ORGANISM: artificial
<220> FEATURE:
<223> OTHER INFORMATION: Nle.SMB_eagd_ser
<220> FEATURE:
<221> NAME/KEY: MISC_FEATURE
<222> LOCATION: (21)..(21)
<223> OTHER INFORMATION: Xaa represents Nle
<220> FEATURE:
<221> NAME/KEY: MISC_FEATURE
<222> LOCATION: (28)..(28)
<223> OTHER INFORMATION: Xaa represents Nle

<400> SEQUENCE: 498

Phe Pro Ile Pro Leu Pro Tyr Ser Trp Leu Ser Arg Ala Leu Ile Lys
1               5                   10                  15

Arg Ile Gln Ala Xaa Ile Glu Ala Gly Asp Arg Xaa Leu Pro Gln Leu
            20                  25                  30

Val Ser Arg Leu Val Leu Arg Ser Ser
        35                  40

<210> SEQ ID NO 499
<211> LENGTH: 102
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (1)..(3)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
<222> LOCATION: (10)..(12)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
<222> LOCATION: (40)..(42)
<223> OTHER INFORMATION: 3 n's can be CTT, CTC, CTA, CTG, TTA, TTG, ATT,
      ATC, or ATA FEATURE:
<221> NAME/KEY: misc_feature
<222> LOCATION: (46)..(48)
<223> OTHER INFORMATION: 3 n's can be any codon that encodes a turn or
      loop sequence containing at least four amino acids
<220> FEATURE:
<221> NAME/KEY: misc_feature
<222> LOCATION: (49)..(51)
<223> OTHER INFORMATION: 3 n's can be any codon that encodes a turn or
      loop sequence containing at least four amino acids
<220> FEATURE:
<221> NAME/KEY: misc_feature
<222> LOCATION: (52)..(54)
<223> OTHER INFORMATION: 3 n's can be any codon that encodes a turn or
      loop sequence containing at least four amino acids
<220> FEATURE:
<221> NAME/KEY: misc_feature
<222> LOCATION: (55)..(57)
<223> OTHER INFORMATION: 3 n's can be any codon that encodes a turn or
      loop sequence containing at least four amino acids
<220> FEATURE:
<221> NAME/KEY: misc_feature
<222> LOCATION: (61)..(63)
<223> OTHER INFORMATION: 3 n's can be CTT, CTC, CTA, CTG, TTA, TTG, ATT,
      ATC, or ATA
<220> FEATURE:
<221> NAME/KEY: misc_feature
<222> LOCATION: (79)..(81)
<223> OTHER INFORMATION: 3 n's can be GCT, GCC, GCA, GCG, TCT, TCC, TCA,
      TCG, AGT, AGC, TGT, or TGC
<220> FEATURE:
<221> NAME/KEY: misc_feature
```

```
<222> LOCATION: (97)..(99)
<223> OTHER INFORMATION: 3 n's can be GCT, GCC, GCA, GCG, TCT, TCC, TCA,
      TCG, AGT, AGC, TGT, or TGC

<400> SEQUENCE: 499
nnntggttan nnagagcatt aataaaaaga atacaagcan nnatannnnn nnnnnnnaga        60
nnnttaccac aattagtann nagattagta ttaagannna gt                          102

<210> SEQ ID NO 500
<211> LENGTH: 4
<212> TYPE: PRT
<213> ORGANISM: artificial
<220> FEATURE:
<223> OTHER INFORMATION: loop sequence for consensus sequence

<400> SEQUENCE: 500

Pro Lys Gly Gly
1

<210> SEQ ID NO 501
<211> LENGTH: 4
<212> TYPE: PRT
<213> ORGANISM: artificial
<220> FEATURE:
<223> OTHER INFORMATION: loop sequence for consensus sequence

<400> SEQUENCE: 501

Asp Ala Thr Lys
1

<210> SEQ ID NO 502
<211> LENGTH: 4
<212> TYPE: PRT
<213> ORGANISM: artificial
<220> FEATURE:
<223> OTHER INFORMATION: loop sequence for consensus sequence

<400> SEQUENCE: 502

Asp His Gly Ser
1

<210> SEQ ID NO 503
<211> LENGTH: 4
<212> TYPE: PRT
<213> ORGANISM: artificial
<220> FEATURE:
<223> OTHER INFORMATION: loop sequence for consensus sequence

<400> SEQUENCE: 503

His Ser Gly Asp
1

<210> SEQ ID NO 504
<211> LENGTH: 4
<212> TYPE: PRT
<213> ORGANISM: artificial
<220> FEATURE:
<223> OTHER INFORMATION: loop sequence for consensus sequence

<400> SEQUENCE: 504

Glu Ala Gly Asp
1
```

SP-B AND SP-C PEPTIDES, SYNTHETIC LUNG SURFACTANTS, AND USE THEREOF

This application is a national stage application under 35 U.S.C. §371 from PCT Application No. PCT/US2013/025532, filed Feb. 11, 2013, which claims the priority benefit of U.S. Provisional Patent Application Ser. No. 61/596,913, filed Feb. 9, 2012 which is hereby incorporated by reference in its entirety.

This invention was made with government support under grant numbers HL094641, HL092158, and ES015330 awarded by the National Institutes of Health. The government has certain rights in the invention.

FIELD OF THE INVENTION

The present invention relates to novel peptides and their use in surfactant compositions, as well as various uses of the surfactant compositions.

BACKGROUND OF THE INVENTION

The airsacs in the lungs of mammals are stabilized by pulmonary surfactant, a complex mixture containing glycerophospholipids and specific surfactant proteins (SP) that is synthesized by type II epithelial cells in the alveolar lining (for review see text by Notter (Notter, *Lung Surfactants: Basic Science and Clinical Applications*, Marcel Dekker, Inc, New York (2000)). The mammalian lungs have a huge internal surface area of the order 1 $m^2$/kg body weight at total lung capacity, and much of this surface is lined by a thin liquid film or "alveolar hypophase". Surface tension forces at the extensive air-hypophase interface are a major contributor to the work of breathing. Pulmonary surfactant plays crucial roles in respiratory physiology by moderating these surface tension forces. Endogenous surfactant secreted by alveolar type II epithelial cells adsorbs at the air-hypophase interface and lowers and varies surface tension as a function of alveolar size during breathing. This regulation of surface tension reduces the work of breathing while stabilizing different sized alveoli against collapse and overdistension. It also leads to a smaller hydrostatic pressure driving force for edema fluid to move into the lung interstitium from the pulmonary capillaries. Functional pulmonary surfactant is necessary for life, and its deficiency or dysfunction is associated with severe impairments in respiratory function that can be lethal if not treated effectively.

A major disease where lung surfactant deficiency causes respiratory failure is the neonatal respiratory distress syndrome ("NRDS"), also called Hyaline Membrane Disease ("HMD"). NRDS is most prevalent in premature infants <32 weeks gestation (term=40 weeks in humans), but it can also occur in older premature infants of 32-36 weeks gestation. NRDS is caused by a deficiency of endogenous surfactant in the lungs of premature infants at birth (although elements of lung injury with acquired surfactant dysfunction can subsequently arise during its clinical course). The major clinical conditions associated with lung surfactant dysfunction are the syndromes of acute lung injury ("ALI") and the acute respiratory distress syndrome ("ARDS"). ALI and ARDS are lethal manifestations of inflammatory lung injury that can result from multiple direct and indirect causes ranging from respiratory infection, gastric aspiration, meconium aspiration, blunt chest trauma with lung contusion, hyperoxia, near drowning, hypovolemic shock, bacterial sepsis, and many others (for review see Notter et al., editors, *Lung Injury: Mechanisms, Pathophysiology and Therapy*, Taylor Francis Group, Inc, Boca Raton (2005)). ALI/ARDS can affect patients of all ages from infants to adults, although different age groups vary somewhat in the etiology and specifics of disease. The American-European Consensus Committee in 1994 defined clinical ARDS more specifically as requiring an acute onset, bilateral infiltrates on frontal chest radiograph, a $PaO_2/FiO_2$ ratio 200 mmHg, and a pulmonary capillary wedge pressure mmHg (if measured) or no evidence of left atrial hypertension (Bernard et al., "The American-European Consensus Conference on ARDS: Definitions, Mechanisms, Relevant Outcomes, and Clinical Trial Coordination," *Am J Respir Crit Care Med* 149:818-824 (1994)). The Consensus Committee defined ALI identically to ARDS except for a $PaO_2/FiO_2$ ratio 300 mmHg (Bernard et al., "The American-European Consensus Conference on ARDS: Definitions, Mechanisms, Relevant Outcomes, and Clinical Trial Coordination,"*Am J Respir Crit Care Med* 149:818-824 (1994)). ARDS affects 50,000 to 150,000 patients in the United States each year, and the incidence of ALI is estimated at 22-86 cases per 100,000 people per year. Both conditions have substantial mortality rates of 30-50% despite sophisticated intensive care (Bernard et al., "The American-European Consensus Conference on ARDS: Definitions, Mechanisms, Relevant Outcomes, and Clinical Trial Coordination," *Am J Respir Crit Care Med* 149:818-824 (1994); Rubenfeld et al., "Incidence and Outcomes of Acute Lung Injury," *N Engl J Med* 363:1685-1693 (2005); Hyers, "Prediction of Survival and Mortality in Patients With the Adult Respiratory Distress Syndrome," *New Horizons* 1:466-470 (1993); Doyle et al., "Identification of Patients With Acute Lung Injury: Predictors of Mortality," *Am J Respir Crit Care Med* 152:1818-1824 (1995); Krafft et al., "The Acute Respiratory Distress Syndrome; Definitions, Severity, and Clinical Outcome. An Analysis of 101 Clinical Investigations," *Intensive Care Med* 22:519-529 (1996); Goss et al., "Incidence of Acute Lung Injury in the United States," *Crit Care Med* 31:1607-1611 (2003)). Multiple studies have identified surfactant abnormalities in bronchoalveolar lavage (lung washings) from patients with ALI/ARDS (e.g., Petty et al., "Characteristics of Pulmonary Surfactant in Adult Respiratory Distress Syndrome Associated With Trauma and Shock," *Am Rev Respir Dis* 115:531-536 (1977); Hallman et al., "Evidence of Lung Surfactant Abnormality in Respiratory Failure," *J Clin Invest* 70:673-683 (1982); Seeger et al., "Surfactant Abnormalities and Adult Respiratory Failure," *Lung* 168 (Suppl):891-902 (1990); Pison et al., "Surfactant Abnormalities in Patients With Respiratory Failure After Multiple Trauma," *Am Rev Respir Dis* 140:1033-1039 (1989); Gregory et al., "Surfactant Chemical Composition and Biophysical Activity in Acute Respiratory Distress Syndrome," *J Clin Invest* 88:1976-1981 (1991); Veldhuizen et al., "Pulmonary Surfactant Subfractions in Patients With the Acute Respiratory Distress Syndrome," *Am J Respir Crit Care Med* 152:1867-1871 (1995); Griese, "Pulmonary Surfactant in Health and Human *Lung* Diseases: State of the Art," *Eur Respir J* 13:1455-1476 (1999); Gunther et al., "Surfactant Alterations in Severe Pneumonia, Acute Respiratory Distress Syndrome, and Cardiogenic Lung Edema," *Am J Respir Crit Care Med* 153:176-184 (1996)).

Surfactant dysfunction in ALI/ARDS occurs by several mechanisms including physical and chemical interactions with inhibitors in edema fluid or lung tissue (Notter, *Lung Surfactants: Basic Science and Clinical Applications*, Marcel Dekker, Inc, New York (2000); Notter et al., "Pulmonary Surfactant: Physical Chemistry, Physiology and Replacement," *Rev Chem Eng* 13:1-118 (1997); Wang et al., "Surfactant Activity and Dysfunction in Lung Injury," In: Notter et al., editors, *Lung Injury: Mechanisms, Pathophysiology, and Therapy*, Taylor Francis Group, Inc, Boca Raton, pp. 297-352 (2005)). To be optimally effective, exogenous surfactants used in treating ALI/ARDS and/or severe NRDS must have very high surface activity and resistance to biophysical inhibition and/or chemical degradation.

If endogenous surfactant is deficient or dysfunctional, it can in principle be treated by the delivery of active exogenous surface-active material to the alveoli by airway instillation or by other techniques such as aerosolization or nebulization. Exogenous surfactant therapy is intended to preserve lung function over the short term while the patient's lungs develop or recover the ability to produce and maintain adequate levels of endogenous surfactant. The utility of exogenous surfactant therapy with first-generation animal-derived clinical surfactant drugs to prevent or treat NRDS in premature infants is well documented (for review see: Notter, *Lung Surfactants: Basic Science and Clinical Applications*, Marcel Dekker, Inc, New York (2000); Soll, "Surfactant Therapy in The USA: Trials and Current Routines," *Biol Neonate* 71:1-7 (1997); Soll et al., "Surfactant in the Prevention and Treatment of Respiratory Distress Syndrome," In: *New Therapies for Neonatal Respiratory Failure*, Boynton et al., editors, Cambridge University Press, New York, pp. 49-80 (1994); Jobe, "Pulmonary Surfactant Therapy," *N Engl J Med* 328:861-868 (1993)). Exogenous surfactant therapy is still under development for ALI/ARDS, but the existence of surfactant dysfunction in patients with this condition provides a clear conceptual rationale for the potential benefits of such therapy (Chess et al., "Surfactant Replacement Therapy in Lung Injury," In: *Lung Injury: Mechanisms, Pathophysiology, and Therapy*, Notter et al., editors, Taylor Francis Group, Inc, Boca Raton, pp. 617-663 (2005); Raghavendran, et al., "Pharmacotherapy of Acute Lung Injury and Acute Respiratory Distress Syndrome," *Curr Med Chem* 15:1911-1924 (2008); Willson et al., "Surfactant for Pediatric Acute Lung Injury," *Pediatr Clin N Am* 55:545-575 (2008)).

Published research shows that current animal-derived clinical exogenous surfactants, e.g., Infasurf® (CLSE), Survanta®, and Curosurf®, are more active biophysically and physiologically than first-generation synthetic surfactants such as Exosurf® and ALEC (Notter, *Lung Surfactants: Basic Science and Clinical Applications*, Marcel Dekker, Inc, New York (2000); Soll, "Surfactant Therapy in The USA: Trials and Current Routines," *Biol Neonate* 71:1-7 (1997); Soll et al., "Surfactant in the Prevention and Treatment of Respiratory Distress Syndrome," In: *New Therapies for Neonatal Respiratory Failure*, Boynton et al., editors, Cambridge University Press, New York, pp. 49-80 (1994); Jobe, "Pulmonary Surfactant Therapy," *N Engl J Med* 328:861-868 (1993)). These animal-derived clinical surfactants all contain one or both of the lung surfactant proteins (SP)-B and/or SP-C as essential ingredients (Notter, *Lung Surfactants: Basic Science and Clinical Applications*, Marcel Dekker, Inc, New York (2000).

However, synthetic lung surfactants manufactured under controlled conditions have significant potential advantages in purity, compositional reproducibility, activity reproducibility, quality-control, and manufacturing economy compared to animal-derived preparations. In addition, constituents in synthetic surfactants can incorporate special and useful molecular properties, such as resistance to degradation by phospholipases during inflammatory lung injury ((Notter, *Lung Surfactants: Basic Science and Clinical Applications*, Marcel Dekker, Inc, New York (2000); Wang et al., "Surface Activity of a Synthetic Lung Surfactant Containing a Phospholipase-resistant Phosphonolipid Analog of Dipalmitoyl Phosphatidylcholine," *Am J Physiol* 285:L550-L559 (2003); Wang et al., "Activity and Inhibition Resistance of a Phospholipase-Resistant Synthetic Exogenous Surfactant in Excised Rat Lungs," *Am J Respir Cell Mol Biol* 37:387-394 (2007)). Synthetic surfactants are also free from concerns about prion-caused diseases (e.g., bovine spongiform encephalitis) that are relevant for animal-derived surfactants, and synthetic surfactants are not subject to cultural or religious considerations that potentially affect bovine- or porcine-derived preparations.

Despite significant advances in recent years, there remains a need to identify improved synthetic SP-B peptides and SP-C peptides that show enhanced activity and/or stability, can be easily produced in pure form and in a cost-effective manner, and can be used to generate synthetic surfactant compositions having activity comparable to or better than the activities of commercially available animal-derived surfactants.

The present invention is directed to overcoming these and other deficiencies in the art.

SUMMARY OF THE INVENTION

A first aspect of the present invention relates to a novel surface active peptide.

In one embodiment, the surface active peptide is derived from SP-B and comprises the consensus amino acid sequence of:

XWLXRALIKRIQAMI-Z-RMLPQLVXRLVLRXS (SEQ ID NO: 1)

where Z is a loop or turn sequence containing at least four amino acids, and each X independently represents an uncharged amino acid residue, except that Z is not PKGG (SEQ ID NO: 500) when each X is cysteine.

In a related embodiment, the surface active peptide is derived from SP-B and comprises the consensus amino acid sequence of:

(SEQ ID NO: 414)
XWLXRALIKRIQAXI-Z-RXLPQLVXRLVLRXS where Z is a loop or turn sequence containing at least four amino acids, each X at positions 1, 4, 24, and 30 independently represents an uncharged amino acid residue and each X at positions 14 and 18 independently represent leucine, isoleucine, or norleucine, except that Z is not PKGG (SEQ ID NO: 500) when each X at positions 1, 4, 24, and 30 is cysteine.

In another embodiment, the surface active peptide is derived from SP-C and comprises the consensus amino acid sequence of:

XXIPXXPXXLKRLLXXXXX (SEQ ID NO: 30)

where X at the first position is Leu or Phe, X at the second position is Gly or Arg, X at the fifth position is Phe, Cys, or Tyr, X at the sixth position is Phe or Tyr, X at the eighth position is Ser or Val, X at the ninth position is Ser or His, X at the fifteenth and sixteenth positions is independently Ile or Val, and X at the seventeenth to nineteenth positions is independently Val or Leu.

In a further embodiment, the surface active peptide is derived from SP-C and comprises the consensus amino acid sequence of:

(SEQ ID NO: 36)
GIPXXPXXLKRLLIXVVVXXLXVXVIVGALLMG where X at the fourth and fifth positions are independently Ser or Phe; X at the seventh position is Val or Ser; X at the eighth position is His or Ser; X at positions 15 and 19 and 20 and 24 represent one or two pairs of residues that can form an ion lock, except that when only one pair forms an ion lock, then the other residues are a hydrophobic amino acid selected from Leu, Ile, and Val; and X at position 22 is Ile or Val; wherein the amino acids residues that can form the ion lock are positively-charged or negatively-charged amino acids.

In yet another embodiment, the surface active peptide is derived from SP-C and comprises the consensus amino acid sequence of:

(SEQ ID NO: 325)
IPXXPXXLKRLKLLXLLLXXILLXILGALLMGL where X at positions 3 and 4 are independently Ser or Phe; X at position 6 is Val or Ser; X at position 7 is His or Ser; X at positions 15 and 19 and 20 and 24 represent one or two pairs of residues that can form an ion lock, except that when only one pair forms an ion lock, then the other residues are a hydrophobic amino acid selected from Leu, Ile, and Val.

A second aspect of the present invention relates to a surfactant composition that includes a surface active peptide of the first aspect of the invention.

In certain embodiments, the surfactant composition also includes one or more synthetic phospholipids. According to this aspect of the present invention, the synthetic phospholipids can be one or more glycerophospholipids found in endogenous surfactants (including exogenous surfactant formulations), one or more phospholipase-resistant phospho-glycerol derivatives, one or more phospholipase-resistant phospho-choline derivatives, or a combination thereof.

A third aspect of the present invention relates to a method of treating endogenous surfactant dysfunctional lung tissue. This includes providing a surfactant composition according to the second aspect of the present invention, and administering the surfactant composition to a patient having lung tissue characterized by endogenous surfactant deficiency and/or dysfunction. The administering is carried out under conditions effective to coat alveolar surfaces of the affected lung tissue with the surfactant composition, thereby treating the surfactant deficient and/or dysfunctional lung tissue.

A fourth aspect of the present invention relates to a method of delivering a therapeutic agent. The method includes introducing a therapeutic agent into a surfactant composition according to the second aspect of the present invention under conditions effective to encapsulate the therapeutic agent in liposomal vesicles. The method also involves administering the composition to a subject under conditions effective to deliver the therapeutic agent to a target tissue, including airway instillation or aerosol delivery.

The present invention achieves a synthetic lung surfactant composition that overcomes the above-identified deficiencies through the use of synthetic surface-active peptides that are remarkably stable and easy to synthesize. In particular, several synthetic compositions of the present invention can achieve high surface activity approaching, equaling or exceeding animal-derived surfactants, while incorporating commercially relevant advantages in synthesis, purity, compositional reproducibility, manufacturing quality control, and/or stability compared to animal-derived materials. The synthetic surfactants of this invention are also free from the risk of transmitting animal pathogens such as prions (e.g., bovine spongiform encephalitis).

DETAILED DESCRIPTION OF THE INVENTION

Figure 1:
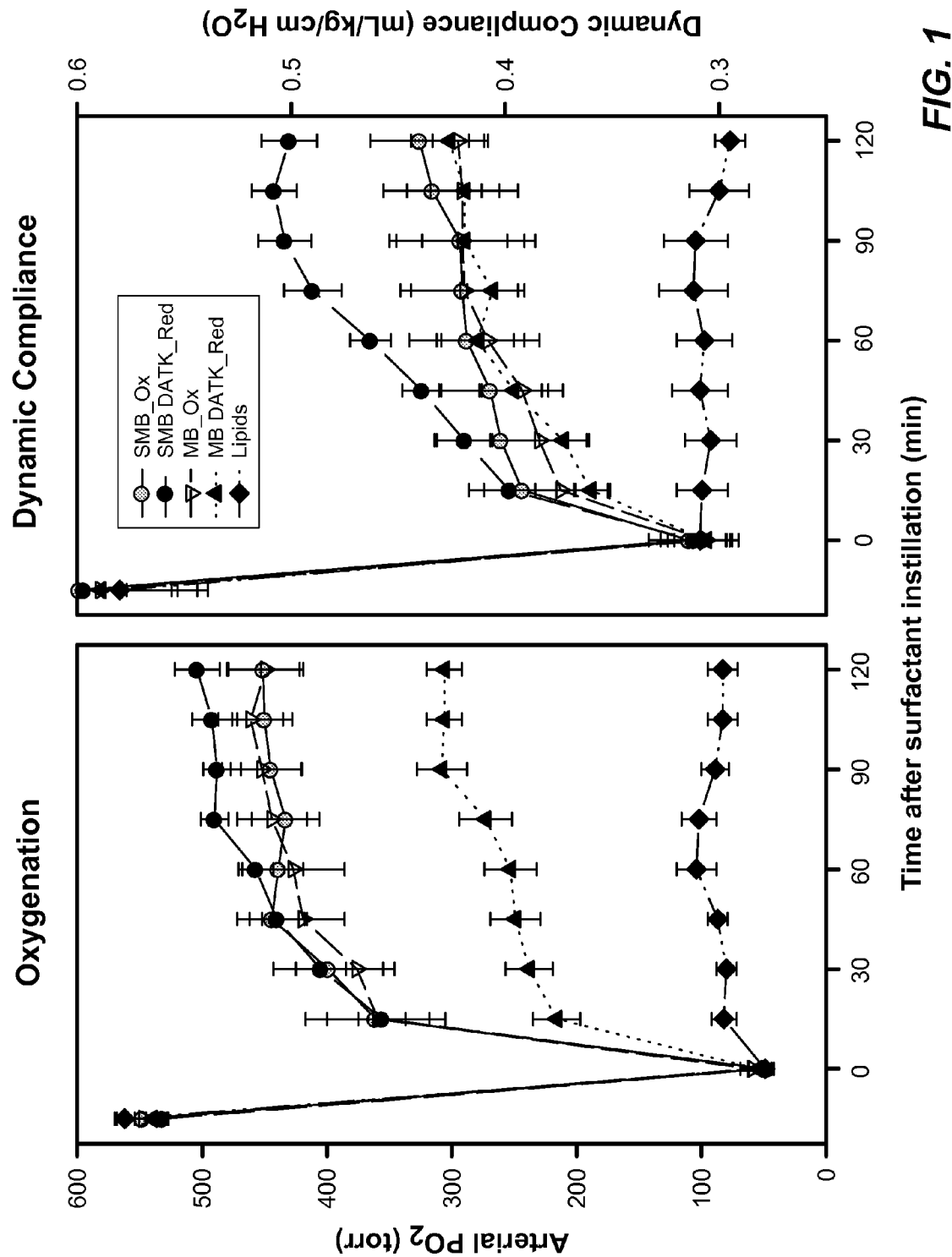
FIG. 1 is a pair of graphs illustrating arterial oxygenation and dynamic compliance in surfactant SP-B mimic-treated, ventilated rabbits with ARDS induced by in vivo lavage. Arterial partial pressure of oxygen and dynamic compliance are shown for groups of rabbits treated with synthetic preparations containing synthetic lipids with 3.0% by weight SMB_Ox=Oxidized Super Mini-B, SMB DATK_Red [SEQ ID NO: 18 (reduced)], MB_Ox=Oxidized Mini-B, MB DATK_Red [SEQ ID NO: 4 (reduced)]. Lipids=Synthetic lipids alone. Synthetic lipids are DPPC:POPC:POPG (5:3:2, weight ratio). Data for the oxygenation and dynamic compliance curves are shown as means±SEM at selected intervals for SMB_Ox (n=9), SMB DATK_Red (n=4), MB_Ox (n=6), MB DATK_Red (n=5) and Lipids alone (n=6).

The present invention relates to surface-active synthetic peptides and lung surfactant compositions that contain one or more of these peptides.

The term "surface-active synthetic peptide" is meant to include a synthetic peptide that increases the ability of the surfactant composition to lower surface tension during adsorption and/or during dynamic compression in a spread or adsorbed interfacial (surface) film. Preferred "surface-active synthetic peptides" are amphipathic or hydrophobic.

The surface-active synthetic peptides of the present invention have been designed to have optimal surface-active interactions with phospholipids, including phospholipase-resistant phospholipids, when present in surfactant compositions of the present invention. These peptides can also be used to form highly-active synthetic surfactants in combination with non phospholipase-resistant phospholipids, including phospholipids present in endogenous surfactant or commercially available exogenous surfactant preparations.

The surface-active synthetic peptides of this invention can be related in primary sequence to regions of surfactant proteins (SP)-B or SP-C, and may also incorporate features such as homo- or hetero-dimerization.

Particularly preferred amphipathic peptides for this invention are those related to the regional or full-length sequence of human or animal SP-B, including dimer forms, which may be used in synthetic lung surfactants with lipids as single peptides or in combination with preferred synthetic peptides related to the regional or full sequence of SP-C. Preferred peptides can be combined in synthetic exogenous surfactants with 'regular' (e.g., ester-linked) synthetic phospholipids including those found in native lung surfactant or with phospholipase-resistant synthetic phospholipids.

The structural features of the full-length mature SP-B and SP-C proteins are well known and reported as Genbank Accession Nos. L11573, AF400074, BC032785, NM_000542, and NM_198843 for SP-B; and J03890, U02948, AY357924, AY337315, BC005913, and NM_003018 for SP-C. Each of the above-listed Genbank Accessions is hereby incorporated by reference in its entirety.

When fragments of the mature SP-B and/or SP-C are employed in the surfactant compositions of the present invention, it is preferable to utilize fragments thereof that contain at least a portion of a lipid associating region. Lipid associating regions are those portions of the mature protein that are capable of molecular interaction with lipids (either native glycerophospholipids or synthetic phospholipase-resistant lipids) to promote surface activity of the resulting composition in which they are introduced. Such fragments include, without limitation, fragments of SP-B that contain an amphipathic or hydrophobic region capable of associating with lipids, fragments of SP-C that contain an amphipathic or hydrophobic region capable of associating with lipids, as well as any number of synthetic peptides or combinations thereof.

The synthetic peptides can be modified not only with respect to their primary amino acid sequence (i.e., relative to SP-B or SP-C), but also by the presence of structural features that affect tertiary structure of the peptide. These structural features may include, among others, the presence of modified beta-turn peptide structures, ion-lock residues, the presence of di-sulfide linkages between two peptide sequences to form a single dimeric molecule, and the presence of fatty acid chains tethered via disulfide bond to a Cys residue in the peptide.

A first synthetic peptide family of the present invention has molecular features analogous to SP-B and is designed to include peptides comprising the consensus amino acid sequence of:

(SEQ ID NO: 1)
XWLXRALIKRIQAMI-Z-RMLPQLVXRLVLRXS where Z is a loop or turn sequence containing at least four amino acids, and each X independently represents an uncharged amino acid residue. The loop or turn sequence (-Z-) can be any suitable sequence, but is preferably selected from the group of four to ten amino acid residues that include the peptides PKGG (SEQ ID NO: 500), DATK (SEQ ID NO: 501), DHGS (SEQ ID NO: 502), HSGD (SEQ ID NO: 503), or EAGD (SEQ ID NO: 504). In certain embodiments, the loop or turn sequence (-Z-) consists of PKGG (SEQ ID NO: 500), DATK (SEQ ID NO: 501), DHGS (SEQ ID NO: 502), HSGD (SEQ ID NO: 503), or EAGD (SEQ ID NO: 504). The hydrophobic amino acid residues (X) can be valine, isoleucine, leucine, methionine, phenylalanine, tryptophan, histidine, tyrosine, glycine, alanine, threonine, cysteine, proline, asparagine, glutamine, and serine. Of these, alanine, serine, threonine, and cysteine are preferred, with cysteine, alanine, and serine being most preferred.

In certain embodiments of the invention, the scope of SEQ ID NO: 1 is intended to include peptide sequences where Z consists of PKGG (SEQ ID NO: 500) and each X is cysteine. Peptide sequences of this type have been previously identified as Mini-B (Waring et al., "The Role of Charged Amphipathic Helices in the Structure and Function of Surfactant Protein B," *Journal Peptide Research* 66:364-374 (2005); U.S. Pat. No. 7,538,090 to Waring et al., each of which is hereby incorporated by reference in its entirety) and Super Mini-B (PCT Application Publ. No. WO 2008/011559; Walther et al., "Critical Structural and Functional Roles for the N-terminal Insertion Sequence in Surfactant Protein B Analogs," *PLoS One* 5:e8672.10.1371 (2010), which is hereby incorporated by reference in its entirety). Embodiments where these peptides are included within the scope of the present invention include surfactant formulations where these peptides are included in combination with a novel SP-C-like peptide.

In certain other embodiments of the invention, the scope of SEQ ID NO: 1 is intended specifically to exclude such peptide sequences where Z consists of PKGG (SEQ ID NO: 500) and each X is cysteine, as described in the preceding paragraph. Embodiments where these peptides are specifically excluded from the scope of the present invention relate to the peptides of SEQ ID NO: 1, per se, and surfactant formulations where the SEQ ID NO: 1 peptides are included in combination with a previously known SP-C-like peptide.

Exemplary peptides that correspond to the peptide of SEQ ID NO: 1 include, without limitation, those listed in Table 1 below, as well as combinations thereof

TABLE 1

Members of SP-B-like Peptides

| Name | Sequence | SEQ ID NO: |
|---|---|---|
| MB-ala | AWLARALIKRIQAMIPKGGRMLPQLVARLVLRAS | 2 |
| MB-ser | SWLSRALIKRIQAMIPKGGRMLPQLVSRLVLRSS | 3 |
| MB_datk | CWLCRALIKRIQAMIDATKRMLPQLVCRLVLRCS | 4 |
| MB-datk_ala | AWLARALIKRIQAMIDATKRMLPQLVARLVLRAS | 5 |
| MB_datk_ser | SWLSRALIKRIQAMIDATKRMLPQLVSRLVLRSS | 6 |
| MB_dhgs | CWLCRALIKRIQAMIDHGSRMLPQLVCRLVLRCS | 7 |
| MB_dhgs_ala | AWLARALIKRIQAMIDHGSRMLPQLVARLVLRAS | 8 |

TABLE 1-continued

Members of SP-B-like Peptides

| Name | Sequence | SEQ ID NO: |
|---|---|---|
| MB_dhgs_ser | SWLSRALIKRIQAMIDHGSRMLPQLVSRLVLRSS | 9 |
| MB_hsgd | CWLCRALIKRIQAMIHSGDRMLPQLVCRLVLRCS | 10 |
| MB_hsgd_ala | AWLARALIKRIQAMIHSGDRMLPQLVARLVLRAS | 11 |
| MB_hsgd_ser | SWLSRALIKRIQAMIHSGDRMLPQLVSRLVLRSS | 12 |
| MB_eagd | CWLCRALIKRIQAMIEAGDRMLPQLVCRLVLRCS | 13 |
| MB_eagd_ala | AWLARALIKRIQAMIEAGDRMLPQLVARLVLRAS | 14 |
| MB_eagd_ser | SWLSRALIKRIQAMIEAGDRMLPQLVSRLVLRSS | 15 |
| SMB_ala | FPIPLPYAWLARALIKRIQAMIPKGGRMLPQLVARLVLRAS | 16 |
| SMB_ser | FPIPLPYSWLSRALIKRIQAMIPKGGRMLPQLVSRLVLRSS | 17 |
| SMB_datk | FPIPLPYCWLCRALIKRIQAMIDATKRMLPQLVCRLVLRCS | 18 |
| SMB_datk_ala | FPIPLPYAWLARALIKRIQAMIDATKRMLPQLVARLVLRAS | 19 |
| SMB_datk_ser | FPIPLPYSWLSRALIKRIQAMIDATKRMLPQLVSRLVLRSS | 20 |
| SMB_dhgs | FPIPLPYCWLCRALIKRIQAMIDHGSRMLPQLVCRLVLRCS | 21 |
| SMB_dhgs_ala | FPIPLPYAWLARALIKRIQAMIDHGSRMLPQLVARLVLRAS | 22 |
| SMB_dhgs_ser | FPIPLPYSWLSRALIKRIQAMIDHGSRMLPQLVSRLVLRSS | 23 |
| SMB_hsgd | FPIPLPYCWLCRALIKRIQAMIHSGDRMLPQLVCRLVLRCS | 24 |
| SMB_hsgd_ala | FPIPLPYAWLARALIKRIQAMIHSGDRMLPQLVARLVLRAS | 25 |
| SMB_hsgd_ser | FPIPLPYSWLSRALIKRIQAMIHSGDRMLPQLVSRLVLRSS | 26 |
| SMB_eagd | FPIPLPYCWLCRALIKRIQAMIEAGDRMLPQLVCRLVLRCS | 27 |
| SMB_eagd_ala | FPIPLPYAWLARALIKRIQAMIEAGDRMLPQLVARLVLRAS | 28 |
| SMB_eagd_ser | FPIPLPYSWLSRALIKRIQAMIEAGDRMLPQLVSRLVLRSS | 29 |

In each peptide name, MB means that the sequence is related to the peptide "Mini-B" (Waring et al., "The Role of Charged Amphipathic Helices in the Structure and Function of Surfactant Protein B," Journal Peptide Research 66: 364-374 (2005); U.S. Pat. No. 7,538,090 to Waring et al.) and SMB means that the sequence is related to the peptide "Super-Mini-B" (PCT Application Publ. No. WO 2008/011559; Walther et al., "Critical Structural and Functional Roles for the N-terminal Insertion Sequence in Surfactant Protein B Analogs," PLoS One 5: e8672.10.1371 (2010)). Each reference is incorporated herein in its entirety.

Peptides within the consensus family of SEQ ID NO: 1 include peptide sequences that comprise one of SEQ ID NOS: 2-29, as well as peptide sequences that consist of one of SEQ ID NOS: 2-29.

A second synthetic peptide family of the present invention has molecule features analogous to SP-B and is designed to include peptides comprising the consensus amino acid sequence of:

(SEQ ID NO: 414)
XWLXRALIKRIQAXI-Z-RXLPQLVXRLVLRXS where Z is a loop or turn sequence containing at least four amino acids, each X at positions 1, 4, 24, and 30 independently represents an uncharged amino acid residue and each X at positions 14 and 18 independently represents leucine, isoleucine, or norleucine, except that Z is not PKGG (SEQ ID NO: 500) when each X at positions 1, 4, 24, and 30 is cysteine. The peptide sequences of SEQ ID NO: 414 therefore differ from the peptides of SEQ ID NO: 1 with respect to the methionine residues at positions 14 and 18 of SEQ ID NO: 1, which are replaced in SEQ ID NO: 414 by leucine, isoleucine, or norleucine to prevent the methionine from oxidizing and making the peptide sequence more polar. The loop or turn sequence (-Z-) can be any suitable sequence, but is preferably selected from the group of four to ten amino acid residues that include the peptides PKGG (SEQ ID NO: 500), DATK (SEQ ID NO: 501), DHGS (SEQ ID NO: 502), HSGD (SEQ ID NO: 503), or EAGD (SEQ ID NO: 504). In certain embodiments, the loop or turn sequence (-Z-) consists of PKGG (SEQ ID NO: 500), DATK (SEQ ID NO: 501), DHGS (SEQ ID NO: 502), HSGD (SEQ ID NO: 503), or EAGD (SEQ ID NO: 504). The hydrophobic amino acid residues (X) can be valine, isoleucine, leucine, methionine, phenylalanine, tryptophan, histidine, tyrosine, glycine, alanine, threonine, cysteine, proline, asparagine, glutamine, and serine. Of these, alanine, serine, threonine, and cysteine are preferred, with cysteine, alanine, and serine being most preferred.

In certain embodiments of the invention, the scope of SEQ ID NO: 414 is intended to include peptide sequences where Z consists of PKGG (SEQ ID NO: 500) and X at positions 1, 4, 24, and 30 is cysteine. Peptide sequences of this type have been previously identified in U.S. Publ. No. 2011/0003733 to Pivetti et al. and Seehase et al., "New Surfactant with SP-B and C Analogs Gives Survival Benefit after Inactivation in Preterm Lambs," *PLoS One* 7(10): e47631 (2012), each of which is hereby incorporated by reference in its entirety. Embodiments where these peptides are included within the scope of the present invention include surfactant formulations where these peptides are included in combination with a novel SP-C-like peptide.

In certain other embodiments of the invention, the scope of SEQ ID NO: 414 is intended specifically to exclude such peptide sequences where Z consists of PKGG (SEQ ID NO: 500) and X at positions 1, 4, 24, and 30 is cysteine, as described in the preceding paragraph. Embodiments where these peptides are specifically excluded from the scope of the present invention relate to the peptides of SEQ ID NO: 414, per se, and surfactant formulations where the SEQ ID NO: 414 peptides are included in combination with a previously known SP-C-like peptide.

Exemplary peptides that correspond to the peptide of SEQ ID NO: 414 include, without limitation, those listed in Table 2 below, as well as combinations thereof

TABLE 2

Members of SP-B-like Peptides

| Name | Sequence | SEQ ID NO: |
|---|---|---|
| L.MB_ala | AWLARALIKRIQALIPKGGRLLPQLVARLVLRAS | 415 |
| L.MB_ser | SWLSRALIKRIQALIPKGGRLLPQLVSRLVLRSS | 416 |
| L.MB_datk | CWLCRALIKRIQALIDATKRLLPQLVCRLVLRCS | 417 |
| L.MB_datk_ala | AWLARALIKRIQALIDATKRLLPQLVARLVLRAS | 418 |
| L.MB_datk_ser | SWLSRALIKRIQALIDATKRLLPQLVSRLVLRSS | 419 |
| L.MB_dhgs | CWLCRALIKRIQALIDHGSRLLPQLVCRLVLRCS | 420 |
| L.MB_dhgs_ala | AWLARALIKRIQALIDHGSRLLPQLVARLVLRAS | 421 |
| L.MB_dhgs_ser | SWLSRALIKRIQALIDHGSRLLPQLVSRLVLRSS | 422 |
| L.MB_hsgd | CWLCRALIKRIQALIHSGDRLLPQLVCRLVLRCS | 423 |
| L.MB_hsgd_ala | AWLARALIKRIQALIHSGDRLLPQLVARLVLRAS | 424 |
| L.MB_hsgd_ser | SWLSRALIKRIQALIHSGDRLLPQLVSRLVLRSS | 425 |
| L.MB_eagd | CWLCRALIKRIQALIEAGDRLLPQLVCRLVLRCS | 426 |
| L.MB_eagd_ala | AWLARALIKRIQALIEAGDRLLPQLVARLVLRAS | 427 |
| L.MB_eagd_ser | SWLSRALIKRIQALIEAGDRLLPQLVSRLVLRSS | 428 |
| L.SMB_ala | FPIPLPYAWLARALIKRIQALIPKGGRLLPQLVARLVLRAS | 429 |
| L.SMB_ser | FPIPLPYSWLSRALIKRIQALIPKGGRLLPQLVSRLVLRSS | 430 |
| L.SMB_datk | FPIPLPYCWLCRALIKRIQALIDATKRLLPQLVCRLVLRCS | 431 |
| L.SMB_datk_ala | FPIPLPYAWLARALIKRIQALIDATKRLLPQLVARLVLRAS | 432 |
| L.SMB_datk_ser | FPIPLPYSWLSRALIKRIQALIDATKRLLPQLVSRLVLRSS | 433 |
| L.SMB_dhgs | FPIPLPYCWLCRALIKRIQALIDHGSRLLPQLVCRLVLRCS | 434 |
| L.SMB_dhgs_ala | FPIPLPYAWLARALIKRIQALIDHGSRLLPQLVARLVLRAS | 435 |
| L.SMB_dhgs_ser | FPIPLPYSWLSRALIKRIQALIDHGSRLLPQLVSRLVLRSS | 436 |
| L.SMB_hsgd | FPIPLPYCWLCRALIKRIQALIHSGDRLLPQLVCRLVLRCS | 437 |
| L.SMB_hsgd_ala | FPIPLPYAWLARALIKRIQALIHSGDRLLPQLVARLVLRAS | 438 |
| L.SMB_hsgd_ser | FPIPLPYSWLSRALIKRIQALIHSGDRLLPQLVSRLVLRSS | 439 |
| L.SMB_eagd | FPIPLPYCWLCRALIKRIQALIEAGDRLLPQLVCRLVLRCS | 440 |
| L.SMB_eagd_ala | FPIPLPYAWLARALIKRIQALIEAGDRLLPQLVARLVLRAS | 441 |
| L.SMB_eagd_ser | FPIPLPYSWLSRALIKRIQALIEAGDRLLPQLVSRLVLRSS | 442 |
| I.MB_ala | AWLARALIKRIQAIIPKGGRILPQLVARLVLRAS | 443 |

TABLE 2-continued

Members of SP-B-like Peptides

| Name | Sequence | SEQ ID NO: |
|---|---|---|
| I.MB_ser | SWLSRALIKRIQAIIPKGGRILPQLVSRLVLRSS | 444 |
| I.MB_datk | CWLCRALIKRIQAIIDATKRILPQLVCRLVLRCS | 445 |
| I.MB_datk_ala | AWLARALIKRIQAIIDATKRILPQLVARLVLRAS | 446 |
| I.MB_datk_ser | SWLSRALIKRIQAIIDATKRILPQLVSRLVLRSS | 447 |
| I.MB_dhgs | CWLCRALIKRIQAIIDHGSRILPQLVCRLVLRCS | 448 |
| I.MB_dhgs_ala | AWLARALIKRIQAIIDHGSRILPQLVARLVLRAS | 449 |
| I.MB_dhgs_ser | SWLSRALIKRIQAIIDHGSRILPQLVSRLVLRSS | 450 |
| I.MB_hsgd | CWLCRALIKRIQAIIHSGDRILPQLVCRLVLRCS | 451 |
| I.MB_hsgd_ala | AWLARALIKRIQAIIHSGDRILPQLVARLVLRAS | 452 |
| I.MB_hsgd_ser | SWLSRALIKRIQAIIHSGDRILPQLVSRLVLRSS | 453 |
| I.MB_eagd | CWLCRALIKRIQAIIEAGDRILPQLVCRLVLRCS | 454 |
| I.MB_eagd_ala | AWLARALIKRIQAIIEAGDRILPQLVARLVLRAS | 455 |
| I.MB_eagd_ser | SWLSRALIKRIQAIIEAGDRILPQLVSRLVLRSS | 456 |
| I.SMB_ala | FPIPLPYAWLARALIKRIQAIIPKGGRILPQLVARLVLRAS | 457 |
| I.SMB_ser | FPIPLPYSWLSRALIKRIQAIIPKGGRILPQLVSRLVLRSS | 458 |
| I.SMB_datk | FPIPLPYCWLCRALIKRIQAIIDATKRILPQLVCRLVLRCS | 459 |
| I.SMB_datk_ala | FPIPLPYAWLARALIKRIQAIIDATKRILPQLVARLVLRAS | 460 |
| I.SMB_datk_ser | FPIPLPYSWLSRALIKRIQAIIDATKRILPQLVSRLVLRSS | 461 |
| I.SMB_dhgs | FPIPLPYCWLCRALIKRIQAIIDHGSRILPQLVCRLVLRCS | 462 |
| I.SMB_dhgs_ala | FPIPLPYAWLARALIKRIQAIIDHGSRILPQLVARLVLRAS | 463 |
| I.SMB_dhgs_ser | FPIPLPYSWLSRALIKRIQAIIDHGSRILPQLVSRLVLRSS | 464 |
| I.SMB_hsgd | FPIPLPYCWLCRALIKRIQAIIHSGDRILPQLVCRLVLRCS | 465 |
| I.SMB_hsgd_ala | FPIPLPYAWLARALIKRIQAIIHSGDRILPQLVARLVLRAS | 466 |
| I.SMB_hsgd_ser | FPIPLPYSWLSRALIKRIQAIIHSGDRILPQLVSRLVLRSS | 467 |
| I.SMB_eagd | FPIPLPYCWLCRALIKRIQAIIEAGDRILPQLVCRLVLRCS | 468 |
| I.SMB_eagd_ala | FPIPLPYAWLARALIKRIQAIIEAGDRILPQLVARLVLRAS | 469 |
| I.SMB_eagd_ser | FPIPLPYSWLSRALIKRIQAIIEAGDRILPQLVSRLVLRSS | 470 |
| Nle.MB_ala | AWLARALIKRIQAXIPKGGRXLPQLVARLVLRAS | 471 |
| Nle.MB_ser | SWLSRALIKRIQAXIPKGGRXLPQLVSRLVLRSS | 472 |
| Nle.MB_datk | CWLCRALIKRIQAXIDATKRXLPQLVCRLVLRCS | 473 |
| Nle.MB_datk_ala | AWLARALIKRIQAXIDATKRXLPQLVARLVLRAS | 474 |
| Nle.MB_datk_ser | SWLSRALIKRIQAXIDATKRXLPQLVSRLVLRSS | 475 |
| Nle.MB_dhgs | CWLCRALIKRIQAXIDHGSRXLPQLVCRLVLRCS | 476 |
| Nle.MB_dhgs_ala | AWLARALIKRIQAXIDHGSRXLPQLVARLVLRAS | 477 |
| Nle.MB_dhgs_ser | SWLSRALIKRIQAXIDHGSRXLPQLVSRLVLRSS | 478 |
| Nle.MB_hsgd | CWLCRALIKRIQAXIHSGDRXLPQLVCRLVLRCS | 479 |
| Nle.MB_hsgd_ala | AWLARALIKRIQAXIHSGDRXLPQLVARLVLRAS | 480 |

TABLE 2-continued

Members of SP-B-like Peptides

| Name | Sequence | SEQ ID NO: |
|---|---|---|
| Nle.MB_hsgd_ser | SWLSRALIKRIQAXIHSGDRXLPQLVSRLVLRSS | 481 |
| Nle.MB_eagd | CWLCRALIKRIQAXIEAGDRXLPQLVCRLVLRCS | 482 |
| Nle.MB_eagd_ala | AWLARALIKRIQAXIEAGDRXLPQLVARLVLRAS | 483 |
| Nle.MB_eagd_ser | SWLSRALIKRIQAXIEAGDRXLPQLVSRLVLRSS | 484 |
| Nle.SMB_ala | FPIPLPYAWLARALIKRIQAXIPKGGRXLPQLVARLVLRAS | 485 |
| Nle.SMB_ser | FPIPLPYSWLSRALIKRIQAXIPKGGRXLPQLVSRLVLRSS | 486 |
| Nle.SMB_datk | FPIPLPYCWLCRALIKRIQAXIDATKRXLPQLVCRLVLRCS | 487 |
| Nle.SMB_datk_ala | FPIPLPYAWLARALIKRIQAXIDATKRXLPQLVARLVLRAS | 488 |
| Nle.SMB_datk_ser | FPIPLPYSWLSRALIKRIQAXIDATKRXLPQLVSRLVLRSS | 489 |
| Nle.SMB_dhgs | FPIPLPYCWLCRALIKRIQAXIDHGSRXLPQLVCRLVLRCS | 490 |
| Nle.SMB_dhgs_ala | FPIPLPYAWLARALIKRIQAXIDHGSRXLPQLVARLVLRAS | 491 |
| Nle.SMB_dhgs_ser | FPIPLPYSWLSRALIKRIQAXIDHGSRXLPQLVSRLVLRSS | 492 |
| Nle.SMB_hsgd | FPIPLPYCWLCRALIKRIQAXIHSGDRXLPQLVCRLVLRCS | 493 |
| Nle.SMB_hsgd_ala | FPIPLPYAWLARALIKRIQAXIHSGDRXLPQLVARLVLRAS | 494 |
| Nle.SMB_hsgd_ser | FPIPLPYSWLSRALIKRIQAXIHSGDRXLPQLVSRLVLRSS | 495 |
| Nle.SMB_eagd | FPIPLPYCWLCRALIKRIQAXIEAGDRXLPQLVCRLVLRCS | 496 |
| Nle.SMB_eagd_ala | FPIPLPYAWLARALIKRIQAXIEAGDRXLPQLVARLVLRAS | 497 |
| Nle.SMB_eagd_ser | FPIPLPYSWLSRALIKRIQAXIEAGDRXLPQLVSRLVLRSS | 498 |

In each of SEQ ID NOS: 471-498, X represents Norleucine (Nle).

Peptides within the consensus family of SEQ ID NO: 414 include peptide sequences that comprise one of SEQ ID NOS: 415-498, as well as peptide sequences that consist of one of SEQ ID NOS: 415-498.

A third synthetic peptide family of the present invention has molecular features analogous to SP-C and is designed to include peptides comprising the consensus amino acid sequence of:

XXIPXXPXXLKRLLXXXXX    (SEQ ID NO: 30)

where X at the first position is optional, and can be Leu or Phe, X at the second position is optional, and can be Gly or Arg, X at the fifth position is Phe, Cys, or Tyr, X at the sixth position is Phe or Tyr, X at the eighth position is Ser or Val, X at the ninth position is Ser or His, X at fourteenth position is Leu or Lys, X at the fifteenth and sixteenth positions is independently Ile, Leu, or Val, and X at the seventeenth to nineteenth positions is independently Val or Leu.

Exemplary peptides that correspond to the peptide of SEQ ID NO: 30 include, without limitation, those listed in Table 3 below, as well as combinations thereof

TABLE 3

Members of SP-C-like Peptides

| Name | Sequence | SEQ ID NO: |
|---|---|---|
| Mini-SPCff_dog | LGIPFFPSSLKRLLIIVVV-CONH$_2$ | 31 |
| Mini-SPCff_dog_leu | LGIPFFPSSLKRLLIILLL-CONH$_2$ | 32 |
| Mini-C dog cf_cys5 | LGIPCFPSSLKRLLIIVVV-CONH$_2$ | 33 |
| (disulfide dimer shown) | LGIPCFPSSLKRLLIIVVV-CONH$_2$ | |

TABLE 3-continued

Members of SP-C-like Peptides

| Name | Sequence | SEQ ID NO: |
|---|---|---|
| Mini-SPCff_2_leu | FGIPFFPVHLKRLLILLLL-CONH$_2$ | 34 |
| Super Mini-C | FRIPYYPVHLKRLLVVVVVIVGALLMGL | 35 |
| SP-C33FF | IPFFPVHLKRLKLLLLLLLLILLLILGALLMGL | 390 |

Peptides within the consensus family of SEQ ID NO: 30 include peptide sequences that comprise one of SEQ ID NOS: 31-35 and 390, as well as peptide sequences that consist of one of SEQ ID NOS: 31-35 and 390.

A fourth synthetic peptide family of the present invention has molecular features analogous to SP-C, but is modified to include one or more pairs of oppositely charged amino acid residues designed to form an ion lock. The peptides of this family comprise the consensus amino acid sequence of:

(SEQ ID NO: 36)
GIPXXPXXLKRLLIXVVVXXLXVXVIVGALLMG where X at the fourth and fifth positions are independently Ser or Phe; X at the seventh position is Val or Ser; X at the eighth position is His or Ser; X at positions 15 and 19 and 20 and 24 represent one or two pairs of residues that can form an ion lock, except that when only one pair forms an ion lock, then the other residues are a hydrophobic amino acid selected from Leu, Ile, and Val; and X at position 22 is Ile or Val. For the one or two pairs of residues at positions 15/19 and 20/24, the amino acids capable of forming an ion lock are positively-charged or negatively-charged amino acids, preferably Lys, Arg, Glu, or Asp, whereby when the amino acid at position 15 is positively charged then the amino acid at position 19 is negatively charged, or vice versa, and when the amino acid at position 20 is positively charged then the amino acid at position 24 is negatively charged, or vice versa. As noted above, one ion lock pair may be present at positions 15/19, in which case the amino acids at positions 20/24 are hydrophobic; one ion lock pair may be present at positions 20/24, in which case the amino acids at positions 15/19 are hydrophobic; or two ion lock pairs can be present at positions 15/19 and at positions 20/24.

Exemplary peptides that correspond to the peptide of SEQ ID NO: 36 include, without limitation, those listed in Table 4 below, as well as combinations thereof

TABLE 4

Members of SP-C-like Peptides with Ion-Lock

| Family and Name | Sequence | SEQ ID NO: |
|---|---|---|
| SP-C SS Ion Lock | | |
| E20/K24 | GIPSSPVHLKRLLIVVVVVELIVKVIVGALLMG | 37 |
| E20/R24 | GIPSSPVHLKRLLIVVVVVELIVRVIVGALLMG | 38 |
| D20/K24 | GIPSSPVHLKRLLIVVVVVDLIVKVIVGALLMG | 39 |
| D20/R24 | GIPSSPVHLKRLLIVVVVVDLIVRVIVGALLMG | 40 |
| K20/E24 | GIPSSPVHLKRLLIVVVVVKLIVEVIVGALLMG | 41 |
| R20/E24 | GIPSSPVHLKRLLIVVVVVRLIVEVIVGALLMG | 42 |
| K20/D24 | GIPSSPVHLKRLLIVVVVVKLIVDVIVGALLMG | 43 |
| R20/D24 | GIPSSPVHLKRLLIVVVVVRLIVDVIVGALLMG | 44 |
| SP-C SS Ion Lock + L | | |
| E20/K24 | GIPSSPVHLKRLLIVVVVVELIVKVIVGALLMGL | 45 |
| E20/R24 | GIPSSPVHLKRLLIVVVVVELIVRVIVGALLMGL | 46 |
| D20/K24 | GIPSSPVHLKRLLIVVVVVDLIVKVIVGALLMGL | 47 |
| D20/R24 | GIPSSPVHLKRLLIVVVVVDLIVRVIVGALLMGL | 48 |
| K20/E24 | GIPSSPVHLKRLLIVVVVVKLIVEVIVGALLMGL | 49 |
| R20/E24 | GIPSSPVHLKRLLIVVVVVRLIVEVIVGALLMGL | 50 |

TABLE 4-continued

Members of SP-C-like Peptides with Ion-Lock

| Family and Name | Sequence | SEQ ID NO: |
|---|---|---|
| K20/D24 | GIPSSPVHLKRLLIVVVVKLIVDVIVGALLMGL | 51 |
| R20/D24 | GIPSSPVHLKRLLIVVVVRLIVDVIVGALLMGL | 52 |
| SP-C FF Ion Lock | | |
| E20/K24 | GIPFFPVHLKRLLIVVVVELIVKVIVGALLMG | 398 |
| E20/R24 | GIPFFPVHLKRLLIVVVVELIVRVIVGALLMG | 399 |
| D20/K24 | GIPFFPVHLKRLLIVVVVDLIVKVIVGALLMG | 400 |
| D20/R24 | GIPFFPVHLKRLLIVVVVDLIVRVIVGALLMG | 401 |
| K20/E24 | GIPFFPVHLKRLLIVVVVKLIVEVIVGALLMG | 402 |
| R20/E24 | GIPFFPVHLKRLLIVVVVRLIVEVIVGALLMG | 403 |
| K20/D24 | GIPFFPVHLKRLLIVVVVKLIVDVIVGALLMG | 404 |
| R20/D24 | GIPFFPVHLKRLLIVVVVRLIVDVIVGALLMG | 405 |
| SP-C FF Ion Lock + L | | |
| E20/K24 | GIPFFPVHLKRLLIVVVVELIVKVIVGALLMGL | 406 |
| E20/R24 | GIPFFPVHLKRLLIVVVVELIVRVIVGALLMGL | 407 |
| D20/K24 | GIPFFPVHLKRLLIVVVVDLIVKVIVGALLMGL | 408 |
| D20/R24 | GIPFFPVHLKRLLIVVVVDLIVRVIVGALLMGL | 409 |
| K20/E24 | GIPFFPVHLKRLLIVVVVKLIVEVIVGALLMGL | 410 |
| R20/E24 | GIPFFPVHLKRLLIVVVVRLIVEVIVGALLMGL | 411 |
| K20/D24 | GIPFFPVHLKRLLIVVVVKLIVDVIVGALLMGL | 412 |
| R20/D24 | GIPFFPVHLKRLLIVVVVRLIVDVIVGALLMGL | 413 |
| SP-C SF Ion Lock | | |
| E20/K24 | GIPSFPSSLKRLLIVVVVELIVKVIVGALLMG | 53 |
| E20/R24 | GIPSFPSSLKRLLIVVVVELIVRVIVGALLMG | 54 |
| D20/K24 | GIPSFPSSLKRLLIVVVVDLIVKVIVGALLMG | 55 |
| D20/R24 | GIPSFPSSLKRLLIVVVVDLIVRVIVGALLMG | 56 |
| K20/E24 | GIPSFPSSLKRLLIVVVVKLIVEVIVGALLMG | 57 |
| R20/E24 | GIPSFPSSLKRLLIVVVVRLIVEVIVGALLMG | 58 |
| K20/D24 | GIPSFPSSLKRLLIVVVVKLIVDVIVGALLMG | 59 |
| R20/D24 | GIPSFPSSLKRLLIVVVVRLIVDVIVGALLMG | 60 |
| SP-C SF Ion Lock + L | | |
| E20/K24 | GIPSFPSSLKRLLIVVVVELIVKVIVGALLMGL | 61 |
| E20/R24 | GIPSFPSSLKRLLIVVVVELIVRVIVGALLMGL | 62 |
| D20/K24 | GIPSFPSSLKRLLIVVVVDLIVKVIVGALLMGL | 63 |
| D20/R24 | GIPSFPSSLKRLLIVVVVDLIVRVIVGALLMGL | 64 |
| K20/E24 | GIPSFPSSLKRLLIVVVVKLIVEVIVGALLMGL | 65 |
| R20/E24 | GIPSFPSSLKRLLIVVVVRLIVEVIVGALLMGL | 66 |

TABLE 4-continued

Members of SP-C-like Peptides with Ion-Lock

| Family and Name | Sequence | SEQ ID NO: |
|---|---|---|
| K20/D24 | GIPSFPSSLKRLLIVVVVKLIVDVIVGALLMGL | 67 |
| R20/D24 | GIPSFPSSLKRLLIVVVVRLIVDVIVGALLMGL | 68 |

SP-C FF Ion Lock2

| Family and Name | Sequence | SEQ ID NO: |
|---|---|---|
| K15/E19; E20/K24 | GIPFFPVHLKRLLIKVVVEELIVKVIVGALLMGL | 69 |
| K15/D19; E20/K24 | GIPFFPVHLKRLLIKVVVDELIVKVIVGALLMGL | 70 |
| K15/E19; D20/K24 | GIPFFPVHLKRLLIKVVVEDLIVKVIVGALLMGL | 71 |
| K15/D19; D20/K24 | GIPFFPVHLKRLLIKVVVDDLIVKVIVGALLMGL | 72 |
| K15/E19; E20/R24 | GIPFFPVHLKRLLIKVVVEELIVRVIVGALLMGL | 73 |
| K15/D19; E20/R24 | GIPFFPVHLKRLLIKVVVDELIVRVIVGALLMGL | 74 |
| K15/E19; D20/R24 | GIPFFPVHLKRLLIKVVVEDLIVRVIVGALLMGL | 75 |
| K15/D19; D20/R24 | GIPFFPVHLKRLLIKVVVDDLIVRVIVGALLMGL | 76 |
| K15/E19; K20/E24 | GIPFFPVHLKRLLIKVVVEKLIVEVIVGALLMGL | 77 |
| K15/D19; K20/E24 | GIPFFPVHLKRLLIKVVVDKLIVEVIVGALLMGL | 78 |
| K15/E19; K20/D24 | GIPFFPVHLKRLLIKVVVEKLIVDVIVGALLMGL | 79 |
| K15/D19; K20/D24 | GIPFFPVHLKRLLIKVVVDKLIVDVIVGALLMGL | 80 |
| K15/E19; R20/E24 | GIPFFPVHLKRLLIKVVVERLIVEVIVGALLMGL | 81 |
| K15/D19; R20/E24 | GIPFFPVHLKRLLIKVVVDRLIVEVIVGALLMGL | 82 |
| K15/E19; R20/D24 | GIPFFPVHLKRLLIKVVVERLIVDVIVGALLMGL | 83 |
| K15/D19; R20/D24 | GIPFFPVHLKRLLIKVVVDRLIVDVIVGALLMGL | 84 |
| R15/E19; E20/K24 | GIPFFPVHLKRLLIRVVVEELIVKVIVGALLMGL | 85 |
| R15/D19; E20/K24 | GIPFFPVHLKRLLIRVVVDELIVKVIVGALLMGL | 86 |
| R15/E19; D20/K24 | GIPFFPVHLKRLLIRVVVEDLIVKVIVGALLMGL | 87 |
| R15/D19; D20/K24 | GIPFFPVHLKRLLIRVVVDDLIVKVIVGALLMGL | 88 |
| R15/E19; E20/R24 | GIPFFPVHLKRLLIRVVVEELIVRVIVGALLMGL | 89 |
| R15/D19; E20/R24 | GIPFFPVHLKRLLIRVVVDELIVRVIVGALLMGL | 90 |
| R15/E19; D20/R24 | GIPFFPVHLKRLLIRVVVEDLIVRVIVGALLMGL | 91 |
| R15/D19; D20/R24 | GIPFFPVHLKRLLIRVVVDDLIVRVIVGALLMGL | 92 |
| R15/E19; K20/E24 | GIPFFPVHLKRLLIRVVVEKLIVEVIVGALLMGL | 93 |
| R15/D19; K20/E24 | GIPFFPVHLKRLLIRVVVDKLIVEVIVGALLMGL | 94 |
| R15/E19; K20/D24 | GIPFFPVHLKRLLIRVVVEKLIVDVIVGALLMGL | 95 |
| R15/D19; K20/D24 | GIPFFPVHLKRLLIRVVVDKLIVDVIVGALLMGL | 96 |
| R15/E19; R20/E24 | GIPFFPVHLKRLLIRVVVERLIVEVIVGALLMGL | 97 |
| R15/D19; R20/E24 | GIPFFPVHLKRLLIRVVVDRLIVEVIVGALLMGL | 98 |
| R15/E19; R20/D24 | GIPFFPVHLKRLLIRVVVERLIVDVIVGALLMGL | 99 |
| R15/D19; R20/D24 | GIPFFPVHLKRLLIRVVVDRLIVDVIVGALLMGL | 100 |
| E15/K19; E20/K24 | GIPFFPVHLKRLLIEVVVKELIVKVIVGALLMGL | 101 |
| E15/R19; E20/K24 | GIPFFPVHLKRLLIEVVVRELIVKVIVGALLMGL | 102 |

TABLE 4-continued

Members of SP-C-like Peptides with Ion-Lock

| Family and Name | Sequence | SEQ ID NO: |
|---|---|---|
| E15/K19; D20/K24 | GIPFFPVHLKRLLIEVVVKDLIVKIVGALLMGL | 103 |
| E15/R19; D20/K24 | GIPFFPVHLKRLLIEVVVRDLIVKIVGALLMGL | 104 |
| E15/K19; E20/R24 | GIPFFPVHLKRLLIEVVVKELIVRIVGALLMGL | 105 |
| E15/R19; E20/R24 | GIPFFPVHLKRLLIEVVVRELIVRIVGALLMGL | 106 |
| E15/K19; D20/R24 | GIPFFPVHLKRLLIEVVVKDLIVRIVGALLMGL | 107 |
| E15/R19; D20/R24 | GIPFFPVHLKRLLIEVVVRDLIVRIVGALLMGL | 108 |
| E15/K19; K20/E24 | GIPFFPVHLKRLLIEVVVKKLIVEIVGALLMGL | 109 |
| E15/R19; K20/E24 | GIPFFPVHLKRLLIEVVVRKLIVEIVGALLMGL | 110 |
| E15/K19; K20/D24 | GIPFFPVHLKRLLIEVVVKKLIVDIVGALLMGL | 111 |
| E15/R19; K20/D24 | GIPFFPVHLKRLLIEVVVRKLIVDIVGALLMGL | 112 |
| E15/K19; R20/E24 | GIPFFPVHLKRLLIEVVVKRLIVEIVGALLMGL | 113 |
| E15/R19; R20/E24 | GIPFFPVHLKRLLIEVVVRRLIVEIVGALLMGL | 114 |
| E15/K19; R20/D24 | GIPFFPVHLKRLLIEVVVKRLIVDIVGALLMGL | 115 |
| E15/R19; R20/D24 | GIPFFPVHLKRLLIEVVVRRLIVDIVGALLMGL | 116 |
| D15/K19; E20/K24 | GIPFFPVHLKRLLIDVVVKELIVKIVGALLMGL | 117 |
| D15/R19; E20/K24 | GIPFFPVHLKRLLIDVVVRELIVKIVGALLMGL | 118 |
| D15/K19; D20/K24 | GIPFFPVHLKRLLIDVVVKDLIVKIVGALLMGL | 119 |
| D15/R19; D20/K24 | GIPFFPVHLKRLLIDVVVRDLIVKIVGALLMGL | 120 |
| D15/K19; E20/R24 | GIPFFPVHLKRLLIDVVVKELIVRIVGALLMGL | 121 |
| D15/R19; E20/R24 | GIPFFPVHLKRLLIDVVVRELIVRIVGALLMGL | 122 |
| D15/K19; D20/R24 | GIPFFPVHLKRLLIDVVVKDLIVRIVGALLMGL | 123 |
| D15/R19; D20/R24 | GIPFFPVHLKRLLIDVVVRDLIVRIVGALLMGL | 124 |
| D15/K19; K20/E24 | GIPFFPVHLKRLLIDVVVKKLIVEIVGALLMGL | 125 |
| D15/R19; K20/E24 | GIPFFPVHLKRLLIDVVVRKLIVEIVGALLMGL | 126 |
| D15/K19; R20/D24 | GIPFFPVHLKRLLIDVVVKRLIVDIVGALLMGL | 127 |
| D15/R19; K20/D24 | GIPFFPVHLKRLLIDVVVRKLIVDIVGALLMGL | 128 |
| D15/K19; R20/E24 | GIPFFPVHLKRLLIDVVVKRLIVEIVGALLMGL | 129 |
| D15/R19; R20/E24 | GIPFFPVHLKRLLIDVVVRRLIVEIVGALLMGL | 130 |
| D15/K19; K20/D24 | GIPFFPVHLKRLLIDVVVKKLIVDIVGALLMGL | 131 |
| D15/R19; R20/D24 | GIPFFPVHLKRLLIDVVVRRLIVDIVGALLMGL | 132 |
| SP-C FF Ion Lock2 - L | | |
| K15/E19; E20/K24 | GIPFFPVHLKRLLIKVVVEELIVKIVGALLMG | 133 |
| K15/D19; E20/K24 | GIPFFPVHLKRLLIKVVVDELIVKIVGALLMG | 134 |
| K15/E19; D20/K24 | GIPFFPVHLKRLLIKVVVEDLIVKIVGALLMG | 135 |
| K15/D19; D20/K24 | GIPFFPVHLKRLLIKVVVDDLIVKIVGALLMG | 136 |
| K15/E19; E20/R24 | GIPFFPVHLKRLLIKVVVEELIVRIVGALLMG | 137 |
| K15/E19; D20/K24 | GIPFFPVHLKRLLIKVVVDELIVRIVGALLMG | 138 |
| K15/E19; D20/K24 | GIPFFPVHLKRLLIKVVVEDLIVRIVGALLMG | 139 |

TABLE 4-continued

Members of SP-C-like Peptides with Ion-Lock

| Family and Name | Sequence | SEQ ID NO: |
|---|---|---|
| K15/D19; D20/K24 | GIPFFPVHLKRLLIKVVVDDLIVRVIVGALLMG | 140 |
| K15/E19; K20/E24 | GIPFFPVHLKRLLIKVVVEKLIVEVIVGALLMG | 141 |
| K15/D19; K20/E24 | GIPFFPVHLKRLLIKVVVDKLIVEVIVGALLMG | 142 |
| K15/E19; K20/D24 | GIPFFPVHLKRLLIKVVVEKLIVDVIVGALLMG | 143 |
| K15/D19; K20/D24 | GIPFFPVHLKRLLIKVVVDKLIVDVIVGALLMG | 144 |
| K15/E19; R20/E24 | GIPFFPVHLKRLLIKVVVERLIVEVIVGALLMG | 145 |
| K15/D19; R20/E24 | GIPFFPVHLKRLLIKVVVDRLIVEVIVGALLMG | 146 |
| K15/E19; R20/D24 | GIPFFPVHLKRLLIKVVVERLIVDVIVGALLMG | 147 |
| K15/D19; R20/D24 | GIPFFPVHLKRLLIKVVVDRLIVDVIVGALLMG | 148 |
| R15/E19; E20/K24 | GIPFFPVHLKRLLIRVVVEELIVKVIVGALLMG | 149 |
| R15/D19; E20/K24 | GIPFFPVHLKRLLIRVVVDELIVKVIVGALLMG | 150 |
| R15/E19; D20/K24 | GIPFFPVHLKRLLIRVVVEDLIVKVIVGALLMG | 151 |
| R15/D19; D20/K24 | GIPFFPVHLKRLLIRVVVDDLIVKVIVGALLMG | 152 |
| R15/E19; E20/R24 | GIPFFPVHLKRLLIRVVVEELIVRVIVGALLMG | 153 |
| R15/D19; E20/R24 | GIPFFPVHLKRLLIRVVVDELIVRVIVGALLMG | 154 |
| R15/E19; D20/R24 | GIPFFPVHLKRLLIRVVVEDLIVRVIVGALLMG | 155 |
| R15/D19; D20/R24 | GIPFFPVHLKRLLIRVVVDDLIVRVIVGALLMG | 156 |
| R15/E19; K20/E24 | GIPFFPVHLKRLLIRVVVEKLIVEVIVGALLMG | 157 |
| R15/D19; K20/E24 | GIPFFPVHLKRLLIRVVVDKLIVEVIVGALLMG | 158 |
| R15/E19; K20/D24 | GIPFFPVHLKRLLIRVVVEKLIVDVIVGALLMG | 159 |
| R15/D19; K20/D24 | GIPFFPVHLKRLLIRVVVDKLIVDVIVGALLMG | 160 |
| R15/E19; R20/E24 | GIPFFPVHLKRLLIRVVVERLIVEVIVGALLMG | 161 |
| R15/D19; R20/E24 | GIPFFPVHLKRLLIRVVVDRLIVEVIVGALLMG | 162 |
| R15/E19; R20/D24 | GIPFFPVHLKRLLIRVVVERLIVDVIVGALLMG | 163 |
| R15/D19; R20/D24 | GIPFFPVHLKRLLIRVVVDRLIVDVIVGALLMG | 164 |
| E15/K19; E20/K24 | GIPFFPVHLKRLLIEVVVKELIVKVIVGALLMG | 165 |
| E15/R19; E20/K24 | GIPFFPVHLKRLLIEVVVRELIVKVIVGALLMG | 166 |
| E15/K19; D20/K24 | GIPFFPVHLKRLLIEVVVKDLIVKVIVGALLMG | 167 |
| E15/R19; D20/K24 | GIPFFPVHLKRLLIEVVVRDLIVKVIVGALLMG | 168 |
| E15/K19; E20/R24 | GIPFFPVHLKRLLIEVVVKELIVRVIVGALLMG | 169 |
| E15/R19; E20/R24 | GIPFFPVHLKRLLIEVVVRELIVRVIVGALLMG | 170 |
| E15/K19; D20/R24 | GIPFFPVHLKRLLIEVVVKDLIVRVIVGALLMG | 171 |
| E15/R19; D20/R24 | GIPFFPVHLKRLLIEVVVRDLIVRVIVGALLMG | 172 |
| E15/K19; K20/E24 | GIPFFPVHLKRLLIEVVVKKLIVEVIVGALLMG | 173 |
| E15/R19; K20/E24 | GIPFFPVHLKRLLIEVVVRKLIVEVIVGALLMG | 174 |
| E15/K19; K20/D24 | GIPFFPVHLKRLLIEVVVKKLIVDVIVGALLMG | 175 |
| E15/R19; K20/D24 | GIPFFPVHLKRLLIEVVVRKLIVDVIVGALLMG | 176 |

TABLE 4-continued

Members of SP-C-like Peptides with Ion-Lock

| Family and Name | Sequence | SEQ ID NO: |
|---|---|---|
| E15/K19; R20/E24 | GIPFFPVHLKRLLIEVVVKRLIVEIVGALLMG | 177 |
| E15/R19; R20/E24 | GIPFFPVHLKRLLIEVVVRRLIVEIVGALLMG | 178 |
| E15/K19; R20/D24 | GIPFFPVHLKRLLIEVVVKRLIVDIVGALLMG | 179 |
| E15/R19; R20/D24 | GIPFFPVHLKRLLIEVVVRRLIVDIVGALLMG | 180 |
| D15/K19; E20/K24 | GIPFFPVHLKRLLIDVVVKELIVKIVGALLMG | 181 |
| D15/R19; E20/K24 | GIPFFPVHLKRLLIDVVVRELIVKIVGALLMG | 182 |
| D15/K19; D20/K24 | GIPFFPVHLKRLLIDVVVKDLIVKIVGALLMG | 183 |
| D15/R19; D20/K24 | GIPFFPVHLKRLLIDVVVRDLIVKIVGALLMG | 184 |
| D15/K19; E20/R24 | GIPFFPVHLKRLLIDVVVKELIVRIVGALLMG | 185 |
| D15/R19; E20/R24 | GIPFFPVHLKRLLIDVVVRELIVRIVGALLMG | 186 |
| D15/K19; D20/R24 | GIPFFPVHLKRLLIDVVVKDLIVRIVGALLMG | 187 |
| D15/R19; D20/R24 | GIPFFPVHLKRLLIDVVVRDLIVRIVGALLMG | 188 |
| D15/K19; K20/E24 | GIPFFPVHLKRLLIDVVVKKLIVEIVGALLMG | 189 |
| D15/K19; K20/E24 | GIPFFPVHLKRLLIDVVVRKLIVEIVGALLMG | 190 |
| D15/R19; D20/D24 | GIPFFPVHLKRLLIDVVVKRLIVDIVGALLMG | 191 |
| D15/K19; K20/D24 | GIPFFPVHLKRLLIDVVVRKLIVDIVGALLMG | 192 |
| D15/K19; R20/E24 | GIPFFPVHLKRLLIDVVVKRLIVEIVGALLMG | 193 |
| D15/R19; R20/E24 | GIPFFPVHLKRLLIDVVVRRLIVEIVGALLMG | 194 |
| D15/K19; K20/D24 | GIPFFPVHLKRLLIDVVVKKLIVDIVGALLMG | 195 |
| D15/R19; R20/D24 | GIPFFPVHLKRLLIDVVVRRLIVDIVGALLMG | 196 |
| SP-C SS Ion Lock2 | | |
| K15/E19; E20/K24 | GIPSSPVHLKRLLIKVVVEELIVKVIVGALLMGL | 197 |
| K15/D19; E20/K24 | GIPSSPVHLKRLLIKVVVDELIVKVIVGALLMGL | 198 |
| K15/E19; D20/K24 | GIPSSPVHLKRLLIKVVVEDLIVKVIVGALLMGL | 199 |
| K15/D19; D20/K24 | GIPSSPVHLKRLLIKVVVDDLIVKVIVGALLMGL | 200 |
| K15/E19; E20/R24 | GIPSSPVHLKRLLIKVVVEELIVRVIVGALLMGL | 201 |
| K15/D19; E20/R24 | GIPSSPVHLKRLLIKVVVDELIVRVIVGALLMGL | 202 |
| K15/E19; D20/R24 | GIPSSPVHLKRLLIKVVVEDLIVRVIVGALLMGL | 203 |
| K15/D19; D20/R24 | GIPSSPVHLKRLLIKVVVDDLIVRVIVGALLMGL | 204 |
| K15/E19; K20/E24 | GIPSSPVHLKRLLIKVVVEKLIVEVIVGALLMGL | 205 |
| K15/D19; K20/E24 | GIPSSPVHLKRLLIKVVVDKLIVEVIVGALLMGL | 206 |
| K15/E19; K20/D24 | GIPSSPVHLKRLLIKVVVEKLIVDVIVGALLMGL | 207 |
| K15/D19; K20/D24 | GIPSSPVHLKRLLIKVVVDKLIVDVIVGALLMGL | 208 |
| K15/E19; R20/E24 | GIPSSPVHLKRLLIKVVVERLIVEVIVGALLMGL | 209 |
| K15/D19; R20/E24 | GIPSSPVHLKRLLIKVVVDRLIVEVIVGALLMGL | 210 |
| K15/E19; R20/D24 | GIPSSPVHLKRLLIKVVVERLIVDVIVGALLMGL | 211 |
| K15/D19; R20/D24 | GIPSSPVHLKRLLIKVVVDRLIVDVIVGALLMGL | 212 |
| R15/E19; E20/K24 | GIPSSPVHLKRLLIRVVVEELIVKVIVGALLMGL | 213 |

TABLE 4-continued

Members of SP-C-like Peptides with Ion-Lock

| Family and Name | Sequence | SEQ ID NO: |
|---|---|---|
| R15/D19; E20/K24 | GIPSSPVHLKRLLIRVVVDELIVKVIVGALLMGL | 214 |
| R15/E19; D20/K24 | GIPSSPVHLKRLLIRVVVEDLIVKVIVGALLMGL | 215 |
| R15/D19; D20/K24 | GIPSSPVHLKRLLIRVVVDDLIVKVIVGALLMGL | 216 |
| R15/E19; E20/R24 | GIPSSPVHLKRLLIRVVVEELIVRVIVGALLMGL | 217 |
| R15/D19; E20/R24 | GIPSSPVHLKRLLIRVVVDELIVRVIVGALLMGL | 218 |
| R15/E19; D20/R24 | GIPSSPVHLKRLLIRVVVEDLIVRVIVGALLMGL | 219 |
| R15/D19; D20/R24 | GIPSSPVHLKRLLIRVVVDDLIVRVIVGALLMGL | 220 |
| R15/E19; K20/E24 | GIPSSPVHLKRLLIRVVVEKLIVEVIVGALLMGL | 221 |
| R15/D19; K20/E24 | GIPSSPVHLKRLLIRVVVDKLIVEVIVGALLMGL | 222 |
| R15/E19; K20/D24 | GIPSSPVHLKRLLIRVVVEKLIVDVIVGALLMGL | 223 |
| R15/D19; K20/D24 | GIPSSPVHLKRLLIRVVVDKLIVDVIVGALLMGL | 224 |
| R15/E19; R20/E24 | GIPSSPVHLKRLLIRVVVERLIVEVIVGALLMGL | 225 |
| R15/D19; R20/E24 | GIPSSPVHLKRLLIRVVVDRLIVEVIVGALLMGL | 226 |
| R15/E19; R20/D24 | GIPSSPVHLKRLLIRVVVERLIVDVIVGALLMGL | 227 |
| R15/D19; R20/D24 | GIPSSPVHLKRLLIRVVVDRLIVDVIVGALLMGL | 228 |
| E15/K19; E20/K24 | GIPSSPVHLKRLLIEVVVKELIVKVIVGALLMGL | 229 |
| E15/R19; E20/K24 | GIPSSPVHLKRLLIEVVVRELIVKVIVGALLMGL | 230 |
| E15/K19; D20/K24 | GIPSSPVHLKRLLIEVVVKDLIVKVIVGALLMGL | 231 |
| E15/R19; D20/K24 | GIPSSPVHLKRLLIEVVVRDLIVKVIVGALLMGL | 232 |
| E15/K19; E20/R24 | GIPSSPVHLKRLLIEVVVKELIVRVIVGALLMGL | 233 |
| E15/R19; E20/R24 | GIPSSPVHLKRLLIEVVVRELIVRVIVGALLMGL | 234 |
| E15/K19; D20/R24 | GIPSSPVHLKRLLIEVVVKDLIVRVIVGALLMGL | 235 |
| E15/R19; D20/R24 | GIPSSPVHLKRLLIEVVVRDLIVRVIVGALLMGL | 236 |
| E15/K19; K20/E24 | GIPSSPVHLKRLLIEVVVKKLIVEVIVGALLMGL | 237 |
| E15/R19; K20/E24 | GIPSSPVHLKRLLIEVVVRKLIVEVIVGALLMGL | 238 |
| E15/K19; K20/D24 | GIPSSPVHLKRLLIEVVVKKLIVDVIVGALLMGL | 239 |
| E15/R19; K20/D24 | GIPSSPVHLKRLLIEVVVRKLIVDVIVGALLMGL | 240 |
| E15/K19; R20/E24 | GIPSSPVHLKRLLIEVVVKRLIVEVIVGALLMGL | 241 |
| E15/R19; R20/E24 | GIPSSPVHLKRLLIEVVVRRLIVEVIVGALLMGL | 242 |
| E15/K19; R20/D24 | GIPSSPVHLKRLLIEVVVKRLIVDVIVGALLMGL | 243 |
| E15/R19; R20/D24 | GIPSSPVHLKRLLIEVVVRRLIVDVIVGALLMGL | 244 |
| D15/K19; E20/K24 | GIPSSPVHLKRLLIDVVVKELIVKVIVGALLMGL | 245 |
| D15/R19; E20/K24 | GIPSSPVHLKRLLIDVVVRELIVKVIVGALLMGL | 246 |
| D15/K19; D20/K24 | GIPSSPVHLKRLLIDVVVKDLIVKVIVGALLMGL | 247 |
| D15/R19; D20/K24 | GIPSSPVHLKRLLIDVVVRDLIVKVIVGALLMGL | 248 |
| D15/K19; E20/R24 | GIPSSPVHLKRLLIDVVVKELIVRVIVGALLMGL | 249 |
| D15/R19; E20/R24 | GIPSSPVHLKRLLIDVVVRELIVRVIVGALLMGL | 250 |

TABLE 4-continued

Members of SP-C-like Peptides with Ion-Lock

| Family and Name | Sequence | SEQ ID NO: |
|---|---|---|
| D15/K19; D20/R24 | GIPSSPVHLKRLLIDVVVKDLIVRIVGALLMGL | 251 |
| D15/R19; D20/R24 | GIPSSPVHLKRLLIDVVVRDLIVRIVGALLMGL | 252 |
| D15/K19; K20/E24 | GIPSSPVHLKRLLIDVVVKKLIVEIVGALLMGL | 253 |
| D15/K19; K20/E24 | GIPSSPVHLKRLLIDVVVRKLIVEIVGALLMGL | 254 |
| D15/K19; R20/D24 | GIPSSPVHLKRLLIDVVVKRLIVDIVGALLMGL | 255 |
| D15/K19; K20/D24 | GIPSSPVHLKRLLIDVVVRKLIVDIVGALLMGL | 256 |
| D15/K19; R20/E24 | GIPSSPVHLKRLLIDVVVKRLIVEIVGALLMGL | 257 |
| D15/R19; R20/E24 | GIPSSPVHLKRLLIDVVVRRLIVEIVGALLMGL | 258 |
| D15/K19; K20/D24 | GIPSSPVHLKRLLIDVVVKKLIVDIVGALLMGL | 259 |
| D15/R19; R20/D24 | GIPSSPVHLKRLLIDVVVRRLIVDIVGALLMGL | 260 |

SP-C SS Ion Lock2 - L

| Family and Name | Sequence | SEQ ID NO: |
|---|---|---|
| K15/E19; E20/K24 | GIPSSPVHLKRLLIKVVVEELIVKIVGALLMG | 261 |
| K15/E19; E20/K24 | GIPSSPVHLKRLLIKVVVDELIVKIVGALLMG | 262 |
| K15/E19; E20/K24 | GIPSSPVHLKRLLIKVVVEDLIVKIVGALLMG | 263 |
| K15/E19; E20/K24 | GIPSSPVHLKRLLIKVVVDDLIVKIVGALLMG | 264 |
| K15/E19; E20/K24 | GIPSSPVHLKRLLIKVVVEELIVRIVGALLMG | 265 |
| K15/E19; E20/K24 | GIPSSPVHLKRLLIKVVVDELIVRIVGALLMG | 266 |
| K15/E19; E20/K24 | GIPSSPVHLKRLLIKVVVEDLIVRIVGALLMG | 267 |
| K15/E19; E20/K24 | GIPSSPVHLKRLLIKVVVDDLIVRIVGALLMG | 268 |
| K15/E19; E20/K24 | GIPSSPVHLKRLLIKVVVEKLIVEIVGALLMG | 269 |
| K15/E19; E20/K24 | GIPSSPVHLKRLLIKVVVDKLIVEIVGALLMG | 270 |
| K15/E19; E20/K24 | GIPSSPVHLKRLLIKVVVEKLIVDIVGALLMG | 271 |
| K15/E19; E20/K24 | GIPSSPVHLKRLLIKVVVDKLIVDIVGALLMG | 272 |
| K15/E19; E20/K24 | GIPSSPVHLKRLLIKVVVERLIVEIVGALLMG | 273 |
| K15/E19; E20/K24 | GIPSSPVHLKRLLIKVVVDRLIVEIVGALLMG | 274 |
| K15/E19; E20/K24 | GIPSSPVHLKRLLIKVVVERLIVDIVGALLMG | 275 |
| K15/E19; E20/K24 | GIPSSPVHLKRLLIKVVVDRLIVDIVGALLMG | 276 |
| K15/E19; E20/K24 | GIPSSPVHLKRLLIRVVVEELIVKIVGALLMG | 277 |
| K15/E19; E20/K24 | GIPSSPVHLKRLLIRVVVDELIVKIVGALLMG | 278 |
| K15/E19; E20/K24 | GIPSSPVHLKRLLIRVVVEDLIVKIVGALLMG | 279 |
| K15/E19; E20/K24 | GIPSSPVHLKRLLIRVVVDDLIVKIVGALLMG | 280 |
| K15/E19; E20/K24 | GIPSSPVHLKRLLIRVVVEELIVRIVGALLMG | 281 |
| K15/E19; E20/K24 | GIPSSPVHLKRLLIRVVVDELIVRIVGALLMG | 282 |
| K15/E19; E20/K24 | GIPSSPVHLKRLLIRVVVEDLIVRIVGALLMG | 283 |
| K15/E19; E20/K24 | GIPSSPVHLKRLLIRVVVDDLIVRIVGALLMG | 284 |
| K15/E19; E20/K24 | GIPSSPVHLKRLLIRVVVEKLIVEIVGALLMG | 285 |
| K15/E19; E20/K24 | GIPSSPVHLKRLLIRVVVDKLIVEIVGALLMG | 286 |
| K15/E19; E20/K24 | GIPSSPVHLKRLLIRVVVEKLIVDIVGALLMG | 287 |

TABLE 4-continued

Members of SP-C-like Peptides with Ion-Lock

| Family and Name | Sequence | SEQ ID NO: |
|---|---|---|
| K15/E19; E20/K24 | GIPSSPVHLKRLLIRVVVDKLIVDIVGALLMG | 288 |
| K15/E19; E20/K24 | GIPSSPVHLKRLLIRVVVERLIVEIVGALLMG | 289 |
| K15/E19; E20/K24 | GIPSSPVHLKRLLIRVVVDRLIVEIVGALLMG | 290 |
| K15/E19; E20/K24 | GIPSSPVHLKRLLIRVVVERLIVDIVGALLMG | 291 |
| K15/E19; E20/K24 | GIPSSPVHLKRLLIRVVVDRLIVDIVGALLMG | 292 |
| K15/E19; E20/K24 | GIPSSPVHLKRLLIEVVVKELIVKIVGALLMG | 293 |
| K15/E19; E20/K24 | GIPSSPVHLKRLLIEVVVRELIVKIVGALLMG | 294 |
| K15/E19; E20/K24 | GIPSSPVHLKRLLIEVVVKDLIVKIVGALLMG | 295 |
| K15/E19; E20/K24 | GIPSSPVHLKRLLIEVVVRDLIVKIVGALLMG | 296 |
| K15/E19; E20/K24 | GIPSSPVHLKRLLIEVVVKELIVRIVGALLMG | 297 |
| K15/E19; E20/K24 | GIPSSPVHLKRLLIEVVVRELIVRIVGALLMG | 298 |
| K15/E19; E20/K24 | GIPSSPVHLKRLLIEVVVKDLIVRIVGALLMG | 299 |
| K15/E19; E20/K24 | GIPSSPVHLKRLLIEVVVRDLIVRIVGALLMG | 300 |
| K15/E19; E20/K24 | GIPSSPVHLKRLLIEVVVKKLIVEIVGALLMG | 301 |
| K15/E19; E20/K24 | GIPSSPVHLKRLLIEVVVRKLIVEIVGALLMG | 302 |
| K15/E19; E20/K24 | GIPSSPVHLKRLLIEVVVKKLIVDIVGALLMG | 303 |
| K15/E19; E20/K24 | GIPSSPVHLKRLLIEVVVRKLIVDIVGALLMG | 304 |
| K15/E19; E20/K24 | GIPSSPVHLKRLLIEVVVKRLIVEIVGALLMG | 305 |
| K15/E19; E20/K24 | GIPSSPVHLKRLLIEVVVRRLIVEIVGALLMG | 306 |
| K15/E19; E20/K24 | GIPSSPVHLKRLLIEVVVKRLIVDIVGALLMG | 307 |
| K15/E19; E20/K24 | GIPSSPVHLKRLLIEVVVRRLIVDIVGALLMG | 308 |
| K15/E19; E20/K24 | GIPSSPVHLKRLLIDVVVKELIVKIVGALLMG | 309 |
| K15/E19; E20/K24 | GIPSSPVHLKRLLIDVVVRELIVKIVGALLMG | 310 |
| K15/E19; E20/K24 | GIPSSPVHLKRLLIDVVVKDLIVKIVGALLMG | 311 |
| K15/E19; E20/K24 | GIPSSPVHLKRLLIDVVVRDLIVKIVGALLMG | 312 |
| K15/E19; E20/K24 | GIPSSPVHLKRLLIDVVVKELIVRIVGALLMG | 313 |
| K15/E19; E20/K24 | GIPSSPVHLKRLLIDVVVRELIVRIVGALLMG | 314 |
| K15/E19; E20/K24 | GIPSSPVHLKRLLIDVVVKDLIVRIVGALLMG | 315 |
| K15/E19; E20/K24 | GIPSSPVHLKRLLIDVVVRDLIVRIVGALLMG | 316 |
| K15/E19; E20/K24 | GIPSSPVHLKRLLIDVVVKKLIVEIVGALLMG | 317 |
| K15/E19; E20/K24 | GIPSSPVHLKRLLIDVVVRKLIVEIVGALLMG | 318 |
| K15/E19; E20/K24 | GIPSSPVHLKRLLIDVVVKRLIVDIVGALLMG | 319 |
| K15/E19; E20/K24 | GIPSSPVHLKRLLIDVVVRKLIVDIVGALLMG | 320 |
| K15/E19; E20/K24 | GIPSSPVHLKRLLIDVVVKRLIVEIVGALLMG | 321 |
| K15/E19; E20/K24 | GIPSSPVHLKRLLIDVVVRRLIVEIVGALLMG | 322 |
| K15/E19; E20/K24 | GIPSSPVHLKRLLIDVVVKKLIVDIVGALLMG | 323 |
| K15/E19; E20/K24 | GIPSSPVHLKRLLIDVVVRRLIVDIVGALLMG | 324 |

Peptides within the consensus family of SEQ ID NO: 36 include peptide sequences that comprise one of SEQ ID NOS: 37-324 and 398-413, as well as peptide sequences that consist of one of SEQ ID NOS: 37-324 and 398-413.

A fifth synthetic peptide family of the present invention has molecular features analogous to SP-C and is designed to include peptides comprising the consensus amino acid sequence of:

IPXXPXXLKRLKLLXLLLXXILLXILGALLMGL (SEQ ID NO: 325)

where X at positions 3 and 4 are independently Ser or Phe; X at position 6 is Val or Ser; X at position 7 is His or Ser; X at positions 15 and 19 and 20 and 24 represent one or two pairs of residues that can form an ion lock, except that when only one pair forms an ion lock, then the other residues are a hydrophobic amino acid selected from Leu, Ile, and Val.

For the one or two pairs of residues at positions 15/19 and 20/24, the amino acids capable of forming an ion lock are positively-charged or negatively-charged amino acids, preferably Lys, Arg, Glu, or Asp, whereby when the amino acid at position 15 is positively charged then the amino acid at position 19 is negatively charged, or vice versa, and when the amino acid at position 20 is positively charged then the amino acid at position 24 is negatively charged, or vice versa. As noted above, one ion lock pair may be present at positions 15/19, in which case the amino acids at positions 20/24 are hydrophobic; one ion lock pair may be present at positions 20/24, in which case the amino acids at positions 15/19 are hydrophobic; or two ion lock pairs can be present at positions 15/19 and at positions 20/24.

Exemplary peptides that correspond to the peptide of SEQ ID NO: 325 include, without limitation, those listed in Table 5 below, as well as combinations thereof

TABLE 5

Members of SP-C-like Peptides with Ion-Lock

| Family and Name | Sequence | SEQ ID NO: |
|---|---|---|
| SP-C33SS Ion Lock2 | | |
| K15/E19; E20/K24 | IPSSPVHLKRLKLLKLLLEEILLKILGALLMGL | 326 |
| K15/D19; E20/K24 | IPSSPVHLKRLKLLKLLLDEILLKILGALLMGL | 327 |
| K15/E19; D20/K24 | IPSSPVHLKRLKLLKLLLEDILLKILGALLMGL | 328 |
| K15/D19; D20/K24 | IPSSPVHLKRLKLLKLLLDDILLKILGALLMGL | 329 |
| K15/E19; E20/R24 | IPSSPVHLKRLKLLKLLLEEILLRILGALLMGL | 330 |
| K15/D19; E20/R24 | IPSSPVHLKRLKLLKLLLDEILLRILGALLMGL | 331 |
| K15/E19; D20/R24 | IPSSPVHLKRLKLLKLLLEDILLRILGALLMGL | 332 |
| K15/D19; D20/R24 | IPSSPVHLKRLKLLKLLLDDILLRILGALLMGL | 333 |
| K15/E19; K20/E24 | IPSSPVHLKRLKLLKLLLEKILLEILGALLMGL | 334 |
| K15/D19; K20/E24 | IPSSPVHLKRLKLLKLLLDKILLEILGALLMGL | 335 |
| K15/E19; K20/D24 | IPSSPVHLKRLKLLKLLLEKILLDILGALLMGL | 336 |
| K15/D19; K20/D24 | IPSSPVHLKRLKLLKLLLDKILLDILGALLMGL | 337 |
| K15/E19; R20/E24 | IPSSPVHLKRLKLLKLLLERILLEILGALLMGL | 338 |
| K15/D19; R20/E24 | IPSSPVHLKRLKLLKLLLEEILLKILGALLMGL | 339 |
| K15/E19; R20/D24 | IPSSPVHLKRLKLLKLLLERILLDILGALLMGL | 340 |
| K15/D19; R20/D24 | IPSSPVHLKRLKLLKLLLDRILLDILGALLMGL | 341 |
| R15/E19; E20/K24 | IPSSPVHLKRLKLLRLLLEEILLKILGALLMGL | 342 |
| R15/D19; E20/K24 | IPSSPVHLKRLKLLRLLLDEILLKILGALLMGL | 343 |
| R15/E19; D20/K24 | IPSSPVHLKRLKLLRLLLEDILLKILGALLMGL | 344 |
| R15/D19; D20/K24 | IPSSPVHLKRLKLLRLLLDDILLKILGALLMGL | 345 |
| R15/E19; E20/R24 | IPSSPVHLKRLKLLRLLLEEILLRILGALLMGL | 346 |
| R15/D19; E20/R24 | IPSSPVHLKRLKLLRLLLDEILLRILGALLMGL | 347 |
| R15/E19; D20/R24 | IPSSPVHLKRLKLLRLLLEDILLRILGALLMGL | 348 |
| R15/D19; D20/R24 | IPSSPVHLKRLKLLRLLLDDILLRILGALLMGL | 349 |
| R15/E19; K20/E24 | IPSSPVHLKRLKLLRLLLEKILLEILGALLMGL | 350 |

TABLE 5-continued

Members of SP-C-like Peptides with Ion-Lock

| Family and Name | Sequence | SEQ ID NO: |
|---|---|---|
| R15/D19; K20/E24 | IPSSPVHLKRLKLLRLLLDKILLEILGALLMGL | 351 |
| R15/E19; K20/D24 | IPSSPVHLKRLKLLRLLLEKILLDILGALLMGL | 352 |
| R15/D19; K20/D24 | IPSSPVHLKRLKLLRLLLDKILLDILGALLMGL | 353 |
| R15/E19; R20/E24 | IPSSPVHLKRLKLLRLLLERILLEILGALLMGL | 354 |
| R15/D19; R20/E24 | IPSSPVHLKRLKLLRLLLEEILLKILGALLMGL | 355 |
| R15/E19; R20/D24 | IPSSPVHLKRLKLLRLLLERILLDILGALLMGL | 356 |
| R15/D19; R20/D24 | IPSSPVHLKRLKLLRLLLDRILLDILGALLMGL | 357 |
| E15/K19; E20/K24 | IPSSPVHLKRLKLLELLLKEILLKILGALLMGL | 358 |
| E15/R19; E20/K24 | IPSSPVHLKRLKLLELLLREILLKILGALLMGL | 359 |
| E15/K19; D20/K24 | IPSSPVHLKRLKLLELLLKDILLKILGALLMGL | 360 |
| E15/R19; D20/K24 | IPSSPVHLKRLKLLELLLRDILLKILGALLMGL | 361 |
| E15/K19; E20/R24 | IPSSPVHLKRLKLLELLLKEILLRILGALLMGL | 362 |
| E15/R19; E20/R24 | IPSSPVHLKRLKLLELLLREILLRILGALLMGL | 363 |
| E15/K19; D20/R24 | IPSSPVHLKRLKLLELLLKDILLRILGALLMGL | 364 |
| E15/R19; D20/R24 | IPSSPVHLKRLKLLELLLRDILLRILGALLMGL | 365 |
| E15/K19; K20/E24 | IPSSPVHLKRLKLLELLLKKILLEILGALLMGL | 366 |
| E15/R19; K20/E24 | IPSSPVHLKRLKLLELLLRKILLEILGALLMGL | 367 |
| E15/K19; K20/D24 | IPSSPVHLKRLKLLELLLKKILLDILGALLMGL | 368 |
| E15/R19; K20/D24 | IPSSPVHLKRLKLLELLLRKILLDILGALLMGL | 369 |
| E15/K19; R20/E24 | IPSSPVHLKRLKLLELLLKRILLEILGALLMGL | 370 |
| E15/R19; R20/E24 | IPSSPVHLKRLKLLELLLRRILLEILGALLMGL | 371 |
| E15/K19; R20/D24 | IPSSPVHLKRLKLLELLLKRILLDILGALLMGL | 372 |
| E15/R19; R20/D24 | IPSSPVHLKRLKLLELLLRRILLDILGALLMGL | 373 |
| D15/K19; E20/K24 | IPSSPVHLKRLKLLDLLLKEILLKILGALLMGL | 374 |
| D15/R19; E20/K24 | IPSSPVHLKRLKLLDLLLREILLKILGALLMGL | 375 |
| D15/K19; D20/K24 | IPSSPVHLKRLKLLDLLLKDILLKILGALLMGL | 376 |
| D15/R19; D20/K24 | IPSSPVHLKRLKLLDLLLRDILLKILGALLMGL | 377 |
| D15/K19; E20/R24 | IPSSPVHLKRLKLLDLLLKEILLRILGALLMGL | 378 |
| D15/R19; E20/R24 | IPSSPVHLKRLKLLDLLLREILLRILGALLMGL | 379 |
| D15/K19; D20/R24 | IPSSPVHLKRLKLLDLLLKDILLRILGALLMGL | 380 |
| D15/R19; D20/R24 | IPSSPVHLKRLKLLDLLLRDILLRILGALLMGL | 381 |
| D15/K19; K20/E24 | IPSSPVHLKRLKLLDLLLKKILLEILGALLMGL | 382 |
| D15/R19; K20/E24 | IPSSPVHLKRLKLLDLLLRKILLEILGALLMGL | 383 |
| D15/K19; R20/D24 | IPSSPVHLKRLKLLDLLLKRILLDILGALLMGL | 384 |
| D15/R19; K20/D24 | IPSSPVHLKRLKLLDLLLRKILLDILGALLMGL | 385 |
| D15/K19; R20/E24 | IPSSPVHLKRLKLLDLLLKRILLEILGALLMGL | 386 |
| D15/R19; R20/E24 | IPSSPVHLKRLKLLDLLLRRILLEILGALLMGL | 387 |

TABLE 5-continued

Members of SP-C-like Peptides with Ion-Lock

| Family and Name | Sequence | SEQ ID NO: |
|---|---|---|
| D15/K19; K20/D24 | IPSSPVHLKRLKLLDLLLKKILLDILGALLMGL | 388 |
| D15/R19; R20/D24 | IPSSPVHLKRLKLLDLLLRRILLDILGALLMGL | 389 |

Peptides within the consensus family of SEQ ID NO: 325 include peptide sequences that comprise one of SEQ ID NOS: 326-389, as well as peptide sequences that consist of one of SEQ ID NOS: 326-389. Specifically excluded from the scope of SEQ ID NO: 325 are peptides that consist of or consist essentially of

IPSSPVHLKRLKLLLLLLLLILLLILGALLMGL.
(SEQ ID NO: 397)

Further modifications in the above-identified peptides can be made without departing from the scope of this invention, including the replacement of any one or more leucine residues with isoleucine or norleucine, the replacement of any one or more isoleucine residues with leucine or norleucine, or the replacement of methionine residues in the peptides within the scope of consensus sequences SEQ ID NOS: 30, 36, and 325 with leucine, isoleucine, or norleucine (as illustrated above in Table 2, i.e., modifying SEQ ID NO: 1 to arrive at peptides within the scope of SEQ ID NO: 414).

The synthetic peptides of the present invention are designed with amino acid sequences that retard the transition of helical structures to non-specific or amyloid-like structures that have attenuated surface activity and/or increased surface or shear viscosity (Gordon et al., "Conformational Mapping of the N-Terminal Peptide of HIV-1 gp41 in Lipid Detergent and Aqueous Environments Using $^{13}$C-Enhanced Fourier Transform Infrared Spectroscopy," Protein Sci 13:1012-1030 (2004), which is hereby incorporated by reference in its entirety). Without being bound by belief, it is believed the synthetic peptides will increase shelf life as well as reduce surface or shear viscosity in synthetic lung surfactants to improve their ease of pulmonary delivery. In addition, the synthetic peptides of this invention are designed to allow the formulation of peptide-containing synthetic lung surfactants with salts containing calcium or other divalent or monovalent ions (as described above) so as to reduce surface or shear viscosity to improve pulmonary delivery as well as maximize shelf life.

The synthetic peptides of the present invention can be synthesized by standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. Using the same synthesis strategies, mimics of the surfactant peptides may also be prepared using either oligo-N-substituted glycines to make surface active surfactant peptoids (Seurynck et al., Chem. Biology 12:77-88 (2005), which is hereby incorporated by reference in its entirety) or by altering amino acid sequence of the surfactant peptide mimetic by introducing non-proteinaceous amino acids that improve resistance to protease cleavage (e.g., α,α-disubstituted aminoacids, and β-homo amino acids) (Yamaguchi et al., "Effect of alpha, alpha-disubstituted Amino Acids on the Protease Resistance of Peptides," Biosci., Biotechnol. Biochem. 67:2269-2272 (2003); Schreiber et al., "On the Biodegradation of beta-Peptides," Chem. Biol. Chem 3:4243-432 (2002), each of which is hereby incorporated by reference in its entirety).

Alternatively, the synthetic peptides can be synthesized in the presence of one or more synthetic lipid analogs described below and in PCT Application Publ. No. WO 2008/011559, which is hereby incorporated by reference in its entirety.

The surface-active peptides may be also prepared by using recombinant expression systems. Generally, this involves inserting the encoding nucleic acid molecule into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The nucleic acid molecules can be derived from the known SP-B and SP-C nucleotides using the above-referenced Genbank Accessions. In certain embodiments, it may be desirable to prepare codon-enhanced nucleic acids that will favor expression of the desired peptide in the transgenic expression system of choice. Alternatively, given their size, the nucleic acid molecules can be synthesized and then used for preparation of recombinant nucleic acid constructs.

By way of example, a consensus DNA sequence encoding the peptides of SEQ ID NO: 1 possesses a codon-optimized sequence for expression in E. coli as follows:

NNN TGG TTA NNN AGA GCA TTA ATA AAA AGA

ATA CAA GCA ATG ATA NNN NNN NNN NNN AGA

ATG TTA CCA CAA TTA GTA NNN AGA TTA GTA

TTA AGA NNN AGT (SEQ ID NO: 391), where the $1^{st}$, $4^{th}$, $27^{th}$, and $33^{rd}$ codons independently encode Ala, Ser, or Cys; and the $16^{th}$-$19^{th}$ codons encode the peptide sequence consisting of the Z sequences noted above (e.g., PKGG (SEQ ID NO: 500), DATK (SEQ ID NO: 501), DHGS (SEQ ID NO: 502), HSGD (SEQ ID NO: 503), or EAGD (SEQ ID NO: 504)). Specific codon-enhanced sequences for peptides of SEQ ID NOS: 2-29 can be identified using the online backtranslation tool available from Entelechon. The sequences can be modified at their ends to facilitate ligation into a nucleic acid construct or the presence of various regulatory sequences as described herein.

As a further example, a consensus DNA sequence encoding the peptides of SEQ ID NO: 414 possesses a codon-optimized sequence for expression in E. coli as follows:

```
NNN TGG TTA NNN AGA GCA TTA ATA AAA AGA

ATA CAA GCA NNN ATA NNN NNN NNN NNN AGA

NNN TTA CCA CAA TTA GTA NNN AGA TTA GTA

TTA AGA NNN AGT
```

(SEQ ID NO: 499), where the $1^{st}$, $4^{th}$, $27^{th}$, and $33^{rd}$ codons independently encode Ala, Ser, or Cys; the $16^{th}$-$19^{th}$ codons encode the peptide sequence consisting of the Z sequences noted above (e.g., PKGG (SEQ ID NO: 500), DATK (SEQ ID NO: 501), DHGS (SEQ ID NO: 502), HSGD (SEQ ID NO: 503), or EAGD (SEQ ID NO: 504)); and the $14^{th}$ and $21^{st}$ codons encode Leu or Iso. Specific codon-enhanced sequences for peptides of SEQ ID NOS: 415-470 can be identified using the online backtranslation tool available from Entelechon. The sequences can be modified at their ends to facilitate ligation into a nucleic acid construct or the presence of various regulatory sequences as described herein.

As another example, a consensus DNA sequence encoding the peptides of SEQ ID NO: 30 possesses a codon-optimized sequence for expression in E. coli as follows:

```
NNN NNN ATA CCA NNN NNN CCA NNN NNN TTA

AAA AGA TTA NNN NNN NNN NNN NNN NNN
```

(SEQ ID NO: 392), where the $1^{st}$ codon encodes Leu or Phe, the $2^{nd}$ codon encodes Gly or Arg, the $5^{th}$ codon encodes Phe, Cys, or Tyr, the $6^{th}$ codon encodes Phe or Tyr, the $8^{th}$ codon encodes Ser or Val, the $9^{th}$ codon encodes Ser or His, the $14^{th}$ codon encodes Leu or Lys, the $15^{th}$ and $16^{th}$ codons independently encode Ile, Leu, or Val, and the $17^{th}$-$19^{th}$ codons independently encode Val or Leu. Specific codon-enhanced sequences for peptides of SEQ ID NOS: 31-35 can be identified using the online backtranslation tool available from Entelechon. The sequences can be modified at their ends to facilitate ligation into a nucleic acid construct or the presence of various regulatory sequences as described herein.

As another example, a consensus DNA sequence encoding the peptides of SEQ ID NO: 36 possesses a codon-optimized sequence for expression in E. coli as follows:

```
GGA ATA CCA NNN NNN CCA NNN NNN TTA AAA

AGA TTA TTA ATA NNN GTA GTA GTA NNN NNN

TTA NNN GTA NNN GTA ATA GTA GGA GCA TTA

TTA ATG GGA
```

(SEQ ID NO: 393), where the $4^{th}$ and $5^{th}$ codons independently encode Ser of Phe; the $7^{th}$ codon encodes Val or Ser; the $8^{th}$ codon encodes His or Ser; at least one pair of the $15^{th}$ and $19^{th}$ codons and the $20^{th}$ and $24^{th}$ codons encode pairs of amino acid residues that can form an ion lock, as described above, except that when only one pair forms an ion lock, then the other pair encodes a hydrophobic amino acid independently selected from Leu, Ile, and Val; and the $22^{nd}$ codon encodes Ile or Val. Specific codon-enhanced sequences for peptides of SEQ ID NOS: 37-324 and 398-413 can be identified using the online backtranslation tool available from Entelechon. The sequences can be modified at their ends to facilitate ligation into a nucleic acid construct or the presence of various regulatory sequences as described herein.

As a further example, a consensus DNA sequence encoding the peptides of SEQ ID NO: 325 possesses a codon-optimized sequence for expression in E. coli as follows:

```
ATA CCA AGT AGT CCA GTA CAT TTA AAA AGA

TTA AAA TTA TTA NNN TTA TTA TTA NNN NNN

ATA TTA TTA NNN ATA TTA GGA GCA TTA TTA

ATG GGA TTA
```

(SEQ ID NO: 394), where the 3d and $4^{th}$ codons independently encode either Ser or Phe; the $6^{th}$ codon encodes Val or Ser; the $7^{th}$ codon encodes His or Ser; at least one pair of the $15^{th}$ and $19^{th}$ codons and the $20^{th}$ and $24^{th}$ codons encode pairs of amino acid residues that can form an ion lock, as described above, except that when only one pair forms an ion lock, then the other pair encodes a hydrophobic amino acid independently selected from Leu, Ile, and Val. Specific codon-enhanced sequences for peptides of SEQ ID NOS: 37-324 and 398-413 can be identified using the online backtranslation tool available from Entelechon. The sequences can be modified at their ends to facilitate ligation into a nucleic acid construct or the presence of various regulatory sequences as described herein.

These DNA molecules can be ligated into a nucleic acid constructs or expression system using methods well known in the art. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. Other vectors are also suitable.

Once a suitable expression vector is selected, the desired nucleic acid sequences are cloned into the vector using standard cloning procedures in the art, as described by Sambrook et al., Molecular Cloning: *A Laboratory Manual, Cold Springs Laboratory*, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used to carry out this and other aspects of the present invention.

Different genetic signals and processing events control many levels of gene expression (e.g., DNA transcription and messenger RNA ("mRNA") translation). Transcription of DNA is dependent upon the presence of a promoter, which is a DNA sequence that directs the binding of RNA polymerase, and thereby promotes mRNA synthesis. The DNA sequences of eukaryotic promoters differ from those of prokaryotic promoters. Furthermore, eukaryotic promoters and accompanying genetic signals may not be recognized in, or may not function in, a prokaryotic system; similarly, prokaryotic promoters are not recognized and do not function in eukaryotic cells.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters to obtain a high level of transcription and, hence, expression of the gene. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

When multiple nucleic acid molecules are inserted, the multiple nucleic acid molecules may all be placed under a single 5' regulatory region and a single 3' regulatory region, where the regulatory regions are of sufficient strength to transcribe and/or express the nucleic acid molecules as desired.

Specific initiation signals are also required for efficient gene transcription and translation in prokaryotic cells. These transcription and translation initiation signals may vary in "strength" as measured by the quantity of gene specific messenger RNA and protein synthesized, respectively. The nucleic acid expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used. Depending on the vector system and host utilized, any number of suitable transcription and/or translation elements, including constitutive, inducible, and repressible promoters, as well as minimal 5' promoter elements, enhancers or leader sequences may be used.

Typically, when a recombinant host is produced, an antibiotic or other compound useful for selective growth of only the transgenic cells is added as a supplement to the media. The compound to be used will be dictated by the selectable marker element present in the plasmid with which the host was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound, or other markers which indicate relevant information regarding the outcome of gene delivery, are also suitable. For example, various luminescent or phosphorescent reporter genes are also appropriate, such that the presence of the heterologous gene may be ascertained visually.

An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., "Primary Structure of the *Aequorea Victoria* Green-Fluorescent Protein," *Gene* 111(2):229-233 (1992); U.S. Pat. No. 5,491,084 to Chalfie et al., which are hereby incorporated by reference in their entirety). A plasmid encoding the GFP of *Aequorea victoria* is available from the ATCC as Accession No. 75547. Mutated forms of GFP that emit more strongly than the native protein are commercially available from Clontech Laboratories, Inc. (Palo Alto, Calif.) and can be used for the same purpose. Indeed, any nucleic acid molecule encoding a fluorescent form of GFP can be used in accordance with the subject invention. Standard techniques are then used to place the nucleic acid molecule encoding GFP under the control of the chosen cell specific promoter.

A nucleic acid molecule encoding a suitable cytokine, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Sambrook et al., *Molecular Cloning: A Laboratory Manual*, Cold Spring Laboratory, Cold Spring Harbor, N.Y. (1989); Ausubel et al., "Short Protocols in Molecular Biology," New York:Wiley (1999), and U.S. Pat. No. 4,237,224 to Cohen and Boyer, which are hereby incorporated by reference in their entirety.

In one embodiment, the recombinant expression system is suited for the secretion of hydrophobic proteins in recombinant organisms such that the hydrophobic protein is properly folded and either directed to the periplasm of Gram-negative bacteria or secreted into the extracellular environment. One example of such an expression system is disclosed in U.S. Application Publ. No. 20110020868 to Coleman et al., which is hereby incorporated by reference in its entirety. The system described in Coleman utilizes a *Pseudomonas fluorescens* (*P. fluorescens*) secretion polypeptide selected from a mutant phosphate binding protein (pbp*), a protein disulfide isomerase A (dsbA), a protein disulfide isomerase C (dsbC), a CupA2, a CupB2, a CupC2, a NikA, a FlgI, a tetratricopeptide repeat family protein (ORF5550), a toluene tolerance protein (Ttg2C), or a methyl accepting chemotaxis protein (ORF8124) secretion signal, a *Bacillus coagulans* Bce secretion signal sequence, as well as biologically active variants, fragments, and derivatives thereof.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, yeast, and mammalian cells.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Application Publ. No. 20110020868 to Coleman et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Whether the peptide of interest is secreted or not, it may also contain a purification tag (such as poly-histidine ($His_6$), a glutathione-S-transferase (GST-), or maltose-binding protein (MBP-)), which assists in the purification but can later be removed, i.e., cleaved from the peptide following recovery. Protease-specific cleavage sites can be introduced between the purification tag and the desired peptide. The desired peptide product can be purified further to remove the cleaved purification tags.

The peptides of the present invention are useful in formulating surfactant compositions for use in treating conditions involving disrupted lung.

The surfactant compositions of the invention include one or more of the above-identified peptides in combination with one or more lipids. In one embodiment, the one or more lipids include one or more synthetic ester-linked phospholipids or one or more phospholipase-resistant phospholipids or phosphonolipids. In an alternative embodiment, the one or more lipids include one or more naturally occurring phospholipids. In yet another embodiment, a mixture of synthetic and naturally occurring phospholipids is utilized.

Preferred synthetic lipid derivatives used in the surfactant compositions of the present invention are designed with molecular structures that are resistant to one or more endogenous phospholipases ($A_1$, $A_2$, and/or D) (Turcotte et al., "Chemical Synthesis and Surface Activity of Lung Surfactant Phospholipid Analogs. II. Racemic N-Substituted Diether Phosphonolipids," *Biochim Biophys Acta* 1084:1-12 (1991); Turcotte et al., "Chemical Synthesis and Surface Properties of an Analog of the Pulmonary Surfactant Dipalmitoyl Phosphatidylcholine Analog," *Biochim Biophys Acta* 488:235-248 (1977), each of which is hereby incorporated by reference in its entirety). Compounds of this type can also have partial resistance to degradation by phospholipase C (Lin et al., "A Diether Phosphonolipid Surfactant Analog, DEPN-8, is Resistant to Phospholipase-C Cleavage," *Respiration* 64:96-101 (1997), which is hereby incorporated by reference in its entirety). Phospholipase $A_2$ ($PLA_2$) is thought to play important roles in the pathogenesis of meconium aspiration syndrome (Kaapa, "Meconium Aspiration Syndrome: A Role for Phospholipase $A_2$ in the Pathogenesis?" *Acta Paediatr.* 90:365-367 (2001); Schrama et al., "Phospholipase $A_2$ is Present in Meconium and Inhibits the Activity of Pulmonary Surfactant: An in vitro Study," *Acta Paediatr.* 90:412-416 (2001)) and ARDS (Touqui et al., "A Role for Phospholipase $A_2$ in ARDS Pathogenesis," *Molec Med Today* 5:244-249 (1999), each of which is hereby incorporated by reference in its entirety). $PLA_2$ present in the lungs as a result of meconium aspiration or other forms of acute inflammatory lung injury can be directly inhibitory to surfactant function (Schrama et al., "Phospholipase $A_2$ is Present in Meconium and Inhibits the Activity of Pulmonary Surfactant: An in vitro Study," *Acta Paediatr.* 90:412-416 (2001); Enhorning et al., "Phospholipases Introduced into the Hypophase Affect the Surfactant Film Outlining a Bubble," *J Appl Physiol* 73:941-945 (1992); Holm et al., "Inhibition of Pulmonary Surfactant by Phospholipases," *J Appl Physiol* 71:317-321 (1991); Duncan et al., "Susceptibility of Exogenous Surfactant to Phospholipase $A_2$ Degradation," *Can J Physiol Pharmacol* 74:957-963 (1996); Arbibe et al., "Generation of Lyso-Phospholipids From Surfactant in Acute Lung Injury is Mediated by Type II Phospholipase $A_2$ and Inhibited by a Direct Surfactant Protein A-Phospholipase $A_2$ Interaction," *J Clin Invest* 102:1152-1160 (1998), each of which is hereby incorporated by reference in its entirety). $PLA_2$ not only can degrade and deplete active surfactant glycerophospholipids, but also produces reaction byproducts such as lysophosphatidylcholine (LPC) and unsaturated free fatty acids that interact biophysically with intact surfactant to further impair surface activity (Holm et al., "Multiple Mechanisms of Lung Surfactant Inhibition," *Pediatr Res* 46:85-93 (1999); Wang et al., "Additivity of Protein and Non-protein Inhibitors of Lung Surfactant Activity," *Am J Respir Crit Care Med* 158:28-35 (1998); Hall et al., "Inhibition of Pulmonary Surfactant by Oleic Acid: Mechanisms and Characteristics," *J Appl Physiol* 72:1708-1716 (1992), each of which is hereby incorporated by reference in its entirety). LPC and excess amounts of unsaturated free fatty acids can also directly injure the alveolocapillary membrane and increase its permeability to worsen pulmonary edema (Niewoehner et al., "Injurious Effects of Lysophosphatidylcholine on Barrier Properties of Alveolar Epithelium," *J Appl Physiol* 63:1979-1986 (1987); Hall et al., "Altered Function of Pulmonary Surfactant in Fatty Acid Lung Injury," *J Appl Physiol* 69:1143-1149 (1990), each of which is hereby incorporated by reference in its entirety).

According to one preferred embodiment, the phospholipase-resistant surfactants of this invention include one or more synthetic peptides combined with one or more phospholipase-resistant phospho-choline derivatives (analogs) and/or one or more phospholipase-resistant phospho-glycerol derivatives (analogs).

As used herein, the term "phospholipase-resistant phospho-choline derivative or analog" refers to a derivative of naturally occurring phospho-choline molecules in lung surfactant, where the derivatives are resistant to one or more of phospholipases $A_1$, $A_2$, C, and D, and have a structural modification in one or more of the fatty acid chain-backbone linkage group (e.g., ether, thioether, etc.), phospho group, or the remainder of the head group including the choline group.

The phospholipase-resistant phospho-choline derivative preferably has a structure according to formula (II)

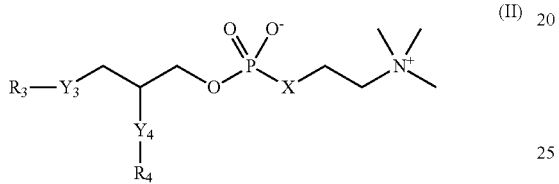

(II)

where X is O or $(CH_2)_n$ where n is an integer from 0 to 5, $Y_3$ and $Y_4$ are independently O, S, or $SO_2$, and $R_3$ and $R_4$ are independently C8-C24 hydrocarbons.

The hydrocarbon groups of $R_3$ and $R_4$ can be the same or different, and can be saturated, monounsaturated, or polyunsaturated hydrocarbons, although saturated and monounsaturated are preferred. Preferred hydrocarbons are C10-C22 hydrocarbons, more preferably C12-C20 hydrocarbons, most preferably C14-C18 hydrocarbons. According to one embodiment, the phospholipase-resistant phospho-choline derivative has a saturated $R_3$ group and a monounsaturated or polyunsaturated $R_4$ group.

When X is $(CH_2)_n$, n is preferably an integer from 0 to 2.

The $Y_3$ and $Y_4$ linker groups can be the same or different. According to one preferred embodiment, at least one of these linker groups is S or $SO_2$, more preferably the $Y_3$ group. According to another embodiment, both $Y_3$ and $Y_4$ are S or $SO_2$. According to a further embodiment, both $Y_3$ and $Y_4$ are O.

Exemplary phospholipase-resistant phospho-choline derivatives include, without limitation, [(±)-trimethyl(3-phosphonopropyl)ammonium, mono(2,3-bis(hexadecyloxy) propyl ester] ("DEPN-8"); [(-±)-trimethyl(3-phosphonopropyl)ammonium, mono(2-hexadec-9-enyloxy-3-hexadecyloxypropyl) ester] ("UnDEPN-8"); [(±)-trimethyl (3-phosphonopropyl)ammonium, mono(2-hexadecyloxy-3-hexadecylsulfanylpropyl) ester] ("S-lipid"); [(±)-trimethyl (3-phosphonopropyl)ammonium, mono(2-hexadecyloxy-3-hexadecylsulfonylpropyl) ester] ("$SO_2$-lipid"); and combinations thereof. Of these phospholipase-resistant phospho-choline derivatives, DEPN-8 and $SO_2$-lipid are preferred.

As used herein, the term "phospholipase-resistant phospho-glycerol derivative or analog" refers to a derivative of naturally occurring phospho-glycerol molecules in lung surfactant, where the derivative is resistant to one or more of phospholipases $A_1$, $A_2$, C, and D, and has a structural modification in one or more of the fatty acid chain-backbone linkage group (e.g., ether, thioether, etc.), phospho group, or the remainder of the head group including the glycerol group.

The phospholipase-resistant phospho-glycerol derivative is preferably a compound having a structure according to formulae (Ia) or (Ib)

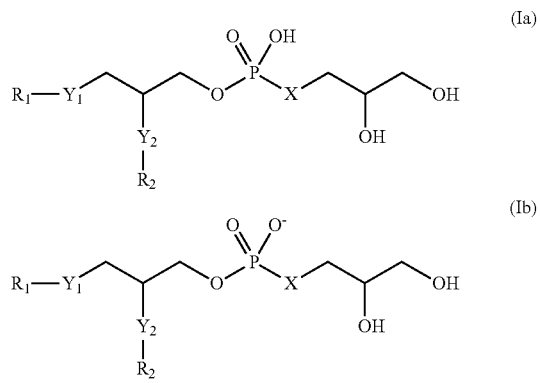

where X is O or $(CH_2)_n$ where n is an integer from 0 to 5, $Y_1$ and $Y_2$ are independently O, S, or $SO_2$, and $R_1$ and $R_2$ are independently C8-C24 hydrocarbons.

The hydrocarbon groups of $R_1$ and $R_2$ can be the same or different, and can be saturated, monounsaturated, or polyunsaturated hydrocarbons, although saturated and monounsaturated are preferred. Preferred hydrocarbons are C10-C22 hydrocarbons, more preferably C12-C20 hydrocarbons, most preferably C14-C18 hydrocarbons. According to one embodiment, the phospholipase-resistant phospho-glycerol derivative has a saturated $R_1$ group and a monounsaturated or polyunsaturated $R_2$ group.

When X is $(CH_2)_n$, n is preferably an integer from 0 to 2. The molecular change at the level of the phosphate group in phosphono-lipid analogs is believed to confer structural resistance to Phospholipase D.

The $Y_1$ and $Y_2$ linker groups can be the same or different. According to one preferred embodiment, at least one of these linker groups is S or $SO_2$, more preferably the $Y_1$ group. According to another embodiment, both $Y_1$ and $Y_2$ are S or $SO_2$. According to a further embodiment, both $Y_1$ and $Y_2$ are O. The synthetic lipids of the present invention are designed to have several important molecular features. One such feature is the molecular modifications used in the $Y_1$ and $Y_2$ linkage groups between the fatty chains and the glycerol backbone, which confer structural resistance to phospholipase $A_1$ ($PLA_1$) and $A_2$ ($PLA_2$).

According to one embodiment, the phospholipase-resistant phospho-glycerol derivative has the structure according to formula (Ib) and is present in the form of a salt, preferably a pharmaceutically acceptable salt. The term "pharmaceutically acceptable salt" refers to those salts that retain the biological effectiveness and properties of the free bases. The salts are formed with any suitable cation including, without limitation, sodium, potassium, calcium, magnesium, zinc, and protonated amino acid residues. Other salts are known to those of skill in the art and can readily be adapted for use in accordance with the present invention.

Exemplary phospholipase-resistant phospho-glycerol derivatives include, without limitation, 2,3-bis(hexadecyloxy)propyl 2,3-dihydroxypropyl hydrogen phosphate ("PG-A"); 2-((Z)-hexadec-9-enyloxy)-3-(hexadecyloxy) propyl 2,3-dihydroxypropyl hydrogen phosphate ("PG-B");

2,3-bis(hexadecyloxy)propyl hydrogen 3,4-dihydroxybutyl-phosphonate ("PG-C"); 2-(hexadecyloxy)-3-(hexadecylthio)propyl 2,3-dihydroxypropyl hydrogen phosphate; 2-(hexadecyloxy)-3-(hexadecylsulfonyl)propyl 2,3-dihydroxypropyl hydrogen phosphate; 2-((E)-hexadec-9-enyloxy)-3-(hexadecylthio)propyl 2,3-dihydroxypropyl hydrogen phosphate; 2-((E)-hexadec-9-enyloxy)-3-(hexadecylsulfonyl)propyl 2,3-dihydroxypropyl hydrogen phosphate; 2-(hexadecyloxy)-3-(hexadecylthio)propyl hydrogen 3,4-dihydroxybutylphosphonate; 2-(hexadecyloxy)-3-(hexadecylsulfonyl)propyl hydrogen 3,4-dihydroxybutylphosphonate; 2-((E)-hexadec-9-enyloxy)-3-(hexadecylthio)propyl hydrogen 3,4-dihydroxybutylphosphonate; 2-((E)-hexadec-9-enyloxy)-3-(hexadecylsulfonyl)propyl hydrogen 3,4-dihydroxybutylphosphonate; (Z)-2-(hexadec-9-enyloxy)-3-(hexadecyloxy)propyl hydrogen (3,4-dihydroxybutyl)phosphonate; (Z)-2-(hexadec-9-enylthio)-3-(hexadecylthio)propyl hydrogen (3,4-dihydroxybutyl)phosphonate; (Z)-2-(hexadec-9-enylsulfonyl)-3-(hexadecylsulfonyl)propyl hydrogen (3,4-dihydroxybutyl)phosphonate; (E)-2-(hexadec-9-enyloxy)-3-(hexadecyloxy)propyl hydrogen (3,4-dihydroxybutyl)phosphonate; (E)-2-(hexadec-9-enylthio)-3-(hexadecylthio)propyl hydrogen (3,4-dihydroxybutyl)phosphonate; (E)-2-(hexadec-9-enylsulfonyl)-3-(hexadecylsulfonyl)propyl hydrogen (3,4-dihydroxybutyl)phosphonate.

In addition to phospholipase resistance, molecular changes in lipid analogs vary the hydrophobicity, molecular flexibility, functional cross-section, bilayer behavior, and surface activity of these compounds. The C16:0 moieties in selected analog compounds in analogy with DPPC (the most prevalent glycerophospholipid in endogenous lung surfactant) promote their ability to form tightly-packed surface films that generate very low surface tensions under dynamic compression.

At the same time, the use of ether or sulfur or other linkages instead of the 'normal' ester linkage between the fatty chains and the glycerol backbone enhances the adsorption and film respreading of analog compounds relative to DPPC. For example, ether linkages increase chain mobility and facilitate film respreading during cycling in the C16:0 diether analog compound DEPN-8 compared to DPPC (Turcotte et al., "Chemical Synthesis and Surface Properties of an Analog of the Pulmonary Surfactant Dipalmitoyl Phosphatidylcholine Analog," *Biochim Biophys Acta* 488:235-248 (1977); Liu et al., "Dynamic Interfacial Properties of Surface-Excess Films of Phospholipids and Phosphonolipid Analogs: I. Effects of pH," *J Colloid Interface Sci* 167:378-390 (1994); Liu et al., "Dynamic Interfacial Properties of Surface-Excess Films of Phospholipid and Phosphonolipid Analogs: II. Effects of Chain Linkage and Headgroup Structure," *J Colloid Interface Sci* 167:391-400 (1994), each of which is hereby incorporated by reference in its entirety). DEPN-8 is also able to form interdigitated as well as normal opposed bilayers (Skita et al., "Bilayer Characteristics of a Diether Phosphonolipid Analog of the Major Lung Surfactant Glycerophospholipid Dipalmitoyl Phosphatidylcholine," *J Lipid Res* 36:1116-1127 (1995), which is hereby incorporated by reference in its entirety), which further modifies its behavior in films and in lipid aggregates in the aqueous phase. The S and $SO_2$ linkages at the chain-backbone in selected analog compounds were chosen in part because sulfur is more hydrophobic than oxygen, and the use of sulfur-containing linkages maintains resistance to $PLA_1$ and $PLA_2$ as is the case with ether linkages. In addition, the headgroup analogy to phosphatidylglycerol (PG), utilized in some analog compounds of the present invention, was chosen because PG is a primary class of anionic glycerophospholipids in endogenous lung surfactant and has specific interactions with lung surfactant proteins (Notter, *Lung Surfactants: Basic Science and Clinical Applications*, Marcel Dekker, Inc, New York (2000)), which is hereby incorporated by reference in its entirety). In particular, the PG-related lipid analogs of the present invention are designed to facilitate interactions with the positive charges present in the headgroup of choline-related analogs and/or with positively charged amino acid residues present in synthetic peptides.

The phospholipase-resistant phospholipids can be synthesized according to the procedures described in PCT Application Publ. No. WO 2008/011559 to Notter et al.; Schwan et al., "Synthesis and Activity of a Novel Diether Phosphonoglycerol in Phospholipase-resistant Synthetic Lipid:Peptide Lung Surfactants," *Med Chem. Commun.* 2:1167 (2011) Wang et al., "Surface Activity of a Synthetic Lung Surfactant Containing a Phospholipase-Resistant Phosphonolipid Analog of Dipalmitoyl Phosphatidylcholine," *J. Physiol. Lung Cell Mol. Physiol* 285:L550-L559 (2003); Chang et al., "Surface Properties of Sulfur- and Ether-Linked Phosphonolipids With and Without Purified Hydrophobic Lung Surfactant Proteins," *Chem Phys Lipids* 137:77-93 (2005); Harlos et al., "Influence of Calcium on Phosphatidylglycerol: Two Separate Lamellar Structures," *Biochemistry* 19:895-899 (1980); Fuji et al., "A Stereoselective and Highly Practical Synthesis of Cytosolic Phospholipase A2 Substrate, 2-S-Arachidonoyl-1-O-hexadecyl-sn-2-thioglycero-3-O-phosphocholine," *J. Org. Chem.* 62:6804-6809 (1997); Turcotte et al., "Chemical Synthesis and Surface Activity of Lung Surfactant Phospholipid Analogs. II. Racemic N-Substituted Diether Phosphonolipids," *Biochim Biophys Acta* 1084:1-12 (1991); Turcotte et al., "Chemical Synthesis and Surface Properties of an Analog of the Pulmonary Surfactant Dipalmitoyl Phosphatidylcholine Analog," *Biochim Biophys Acta* 488:235-248 (1977); Liu et al., "Dynamic Interfacial Properties of Surface-Excess Films of Phospholipids and Phosphonolipid Analogs. I. Effects of pH," *J Colloid Interface Sci* 167:378-390 (1994); Liu et al., "Dynamic Interfacial Properties of Surface-Excess Films of Phospholipid and Phosphonolipid Analogs: II. Effects of Chain Linkage and Headgroup Structure," *J Colloid Interface Sci* 167:391-400 (1994); Liu et al., "Thermotropic Behavior of Structurally-Related Phospholipids and Phosphonolipid Analogs of Lung Surfactant Glycerophospholipids," *Langmuir* 11:101-107 (1995); Wang et al., "Surface Activity of a Synthetic Lung Surfactant Containing a Phospholipase-Resistant Phosphonolipid Analog of Dipalmitoyl Phosphatidylcholine," *Am J Physiol* 285:L550-L559 (2003); Chang et al., "Surface Properties of Sulfur- and Ether-Linked Phosphonolipids With and Without Purified Hydrophobic Lung Surfactant Proteins," *Chem Phys Lipids* 137:77-93 (2005); Notter et al., "Synthesis and Surface Activity of Diether Linked Phosphoglycerols: Potential Applications for Exogenous Lung Surfactants," *Bioorg Med Chem Lett* 17:113-117 (2007); Notter et al, "Novel phospholipase-resistant lipid/peptide synthetic lung surfactants," *Mini Revs Med Chem* 7:932-944 (2007); Schwan et al, "Synthesis and activity of a novel diether phosphonoglycerol in phospholipase-resistant synthetic lipid:peptide lung surfactants", *Med Chem Commun* 2:1167-1173 (2011), each of which is hereby incorporated by reference in its entirety).

The phospholipase-resistant lipid compounds can be present in the surfactant formulations as a racemic mixture, containing substantially equivalent amounts of stereoisomers. In another embodiment, the phospholipase-resistant lipid compounds can be prepared or otherwise isolated, using known procedures, to obtain a single stereoisomer substantially free of its corresponding stereoisomer (i.e., substantially pure). By substantially pure, it is intended that a stereoisomer is at least about 95% pure, more preferably at least about 98% pure, most preferably at least about 99% pure. Both racemic mixtures and substantially pure stereoisomers of the phospholipase-resistant lipid compounds can be used to prepare surfactant compositions of the present invention.

According to another preferred embodiment, the surfactants of this invention include one or more synthetic peptides combined with one or more naturally occurring phospholipids. Exemplary naturally occurring phospholipids include, without limitation, DPPC (16:0 PC; 1,2-dipalmitoyl-sn-glycero-3-phosphocholine); POPC [PC(16:0/18:1 (9Z)); 1-hexadecanoyl 1,2(9Z-octadecenoyl)-sn-glycero-3-phosphocholine; POPG [PG(16:0/18:1(9Z)); 1-hexadecanoyl-2-(9Z-octadecenoyl)-sn-glycero-3-phospho-(1'-rac-glycerol); and combinations thereof.

In certain embodiments where naturally occurring phospholipids are utilized, a mixture of phosphocholine lipids and phosphoglycerol lipids are present, preferably at a mole ratio or weight ratio of total phosphoglycerol lipids to total phosphocholine lipids of between about 1:1 to about 1:100, preferably about 1:3 to about 1:50, more preferably about 1:4 to about 1:25. For example, using a mixture of POPG, DPPC, and POPC to form the lipid component of the synthetic surfactant formulation, the ratio of POPG to total phosphocholines (DPPC+POPC) is between about 1:1 up to about 1:100.

The surfactant compositions of the present invention can further include any one or more of a non-phospho surfactant or a therapeutic agent including a pharmacological agent.

As used herein, the term "non-phospho surfactant" refers to surface active compounds that do not possess a phospho group (e.g., phosphate, phosphonate, etc.). Exemplary non-phospho surfactants include, without limitation, a free fatty acid, hexadecanol, or cholesterol.

Preferred free fatty acids include saturated and monounsaturated C10 to C24 hydrocarbons, more preferably C12-C20 hydrocarbons, most preferably C14-C18 hydrocarbons. Of these, saturated hydrocarbons are preferred.

The therapeutic agent can be any compound, nucleic acid, or peptide that is intended to be administered to the targeted lung tissues for therapeutic treatment of a disease or disorder involving the affected tissue. Exemplary therapeutic agents include, without limitation, antioxidant enzymes, other antioxidant substances, anti-inflammatory agents (drugs, antibodies, receptor antagonists, and soluble receptors, etc.), vasoactive agents or agents synergistic with vasoactive agents, agents affecting leukocyte function or recruitment, agents affecting platelet aggregation, agents affecting resident pulmonary cells involved in host-defense, and agents participating in gene therapy.

According to one embodiment, the surfactant composition includes, in addition to the surface active peptide, both a phospholipase-resistant phospho-glycerol derivative and a phospholipase-resistant phospho-choline derivative. Typically, the phospholipase-resistant phospho-glycerol derivative and the phospholipase-resistant phospho-choline derivative are present at a mole ratio or weight ratio of between about 1:1 to about 1:100, preferably about 1:3 to about 1:50, more preferably about 1:4 to about 1:25.

According to one embodiment, the phospholipase-resistant phospho-choline derivative is present in an amount of about 65 to about 99 wt percent, more preferably between about 75 and about 98 wt percent; the phospholipase-resistant phospho-glycerol derivative is present in an amount up to about 25 wt percent, more preferably between about 1 and about 20 wt percent; and the surface active peptide is present in an amount of about 1 to about 15 wt percent, more preferably about 1 to about 7.5 wt percent, relative to total phospholipid (non-protein components).

In accordance therewith, in the following exemplary example surfactant compositions set forth below, the total weight percentage of the lipid components equals 100 weight percent, and the peptide is added to this as a weight percentage based on the total phospholipid content.

Composition A:

| weight percent | component |
|---|---|
| about 75 to about 95 | DEPN-8 |
| about 5 to about 25 | C16:0 or C16:1 diether phosphono- or phospho-PG |
| about 1 to about 7.5 (relative to total lipid content) | SMB_DATK (SEQ ID NO: 18, reduced or oxidized), MB_DATK (SEQ ID NO: 4, reduced or oxidized), MB_DATK_Ala (SEQ ID NO: 5), or combinations thereof |

Composition B:

| weight percent | component |
|---|---|
| about 80 to about 99 | DEPN-8 |
| about 1 to about 10 | C16:0, C16:1 diether phosphono- or phospho-PG |
| up to about 10 | Palmitic acid |
| about 1 to about 7.5 (relative to total lipid content) | Mini-SPCff_dog (SEQ ID NO: 31), Mini-S PCff_dog_leu (SEQ ID NO: 32), Mini-SPCff_2_leu (SEQ ID NO: 34), Super Mini-SP-C (SEQ ID NO: 35), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), SP-C33ss_ion2 (SEQ ID NO: 326), or combinations thereof |

Composition C:

| weight percent | component |
|---|---|
| about 85 to about 96 | DEPN-8 or diether C16:0 saturated PC analog |
| about 2.5 to about 10 | C16:0, C18:1 diether phosphono- or phospho-PG |
| up to about 7 | Palmitic acid |
| about 1 to about 4 (relative to total lipid content) | at least one of SMB_DATK (SEQ ID NO: 18, reduced or oxidized), MB_DATK (SEQ ID NO: 4, reduced or oxidized), and MB_DATK_Ala (SEQ ID NO: 5) |
| about 1 to about 4 (relative to total lipid content) | at least one of Mini-SPCff_dog (SEQ ID NO: 31), Mini-SPCff_dog_leu (SEQ ID NO: 32), Mini-SPCff_2_leu (SEQ ID NO: 34), Super Mini-SP-C (SEQ ID NO: 35)), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), and SP-C33ss_ion2 (SEQ ID NO: 326) |

Composition D:

| weight percent | component |
|---|---|
| about 70 to about 95 | DPPC |
| about 5 to about 25 | POPG |
| up to about 25 | POPC |

-continued

| weight percent | component |
|---|---|
| about 1 to about 7.5 (relative to total lipid content) | SMB_DATK (SEQ ID NO: 18, reduced or oxidized), MB_DATK (SEQ ID NO: 4, reduced or oxidized), MB_DATK_Ala (SEQ ID NO: 5), or combinations thereof |

Composition E:

| weight percent | component |
|---|---|
| about 70 to about 95 | DPPC |
| about 5 to about 25 | POPG |
| up to about 25 | POPC |
| about 1 to about 7.5 (relative to total lipid content) | Mini-SPCff_dog (SEQ ID NO: 31), Mini-SPCff_dog_leu (SEQ ID NO: 32), Mini-SPCff_2_leu (SEQ ID NO: 34), Super Mini-SP-C (SEQ ID NO: 35), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), SP-C33ss_ion2 (SEQ ID NO: 326), or combinations thereof |

Composition F:

| weight percent | component |
|---|---|
| about 70 to about 95 | DPPC |
| about 5 to about 25 | POPG |
| up to about 25 | POPC |
| up to about 7 | Palmitic acid |
| about 1 to about 4 (relative to total lipid content) | at least one of SMB_DATK (SEQ ID NO: 18, reduced or oxidized), MB_DATK (SEQ ID NO: 4, reduced or oxidized), and MB_DATK_Ala (SEQ ID NO: 5) |
| about 1 to about 4 (relative to total lipid content) | at least one of Mini-SPCff_dog (SEQ ID NO: 31), Mini-SPCff_dog_leu (SEQ ID NO: 32), Mini-SPCff_2_leu (SEQ ID NO: 34), Super Mini-SP-C (SEQ ID NO: 35)), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), and SP-C33ss_ion2 (SEQ ID NO: 326) |

The surfactant compositions of the present invention can be used to treat lung tissue that is characterized by deficiency and/or dysfunction of endogenous surfactant (i.e., "surfactant deficient or dysfunctional lung tissue"). In certain embodiments, the deficiency of endogenous surfactant can be a reduced amount or an abnormal composition of endogenous surfactant (i.e., not enough is present or the composition thereof is ineffective) or the complete absence of an endogenous surfactant, and the surfactant dysfunction can be a reduced activity of endogenous surfactant either present intrinsically or acquired during disease. Thus, the term "treatment" of surfactant deficient and/or dysfunctional lung tissue is meant to include a prophylactic or therapeutic regimen that can inhibit onset of NRDS, for example, in premature infants, or the onset of acute lung injury (ALI) or the acute respiratory distress syndrome (ARDS) in patients of any age, or otherwise improve respiratory function, lung pressure-volume mechanics, or clinical outcome when administered for therapeutic treatment of a pre-existing conditions such as acute or neonatal NRDS, or ALI, or ARDS. As used herein, "treatment" contemplates complete therapeutic resolution of a condition as well as improving conditions to minimize symptoms of NRDS or ALI/ARDS.

The treatments in accordance with this aspect of the invention involve administering a surfactant composition of the present invention to a patient having lung tissue characterized by endogenous surfactant deficiency and/or dysfunction, where the administering is carried out under conditions effective to coat alveolar surfaces of the affected lung tissue with the surfactant composition, thereby treating the surfactant deficient and/or dysfunctional lung tissue.

The patient to be treated can be a premature infant who is characterized by either the complete absence of endogenous surfactant or an ineffective amount of endogenous surfactant or an acquired dysfunction of endogenous surfactant during the clinical course. In either case, the surfactant composition of the present invention can be administered in a manner effective to prevent onset of neonatal respiratory distress syndrome (when administered immediately following intubation), or reduce the severity of respiratory deficit in neonatal respiratory distress syndrome and/or acute lung injury (when administered some time after initial intubation). Administration of the surfactant composition is preferably via aspiration, airway instillation, aerosolization, or nebulization. Administration of the surfactant can be administered periodically over a course of treatment to maintain lung function in the infant, preferably until the infant's lung tissue is capable of producing sufficient endogenous surfactant to maintain lung function in the absence of intervention.

The patient to be treated can also be an individual that otherwise should be able to produce active endogenous surfactant, but due to lung tissue disease or disorder either has deficient levels of endogenous surfactant or existing endogenous surfactant has become inhibited or inactivated in activity. In this embodiment, the patient is a full-term infant, child, or adult. Endogenous surfactant production can be deficient or inactivated due to acute lung injury caused by pulmonary disease or infection, systemic disease or infection, or other direct or indirect causes such as burns, trauma, shock, aspiration syndromes, drug overdose, multiple blood transfusions, pancreatitis, or other known causes of ALI/ARDS. In either acquired surfactant deficiency or dysfunction, the surfactant composition of the present invention can be administered in a manner effective to reduce the severity of respiratory deficit in acute respiratory distress syndrome and/or acute lung injury. The surfactant composition may also be administered prophylactically to such patients to prevent the onset of ALI/ARDS. Administration of the surfactant composition is preferably via aspiration, airway instillation, aerosolization, or nebulization. Administration of the surfactant can be administered periodically over a course of treatment to maintain lung function in the individual being treated.

Another aspect of the present invention relates to a method of delivering a therapeutic agent. By virtue of the surface activity of the compositions of the present invention, it is believed that the surfactant compositions of the present invention will readily form liposomal vesicles that can be used to deliver therapeutic agents to a patient. Thus, this method of the present invention includes introducing a therapeutic agent into a surfactant composition of the present invention under conditions effective to encapsulate the therapeutic agent in liposomal vesicles, and then administering the composition to a subject under conditions effective to deliver the therapeutic agent to a target tissue. The administration can be any suitable approach for delivery of the therapeutic agent to a target tissue, but preferably aspiration, airway instillation, aerosolization, nebulization, intranasal instillation, oral or nasogastic instillation, intraperitoneal injection, or intravascular injection. The target tissue can be lung tissue or a systemic tissue. The agent or agents to be delivered can be any pharmaceutical or therapeutic agent including those listed above as well as a systemic or local anti-tumor agent, a systemic or local gene therapy agent, a systemic or local anti-inflammatory agent or antioxidant, a systemic or local vasoactive agent, a systemic or local agent modifying immune responses, blood cells, or host-defense.

EXAMPLES

The following examples are intended to illustrate the present invention, but are not intended to limit the scope of the appended claims.

Example 1—Bioengineering of Novel Peptide Mimics Based on the SP-B Consensus Amino Acid Sequence (SEQ ID NO: 1) with an Optimized Turn Region and Enhanced Surfactant Activities Novel surfactant peptide (SP-B) mimics with an optimized turn region were developed using an iterative design process, in which key structural features of potential mimics were identified using a variety of computer algorithms and promising candidates were then synthesized for experimental testing.

As one example of this new peptide family with the SP-B consensus sequence (SEQ ID NO: 1), the SP-B mimics MB_datk (SEQ ID NO:4) and SMB_datk (SEQ ID NO:18) were engineered after first noting that the bend region in either Mini-B (MB) or Super Mini-B (SMB) (i.e., -PKGG- (SEQ ID NO: 500)) promoted a compact helix-turn-helix motif, with the central bend region flanked by N- and C-terminal α-helices (Waring et al., "The Role of Charged Amphipathic Helices in the Structure and Function of Surfactant Protein B,"*J Peptide Res* 66:364-374 (2005); Sarker et al., "Structure of Mini-B, a Functional Fragment of Surfactant Protein B, in Detergent Micelles," *Biochemistry* 46:11047-11056 (2007); Walther et al., "Critical Structural and Functional Roles for the N-terminal Insertion Sequence in Surfactant Protein B Analogs," *PLoS One* 5:e8672 (2010), each of which is hereby incorporated by reference in its entirety). The high surfactant activity observed with either MB or SMB was at least partially due to the close physical juxtaposition of the N- and C-terminal helices, facilitated by the presence of the -PKGG- (SEQ ID NO: 500) turn (see Research Collaboratory for Structural Bioinformatics (RCSB), PDB accession codes: 1SSZ and 2DWF) (Waring et al., "The Role of Charged Amphipathic Helices in the Structure and Function of Surfactant Protein B,"*J Peptide Res* 66:364-374 (2005); Sarker et al., "Structure of Mini-B, a Functional Fragment of Surfactant Protein B, in Detergent Micelles," *Biochemistry* 46:11047-11056 (2007); Walther et al., "Critical Structural and Functional Roles for the N-terminal Insertion Sequence in Surfactant Protein B Analogs," *PLoS One* 5:e8672 (2010), each of which is hereby incorporated by reference in its entirety).

Theoretical predictions, based on internet-accessible support vector machines ("SVM") (Kountouris and Hirst, "Prediction of Backbone Dihedral Angles and Protein Secondary Structure Using Support Vector Machines," *BMC Bioinformatics* 10:437 (2009); Kountouris and Hirst, "Predicting Beta-turns and Their Types Using Predicted Backbone Dihedral Angles and Secondary Structures," *BMC Bioinformatics* 11:407 (2010), each of which is hereby incorporated by reference in its entirety) employing multiple sequence alignments and predicted secondary structures and dihedral angles also confirmed that the -PKGG- (SEQ ID NO: 500) region folds as a turn in either MB or SMB. Specifically, submission of the respective primary sequences to the DEBT website at the University of Nottingham (Kountouris and Hirst, "Prediction of Backbone Dihedral Angles and Protein Secondary Structure Using Support Vector Machines," *BMC Bioinformatics* 10:437 (2009); Kountouris and Hirst, "Predicting Beta-turns and Their Types Using Predicted Backbone Dihedral Angles and Secondary Structures," *BMC Bioinformatics* 11:407 (2010), each of which is hereby incorporated by reference in its entirety) indicated theoretical predictions of beta-turns for the -PKGG- (SEQ ID NO: 500) regions in either MB or SMB.

The primary sequences for the MB_datk (SEQ ID NO:4) and SMB_datk (SEQ ID NO:18) peptides were engineered by replacing the -PKGG- (SEQ ID NO: 500) turn sequence with the sequence -DATK- (residues 16-19 of SEQ ID NO: 4). The MB_datk and SMB_datk sequences were also submitted to the DEBT website, and theoretical predictions similarly showed beta-turns encompassing the respective -DATK- regions. Homology modeling of the MB_datk peptide (SEQ ID NO:4) using the GROMACS suite of programs (Lindahl et al., "GROMACS 3.0: A Package for Molecular Simulation and Trajectory Analysis," *J Mol Model* 7:306-317 (2001), which is hereby incorporated by reference in its entirety) was performed to further assess the three-dimensional (3D) folding of this SP-B mimic. Using the GROMACS suite of programs (Lindahl et al., "GROMACS 3.0: A Package for Molecular Simulation and Trajectory Analysis," *J Mol Model* 7:306-317 (2001), which is hereby incorporated by reference in its entirety), the -PKGG- (SEQ ID NO: 500) bend was mutated to -DATK-, and the homologous MB_datk structure was placed in a periodic 65 cubic Å box of HFIP (hexafluoroisopropanol)/water to emulate a surfactant lipid environment (Walther et al., "Critical Structural and Functional Roles for the N-terminal Insertion Sequence in Surfactant Protein B Analogs," *PLoS One* 5:e8672 (2010), which is hereby incorporated by reference in its entirety). The ensemble containing the MB_datk peptide was minimized by the steepest descent method as implemented in the GROMACS 4.5.5 environment (Lindahl et al., "GROMACS 3.0: A Package for Molecular Simulation and Trajectory Analysis," *J Mol Model* 7:306-317 (2001), which is hereby incorporated by reference in its entirety). Chloride counter ions were added to the solvent box with the peptide to neutralize its charge with constraints on the peptide; the ensemble was then subjected to 100 psec of molecular dynamics (MD) at 300K using the ffG53a6 force field option that allows the solvent to equilibrate while restraining the peptide. The resulting homology-based MB_datk structure confirmed that replacement of -PKGG- (SEQ ID NO: 500) with -DATK- produced a structure that was very similar to that of its parent MB (PDB Accession Code: 1SSZ), with a turn at the -DATK- region and closely neighboring N- and C-terminal α-helices.

Using these initial, computer-based screens, the MB_datk (SEQ ID NO:4) and SMB_datk (SEQ ID NO:18) peptides were synthesized and purified as described in Example 4 below, with high purity for each confirmed by mass spectrometry.

Example 2—Bioengineering of Shortened Novel Peptide Mimics Based on the SP-C Consensus Amino Acid Sequence (SEQ ID NO: 30) with Enhanced Surfactant Activities New surfactant peptide mimics based on native SP-C proteins were also developed with an iterative design process, in which native SP-C and potential SP-C mimic peptides were analyzed with computer algorithms and candidates were then synthesized for further testing. The focus in this example is on engineering SP-C mimics with short amino acid sequences that lack the covalently attached palmitoyl groups found in native SP-C proteins, both to simplify peptide synthesis and purification and also to minimize preparative costs.

As one example of specific molecular design, the Mini-SPCff_dog_leu (SEQ ID NO: 32) was identified by screening SP-C mimics based on the parent, native dog SP-C sequence (i.e., GIPCFPSSLKRLLIIVVVIVLVVVVIV-GALLMGL, SEQ ID NO: 395). Prior studies have shown that native dog SP-C is a 34-residue SP-C protein, palmitoylated at Cys-4, which exhibits high α-helix and low β-sheet on Circular Dichroism (CD) spectroscopy and has good surfactant activity in vitro (Creuwels et al., "Characterization of a Dimeric Canine Form of Surfactant Protein C (SP-C)," *Biochim Biophys Acta* 1254:326-332 (1995), which is hereby incorporated by reference in its entirety). Elevated α-helix and high surfactant activity has been observed for other native SP-C proteins (dipalmitoylated at adjacent Cys residues), suggesting that helical SP-C domains are directly important for in vitro and in vivo surfactant activities (Johansson, "Structure and Properties of Surfactant Protein C," *Biochim Biophys Acta* 1408:161-172 (1998); Walther et al., "Surfactant Protein B and C Analogues," Mol Genet Metab 71: 342-351 (2000); Walther et al., "Hydrophobic Surfactant Proteins and Their Analogues," *Neonatology* 91:303-310 (2007), each of which is hereby incorporated by reference in its entirety).

In analyses here, native dog SP-C(SEQ ID NO: 395) was scanned for those regions likely to form β-sheets by submitting its primary sequence to the PASTA website (Trovato et al., "Insight into the Structure of Amyloid Fibrils from the Analysis of Globular Proteins," *PloS Comput Biol* 2:e170 (2006); Trovato et al., "The PASTA Server for Protein Aggregation Prediction," *Protein Eng Des Sel* 20:521-523 (2007), each of which is hereby incorporated by reference in its entirety). PASTA assigns relative energies to specific β-pairings of two sequence stretches of the same length (i.e., 10-100 pairings), and assumes that lower relative energies reflect enhanced β-sheet aggregation. With dog SP-C, PASTA calculated an exceptionally low energy of −28.5 for the segment 12-27 in a parallel pairing (Walther et al., "Critical Structural and Functional Roles for the N-terminal Insertion Sequence in Surfactant Protein B Analogs," *PLoS One* 5:e8672 (2010), which is hereby incorporated by reference in its entirety). Despite the PASTA prediction that dog SP-C will have a high tendency to form β-sheet, however, CD spectroscopy primarily indicated high α-helix and only minimal β-sheet in dog SP-C (Creuwels et al., "Characterization of a Dimeric Canine Form of Surfactant Protein C (SP-C)," *Biochim Biophys Acta* 1254:326-332 (1995), which is hereby incorporated by reference in its entirety). The apparent contradiction may be resolved by noting that the PASTA algorithm does not explicitly account for the palmitoyl group linked to dog SP-C. An important function for the palmitoyl of dog SP-C may be to protect against the formation of inactive β-sheet from active α-helical conformers (Johansson, "Structure and Properties of Surfactant Protein C," *Biochim Biophys Acta* 1408:161-172 (1998), which is hereby incorporated by reference in its entirety), as has been observed with other SP-C proteins (Wang et al., "Acylation of Pulmonary Surfactant Protein-C Is Required for its Optimal Surface Active Interactions with Phospholipids," *J Biol Chem* 271:19104-19109 (1996); Dluhy et al., "Deacylated Pulmonary Surfactant Protein SP-C Transforms from alpha-Helical to Amyloid Fibril Structure via a pH-Dependent Mechanism: An Infrared Structural Investigation," *Biophys J* 85:2417-2429 (2003), each of which is hereby incorporated by reference in its entirety). Further MPEx hydropathy analysis of dog SP-C indicated a high hydropathy value (i.e., +11.97 for residues 12-30), consistent with the helical region inserting into surfactant lipids with high affinity (see Internet site for the White laboratory at US Irvine) (Snider et al., "MPEx: A Tool for Exploring Membrane Proteins," *Protein Sci* 18:2624-2628 (2009), which is hereby incorporated by reference in its entirety).

Several dog SP-C mimics lacking the palmitoyl were next screened with PASTA and MPEx, using as a minimum criteria that successful SP-C mimics have a PASTA energy higher than −28.5 and a positive MPEx hydropathy. Such screening indicated that Mini-SPCff_dog_leu (SEQ ID NO: 32) was a promising surfactant-active mimic, with PASTA energy of −7.8 for the parallel segment 13-19 and a MPEx hydropathy of +8.57 for residues 1-19. This peptide was then synthesized (Example 4) and tested for adsorption activity in vitro (Example 7).

Example 3—Bioengineering of Novel Peptide Mimics Based on the SP-C Consensus Amino Acid Sequence (SEQ ID NO: 36) with an Ion-Lock and Enhanced Surfactant Activities Another iterative design strategy for obtaining highly active SP-C mimics involved computer analysis of SP-C peptides containing charged ion-pairs (i.e., 'salt-bridges' or 'ion-locks', in which the cationic $Arg^+$ or $Lys^+$ residues interact with anionic $Glu^-$ or $Asp^-$ residues), with follow-up synthesis and characterization of promising SP-C ion-lock mimics. In an earlier CD study, Marqusee and Baldwin (Marqusee et al., "Helix Stabilization by $Glu^-$-$Lys^+$ Salt Bridges in Short Peptides of de novo Design," *Proc Natl Acad Sci USA* 84:8898-8902 (1987), each of which is hereby incorporated by reference in its entirety) showed that incorporation of $Lys^+$ and $Glu^-$ at intervals of 4 residues (i.e., "i+4") in the sequence substantially increased the helix content of the host peptide. This stabilization of the α-helix is due to the formation of an electrostatically neutral ion-pair via the positively- and negative-charged side groups for the $Lys^+$ and $Glu^-$ residues. More recent hydropathy analysis using the MPEx website (see Internet site for the White laboratory at US Irvine) and the augmented Wimley-White hydrophobicity scale indicated that insertion of such 'salt-bridges or 'ion-locks' could increase the helicity of both soluble and membrane-bound peptides and proteins (Snider et al., "MPEx: A Tool for Exploring Membrane Proteins," *Protein Sci* 18:2624-2628 (2009); Jayasinghe et al., "Energetics, Stability, and Prediction of Transmembrane Helices," *J Mol Biol* 312:927-934 (2001), each of which is hereby incorporated by reference in its entirety). Because the formation of an ion pair is electrostatically neutral, there is only a small thermodynamic penalty for replacing the hydrophobic residues of a transmembrane sequence with an 'ion-lock' pairing (e.g., $Lys^+$ and $Glu^-$) (Jayasinghe et al., "Energetics, Stability, and Prediction of Transmembrane Helices," *J Mol Biol* 312:927-934 (2001), which is hereby incorporated by reference in its entirety). The insertion of ion-locks has been earlier used in several designer peptides for specific purposes, such as the enhancement of α-helix and anti-HIV activity in sifuvirtide (He et al., "Design and Evaluation of Sifuvirtide, a Novel HIV-1 Fusion Inhibitor," *J Biol Chem*

283:11126-11134 (2008), which is hereby incorporated by reference in its entirety), and the trapping of otherwise unstable structural features such as π-helix (Chapman et al., "Trapping a Folding Intermediate of the alpha-Helix: Stabilization of the pi-Helix," *Biochemistry* 47:4189-4195 (2008), which is hereby incorporated by reference in its entirety) and the second β-hairpin of the B1 domain of protein G (Huyghues-Despointes et al., "Terminal Ion Pairs Stabilize the Second beta-Hairpin of the B1 Domain of Protein G," *Proteins* 63:1005-1017 (2006), which is hereby incorporated by reference in its entirety). However, analyses of the effects of ion-locks on SP-C have not previously been done, and this deficiency in the art was first addressed here by new molecular modeling and web-based computer algorithms to predict the tolerance of SP-C to introduction of an ion lock.

As one example of a SP-C ion-lock mimic, SP-Css ion-lock (SEQ ID NO: 45) was identified by screening SP-C mimics based on the parent SP-Cff sequence (i.e., GIPFF-PVHLKRLLIVVVVVVLIVVVIVGALLMGL, SEQ ID NO: 396). SP-Cff principally uses the human SP-C sequence or recombinant rSP-C(34 residues) as a template, but additionally substitutes Phe residues for the palmitoyl-Cys groups (Veldhuizen et al., "Production of Surfactant Protein C in the Baculovirus Expression System: The Information Required for Correct Folding and Palmitoylation of SP-C is Contained within the Mature Sequence," *Biochim Biophys Acta* 1416:295-308 (1999), which is hereby incorporated by reference in its entirety). Although recombinant rSP-C was reportedly helical in chloroform-methanol (Luy et al., "Structure and Potential C-terminal Dimerization of a Recombinant Mutant of Surfactant-associated Protein C in Chloroform/Methanol," *Eur J Biochem* 271:2076-2085 (2004), which is hereby incorporated by reference in its entirety) and exhibited in vivo surfactant activities closely resembling those of native SP-C (Ikegami and Jobe, "Surfactant Protein-C in Ventilated Premature Lamb Lung," *Pediatr Res* 44:860-864 (1998), which is hereby incorporated by reference in its entirety), a recent clinical trial of patients with acute lung injury (ALI) showed no therapeutic benefits for rSP-C, possibly due to surfactant inactivation and/or delivery issues during the course of the trial (Spragg et al., "Recombinant Surfactant Protein C-based Surfactant for Patients with Severe Direct Lung Injury," *Am J Respir Crit Care Med* 183:1055-1061 (2011), which is hereby incorporated by reference in its entirety). Possible instability of rSP-C preparations may be related to the finding that synthetic SP-Cff shows low solubility in chloroform-methanol and is difficult to formulate with lipids in an active α-helical conformation (Walther et al., "Surfactant Protein B and C Analogues," *Mol Genet Metab* 71: 342-351 (2000), which is hereby incorporated by reference in its entirety). Studies with FTIR spectroscopy also indicate that, upon storage in organic solvent or in surfactant lipids for 4-6 weeks, synthetic SP-Cff self-associates to form β-sheet aggregates that eventually result in inactive 'amyloid-like' fibrils (Walther et al., "Hydrophobic Surfactant *Proteins* and Their Analogues," *Neonatology* 91:303-310 (2007), which is hereby incorporated by reference in its entirety).

Bioengineering analyses were performed to further determine whether SP-Cff is amyloidogenic. Specifically, the peptide was assessed for those regions likely to form β-sheets by submitting its primary sequence to the PASTA website. PASTA calculated a relative energy of −29.3 for the segment 7-27 in a parallel pairing, sufficiently low for SP-Cff to be classified as 'amyloid-like' with a high tendency to form β-sheet (Walther et al., "Critical Structural and Functional Roles for the N-terminal Insertion Sequence in Surfactant Protein B Analogs," *PLoS One* 5:e8672 (2010); Trovato et al., "Insight into the Structure of Amyloid Fibrils from the Analysis of Globular Proteins," *PloS Comput Biol* 2:e170 (2006); Trovato et al., "The PASTA Server for Protein Aggregation Prediction," *Protein Eng Des Sel* 20:521-523 (2007), each of which is hereby incorporated by reference in its entirety). Further, MPEx analysis of SP-Cff indicated a high hydropathy value (i.e., +11.31 for residues 12-30), consistent with this peptide inserting into surfactant lipids when α-helical (Snider et al., "MPEx: A Tool for Exploring Membrane Proteins," *Protein Sci* 18:2624-2628 (2009), which is hereby incorporated by reference in its entirety).

Potential SP-Cff ion-lock mimics lacking palmitoyls were next screened with PASTA and MPEx, using as a minimum criteria that successful SP-C mimics had a PASTA energy higher than −29.3 and a positive MPEx hydropathy. Such screening indicated that SP-Css ion-lock (SEQ ID NO: 45) was a promising surfactant-active mimic, with a PASTA energy of −22.2 for the parallel segment residues 7-27 and an MPEx hydropathy of +10.36 for residues 12-30. Hydropathy was calculated using the augmented Wimley-White whole-residue hydrophobicity scale with an explicit salt-bridge between Glu-20 and Lys-24 (Snider et al., "MPEx: A Tool for Exploring Membrane Proteins," *Protein Sci* 18:2624-2628 (2009); Jayasinghe et al., "Energetics, Stability, and Prediction of Transmembrane Helices," *J Mol Biol* 312:927-934 (2001), each of which is hereby incorporated by reference in its entirety). Thus, SP-Css ion-lock (SEQ ID NO: 45) and several other SP-C ion-lock peptides were synthesized (Example 4) and tested for adsorption activity in vitro and/or in rabbits with ARDS in vivo (Example 8).

Example 4—Synthesis and Purification of Representative New SP-B and SP-C Peptide Materials Selected new SP-B and SP-C peptides were synthesized by solid-state methods, purified, and examined spectroscopically for use in subsequent examples documenting their activity when combined with synthetic glycerophospholipids or with phospholipase-resistant lipids in synthetic surfactant compositions (activity assessments are in subsequent examples).

A listing of representative novel peptides synthesized and studied for activity in the subsequent examples is as follows:

TABLE 6

List of Synthesized Peptides

| Name | Description | SEQ ID NO: |
|---|---|---|
| MB DATK_Red | Mini-B having N-ethylmaleimide-blocked Cys1 and Cys33 residues, and DATK turn sequence | 4 |
| MB DATK_Ox | Mini-B with disulfide bond between Cys1 and Cys33 and DATK turn sequence | 4 |
| MB DATK_Ala | MB DATK with Ala for Cys substitutions | 5 |
| MB DATK_Ser | MB DATK with Ser for Cys substitutions | 6 |
| SMB DATK_Red | Super Mini-B having N-ethylmaleimide-blocked Cys8 and Cys40 residues, and DATK turn sequence | 18 |
| Mini-SPCff_dog | Truncated SP-C dog peptide with Phe substitutions at positions 5 and 6 | 31 |
| Mini-SPCff_dog_leu | Truncated SP-C dog peptide with Phe substitutions at positions 5 and 6, and Leu substitutions at positions 17-19 | 32 |
| Mini-SPCff_2_leu | Truncated SP-C human peptide with Phe substitutions at positions 5 and 6 | 34 |
| Monomer and Dimer Mini-C dog cf_cys 5 | Identical to Mini-SPCff_dog (SEQ ID NO: 31) except having a Cys at position 5 | 33 |
| SP-C ion-lock | SP-C human sequence bearing Phe substitutions at positions 4 and 5, and a Glu20/Lys24 ion lock; 34 residues in length | 406 |
| SP-Css ion-lock | SP-C human sequence bearing Ser substitutions at positions 4 and 5, and a Glu20/Lys24 ion lock; 34 residues in length | 45 |
| SP-C ion-lock-dog | SP-C hybrid sequence (N-terminus dog, and C-terminus human) with Glu20/Lys24 ion lock; 34 residues in length | 61 |
| SP-C ion-lock2ff | SP-C peptide bearing Phe substitutions at positions 4 and 5, and Lys15/Glu19, Glu20/Lys24 ion locks; 34 residues in length | 69 |
| SP-C ion-lock2ss | SP-C human sequence bearing Ser substitutions at positions 4 and 5, and Lys15/Glu19, Glu20/Lys24 ion locks; 34 residues in length | 197 |
| SP-C33ss_ion2 | SP-C peptide bearing Ser substitutions at positions 4 and 5, Lys15/Glu19, Glu20/Lys24 ion locks, and truncated at C terminus to total length of 33 amino acids | 326 |

The synthesis, purification and folding of the new SP-B and SP-C mimic peptides described in this application are based on procedures developed earlier for the parent peptides, Mini-B (Waring et al., "The Role of Charged Amphipathic Helices in the Structure and Function of Surfactant Protein B," *J Peptide Res* 66:364-374 (2005); Walther et al., "Dynamic Surface Activity of a Fully Synthetic Phospholipase-resistant Lipid/Peptide Lung Surfactant," *PLoS ONE* 2:e1039 (2007), each of which is hereby incorporated by reference in its entirety), Super Mini-B (Walther et al., "Critical Structural and Functional Roles for the N-terminal Insertion Sequence in Surfactant Protein B Analogs," *PLoS One* 5:e8672 (2010), which is hereby incorporated by reference in its entirety), and SP-Cff (Alonso et al., "Keeping Lung Surfactant Where It Belongs: Protein Regulation of Two-dimensional Viscosity," *Biophys J* 89:266-273 (2005), which is hereby incorporated by reference in its entirety).

As an example of synthesis methods for new peptides with the SP-B consensus sequence (SEQ ID NO: 1), the SP-B mimic MB DATK (SEQ ID NO: 4) was synthesized employing the protocol developed for the parent Mini-B peptide (Waring et al., "The Role of Charged Amphipathic Helices in the Structure and Function of Surfactant Protein B," *J Peptide Res* 66:364-374 (2005); Walther et al., "Dynamic Surface Activity of a Fully Synthetic Phospholipase-resistant Lipid/Peptide Lung Surfactant," *PLoS ONE* 2:e1039 (2007); Walther et al., "Critical Structural and Functional Roles for the N-terminal Insertion Sequence in Surfactant Protein B Analogs," *PLoS One* 5:e8672 (2010), each of which is hereby incorporated by reference in its entirety). Synthesis of MB_datk was easily accomplished on a 0.25 mmole scale by FastMoc™ using an ABI 431A Solid Phase Peptide Synthesizer (Applied Biosystems, Foster City, Calif.). Peptides from this consensus family that are carboxylated at the C-terminus are readily made with the ABI 431A Solid Phase Peptide, Symphony Multiple Peptide (Protein Technologies, Tucson, Ariz.), or Liberty Microwave Peptide (CEM Corp., Matthews, N.C.) Synthesizers, using FastMoc™ or standard Fmoc protocols on a H-Ser(OtBu)-HMPB NovaPEG resin or alternatively a more common Wang-Ser(OtBu) resin with double coupling for all residues to insure optimal yield (70% or better desired product) (Waring et al., "The Role of Charged Amphipathic Helices in the Structure and Function of Surfactant Protein B," *J Peptide Res* 66:364-374 (2005); Walther et al., "Dynamic Surface Activity of a Fully Synthetic Phospholipase-resistant Lipid/Peptide Lung Surfactant," *PLoS ONE* 2:e1039 (2007); Walther et al., "Critical Structural and Functional Roles for the N-terminal Insertion Sequence in Surfactant Protein B Analogs," *PLoS One* 5:e8672 (2010); Alonso et al., "Keeping Lung Surfactant Where It Belongs: Protein Regulation of Two-dimensional Viscosity," *Biophys J* 89:266-273 (2005), each of which is hereby incorporated by reference in its entirety). The Symphony Multiple Peptide Synthesizer (Protein Technologies, Tucson, Ariz.) has 12 reaction vial positions, permitting large-scale synthesis of SP-B mimic peptides (i.e., 3 mmole) in a single 48 hour run. Here, C-terminal carboxyl MB_datk was cleaved from the resin using the standard phenol:thioanisole:ethanedithiol:water: trifluoracetic acid (0.75:0.25:0.5:0.5:10, v:v) cleavage-deprotection mixture (Applied Biosystems Manual, Strategies in Peptide Synthesis, "Introduction to Cleavage Techniques," pp. 10-11 (1990), which is hereby incorporated by reference in its entirety). The crude peptide was then purified (better than 95%) by preparative HPLC using a VYDAC diphenyl or C8 (1" by 12" width by length) column at 20 ml/min. MB_DATK was eluted from the column with a 0 to 100% (water to acetonitrile with 0.1% TFA as an ion pairing agent added to both aqueous and organic phases) linear gradient in one hour. The purified product was freeze-dried directly and the mass confirmed by Maldi TOF mass spectrometry.

To fold the oxidized Mini-B DATK [i.e., MB DATK_Ox (SEQ ID NO: 4)] as a compact helix-turn-helix motif, the disulfide linkages of the purified MB_datk peptide (SEQ ID NO: 4) were directed by using acid labile trityl (Trt)-protecting groups at cysteine positions 1 and 33, and at cysteine positions 4 and 27. The disulfide bonds between Cys-1 and Cys-33 and at 4 and 27 were formed by air oxidation for 24 h in trifluoroethanol:ammonium bicarbonate buffer (10 mM, pH 8.0). The disulfide connectivity was confirmed by mass spectrometry of the enzyme-digested fragments (trypsin, chymotrypsin). The oxidation of Cys-1 and -33 for MB-datk proceeded more rapidly than for the parent MB, probably due to the enhanced propensity of the DATK sequence to form a β-hairpin which promotes a faster development of the characteristic helix-turn-helix motif of Mini-B.

A reduced Mini-B DATK peptide (MB DATK_Red) was similarly prepared, except that the oxidizing steps were omitted and the sulfide groups on cysteine residues 1 and 33 were blocked with N-ethylmaleimide (Waring et al., "The Role of Charged Amphipathic Helices in the Structure and Function of Surfactant Protein B," *J Peptide Res* 66:364-374 (2005), which is hereby incorporated by reference in its entirety).

Similar procedures (without the subsequent oxidation or reduction steps) were used to prepare MB DATK_Ala (SEQ ID NO: 5), MB DATK_Ser (SEQ ID NO: 6), and SMB DATK_Red (SEQ ID NO: 18).

As an example of new SP-C peptides with an ion-lock sequence (i.e., consensus SEQ ID NO: 36), the SP-Css ion-lock (SEQ ID NO: 45) peptide was synthesized using a similar protocol developed for the parent SP-Cff peptide (Alonso et al., "Keeping Lung Surfactant Where It Belongs: Protein Regulation of Two-dimensional Viscosity," *Biophys J* 89:266-273 (2005), which is hereby incorporated by reference in its entirety). The SP-Css ion-lock (SEQ ID NO: 45) carboxylated at the C-terminus was synthesized with the ABI 431A Synthesizer using standard Fmoc protocols on a Leu-HMPB NOVAPEG resin. C-terminal carboxylated mimics from these SP-C peptide families are readily prepared with FastMoc™ or standard Fmoc procedures on a Leu-HMPB NOVA resin using ABI 431A, Symphony Multiple Peptide or Liberty Microwave Synthesizers. The cleavage procedure for the SP-Css ion-lock (SEQ ID NO: 45) was the same as that described above for the SP-B mimic MB_DATK. Purification of SP-Css ion-lock (SEQ ID NO: 45) (better than 95%) by HPLC was performed with a linear gradient of either water (0.1% TFA) to 100% acetonitrile: isopropanol (1:7, v:v with 0.1% TFA) or ethanol:water (1:1, v:v with 0.1% TFA) to 100% isopropanol with 0.1% TFA. This HLPC procedure better elutes hydrophobic peptides such as SP-Css ion-lock (SEQ ID NO: 45) with a run time of 1 h. The purified product was freeze-dried directly and the mass confirmed by Maldi TOF mass spectrometry as described above.

Fmoc synthesis procedures were used to prepare the SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69) and SP-C33ss_ion2 (SEQ ID NO: 326) peptides. These peptides were prepared by triple coupling all of the hydrophobic residues.

As examples of new SP-C peptides with shortened monomer and covalently-linked dimer (i.e., consensus SEQ ID NO: 30) sequences, the respective shortened Monomer and Dimer Mini-C dog cf_cys 5 (SEQ ID NO: 33) peptides were synthesized using similar protocols developed for the parent SP-Cff peptide (Alonso et al., "Keeping Lung Surfactant Where It Belongs: Protein Regulation of Two-dimensional Viscosity," *Biophys J* 89:266-273 (2005), which is hereby incorporated by reference in its entirety). Here, Monomer Mini-C dog cf_cys 5 that was carboxyl amidated at the C-terminus was synthesized using standard Fmoc protocol with double coupling for all residues and a Novachem Rink Amide MBHA resin (100-200 mesh) with the Symphony Multiple Peptide Synthesizer. Versions of SP-C peptides that are carboxyl amidated at the C-terminus may be synthesized similarly to those that are carboxylated at the C-terminus, replacing the Leu-HMPB NovaPEG resin with either the NovaPEG Rink Amide resin or, alternatively, the more common Wang-Leu or Rink Amide MBHA resin which produces slightly lower peptide yields. More hydrophobic SP-C mimic peptides require triple coupling for multiple valine sequences and double coupling for all other residues to insure optimal yield (75% or better desired product). The cleavage procedure for the Monomer Mini-C dog cf_cys 5 involved standard Fmoc cleavage solution, i.e., neat TFA, with phenol-water, thioanisole, 1,2-ethanedithiol (10:1:0.5: 0.25, v:v), and the mass of the crude monomer peptide was confirmed by Maldi TOFI in low mass reflectance mode using alpha matrix. To produce the disulfide-linked dimeric peptide, the reduced crude monomer Mini-C dog cf_cys 5 was oxidized in 20% DMSO for 48 hours at pH 7.0 (5 mM acetate buffer), then dried down in a speed-vac for 12 hours. Crude dimer peptide was dispersed in HFIP:10 mM HCl (1:1, v:v), and purified (95% or better) by Jasco preparative HPLC with a 1"×12" Vydac reverse phase diphenyl column using a 0 to 100% ACN binary linear gradient (100% $H_2O$ to 100% acetonitrile:isopropanol 1:7, v:v with 0.1% TFA as an ion-pairing agent. The mass of the purified dimer Mini-C dog cf_cys 5 was confirmed by Maldi TOFI in low mass linear mode using alpha matrix.

Similar procedures, without the dimerization, were used to prepare Mini-SPCff_dog (SEQ ID NO: 31), Mini-SPCff_dog_leu (SEQ ID NO: 32), Mini-SPCff_2 leu (SEQ ID NO: 34).

FTIR analysis of purified Mini-SPCff_dog_leu in lipid-mimic (i.e., 35% HFIP/65% sodium phosphate buffer, pH 7.4) showed that the principal secondary conformation was α-helix (~45%), with minimal contributions from β-sheet (-10%). Mini-SPCff_dog_leu may exhibit high α-helix because it omits the C-terminal VVLIVVVIVGALLMGL sequence found in dog SP-C, which limits the number of H-bonded residues participating in β-sheet, and also because of the replacement of Val with Leu at residues 17, 18 and 19 (Almlen et al., "Concentration Dependence of a Poly-leucine Surfactant Protein C Analogue on in vitro and in vivo Surfactant Activity," *Neonatology* 92:194-200 (2007); Almlen et al., "Alterations of the C-terminal End Do Not Affect in vitro or in vivo Activity of Surfactant Protein C Analogs,"

Biochim Biophys Acta S0005-2736(11)00028-9 (2011), each of which is hereby incorporated by reference in its entirety).

Example 5—Formulation of Synthetic Lung Surfactant Compositions for Activity Testing The formulation of these synthetic SP-B and/or SP-C peptides with lipids in synthetic surfactants was accomplished using procedures reported earlier (Waring et al., "The Role of Charged Amphipathic Helices in the Structure and Function of Surfactant Protein B," *J Peptide Res* 66:364-374 (2005); Walther et al., "Dynamic Surface Activity of a Fully Synthetic Phospholipase-resistant Lipid/Peptide Lung Surfactant," *PLoS ONE* 2:e1039 (2007); Walther et al., "Critical Structural and Functional Roles for the N-terminal Insertion Sequence in Surfactant Protein B Analogs," *PLoS One* 5:e8672 (2010), each of which is hereby incorporated by reference in its entirety).

As one brief example, an SP-B mimic peptide (MB DATK_Ox, MB DATK_Red, MB DATK_Ala, or MB DATK_Ser) was dissolved in 2,2,2-trifluoroethanol (TFE) and co-solvated with desired lipids dispersed in chloroform (TFE:Chloroform, 1:1, v:v). The desired lipids included one or more of: DEPN-8 (a phospholipase-resistant C16:0, C16:0 diether phosphono-phosphatidylcholine); PG-1 (a phospholipase-resistant C16:0, C16:1 diether phosphono-phosphatidylglycerol); DPPC (dipalmitoyl phosphatidylcholine); POPC (palmitoyl-oleoyl-phosphatidylcholine); and POPG (palmitoyl-oleoyl-phosphatidylglycerol). The solvent was removed by evaporation or flash evaporation to form a peptide-lipid film. The peptide-lipid film was then placed under high vacuum (1 mT) for 12 hours to remove residual solvent and sterile normal saline (0.9% by weight NaCl) adjusted to pH 7.0 with sodium bicarbonate (0.1 N). The hydrated film was then dispersed using a rotary evaporator at a temperature of 65° C. for one hour prior to refrigerated storage at 5° C. Similar formulation procedures were used for synthetic surfactant compositions containing other SP-B mimic peptides and/or SP-C mimic peptides that were tested for activity in subsequent examples.

Example 6—Activity Testing of a Resistant Synthetic Lung Surfactant Composition Containing SP-B Peptides Plus Resistant Phosphonolipid Analogs Surface activity of synthetic peptide/lipid surfactant compositions was assessed by either or both of the following methods: (1) measurement of the adsorption of surfactant compositions to the air-water interface as a function of time, and (2) measurement of overall dynamic surface activity on a pulsating bubble surfactometer (general methodological details of these two experimental techniques are described by Notter, *Lung Surfactants: Basic Science and Clinical Applications*, Marcel Dekker, Inc, New York (2000), which is hereby incorporated by reference in its entirety).

In adsorption studies, a given surfactant mixture was injected at time zero beneath the surface of a stirred surfactant-free subphase, and surface pressure (defined as surface tension lowering below that of the pure subphase) was measured as a function of time from the force on a hanging platinum slide ("Wilhelmy" method). By definition, higher surface pressure corresponds to lower surface tension (Notter, *Lung Surfactants: Basic Science and Clinical Applications*, Marcel Dekker, Inc, New York (2000)).

In pulsating bubble studies, surface tension at minimum bubble radius (minimum surface tension) was determined as a function of time during pulsation on a bubble surfactometer (General Transco, Largo, Fla.) (37° C., 20 cycles/min, 50% area compression). A tiny air bubble was formed and pulsated between maximum and minimum radii of 0.55 and 0.4 mm, respectively, and the pressure drop across the air-water interface of the bubble was measured with a precision transducer. Minimum surface tension was calculated from the measured pressure drop at minimum radius (0.4 mm) from the Laplace equation (Enhorning, "Pulsating Bubble Technique for Evaluation of Pulmonary Surfactant," *J Appl Physiol* 43:198-203 (1977); Hall et al., "Approximations in the Measurement of Surface Tension with the Oscillating Bubble Surfactometer,"*J Appl Physiol* 75:468-477 (1993), each of which is hereby incorporated by reference in its entirety). Measurements of overall surface activity on this instrument reflect the combined effects of adsorption and dynamic film compression at a cycling rate (20 cycles/min), temperature (37° C.), and area compression (50% compression from maximum to minimum area) relevant for the mammalian lungs in vivo (Notter, *Lung Surfactants: Basic Science and Clinical Applications*, Marcel Dekker, Inc, New York (2000); Enhorning, "Pulsating Bubble Technique for Evaluation of Pulmonary Surfactant," *J Appl Physiol* 43:198-203 (1977); Notter et al., "Pulmonary Surfactant: Physical Chemistry, Physiology and Replacement," *Rev Chem Eng* 13:1-118 (1997), each of which is hereby incorporated by reference in its entirety).

Prior publications have shown that adsorption and/or pulsating bubble surface activity as measured above correlate well with the physiological activity of exogenous surfactants in animal lungs (Notter, *Lung Surfactants: Basic Science and Clinical Applications*, Marcel Dekker, Inc, New York (2000); Notter et al., "Pulmonary Surfactant: Physical Chemistry, Physiology and Replacement," *Rev Chem Eng* 13:1-118 (1997); Holm et al., "Effects of Hemoglobin and Cell Membrane Lipids on Pulmonary Surfactant Activity," *J Appl Physiol* 63:1434-1442 (1987), each of which is hereby incorporated by reference in its entirety).

In this example, selected synthetic SP-B peptides were formulated in combination with phospholipase resistant phospholipids as in Example 5 above, and tested for both adsorption and pulsating bubble activity. Tables 7 and 8 (below) show the adsorption and overall surface activity of phospholipase-resistant synthetic surfactants containing DEPN-8 or 9:1 DEPN-8/PG-1 combined with 3% by weight Super Mini-B (S-MB) peptide, which is a major parent compound for the new SP-B peptides of this application. The results document the very high adsorption and dynamic surface activity of resistant surfactants containing this parent peptide combined with DEPN-8. The results also show that the addition of a C16:0, C16:1 diether phosphono-PG (i.e., PG-1) at 10 wt. % relative to DEPN-8 provides a further small but consistent increase in both adsorption and dynamic surface activity. The adsorption and dynamic surface activity of synthetic 9:1 DEPN-8/PG-1+3% S-MB fully equals the natural lung surfactant extract (CLSE, calf lung surfactant extract) and exceeds that of the bovine-derived clinical exogenous surfactant SURVANTA® (Tables 7, 8).

TABLE 7

Adsorption of Resistant Synthetic Surfactants Containing DEPN-8 plus
C16:0, C16:1 Phosphono-PG (PG-1) Plus Super Mini-B (S-MB) Peptide

| Samples | Adsorption Surface Pressure (mN/m), at time (min) | | | | | |
|---|---|---|---|---|---|---|
| | 0 | 1 | 2 | 5 | 10 | 15 |
| DEPN-8 | 0 ± 0.0 | 12.9 ± 2.9 | 16.0 ± 1.6 | 17.8 ± 1.7 | 18.0 ± 1.7 | 18.2 ± 1.7 |
| DEPN-8 + 3% S-MB | 0 ± 0.0 | 44.4 ± 0.4 | 46.4 ± 0.3 | 47.1 ± 0.5 | 47.5 ± 0.6 | 47.6 ± 0.6 |
| DEPN-8 + PG-1 (9:1) +3% S-MB | 0 ± 0.0 | 47.4 ± 0.3 | 47.8 ± 0.1 | 48.1 ± 0.1 | 48.2 ± 0.1 | 48.3 ± 0.1 |
| CLSE | 0 ± 0.0 | 46.4 ± 0.1 | 47.4 ± 0.2 | 48.0 ± 0.1 | 48.1 ± 0.1 | 48.1 ± 0.1 |
| SURVANTA ® | 0 ± 0.0 | 18.8 ± 2.0 | 27.3 ± 1.2 | 37.6 ± 1.4 | 40.2 ± 2.0 | 42.2 ± 1.2 |

Adsorption was measured following injection of a surfactant bolus beneath the interface of a stirred subphase at time zero. Surface pressure is the amount of surface tension lowering below that of the pure subphase (normal saline adjusted to pH 7.0) at 37 ± 0.5° C. Higher surface pressure equates to lower surface tension. Surfactant concentration was 0.0625 mg phospholipid/ml of subphase. Data are Means ± SEM for N = 4. CLSE: calf lung surfactant extract; DEPN-8 = C16:0, C16:0 diether phosphono-PC (phosphatidylcholine); PG-1: C16:0, C16:1 diether phosphono-PG. "S-MB" denotes "Super Mini-B"

TABLE 8

Minimum Surface Tensions of Resistant Synthetic Surfactants Containing DEPN-8,
PG 1, and Super Mini-B (S-MB) During Pulsation on a Bubble Surfactometer

| Samples | Minimum Surface Tension (mN/m), at time (min) of bubble pulsation | | | | | | |
|---|---|---|---|---|---|---|---|
| | 0.25 | 0.5 | 1 | 2 | 5 | 10 | 15 |
| DEPN-8 | 31.2 ± 2.0 | 27.1 ± 1.8 | 21.2 ± 1.5 | 14.6 ± 1.2 | 7.8 ± 1.7 | 1.5 ± 1.0 | <1 |
| DEPN-8 + 3% S-MB | 11.6 ± 2.0 | 5.8 ± 1.7 | 3.0 ± 1.5 | 2.3 ± 1.4 | <1 | | |
| DEPN-8 + PG-1 (9:1) +3% S-MB | 6.8 ± 1.7 | 3.5 ± 1.1 | 2.2 ± 1.0 | 1.2 ± 0.5 | <1 | | |
| CLSE | 6.8 ± 0.7 | 4.2 ± 0.5 | 2.4 ± 0.6 | <1 | <1 | | |
| SURVANTA ® | 10.4 ± 1.3 | 9.6 ± 2.1 | 8.9 ± 1.8 | 7.3 ± 0.7 | 4.8 ± 0.6 | 4.1 ± 0.5 | 3.6 ± 0.4 |

Surface tension at minimum bubble radius (minimum surface tension) is shown as a function of time of pulsation on a bubble surfactometer (37° C., 20 cycles/min, and 50% area compression). Under rapid dynamic compression on this apparatus, lung surfactant films reach significantly lower surface tensions than in adsorption studies, which are limited by the equilibrium spreading pressure. Surfactant mixture concentration was 2.5 mg/ml phospholipid as shown. CLSE: Calf lung surfactant extract; DEPN-8 = C16:0, C16:0 diether phosphono-PC; PG-1: C16:0, C16:1 diether phosphono-PG. Data are Means ± SEM for N = 4. "S-MB" denotes "Super Mini-B."

Table 9 shows the rapid adsorption of representative phospholipase-resistant synthetic surfactants containing 9:1 DEPN-8/PG-1 combined with 3% by weight of two new peptides from this patent application, i.e., reduced MB DATK (MB DATK_Red) and reduced S-MB DATK (S-MB DATK_Red). These peptides both display adsorption activity as high as S-MB in Table 7, and in addition incorporate the folding and stability advantages discussed earlier for these bend-stabilized compounds.

Example 7—Formulation and Activity Testing of Fully Synthetic Lung Surfactants Containing SP-B Peptides and Glycerophospholipids In this example, representative synthetic surfactant compositions containing new SP-B peptides were combined with synthetic ester-linked glycerophospholipids and studied for in vitro and in vivo surfactant activities.

TABLE 9

Adsorption of Synthetic Surfactant Compositions Containing a New Synthetic
SP-B Peptide Combined with Phospholipase-resistant Synthetic Lipids

| Surfactant | Adsorption Surface Pressure (mN/m), at time (min) | | | | | |
|---|---|---|---|---|---|---|
| | 0 | 1 | 2 | 5 | 10 | 15 |
| DEPN-8 9:1DEPN-8:PG-1 | 0.0 ± 0.0 | 12.9 ± 2.9 | 16.0 ± 1.6 | 17.8 ± 1.7 | 18.0 ± 1.7 | 18.2 ± 1.7 |
| +3.0% S-MB DATK_Red | 0.0 ± 0.0 | 46.4 ± 0.3 | 47.5 ± 0.2 | 47.6 ± 0.3 | 47.6 ± 0.3 | 47.6 ± 0.3 |
| +3.0% MB DATK_Red | 0.0 ± 0.0 | 46.4 ± 0.5 | 47.4 ± 0.2 | 47.5 ± 0.2 | 47.6 ± 0.2 | 47.6 ± 0.2 |

Experimental methods for adsorption are as in the legend to Table 7, and final surfactant concentration was constant at 0.0625 mg phospholipid/ml. Data are Means ± SEM for n = 4. Abbreviations: MB DATK_Red = SEQ ID NO: 4 (reduced); S-MB DATK_Red = SEQ ID NO: 18 (reduced); DEPN-8 = C16:0, C16:0 diether phosphono-PC; PG-1 = C16:0, C16:1 diether phosphono-PG. "S-MB" denotes "Super Mini-B."

Selected synthetic surfactant compositions containing new SP-B peptides were combined with synthetic ester-linked glycerophospholipids (5:3:2 weight ratio DPPC:POPC:POPG) and studied for in vitro adsorption activity in analogy with Example 6. Surfactants were formulated in 0.15M NaCl with pH adjusted to 7.0 with 0.1N sodium bicarbonate as described in Example 5. Table 10 (below) shows that the new SP-B peptides of this patent had very high adsorption when combined with synthetic ester linked phospholipids, analogous to their behavior when combined with resistant lipids in the previous example (Table 9). A novel feature for bend-stabilized peptides, illustrated by Mini-B (MB) DATK and Super Mini-B (S-MB) DATK in Table 10, is that reduced forms of these peptides in addition to oxidized forms also have very high activity. Comparisons of reduced MB DATK (MB DATK_Red), reduced S-MB DATK (S-MB DATK_Red), and oxidized MB DATK (MB DATK_Ox) in Table 10 indicate almost identical adsorption activity. This contrasts with prior experience with original MB and S-MB peptides, which lack the DATK bend-stabilization substitution and require significant post-synthesis folding and oxidation for optimal activity (see, e.g., Notter et al, "Novel Phospholipase-Resistant Lipid/Peptide Synthetic Lung Surfactants," *Mini Rev Med Chem* 7:932-944 (2007); Walther et al, "Dynamic Surface activity of a Fully-Synthetic Phospholipase-Resistant Lipid/Peptide Lung Surfactant," *PLoS ONE*, 2(10):1-10: e1039 (2007), each of which is hereby incorporated by reference in its entirety).

(27.4%). These secondary structures are comparable to those for either oxidized MB or SMB bound to DPPC or POPG (Walther et al., "Critical Structural and Functional Roles for the N-terminal Insertion Sequence in Surfactant Protein B Analogs," *PLoS One* 5:e8672 (2010), which is hereby incorporated by reference in its entirety). MB DATK_Red likely adopts the active folding of oxidized MB in surfactant lipids, given that Molecular Dynamics (MD) simulations using GROMACS showed that MB DATK_Red in a lipid-mimic, i.e., 35% TFE:water (35:65, v:v), rapidly assumes (i.e., ~45 nanoseconds) the characteristic MB tertiary structure of helix-turn-helix. Similar to previous MD simulations of oxidized SMB with surfactant lipids (Schwan et al., "Synthesis and activity of a novel diether phosphonoglycerol in phospholipase-resistant synthetic lipid peptide lung surfactants," *Med Chem Commun* 2:1167 (2011), which is hereby incorporated by reference in its entirety), MD simulations (100-nsec) show that reduced MB DATK preferentially binds, though its cationic N- and C-terminal helical domains connected by a beta-turn, to the head groups of anionic lipids in surfactant bilayers (5:3:2 weight ratio DPPC:POPC:POPG). The ability of the DATK substitution to increase SP-B peptide activity while also simplifying post-synthesis processing (folding/oxidation) enhances the potential pharmaceutical utility of these or related novel materials.

While in vitro studies of an experimental surfactant preparation are invaluable and predictive of overall functionality, such studies do not directly measure pulmonary

TABLE 10

Adsorption of synthetic surfactant compositions containing representative new synthetic SP-B peptides combined at 3% by weight with synthetic glycerophospholipids (5:3:2 molar ratio DPPC:POPC:POPG).

| Surfactant | Adsorption Surface Pressure (mN/m), at time (min) | | | | | |
| --- | --- | --- | --- | --- | --- | --- |
|  | 0 | 1 | 2 | 5 | 10 | 15 |
| 5:3:2 DPPC:POPC:POPG | 0.0 ± 0.0 | 4.4 ± 0.8 | 6.2 ± 1.1 | 7.8 ± 0.3 | 9.4 ± 0.7 | 11.2 ± 0.8 |
| 5:3:2 DPPC:POPC:POPG |  |  |  |  |  |  |
| +3.0% MB DATK_Red | 0.0 ± 0.0 | 45.5 ± 0.6 | 46.4 ± 0.4 | 47.3 ± 0.1 | 47.3 ± 0.0 | 47.3 ± 0.0 |
| +3.0% MB DATK_Ox | 0.0 ± 0.0 | 46.3 ± 0.3 | 47.1 ± 0.2 | 47.6 ± 0.2 | 47.7 ± 0.2 | 47.7 ± 0.2 |
| +3.0% MB DATK_Ala | 0.0 ± 0.0 | 43.2 ± 0.8 | 44.6 ± 0.7 | 46.0 ± 0.5 | 46.4 ± 0.4 | 46.7 ± 0.4 |
| +3.0% MB DATK_Ser | 0.0 ± 0.0 | 26.4 ± 1.9 | 28.4 ± 1.3 | 31.5 ± 1.0 | 33.1 ± 0.8 | 33.8 ± 0.6 |
| +3.0% S-MB_Ox | 0.0 ± 0.0 | 45.8 ± 0.3 | 46.7 ± 0.2 | 47.4 ± 0.2 | 47.4 ± 0.2 | 47.5 ± 0.2 |
| +3.0% S-MB DATK_Red | 0.0 ± 0.0 | 45.7 ± 0.4 | 46.7 ± 0.2 | 47.5 ± 0.2 | 47.7 ± 0.2 | 47.8 ± 0.2 |

Experimental methods for adsorption are as in the legend to Table 7. Final surfactant concentration was constant at 0.0625 mg phospholipid/ml; Data are Means ± SEM for n = 4. Abbreviations: MB DATK_Red = SEQ ID NO: 4 (reduced); MB DATK_Ox = SEQ ID NO: 4 (oxidized); MB DATK_Ala = SEQ ID NO: 5; MB DATK_Ser = SEQ ID NO: 6; S-MB_Ox = Oxidized Super Mini-B; S-MB DATK_Red = SEQ ID NO: 18 (reduced); DPPC = Dipalmitoyl PC; POPC = Palmitoyl-oleoyl-PC; POPG = Palmitoyl-oleoyl-PG. "S-MB" denotes "Super Mini-B".

The DATK substitution in novel MB DATK_Red and MB DATK_Ox peptides in Table 10 also leads to improved adsorption activity relative to that previously reported for MB without the DATK substitution (for MB activity, see Walther et al, "Dynamic Surface activity of a Fully-Synthetic Phospholipase-Resistant Lipid/Peptide Lung Surfactant," *PLoS ONE*, 2(10):1-10: e1039. (2007), which is hereby incorporated by reference in its entirety). These results suggest that oxidation may be unnecessary to form stable, surfactant-active MB peptides if they also contain turn regions with a high propensity to form β-hairpins. At a peptide/lipid ratio of 1/10, Fourier transform infrared (FTIR) spectra of MB DATK_Red with surfactant lipids (5:3:2 weight ratio DPPC:POPC:POPG) in sodium phosphate buffered saline (10 mM PBS, pH 7.4) indicated high secondary conformations for loop-turn (32.8%) and alpha-helix activity. Thus, supplemental in vivo activity testing was carried out on a selected but representative group of synthetic SP mimics in animals.

Saline lavage produces surfactant deficiency, alveolar collapse and lung edema in ventilated rats and rabbits, and is a useful experimental model for human ARDS. A saline-lavage rabbit model for lung injury was thus used to compare synthetic surfactants, with lipids only as negative control. Restoration of lung function was assessed by serial monitoring of gas exchange and lung mechanics. Physiological activity results for selected synthetic SP-B peptides are shown below, and physiological activity results for selected synthetic SP-C peptides are included in following Example 8.

Animal experiments were performed following established protocols approved by the Animal Care and Use Committee at the Los Angeles Biomedical Research Institute at Harbor-UCLA Medical Center. Anesthesia, surgery, lavage, ventilation, and monitoring methods used have been detailed previously (Walther et al., "Dimeric surfactant protein B peptide SP-B$_{1-25}$ in neonatal and acute respiratory distress syndrome," Exp Lung Res 28: 623 (2002); Almlen et al., "Synthetic surfactant based on analogues of SP-B and SP-C is superior to single-peptides in ventilated premature rabbits," Neonatology 998: 91 (2010), each of which is hereby incorporated by reference in its entirety). In brief, experimental animals were commercially available young adult male New Zealand white rabbits whose respiratory function was followed during mechanical ventilation by measurements of serial arterial blood gases and pulmonary compliance over the first 2 hours after a standardized saline lavage protocol. For this timeframe of study, the model reflected a relatively pure state of surfactant insufficiency in animals with mature lungs. Saline lavage administration was performed after induction of anesthesia, insertion of a venous line in a marginal ear vein, endotracheal intubation and initiation of mechanical ventilation, muscle paralysis, and insertion of a carotid arterial line. Heart rate, arterial blood pressure and rectal temperature were measured continuously. After stabilization on the ventilator, saline lavage was performed with repeated intratracheal instillation and removal of 30 mL of normal saline until the PaO2 dropped below 100 mm Hg (average 3 lavages). Maintenance fluid was provided by a continuous infusion of Lactated Ringer's solution at a rate of 10 ml/kg/h. Edema fluid appearing in the trachea was removed by suctioning. When the PaO2 was stable at less than 100 mm Hg in saline lavaged animals, an experimental or control surfactant mixture was instilled into the trachea at a dose of 100 mg/kg body weight and a concentration of 35 mg/mL. The rabbits were ventilated using a Harvard volume-controlled animal ventilator (tidal volume 7.5 ml/kg, a positive end-expiratory pressure [PEEP] of 3 cm $H_2O$, an inspiratory/expiratory ratio of 1:2, 100% oxygen, and a respiratory rate to maintain a PaCO2 at ~40 mm Hg). Airway flow and pressures and tidal volume were monitored continuously with a pneumotachograph connected to the endotracheal tube and a pneumotach system. Arterial pH and blood gases were done every 15 minutes. Dynamic lung compliance was calculated by dividing tidal volume/kg body weight by changes in airway pressure (peak inspiratory pressure minus positive end-expiratory pressure) (mL/kg/cm$H_2O$). Animals were sacrificed 2 h after surfactant administration with an overdose of pentobarbital. End-points are pulmonary gas exchange (arterial pH, PaCO2 and PaO2) and pulmonary mechanics (dynamic compliance, postmortem pressure-volume curves). Each treatment group consisted of n=4-9 animals.

The in vivo pulmonary activity of reduced MB DATK and SMB DATK was investigated in comparison with oxidized SMB and MB (positive controls) and lipids alone (negative control) over 120 min, following intratracheal instillation of these surfactants into ventilated rabbits with ARDS induced by saline lavage. Oxidized SMB and MB were used as positive controls, because these SP-B mimics previously indicated high in vivo surfactant activities equal to those of native, full-length porcine SP-B in ventilated rats with ARDS (Walther et al., "Critical Structural and Functional Roles for the N-terminal Insertion Sequence in Surfactant Protein B Analogs," PLoS One 5:e8672 (2010), which is hereby incorporated by reference in its entirety). Here, synthetic surfactant preparations were formulated by mixing synthetic lipids, consisting of 5:3:2 (weight ratio) DPPC:POPC:POPG, either alone (Lipids) or with 3.0% by weight SMB_Ox=Oxidized Super Mini-B, SMB DATK_Red (SEQ ID NO: 18, reduced), MB_Ox=Oxidized Mini-B, and MB DATK_Red (SEQ ID NO: 4, reduced) in sodium phosphate buffered saline (PBS, pH 7.4). FIG. 1 reports the arterial oxygenation and dynamic compliance in surfactant treated rabbits, with the oxygenation and compliance curves shown as means±SEM at selected intervals for SMB_Ox (n=9), SMB DATK_Red (n=4), MB_Ox (n=6), MB DATK_Red (n=5) and Lipids alone (n=6). Oxygenation and lung compliance (FIG. 1) increased quickly after instillation of reduced SMB DATK and MB DATK. Instillation of the positive controls SMB_Ox and MB_Ox also rapidly increased oxygenation and lung compliance in FIG. 1, while the negative control of lipids alone (Lipids) had minimal effects. The relative order of pulmonary activity in terms of oxygenation was reduced SMB DATK~SMB_Ox~MB_Ox>reduced MB DATK>Lipids alone. Similarly, the relative pulmonary activity with respect to lung compliance was reduced SMB DATK>SMB_Ox~reduced MB DATK~MB_Ox>Lipids alone. FIG. 1 indicates that SMB mimics with high surfactant activity may be more readily and cost-efficiently prepared, simply by replacing -PKGG- (SEQ ID NO: 500) with the bend-promoting -DATK- in the turn region and omitting the oxidation step. FIG. 1 also shows significantly higher arterial oxygenation and dynamic compliance for reduced SMB DATK than for reduced MB DATK. This may be due to SMB DATK retaining the N-terminal insertion sequence, which may increase surfactant activity by anchoring the peptide to the surfactant lipid bilayer and/or promoting dimer or oligomer formation of the SMB peptides in surfactant lipids (Walther et al., "Critical Structural and Functional Roles for the N-terminal Insertion Sequence in Surfactant Protein B Analogs," PLoS One 5:e8672 (2010); Schwan et al., "Synthesis and activity of a novel diether phosphonoglycerol in phospholipase-resistant synthetic lipid peptide lung surfactants,"Med Chem Commun 2:1167 (2011), each of which is hereby incorporated by reference in its entirety).

Example 8—Formulation and Activity Testing of Fully Synthetic Lung Surfactant Compositions Containing SP-C Peptides and Glycerophospholipids In this example, representative synthetic surfactant compositions containing new synthetic SP-C peptides were combined with synthetic ester-linked glycerophospholipids and studied for in vitro adsorption and/or in vivo surfactant activity using methods as in previous examples.

Table 11 shows several representative Mini-SP-C peptides that all have very high adsorption when combined with synthetic ester linked phospholipids. Synthetic surfactant compositions containing 5:3:2 (molar ratio) DPPC:POPC:POPG combined with 3% by weight of Mini-SPCff_dog, Mini-SPCff_dog_leu, Mini-SPCff_2 leu, or Mini-Ccf_dimer all had adsorption equaling that of lung surfactant (i.e., CLSE in Table 7), and adsorption exceeding that of the bovine-derived clinical exogenous surfactant Survanta (i.e., Table 7). The adsorption of surfactant compositions containing Mini-SPCff_dog, Mini-SPCff_dog_leu, Mini-SP-C, or Mini-C dog cf_cys5 dimer in Table 11 is also significantly greater than that of the previously reported SP-C peptide SP-C33.

TABLE 11

Adsorption of Synthetic Surfactant Compositions Containing Representative
New Synthetic Mini-C Peptides Combined at 3% by Weight With Synthetic
Glycerophospholipids (5:3:2 molar ratio DPPC:POPC:POPG)

| Surfactant | Adsorption Surface Pressure (mN/m), at time (min) | | | | | |
|---|---|---|---|---|---|---|
| | 0 | 1 | 2 | 5 | 10 | 15 |
| 5:3:2 DPPC:POPC:POPG | 0.0 ± 0.0 | 4.4 ± 0.8 | 6.2 ± 1.1 | 7.8 ± 0.3 | 9.4 ± 0.7 | 11.2 ± 0.8 |
| 5:3:2 DPPC:POPC:POPG | | | | | | |
| +3.0% SP-C33 | 0.0 ± 0.0 | 29.5 ± 2.7 | 31.4 ± 2.8 | 36.0 ± 2.7 | 40.3 ± 2.9 | 44.7 ± 0.5 |
| +3.0% Mini-SPCff_dog | 0.0 ± 0.0 | 46.0 ± 0.1 | 46.7 ± 0.2 | 47.1 ± 0.2 | 47.2 ± 0.2 | 47.4 ± 0.2 |
| +3.0% Mini-SPCff_dog_leu | 0.0 ± 0.0 | 46.2 ± 0.2 | 47.2 ± 0.3 | 47.6 ± 0.3 | 47.7 ± 0.2 | 47.8 ± 0.2 |
| +3.0% Mini-SPCff_2_leu | 0.0 ± 0.0 | 46.5 ± 0.3 | 47.2 ± 0.4 | 47.4 ± 0.3 | 47.6 ± 0.3 | 47.7 ± 0.3 |
| +3.0% Mini-C dog cf_cys5 dimer | 0.0 ± 0.0 | 46.0 ± 0.2 | 46.8 ± 0.2 | 47.3 ± 0.1 | 47.4 ± 0.1 | 47.4 ± 0.10 |

Experimental methods for adsorption are as in the legend to Table 7. Final surfactant concentration was constant at 0.0625 mg phospholipid/ml; Data are Means ± SEM for n = 4. Abbreviations: SP-C33 = SEQ ID NO: 397, which is reported in Almlen et al. "Concentration Dependence of a Poly-leucine Surfactant Protein C Analogue on in vitro and in vivo Surfactant Activity," Neonatology 92: 194-200 (2007), which is hereby incorporated by reference in its entirety; Mini-SPCff_dog = SEQ ID NO: 31; Mini-SPCff_dog_leu = SEQ ID NO: 32; Mini-SPCff_2_leu = SEQ ID NO: 34; Mini-C dog cf_cys5 dimer = disulfide-linked dimer of Mini-C dog_cf monomers (SEQ ID NO: 33); DPPC = Dipalmitoyl PC; POPC = Palmitoyl-oleoyl-PC; POPG = Palmitoyl-oleoyl-PG.

In addition to extremely high surface activity, the novel Mini-SP-C peptides in Table 11 also have substantial added synthesis/stability advantages relative to full-length native SP-C or existing SP-C peptides such as SP-C33. In particular, novel Mini-SP-C peptides here have only about half the number of amino acid residues present in native SP-C or SP-C33, making them much easier and more cost-effective to synthesize. In addition, novel Mini-SP-C peptides are much more stable against the formation of amyloid-like forms or related non-specific structures that can increase viscosity and reduce shelf life in pharmaceutical applications.

An additional set of SP-C peptides synthesized and studied for surface activity included several ion-lock SP-C peptides. These peptides were synthesized with standard techniques (Waring et al., "The Role of Charged Amphipathic Helices in the Structure and Function of Surfactant Protein B," J Peptide Res 66:364-374 (2005); Walther et al., "Critical Structural and Functional Roles for the N-terminal Insertion Sequence in Surfactant Protein B Analogs," PLoS One 5:e8672 (2010), each of which is hereby incorporated by reference in its entirety). Surfactants were formulated in 0.15M NaCl with pH adjusted to 7.0 with 0.1N sodium bicarbonate as in Example 5. Several of these ion-lock SP-C peptides had high adsorption facility greatly exceeding that of synthetic phospholipids alone (see Table 12 below). SP-C ion-lock peptides that showed substantial rapid adsorption includes: SP-C33ss_ion2, SP-Css ion-lock, SP-C ion-lock2ff. These favorable results are consistent with the interpretation that the Glu-20, Lys-24 residue pair (and also the Lys-15, Glu-19 pair in double ion-locks) may in part facilitate surfactant activity by blocking the formation of inactive β-sheet aggregates.

To assess the structural properties of selected SP-C peptides with and without an ion-lock, FTIR spectroscopic analyses were performed on a peptide without palmitoyl groups that represents the native sequence of SP-C(i.e., SP-Cff; SEQ ID NO: 396), a SP-C mimic with elevated surfactant activity (i.e., SP-C33; SEQ ID NO: 397) and a SP-C mimic with a salt bridge at Glu-20 and Lys-24 (i.e., SP-Css ion-lock; SEQ ID NO: 45). SP-C33 and SP-Css ion-lock were prepared as described earlier, and SP-Cff was also synthesized with standard techniques (Waring et al., "The Role of Charged Amphipathic Helices in the Structure and Function of Surfactant Protein B," J Peptide Res 66:364-374 (2005); Walther et al., "Critical Structural and Functional Roles for the N-terminal Insertion Sequence in Surfactant Protein B Analogs," PLoS One 5:e8672 (2010), each of which is hereby incorporated by reference in its entirety). FTIR spectra were obtained for the above SP-C mimics in surfactant lipids (5:3:2 weight ratio DPPC:POPC:POPG) in 10 mM PBS (pH 7.4) at a peptide/lipid ratio (P/L) of 1/10. Subsequent spectral deconvolutions were performed to determine the relative proportions of secondary structure, as described earlier (Walther et al., "Critical Structural and Functional Roles for the N-terminal Insertion Sequence in Surfactant Protein B Analogs," PLoS One 5:e8672 (2010), which is hereby incorporated by reference in its entirety). FTIR spectra indicated predominant α-helix (i.e., ~63%) for the SP-Css ion-lock in surfactant lipids, as opposed to the very high β-sheet (i.e., ~59%) observed with the corresponding FTIR spectrum of its related parent SP-Cff without an ion-lock. Consequently, insertion of the ion-lock (i.e., Glu⁻-20 and Lys⁺-24) in the mid-section of the poly-Val sequence produced a remarkable conformation shift in the SP-C structure, from an 'amyloid-like' β-sheet profile to one that is primarily α-helix. It is of interest that the corresponding FTIR spectrum of SP-C33 in surfactant lipids showed considerable overlap with that of SP-Css ion-lock, and indicated similarly high α-helical levels (i.e., 67 vs. 63%, respectively). Importantly, prior CD spectra and functional studies on SP-Cff showed low α-helicity and reduced adsorption surface pressure (Johansson et al., "Secondary structure and biophysical activity of synthetic analogues of the pulmonary surfactant polypeptide SP-C," Biochem J 307:535-541 (1995), which is hereby incorporated by reference in its entirety), while earlier FTIR spectroscopy and captive bubble surfactometry of SP-C33 reported high α-helix and low minimum surface tension (Almlen et al., "Alterations of the C-terminal end do not affect in vitro or in vivo activity of surfactant protein C analogs," Biochim Biophys Acta 1818:27-32 (2011)), which is hereby incorporated by reference in its entirety). In the present studies, FTIR spectra and functional measurements on SP-Css ion-lock in surfactant lipids indicated high α-helix content in correlation with its high in vitro surfactant activity (Table 12). In the case of SP-C33, its significant surface activity is likely related to increased α-helicity produced by the large-scale replacement of the poly-Val region of the native SP-C sequence with multiple Leu residues (Table 11) (Almlen et al., "Alterations of the C-terminal end do not affect in vitro or in vivo activity of surfactant protein C analogs," *Biochim Biophys Acta* 1818:27-32 (2011), which is hereby incorporated by reference in its entirety). The elevated α-helix and in vitro adsorption surface pressure noted for SP-Css ion-lock are similar to those of SP-C33, but here are achieved with a novel mechanism in which a single ion-lock (i.e., Glu-20, Lys-24) is incorporated into the transmembrane poly-Val core.

SP-Css ion-lock was readily synthesized as purified peptide in large quantities using standard solid-phase peptide synthesis (SPPS) techniques. Moreover, the SP-Css ion-lock peptide requires only minimal alterations in the native sequence (i.e., insertion of the single ion-lock, Gly-20, Lys-24) to achieve both elevated α-helicity and high surfactant activity and stability, when compared to the poly-Leu substitution in SP-C33. This indicates that SP-C ion-locks may be cleared (i.e., catabolized) more readily by the normal salvage pathways in the lung. Hence, SP-C ion-lock peptides may be less toxic than the SP-C33 class of peptides, especially when administered in therapeutic applications for chronic conditions.

TABLE 12

Adsorption of Synthetic Surfactant Compositions Containing a New SP-C Ion-lock Peptide Plus Synthetic Glycerophospholipids (5:3:2 molar ratio DPPC:POPC:POPG)

| | Adsorption Surface Pressure (mN/m), at time (min) | | | | | |
|---|---|---|---|---|---|---|
| Surfactant | 0 | 1 | 2 | 5 | 10 | 15 |
| 5:3:2 DPPC:POPC:POPG | 0.0 ± 0.0 | 4.4 ± 0.8 | 6.2 ± 1.1 | 7.8 ± 0.3 | 9.4 ± 0.7 | 11.2 ± 0.8 |
| 5:3:2 DPPC:POPC:POPG | | | | | | |
| +3.0% SP-C ion-lock | 0.0 ± 0.0 | 12.8 ± 2.4 | 13.0 ± 2.4 | 13.5 ± 2.4 | 15.2 ± 2.1 | 17.8 ± 2.2 |
| +3.0% SP-C ion-lock-dog | 0.0 ± 0.0 | 17.4 ± 1.2 | 18.6 ± 1.3 | 21.8 ± 2.0 | 27.8 ± 3.0 | 33.7 ± 2.3 |
| +3.0% SP-Css ion-lock | 0.0 ± 0.0 | 34.2 ± 5.6 | 36.3 ± 5.5 | 39.4 ± 4.3 | 41.8 ± 2.1 | 42.5 ± 1.5 |
| +3.0% SP-C ion-lock2ff | 0.0 ± 0.0 | 40.3 ± 1.8 | 42.1 ± 1.6 | 43.6 ± 1.0 | 43.7 ± 0.7 | 43.7 ± 0.7 |
| +3.0% SP-C33ss__ion2 | 0.0 ± 0.0 | 45.1 ± 0.6 | 45.9 ± 0.4 | 46.3 ± 0.4 | 46.3 ± 0.4 | 46.2 ± 0.5 |

Experimental methods for adsorption are as in the legend to Table 7, and final surfactant concentration was constant at 0.0625 mg phospholipid/ml. Data are Means ± SEM for n = 4. Abbreviations: SP-C ion-lock = SEQ ID NO: 406; SP-C ion-lock-dog = SEQ ID NO: 61; SP-Css ion-lock = SEQ ID NO: 45; SP-C ion-lock2ff = SEQ ID NO: 69; SP-C33ss__ion2 = SEQ ID NO: 326; DPPC = Dipalmitoyl PC; POPC = Palmitoyl-oleoyl-PC; POPG = Palmitoyl-oleoyl-PG.

To supplement in vitro studies, the in vivo pulmonary activities of SP-Css ion-lock and SP-Cff peptides were investigated in lavaged, ventilated rabbits with ARDS in comparison with SP-C33 as a positive control) and lipids alone as a negative control. Animal experimental methods were identical to those detailed above in Example 7. SP-C33 was used as a positive control because it has significant in vitro adsorption (Table 11), and also has previously been reported to have high in vitro and in vivo surfactant activities (Almlen et al., "Synthetic surfactant based on analogues of SP-B and SP-C is superior to single-peptides in ventilated premature rabbits," *Neonatology* 998: 91 (2010); Almlen et al., "Alterations of the C-terminal end do not affect in vitro or in vivo activity of surfactant protein C analogs," *Biochim Biophys Acta* 1818:27-32 (2011) each of which is hereby incorporated by reference in its entirety).

Figure 2:
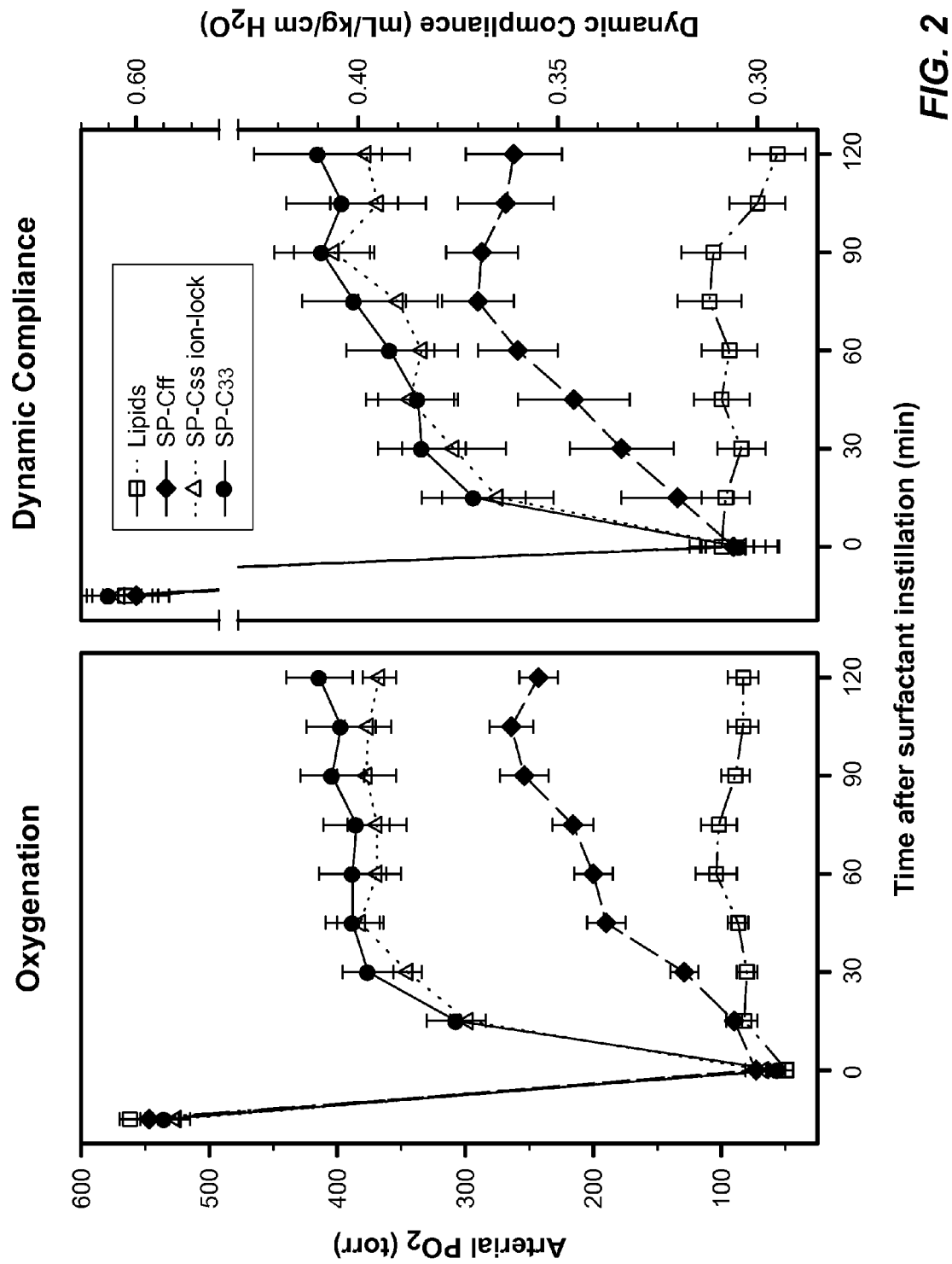
FIG. 2 is a pair of graphs illustrating arterial oxygenation and dynamic compliance in surfactant SP-C mimic-treated, ventilated rabbits with ARDS induced by in vivo lavage. Arterial partial pressure of oxygen and dynamic compliance are shown for groups of rabbits treated with synthetic preparations containing synthetic lipids with 3.0% by weight SP-C33 (SEQ ID NO: 397), SP-C ss ion-lock (SEQ ID NO: 45), SP-Cff (SEQ ID NO: 396). Lipids=Synthetic lipids alone. Synthetic lipids are DPPC:POPC:POPG (5:3:2, weight ratio). Data for the oxygenation and dynamic compliance curves are shown as means±SEM at selected intervals for SP-Css ion-lock (n=7), SP-Cff (n=5), SP-C33 (n=7) and Lipids alone (n=6).

Here, synthetic surfactant preparations were formulated by mixing synthetic lipids, consisting of 5:3:2 (weight ratio) DPPC:POPC:POPG, either alone (Lipids) or with 3.0% by weight SP-Css ion-lock (SEQ ID NO: 45), SP-Cff (SEQ ID NO: 396) and SP-C33 (SEQ ID NO: 397) in sodium phosphate buffered saline (PBS, pH 7.4). FIG. 2 reports the arterial oxygenation and dynamic compliance in surfactant treated rabbits, with the oxygenation and compliance curves shown as means±SEM at selected intervals for SP-Css ion-lock (n=7), SP-Cff (n=5), SP-C33 (n=7) and Lipids alone (n=6). Oxygenation and lung compliance (FIG. 2) increased quickly after instillation of SP-Css ion-lock, but much less so for SP-Cff. Instillation of the positive control SP-C33 also rapidly increased oxygenation and lipid compliance in FIG. 2, while the negative control of lipids alone (Lipids) had minimal effects. The relative order of pulmonary activity in terms of oxygenation and lung compliance was SP-C33~SP-Css ion-lock>SP-Cff>Lipids alone. The substantial in vivo surfactant activity found for SP-Css ion-lock (FIG. 2) correlates well with its high in vitro adsorption (Table 12), as well as with FTIR spectra showing the high α-helix content of both this peptide and SP-C33.

Example 9—Formulation and Activity Testing of Representative Synthetic Lung Surfactant Compositions Containing a New Synthetic SP-B Peptide Plus a New Synthetic SP-C Peptide This example shows the adsorption activity of representative synthetic surfactant compositions containing a new synthetic SP-B peptide and a new synthetic SP-C peptide combined with synthetic ester-linked glycerophospholipids or with phospholipase-resistant lipids. Surfactants were formulated in 0.15M NaCl with pH adjusted to 7.0 with 0.1N sodium bicarbonate as in Example 5, and adsorption methods were as in previous examples.

Table 13 shows that synthetic surfactant compositions containing 5:3:2 (molar ratio) DPPC:POPC:POPG combined with MB DATK_Red+Mini-SPCff_dog (each peptide present at 1.5% by wt relative to phospholipid) had rapid, high adsorption greatly exceeding that of phospholipids alone as a control. Similarly, surfactant compositions containing phospholipase-resistant lipids (9:1 DEPN-8:PG-1) combined with MB DATK_Red+Mini-SPCff_dog (1.5% by wt for each peptide relative to phospholipid) also had rapid, high adsorption greatly exceeding that DEPN-8 alone. The adsorption of these mixed peptide surfactant compositions was equivalent to that of native lung surfactant (CLSE in Table 7) and exceeded the adsorption of the bovine-derived clinical exogenous surfactant Survanta® (Table 7).

TABLE 13

Adsorption of Synthetic Surfactant Compositions Containing a New Synthetic SP-B
Peptide Plus a New Synthetic SP-C Peptide Combined with Phospholipase-Resistant
Lipids or Synthetic Glycerophospholipids (5:3:2 molar ratio DPPC:POPC:POPG)

| Surfactant | Adsorption Surface Pressure (mN/m), at time (min) | | | | | |
| --- | --- | --- | --- | --- | --- | --- |
| | 0 | 1 | 2 | 5 | 10 | 15 |
| 5:3:2 DPPC:POPC:POPG | 0.0 ± 0.0 | 4.4 ± 0.8 | 6.2 ± 1.1 | 7.8 ± 0.3 | 9.4 ± 0.7 | 11.2 ± 0.8 |
| DEPN-8 5:3:2 DPPC:POPC:POPG | 0.0 ± 0.0 | 12.9 ± 2.9 | 16.0 ± 1.6 | 17.8 ± 1.7 | 18.0 ± 1.7 | 18.2 ± 1.7 |
| +MB DATK_Red/ Mini-SPCff_dog (1.5%:1.5%) | 0.0 ± 0.0 | 45.5 ± 0.2 | 46.3 ± 0.2 | 46.8 ± 0.2 | 47.0 ± 0.2 | 46.9 ± 0.1 |
| +S-MB DATK-Red/ Mini-SPCff_dog (1.5%:1.5%) | 0.0 ± 0.0 | 45.1 ± 0.1 | 46.2 ± 0.1 | 46.9 ± 0.2 | 47.3 ± 0.2 | 47.4 ± 0.1 |
| 9:1 DEPN-8:PG-1 +S-MB DATK_Red/ Mini-SPCff_dog (1.5%:1.5%) | 0.0 ± 0.0 | 46.1 ± 0.2 | 46.9 ± 0.3 | 47.2 ± 0.3 | 47.3 ± 0.3 | 47.3 ± 0.3 |

Experimental methods for adsorption are as in the legend to Table 7, and final surfactant concentration was constant at 0.0625 mg phospholipid/ml. Data are Means ± SEM for n = 4. Abbreviations: MB DATK_Red = SEQ ID NO: 4 (reduced); S-MB DATK_Red = SEQ ID NO: 18 (reduced); Mini-SPCff_dog = SEQ ID NO: 31; DEPN-8 = C16:0, C16:0 diether phosphono-PC; DPPC = Dipalmitoyl PC; POPC = Palmitoyl-oleoyl-PC; POPG = Palmitoyl-oleoyl-PG.

Example 10—Activity of a Novel SP-C Peptide After Long-term Room Temperature Storage A direct example of the activity stability of novel Mini-SP-C peptides in this application is provided by the fact that an early synthesis batch of Mini-SPCff_dog was inadvertently stored at room temperature under nitrogen in a laboratory desiccator for a period exceeding 12 months. When this Mini-SPCff_dog peptide material was subsequently studied in a synthetic surfactant preparation combined at 3% by weight with 5:3:2 DPPC:POPC:POPG, the synthetic surfactant had adsorption that was equivalent to that found in Table 11 for analogous surfactant mixtures formulated using new synthesis batches of Mini-SPCff_dog.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated peptide comprising the amino acid sequence according to one of:

(i)

XWLXRALIKRIQAMI-Z-RMLPQLVXRLVLRXS, (SEQ ID NO: 1)

where Z is a loop or turn sequence consisting of four to ten amino acid residues that include peptides DATK (SEQ ID NO: 501), DHGS (SEQ ID NO: 502), HSGD (SEQ ID NO: 503), or EAGD (SEQ ID NO: 504), and each X independently represents an uncharged amino acid residue, and (ii)

XWLXRALIKRIQAXI-Z-RXLPQLVXRLVLRXS, (SEQ ID NO: 414)

where Z is a loop or turn sequence consisting of four to ten amino acid residues that include peptides DATK (SEQ ID NO: 501), DHGS (SEQ ID NO: 502), HSGD (SEQ ID NO: 503), or EAGD (SEQ ID NO: 504), each X at positions 1, 4, 24, and 30 independently represents an uncharged amino acid residue and each X at positions 14 and 18 independently represents leucine, isoleucine, or norleucine.

2. The isolated peptide according to claim 1 wherein the peptide is selected from the group of SEQ ID NOS: 4-15, 18-29, 417-428, 431-442, 445-456, 459-470, 473-484, and 487-498.

3. The isolated peptide according to claim 1 wherein the peptide includes a cysteine residue and the isolated peptide is in the form of a dimer linked via disulfide bond.

4. The isolated peptide according to claim 1 wherein the peptide further comprises a fatty acid chain covalently-linked to an amino acid residue.

5. A surfactant composition comprising a peptide according to claim 1 and a phospholipid.

6. The surfactant composition according to claim 5, wherein the phospholipid is phospholipase-resistant.

7. The surfactant composition according to claim 5, wherein the phospholipid is a naturally occurring phospholipid.

8. The surfactant composition according to claim 5 further comprising a non-phospho surfactant.

9. The surfactant composition according to claim 5 further comprising a therapeutic agent.

10. The surfactant composition according to claim 5 wherein the composition comprises:

| Weight percent | component |
| --- | --- |
| about 85 to about 96 | DEPN-8 or diether C16:0 saturated PC analog |
| about 2.5 to about 10 | C16:0, C18:1 diether phosphono- or phospho-PG |
| up to about 7 | Palmitic acid |
| about 1 to about 4 (relative to total lipid content) | at least one of SMB_DATK (SEQ ID NO: 18, reduced or oxidized), MB_DATK (SEQ ID NO: 4, reduced or oxidized), and MB_DATK_Ala (SEQ ID NO: 5) |
| about 1 to about 4 (relative to total lipid content) | at least one of Mini-SPCff_dog (SEQ ID NO: 31), Mini-SPCff_dog_leu (SEQ ID NO: 32), Mini-SPCff_2_leu (SEQ ID NO: 34), Super Mini-SP-C (SEQ ID NO: 35)), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), and SP-C33ss_ion2 (SEQ ID NO: 326). |

11. The surfactant composition according to claim 5 wherein the composition comprises:

| Weight percent | component |
| --- | --- |
| about 70 to about 95 | dipalmitoyl phosphatidylcholine (DPPC) |
| about 5 to about 25 | palmitoyl-oleoyl-phosphatidylglycerol (POPG) |
| up to about 25 | palmitoyl-oleoyl-phosphatidylcholine (POPC) |
| about 1 to about 7.5 (relative to total lipid content) | SMB_DATK (SEQ ID NO: 18, reduced or oxidized), MB_DATK (SEQ ID NO: 4, reduced or oxidized), MB_DATK_Ala (SEQ ID NO: 5), or combinations thereof. |

12. The surfactant composition according to claim 5 wherein the composition comprises:

| Weight percent | component |
| --- | --- |
| about 70 to about 95 | dipalmitoyl phosphatidylcholine (DPPC) |
| about 5 to about 25 | palmitoyl-oleoyl-phosphatidylglycerol (POPG) |
| up to about 25 | palmitoyl-oleoyl-phosphatidylcholine (POPC) |
| up to about 7 | Palmitic acid |
| about 1 to about 4 (relative to total lipid content) | at least one of SMB_DATK (SEQ ID NO: 18, reduced or oxidized), MB_DATK (SEQ ID NO: 4, reduced or oxidized), and MB_DATK_Ala (SEQ ID NO: 5) |
| about 1 to about 4 (relative to total lipid content) | at least one of Mini-SPCff_dog (SEQ ID NO: 31), Mini-SPCff_dog_leu (SEQ ID NO: 32), Mini-SPCff_2_leu (SEQ ID NO: 34), Super Mini-SP-C (SEQ ID NO: 35) ), SP-Css ion-lock (SEQ ID NO: 45), SP-C ion-lock (SEQ ID NO: 406), SP-C ion-lock2ss (SEQ ID NO: 197), SP-C ion-lock-dog (SEQ ID NO: 61), SP-C ion-lock2ff (SEQ ID NO: 69), and SP-C33ss_ion2 (SEQ ID NO: 326). |

13. The isolated peptide of claim 1, wherein each X at positions 1, 4, 24, and 30 of SEQ ID NO: 1 and SEQ ID NO: 414 independently represents Val, Ile, Leu, Met, Phe, His, Tyr, Gly, Ala, Cys, Pro, Asn, Gln, Ser, or Thr.

14. A method of treating endogenous surfactant deficiency and/or dysfunctional lung tissue comprising:
providing a surfactant composition according to claim 5; and
administering the surfactant composition to a patient having lung tissue characterized by endogenous surfactant deficiency and/or dysfunction, wherein said administering coats alveolar surfaces of the affected lung tissue with the surfactant composition, thereby treating the surfactant deficient and/or dysfunctional lung tissue.

15. A method of delivering a therapeutic agent comprising:
introducing a therapeutic agent into a surfactant composition according to claim 5; and
administering the composition to a subject to deliver the therapeutic agent to a target tissue.

* * * * *

UNITED STATES PATENT AND TRADEMARK OFFICE
CERTIFICATE OF CORRECTION

PATENT NO.        : 9,815,869 B2
APPLICATION NO.   : 14/376726
DATED             : November 14, 2017
INVENTOR(S)       : Robert H. Notter et al.

Page 1 of 1

It is certified that error appears in the above-identified patent and that said Letters Patent is hereby corrected as shown below:

In the Claims

At Claim 10, Column 323, Line 60, delete "DEPN-8 or diether C16:0 saturated PC analog" and insert --C16:0, C16:0 diether phosphono-phosphatidylcholine (DEPN-8) or diether C16:0 saturated phosphatidylcholine--.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*